(12) United States Patent
Barney et al.

(10) Patent No.: US 12,161,760 B2
(45) Date of Patent: Dec. 10, 2024

(54) IMPLANTABLE PARTICLES AND RELATED METHODS

(71) Applicant: SIGILON THERAPEUTICS, INC., Cambridge, MA (US)

(72) Inventors: Lauren Emily Barney, Cambridge, MA (US); Michael Beauregard, Boston, MA (US); Guillaume Carmona, Cambridge, MA (US); Francisco Caballero Gonzalez, Brookline, MA (US); Richard Heidebrecht, Somerville, MA (US); Erika Ellen Johnston, Cambridge, MA (US); Robert James Miller, East Bridgewater, MA (US); Matthias Alexander Oberli, Cambridge, MA (US); Owen O'Connor, Raynham, MA (US); David Peritt, Skokie, IL (US); Jared A. Sewell, Somerville, MA (US); Devyn McKinley Smith, Barrington, RI (US); Omid Veiseh, Bellaire, TX (US); Paul Kevin Wotton, Boston, MA (US)

(73) Assignee: SIGILON THERAPEUTICS, INC., Cambridge, MA (US)

(*) Notice: Subject to any disclaimer, the term of this patent is extended or adjusted under 35 U.S.C. 154(b) by 1043 days.

(21) Appl. No.: 17/045,127

(22) PCT Filed: Mar. 27, 2019

(86) PCT No.: PCT/US2019/024371
§ 371 (c)(1),
(2) Date: Oct. 2, 2020

(87) PCT Pub. No.: WO2019/195055
PCT Pub. Date: Oct. 10, 2019

(65) Prior Publication Data
US 2021/0145759 A1 May 20, 2021

Related U.S. Application Data

(60) Provisional application No. 62/812,568, filed on Mar. 1, 2019, provisional application No. 62/737,838, filed on Sep. 27, 2018, provisional application No. 62/652,880, filed on Apr. 4, 2018.

(51) Int. Cl.
| | |
|---|---|
| *A61K 9/50* | (2006.01) |
| *A61K 35/28* | (2015.01) |
| *A61K 35/30* | (2015.01) |
| *C07K 14/62* | (2006.01) |
| *C07K 14/755* | (2006.01) |
| *C12N 9/64* | (2006.01) |

(52) U.S. Cl.
CPC .......... *A61K 9/5031* (2013.01); *A61K 9/5036* (2013.01); *A61K 9/5073* (2013.01); *A61K 9/5089* (2013.01); *A61K 35/28* (2013.01); *A61K 35/30* (2013.01); *C07K 14/62* (2013.01); *C07K 14/755* (2013.01); *C12N 9/644* (2013.01); *C12Y 304/21022* (2013.01)

(58) Field of Classification Search
None
See application file for complete search history.

(56) References Cited

U.S. PATENT DOCUMENTS

| | | | |
|---|---|---|---|
| 4,784,950 A | 11/1988 | Hagen et al. | |
| 5,578,314 A | 11/1996 | Cochrum et al. | |
| 5,876,742 A * | 3/1999 | Cochrum | A61K 9/5031 264/4.1 |
| 6,361,771 B1 | 3/2002 | Tao et al. | |
| 6,533,819 B1 | 3/2003 | Urry et al. | |
| 8,741,340 B2 | 6/2014 | Kusk et al. | |
| 9,121,037 B2 | 9/2015 | Kusk et al. | |
| 9,422,373 B2 | 8/2016 | Vegas et al. | |
| 9,555,007 B2 * | 1/2017 | Ma | A61K 35/39 |
| 9,867,781 B2 | 1/2018 | Anderson et al. | |
| 9,925,219 B2 | 3/2018 | Kauper et al. | |
| 10,172,791 B2 * | 1/2019 | Ma | A61K 9/0024 |
| 10,278,922 B2 | 5/2019 | Anderson et al. | |
| 10,285,949 B2 | 5/2019 | Vegas et al. | |
| 10,292,936 B2 | 5/2019 | Vegas et al. | |
| 10,426,735 B2 | 10/2019 | Vegas et al. | |
| 10,786,446 B2 * | 9/2020 | Ma | A61K 9/5089 |
| 11,446,239 B2 * | 9/2022 | Ma | A61P 9/00 |
| 2004/0185083 A1 * | 9/2004 | Dionne | A61P 5/24 424/426 |

(Continued)

FOREIGN PATENT DOCUMENTS

| | | |
|---|---|---|
| CN | 104072478 A | 10/2014 |
| CN | 106795225 A | 5/2017 |

(Continued)

OTHER PUBLICATIONS

International Search Report and Written Opinion for Application No. PCT/US2018/053191 mailed Mar. 5, 2019.
Sieving et al., "Ciliary neurotrophic factor (CNTF) for human retinal degeneration: Phase I trial of CNTF delivered by encapsulated cell intraocular implants" Proceedings of the National Academy of Sciences, 2006, vol. 103, No. 10, pp. 3896-3901.
Shintani et al., "Review and update: Current treatment trends for patients with retinitis pigmentosa" Optometry, 2009, vol. 80, No. 7, pp. 384-401.
Wikstrom et al., "Alginate-based microencapsulation of retinal pigment epithelial cell line for cell therapy" Biomaterials, 2008, vol. 29, pp. 869-876.

(Continued)

*Primary Examiner* — Blaine Lankford
(74) *Attorney, Agent, or Firm* — Lando & Anastasi, LLP

(57) ABSTRACT

Described herein are particles comprising a first compartment, a second compartment, and a compound of Formula (I), as well as compositions and methods of making and using the same. The particles may comprise a cell capable of expressing a therapeutic agent useful for the treatment of a disease, disorder, or condition described herein.

27 Claims, 45 Drawing Sheets
Specification includes a Sequence Listing.

(56) References Cited

U.S. PATENT DOCUMENTS

| | | |
|---|---|---|
| 2008/0076174 A1 | 3/2008 | Selden et al. |
| 2013/0259924 A1 | 10/2013 | Bancel et al. |
| 2014/0010861 A1 | 1/2014 | Bancel et al. |
| 2014/0271843 A1 | 9/2014 | Ma et al. |
| 2016/0030359 A1 | 2/2016 | Ma et al. |
| 2016/0030360 A1 | 2/2016 | Vegas et al. |
| 2016/0207978 A1 | 7/2016 | Kelly |
| 2017/0260516 A1 | 9/2017 | Tan et al. |
| 2018/0318612 A1 | 11/2018 | Tzahor et al. |
| 2019/0000932 A1 | 1/2019 | Martini et al. |

FOREIGN PATENT DOCUMENTS

| | | |
|---|---|---|
| JP | 2004-532234 A | 10/2004 |
| JP | 5725475 B2 | 5/2015 |
| JP | 2016-516020 A | 6/2016 |
| JP | 2016-517879 A | 6/2016 |
| JP | 2016-519079 A | 6/2016 |
| JP | 2017-524768 A | 8/2017 |
| WO | 96/28029 A1 | 9/1996 |
| WO | 2008/021388 A1 | 2/2008 |
| WO | 2008/036308 A2 | 3/2008 |
| WO | 2010/005533 A2 | 1/2010 |
| WO | 2012/112982 A2 | 8/2012 |
| WO | 2012/167223 A1 | 12/2012 |
| WO | 2014/147386 A1 | 9/2014 |
| WO | 2014/153126 A1 | 9/2014 |
| WO | 2015/143418 A2 | 9/2015 |
| WO | 2016/019391 A1 | 2/2016 |
| WO | 2016/187225 A1 | 11/2016 |
| WO | 2017/018086 A1 | 2/2017 |
| WO | 2017/075630 A1 | 5/2017 |
| WO | 2017/075631 A1 | 5/2017 |
| WO | 2017/136358 A1 | 8/2017 |
| WO | 2018/067615 A1 | 4/2018 |
| WO | 2018/206168 A1 | 11/2018 |
| WO | 2019/067766 A1 | 4/2019 |
| WO | 2019/195056 A1 | 10/2019 |

OTHER PUBLICATIONS

Carvalho et al., "Click Chemistry' synthesis of a library of 1,2,3-triazole-substituted galactose derivatives and their evaluation against Trypanosoma cruzi and its cell surface trans-sialidase," Bioorganic & Medicinal Chemistry, vol. 18, No. 7, pp. 2412-2427, (2010).

Corbel et al., "Identification of potential cellular targets of aloisine A by affinity chromatography," Bioorganic & Medicinal Chemistry, vol. 17, No. 15, pp. 5572-5582, (2009).

Struthers et al., "'Click-to-Chelate': Design and Incorporation of Triazole-containing Metal-chelating Systems into Biomolecules of Diagnostic and Therapeutic Interest," Chemistry—A European Journal, vol. 14, No. 20, pp. 6173-6183, (2008).

International Search Report and Written Opinion for PCT/US2017/055001 mailed Nov. 27, 2017.

Arunrungvichian et al., "Selectivity optimization of substituted 1,2,3-Triazoles as a7 nicotinic acetylcholine receptor agonists" ACS Chemical Neuroscience, vol. 6, No. 8, 2015, pp. 1317-1330.

RN:1545351-08-3, Database Registry [Online], Retrieved from STN, Feb. 16, 2014.

Panda et al., "A nucleus-imaging probe that selectively stabilizes a minor conformation of c-MYC G-quadruplex and Down-regulates c-MYC Transcription in Human Cancer Cells" Scienctific Reports, 2015, vol. 5, pp. 1-16.

Bochenek et al., "Alginate encapsulation as long-term immune protection of allogeneic pancreatic islet cells transplanted into the omental bursa of macaques" Nature Biomedical Engineering, 2018, vol. 2, No. 11, pp. 810-821.

Vegas et al., "Long-term glycemic control using polymer-encapsulated human stem cell-derived beta cells in immune-competent mice" Nature Medicine, 2016, vol. 22, No. 3, pp. 306-311.

Vegas et al., "Combinatorial hydrogel library enables identification of materials that mitigate the foreign body response in primates" Nature Biotechnology, 2016, vol. 34, No. 3, pp. 345-352.

International Search Report and Written Opinion for Application No. PCT/US2019/024385 mailed Aug. 7, 2019.

Bremond et al., "Formation of liquid-core capsules having a thin hydrogel membrane: liquid pearls" Soft Matter, 2010, vol. 6, No. 11, pp. 2484-2488.

Veiseh et al., "Size- and shape-dependent foreign body immune response to materials implanted in rodents and non-human primates" Nature Materials, 2015, vol. 14, pp. 643-652.

Lee et al., "Size and shape of calcium alginate beads produced by extrusion dripping" Chemical Engineering and Technology, 2013, vol. 36, No. 10, pp. 1627-1642.

International Search Report and Written Opinion for Application No. PCT/US2019/020248 mailed Jun. 26, 2019.

International Search Report and Written Opinion for Application No. PCT/US2019/020405 mailed Jul. 15, 2019.

Llacua et al., "Extracellular matrix molecules and their potential contribution to the function of transplanted pancreatic islets" Diabetologia, 2018, vol. 61, pp. 1261-1272.

Llacua et al., "Laminin and collagen IV inclusion in immunoisolating microcapsules reduces cytokine-mediated cell death in human pancreatic islets" Journal of Tissue Engineering and Regenerative Medicine, 2017, 25 pages.

Orive et al., "Engineering a clinically translatable bioartificial pancreas to treat type I diabetes" Trends in Biotechnology, 2018, 12 pages.

Llacua et al., "Extracellular matrix components supporting human islet function in alginate-based immunoprotective microcapsules for treatment of diabetes" Journal of Biomedical Materials Research Part A, 2018, 10 pages.

Bochenek et al., "Alginate encapsulation as long-term immune protection of allogeneic pancreatic islet cells transplanted into the omental bursa of macaques" Nature Biomedical Engineering, vol. 2, No. 11, pp. 810-821, 2018.

Belhaj, "Enhancements in alginate microencapsulation technology & impacts on cell therapy development", Disseration, Jan. 2018 (109 pages).

Weber et al., "Multifunctional pancreatic islet encapsulation barriers achieved via multilayer PEG hydrogels", Cell Transplantation, vol. 16, No. 10, pp. 1049-1057, 2007.

Jeon et al., "Biodegradable, photocrosslinked alginate hydrogels with independently tailorable physical properties and cell adhesivity", Tissue Engineering, vol. 16, No. 9, pp. 2915-2925, 2010.

International Search Report and Written Opinion for Application No. PCT/US2019/053637 mailed Feb. 14, 2020.

International Search Report and Written Opinion for Application No. PCT/2020/02585 mailed Aug. 28, 2020.

International Search Report and Written Opinion for Application No. PCT/2020/025511 mailed Aug. 28, 2020.

International Search Report and Written Opinion for Application No. PCT/US2019/024371 mailed Aug. 14, 2019.

\* cited by examiner

SEQ ID NO: 1

*MQIELSTCFFLCLLRFCFS*ATRRYYLGAVELSWDYMQSDLGELPVDARFPPRVPKSFPFN
TSVVYKKTLFVEFTDHLFNIAKPRPPWMGLLGPTIQAEVYDTVVITLKNMASHPVSLHAV
GVSYWKASEGAEYDDQTSQREKEDDKVFPGGSHTYVWQVLKENGPMASDPLCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNAIEPRSFSQNPPVLKRHQREITRTTL
QSDQEEIDYDDTISVEMKKEDFDIYDEDENQSPRSFQKKTRHYFIAAVERLWDYGMSSSP
HVLRNRAQSGSVPQFKKVVFQEFTDGSFTQPLYRGELNEHLGLLGPYIRAEVEDNIMVTF
RNQASRPYSFYSSLISYEEDQRQGAEPRKNFVKPNETKTYFWKVQHHMAPTKDEFDCKAW
AYFSDVDLEKDVHSGLIGPLLVCHTNTLNPAHGRQVTVQEFALFFTIFDETKSWYFTENM
ERNCRAPCNIQMEDPTFKENYRFHAINGYIMDTLPGLVMAQDQRIRWYLLSMGSNENIHS
IHFSGHVFTVRKKEEYKMALYNLYPGVFETVEMLPSKAGIWRVECLIGEHLHAGMSTLFL
VYSNKCQTPLGMASGHIRDFQITASGQYGQWAPKLARLHYSGSINAWSTKEPFSWIKVDL
LAPMIIHGIKTQGARQKFSSLYISQFIIMYSLDGKKWQTYRGNSTGTLMVFFGNVDSSGI
KHNIFNPPIIARYIRLHPTHYSIRSTLRMELMGCDLNSCSMPLGMESKAISDAQITASSY
FTNMFATWSPSKARLHLQGRSNAWRPQVNNPKEWLQVDFQKTMKVTGVTTQGVKSLLTSM
YVKEFLISSSQDGHQWTLFFQNGKVKVFQGNQDSFTPVVNSLDPPLLTRYLRIHPQSWVH
QIALRMEVLGCEAQDLY

FIG. 2A

SEQ ID NO: 2

YNSGKLEEFVQGNLERECMEEKCSFEEAREVFENTERTTEFWKQYVDGDQCESNPCLNG
GSCKDDINSYECWCPFGFEGKNCELDVTCNIKNGRCEQFCKNSADNKVVCSCTEGYRLA
ENQKSCEPAVPFPCGRVSVSQTSKLTRAETVFPDVDYVNSTEAETILDNITQSTQSFND
FTRVVGGEDAKPGQFPWQVVLNGKVDAFCGGSIVNEKWIVTAAHCVETGVKITVVAGEH
NIEETEHTEQKRNVIRIIPHHNYNAAINKYNHDIALLELDEPLVLNSYVTPICIADKEY
TNIFLKFGSGYVSGWGRVFHKGRSALVLQYLRVPLVDRATCLRSTKFTIYNNMFCAGFH
EGGRDSCQGDSGGPHVTEVEGTSFLTGIISWGEECAMKGKYGIYTKVSRYVNWIKEKTK
LT

FIG. 2B

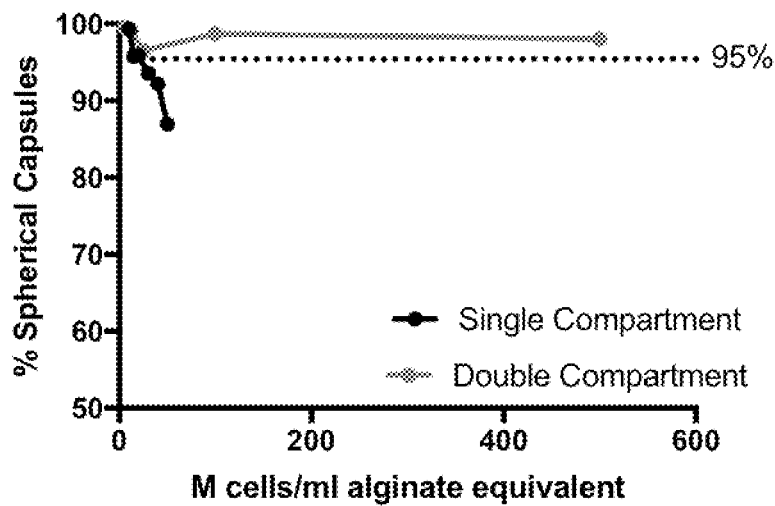

FIG. 3

| Inner Compartment % | Outer Compartment % | Outer Compartment Thicnkess (∞m) |
|---|---|---|
| 20 | 80 | 267 |
| 30 | 70 | 192 |
| 40 | 60 | 122 |
| 50 | 50 | 75 |
| 60 | 40 | 68 |
| 70 | 30 | 28 |
| 80 | 20 | 23 |
| 90 | 10 | 11 |

FIG. 7A Low Conjugation
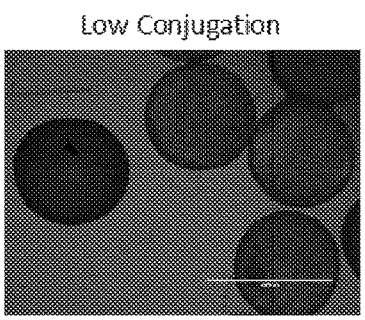
FIG. 7B Medium Conjugation
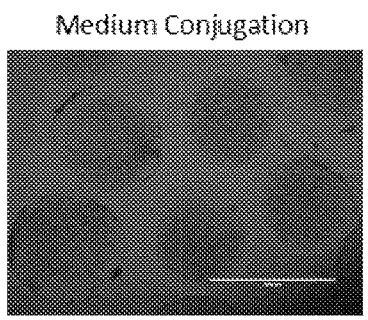
FIG. 7C High Conjugation
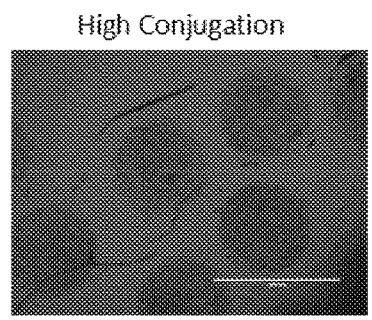
Empty (Medium Conjugation)
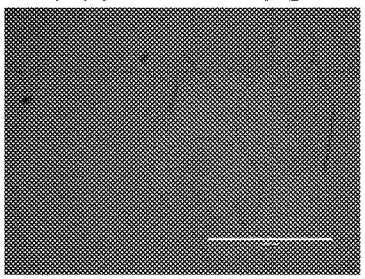
Control
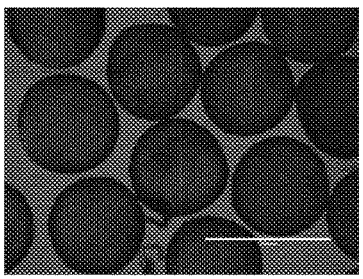
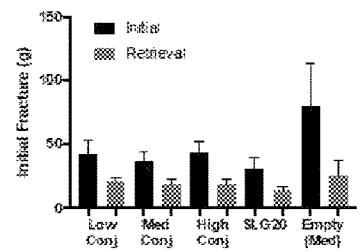
FIG. 7D  FIG. 7E  FIG. 7F
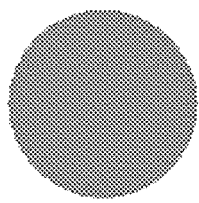
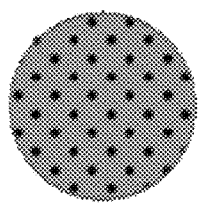
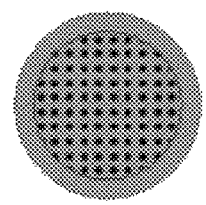
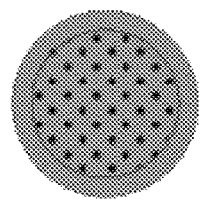
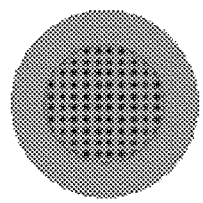
FIG. 8A  FIG. 8B  FIG. 8C  FIG. 8D  FIG. 8E

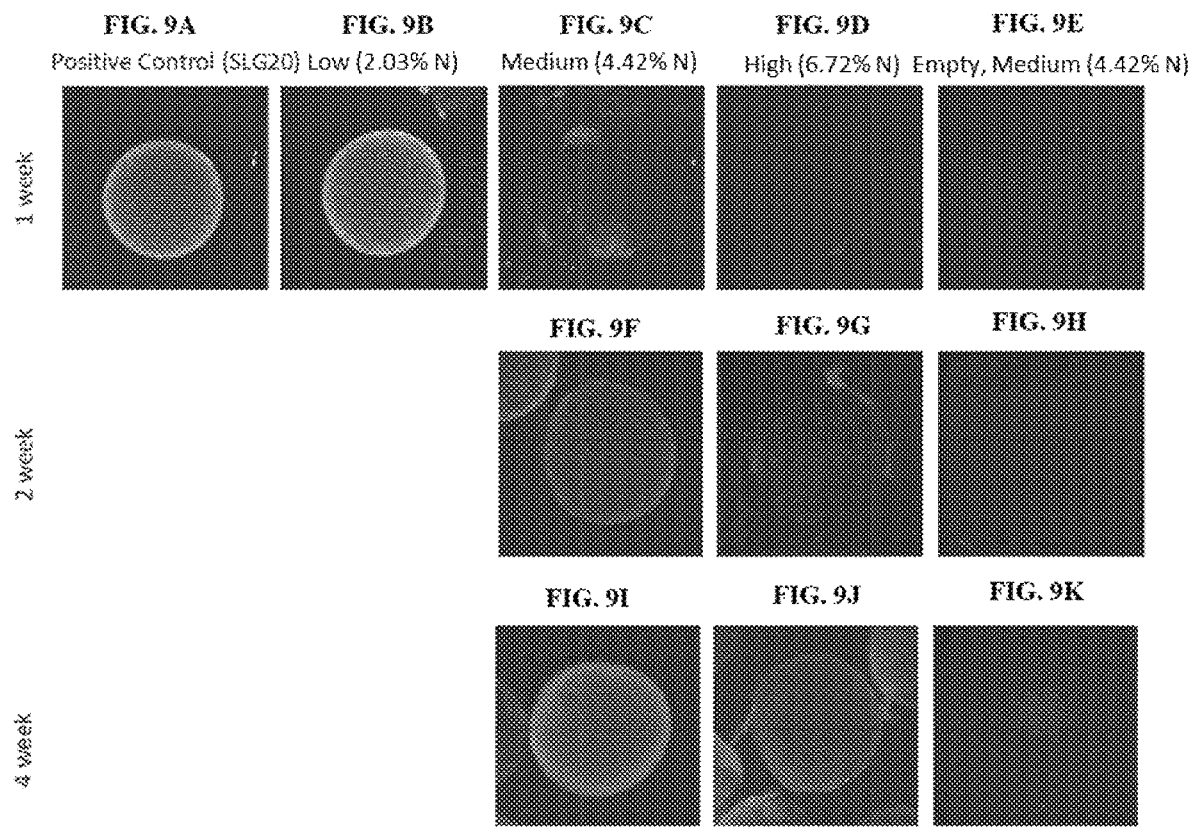

FIG. 10A
Empty, Medium (4.42% N)
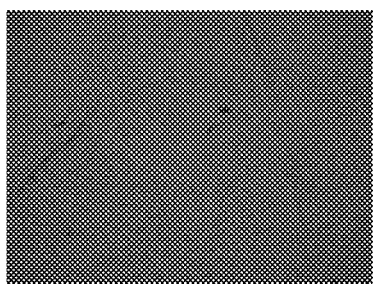
FIG. 10B
Medium (4.42% N)
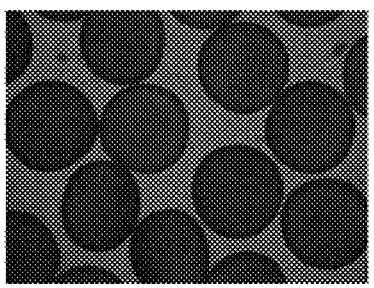
FIG. 10C
Medium-High (4.79% N)
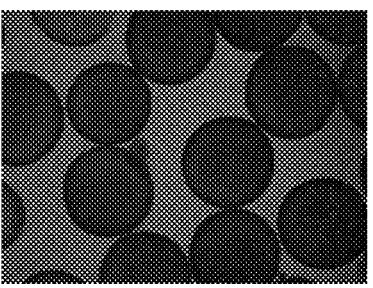
High (6.72% N)
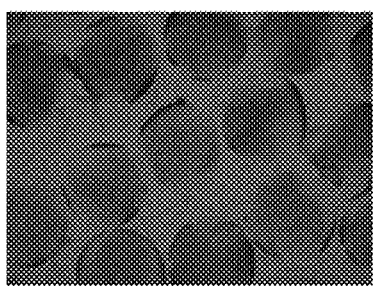
Double High (9.00% N)
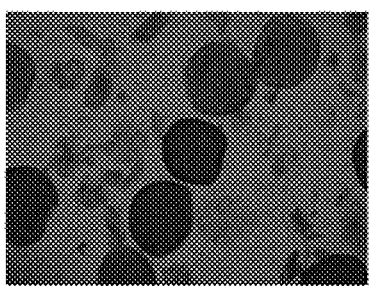
FIG. 10D
FIG. 10E
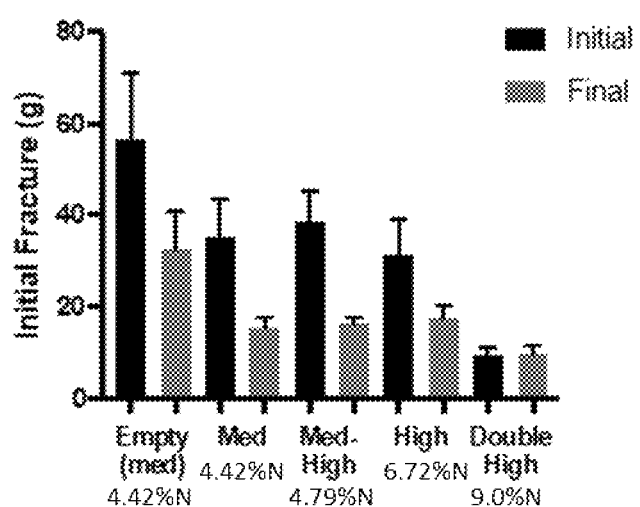
FIG. 11

FIG. 12A
Medium (4.42% N)
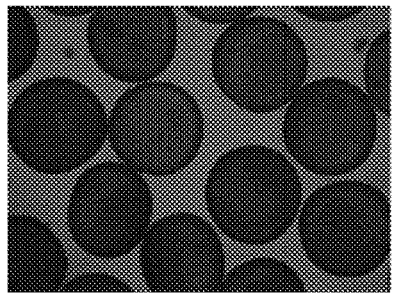
FIG. 12B
High (4.79% N)
FIG. 12C
Amine Added Back (~4.42% N)
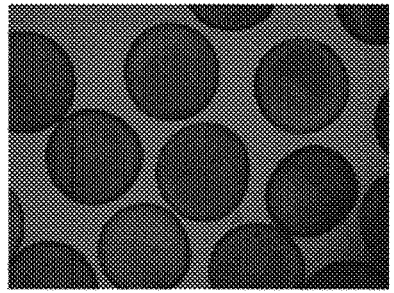
FIG. 13A
Medium (4.42% N)
FIG. 13B
Medium-High (4.79% N)
FIG. 13C
High (6.72% N)
70:30
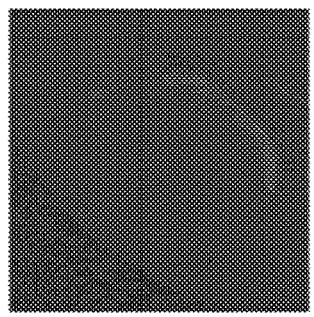
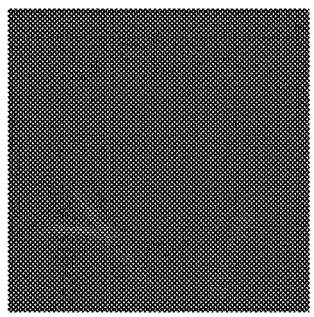
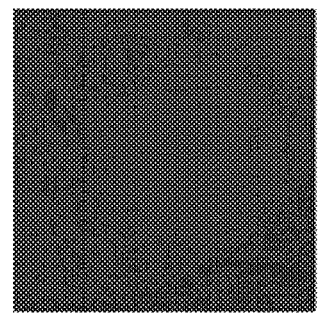
60:40
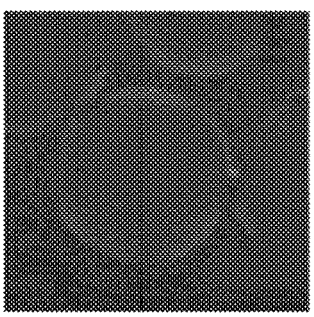
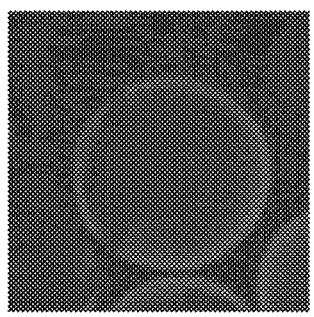
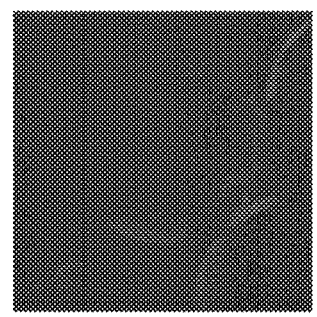
FIG. 13D
FIG. 13E
FIG. 13F

FIG. 14A
Single Compartment
FIG. 14B
Double Compartment
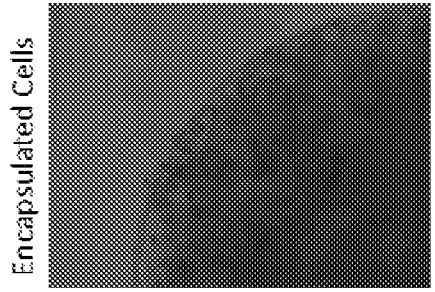
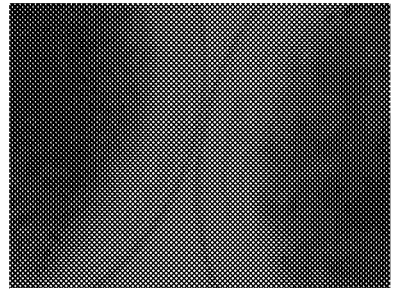
Encapsulated Cells
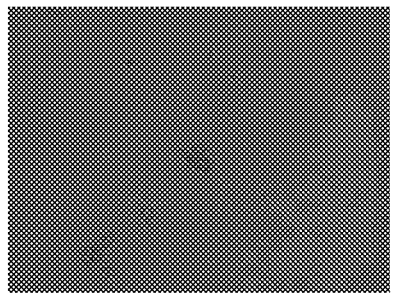
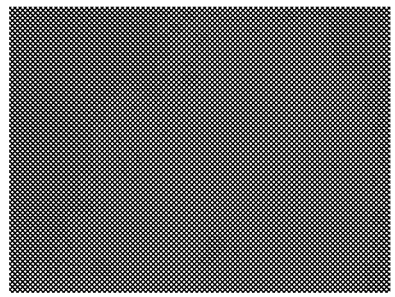
Tissue Culture Plate Surface
FIG. 14C
FIG. 14D

FIG. 17A

Table 4:

| SEQ ID NO. | Protein | Amino Acid Sequence |
|---|---|---|
| 1 | rhFVIII-BDD | MQIELSTCFF LCLLRFCFSA TRRYYLGAVE LSWDYMQSDL GELPVDARFP<br>PRVPKSFPFN TSVVYKKTLF VEFTDHLFNI AKPRPPWMGL LGPTIQAEVY<br>DTVVITLKNM ASHPVSLHAV GVSYWKASEG AEYDDQTSQR EKEDDKVFPG<br>GSHTYVWQVL KENGPMASDP LCLTYSYLSH VDLVKDLNSG LIGALLVCRE<br>GSLAKEKTQT LHKFILLFAV FDEGKSWHSE TKNSLMQDRD AASARAWPKM<br>HTVNGYVNRS LPGLIGCHRK SVYWHVIGMG TTPEVHSIFL EGHTFLVRNH<br>RQASLEISPI TFLTAQTLLM DLGQFLLFCH ISSHQHDGME AYVKVDSCPE<br>EPQLRMKNNE EAEDYDDDLT DSEMDVVRFD DDNSPSFIQI RSVAKKHPKT<br>WVHYIAAEEE DWDYAPLVLA PDDRSYKSQY LNNGPQRIGR KYKKVRFMAY<br>TDETFKTREA IQHESGILGP LLYGEVGDTL LIIFKNQASR PYNIYPHGIT<br>DVRPLYSRRL PKGVKHLKDF PILPGEIFKY KWTVTVEDGP TKSDPRCLTR<br>YYSSFVNMER DLASGLIGPL LICYKESVDQ RGNQIMSDKR NVILFSVFDE<br>NRSWYLTENI QRFLPNPAGV QLEDPEFQAS NIMHSINGYV FDSLQLSVCL<br>HEVAYWYILS IGAQTDFLSV FFSGYTFKHK MVYEDTLTLF PFSGETVFMS<br>MENPGLWILG CHNSDFRNRG MTALLKVSSC DKNTGDYYED SYEDISAYLL<br>SKNNAIEPRS FSQNPPVLKR HQREITRTTL QSDQEEIDYD DTISVEMKKE<br>DFDIYDEDEN QSPRSFQKKT RHYFIAAVER LWDYGMSSSP HVLRNRAQSG<br>SVPQFKKVVF QEFTDGSFTQ PLYRGELNEH LGLLGPYIRA EVEDNIMVTF<br>RNQASRPYSF YSSLISYEED QRQGAEPRKN FVKPNETKTY FWKVQHHMAP<br>TKDEFDCKAW AYFSDVDLEK DVHSGLIGPL LVCHTNTLNP AHGRQVTVQE<br>FALFFTIFDE TKSWYFTENM ERNCRAPCNI QMEDPTFKEN YRFHAINGYI<br>MDTLPGLVMA QDQRIRWYLL SMGSNENIHS IHFSGHVFTV RKKEEYKMAL<br>YNLYPGVFET VEMLPSKAGI WRVECLIGEH LHAGMSTLFL VYSNKCQTPL<br>GMASGHIRDF QITASGQYGQ WAPKLARLHY SGSINAWSTK EPFSWIKVDL<br>LAPMIIHGIK TQGARQKFSS LYISQFIIMY SLDGKKWQTY RGNSTGTLMV<br>FFGNVDSSGI KHNIFNPPII ARYIRLHPTH YSIRSTLRME LMGCDLNSCS<br>MPLGMESKAI SDAQITASSY FTNMFATWSP SKARLHLQGR SNAWRPQVNN<br>PKEWLQVDFQ KTMKVTGVTT QGVKSLLTSM YVKEFLISSS QDGHQWTLFF<br>QNGKVKVFQG NQDSFTPVVN SLDPPLLTRY LRIHPQSWVH QIALRMEVLG<br>CEAQDLY |
| 3 | rhScFVIII-BDD 1 | MQIELSTCFF LCLLRFCFSA TRRYYLGAVE LSWDYMQSDL GELPVDARFP<br>PRVPKSFPFN TSVVYKKTLF VEFTDHLFNI AKPRPPWMGL LGPTIQAEVY<br>DTVVITLKNM ASHPVSLHAV GVSYWKASEG AEYDDQTSQR EKEDDKVFPG<br>GSHTYVWQVL KENGPMASDP LCLTYSYLSH VDLVKDLNSG LIGALLVCRE<br>GSLAKEKTQT LHKFILLFAV FDEGKSWHSE TKNSLMQDRD AASARAWPKM<br>HTVNGYVNRS LPGLIGCHRK SVYWHVIGMG TTPEVHSIFL EGHTFLVRNH<br>RQASLEISPI TFLTAQTLLM DLGQFLLFCH ISSHQHDGME AYVKVDSCPE<br>EPQLRMKNNE EAEDYDDDLT DSEMDVVRFD DDNSPSFIQI RSVAKKHPKT<br>WVHYIAAEEE DWDYAPLVLA PDDRSYKSQY LNNGPQRIGR KYKKVRFMAY<br>TDETFKTREA IQHESGILGP LLYGEVGDTL LIIFKNQASR PYNIYPHGIT<br>DVRPLYSRRL PKGVKHLKDF PILPGEIFKY KWTVTVEDGP TKSDPRCLTR<br>YYSSFVNMER DLASGLIGPL LICYKESVDQ RGNQIMSDKR NVILFSVFDE<br>NRSWYLTENI QRFLPNPAGV QLEDPEFQAS NIMHSINGYV FDSLQLSVCL<br>HEVAYWYILS IGAQTDFLSV FFSGYTFKHK MVYEDTLTLF PFSGETVFMS |

FIG. 17B

| | | | | | | |
|---|---|---|---|---|---|---|
| | | MENPGLWILG | CHNSDFRNRG | MTALLKVSSC | DKNTGDYYED | SYEDISAYLL |
| | | SKNNAIEPRS | FSQNPPVLKH | HQREITRTTL | QSDQEEIDYD | DTISVEMKKE |
| | | DFDIYDEDEN | QSPRSFQKKT | RHYFIAAVER | LWDYGMSSSP | HVLRNRAQSG |
| | | SVPQFKKVVF | QEFTDGSFTQ | PLYRGELNEH | LGLLGPYIRA | EVEDNIMVTF |
| | | RNQASRPYSF | YSSLISYEED | QRQGAEPRKN | FVKPNETKTY | FWKVQHHMAP |
| | | TKDEFDCKAW | AYFSDVDLEK | DVHSGLIGPL | LVCHTNTLNP | AHGRQVTVQE |
| | | FALFFTIFDE | TKSWYFTENM | ERNCRAPCNI | QMEDPTFKEN | YRFHAINGYI |
| | | MDTLPGLVMA | QDQRIRWYLL | SMGSNENIHS | IHFSGHVFTV | RKKEEYKMAL |
| | | YNLYPGVFET | VEMLPSKAGI | WRVECLIGEH | LHAGMSTLFL | VYSNKCQTPL |
| | | GMASGHIRDF | QITASGQYGQ | WAPKLARLHY | SGSINAWSTK | EPFSWIKVDL |
| | | LAPMIIHGIK | TQGARQKFSS | LYISQFIIMY | SLDGKKWQTY | RGNSTGTLMV |
| | | FFGNVDSSGI | KHNIFNPPII | ARYIRLHPTH | YSIRSTLRME | LMGCDLNSCS |
| | | MPLGMESKAI | SDAQITASSY | FTNMFATWSP | SKARLHLQGR | SNAWRPQVNN |
| | | PKEWLQVDFQ | KTMKVTGVTT | QGVKSLLTSM | YVKEFLISSS | QDGHQWTLFF |
| | | QNGKVKVFQG | NQDSFTPVVN | SLDPPLLTRY | LRIHPQSWVH | QIALRMEVLG |
| | | CEAQDLY | | | | |
| 4 | rhScFVIII-BDD 2 | MQIELSTCFF | LCLLRFCFSA | TRRYYLGAVE | LSWDYMQSDL | GELPVDARFP |
| | | PRVPKSFPFN | TSVVYKKTLF | VEFTDHLFNI | AKPRPPWMGL | LGPTIQAEVY |
| | | DTVVITLKNM | ASHPVSLHAV | GVSYWKASEG | AEYDDQTSQR | EKEDDKVFPG |
| | | GSHTYVWQVL | KENGPMASDP | LCLTYSYLSH | VDLVKDLNSG | LIGALLVCRE |
| | | GSLAKEKTQT | LHKFILLFAV | FDEGKSWHSE | TKNSLMQDRD | AASARAWPKM |
| | | HTVNGYVNRS | LPGLIGCHRK | SVYWHVIGMG | TTPEVHSIFL | EGHTFLVRNH |
| | | RQASLEISPI | TFLTAQTLLM | DLGQFLLFCH | ISSHQHDGME | AYVKVDSCPE |
| | | EPQLRMKNNE | EAEDYDDDLT | DSEMDVVRFD | DDNSPSFIQI | RSVAKKHPKT |
| | | WVHYIAAEEE | DWDYAPLVLA | PDDRSYKSQY | LNNGPQRIGR | KYKKVRFMAY |
| | | TDETFKTREA | IQHESGILGP | LLYGEVGDTL | LIIFKNQASR | PYNIYPHGIT |
| | | DVRPLYSRRL | PKGVKHLKDF | PILPGEIFKY | KWTVTVEDGP | TKSDPRCLTR |
| | | YYSSFVNMER | DLASGLIGPL | LICYKESVDQ | RGNQIMSDKR | NVILFSVFDE |
| | | NRSWYLTENI | QRFLPNPAGV | QLEDPEFQAS | NIMHSINGYV | FDSLQLSVCL |
| | | HEVAYWYILS | IGAQTDFLSV | FFSGYTFKHK | MVYEDTLTLF | PFSGETVFMS |
| | | MENPGLWILG | CHNSDFRNRG | MTALLKVSSC | DKNTGDYYED | SYEDISAYLL |
| | | SKNNAIEPRS | FSQNPPVLKA | HQAEITRTTL | QSDQEEIDYD | DTISVEMKKE |
| | | DFDIYDEDEN | QSPRSFQKKT | RHYFIAAVER | LWDYGMSSSP | HVLRNRAQSG |
| | | SVPQFKKVVF | QEFTDGSFTQ | PLYRGELNEH | LGLLGPYIRA | EVEDNIMVTF |
| | | RNQASRPYSF | YSSLISYEED | QRQGAEPRKN | FVKPNETKTY | FWKVQHHMAP |
| | | TKDEFDCKAW | AYFSDVDLEK | DVHSGLIGPL | LVCHTNTLNP | AHGRQVTVQE |
| | | FALFFTIFDE | TKSWYFTENM | ERNCRAPCNI | QMEDPTFKEN | YRFHAINGYI |
| | | MDTLPGLVMA | QDQRIRWYLL | SMGSNENIHS | IHFSGHVFTV | RKKEEYKMAL |
| | | YNLYPGVFET | VEMLPSKAGI | WRVECLIGEH | LHAGMSTLFL | VYSNKCQTPL |
| | | GMASGHIRDF | QITASGQYGQ | WAPKLARLHY | SGSINAWSTK | EPFSWIKVDL |
| | | LAPMIIHGIK | TQGARQKFSS | LYISQFIIMY | SLDGKKWQTY | RGNSTGTLMV |
| | | FFGNVDSSGI | KHNIFNPPII | ARYIRLHPTH | YSIRSTLRME | LMGCDLNSCS |
| | | MPLGMESKAI | SDAQITASSY | FTNMFATWSP | SKARLHLQGR | SNAWRPQVNN |
| | | PKEWLQVDFQ | KTMKVTGVTT | QGVKSLLTSM | YVKEFLISSS | QDGHQWTLFF |
| | | QNGKVKVFQG | NQDSFTPVVN | SLDPPLLTRY | LRIHPQSWVH | QIALRMEVLG |
| | | CEAQDLY | | | | |
| 5 | rhScFVIII-BDD 3 (ΔF) | MQIELSTCFF | LCLLRFCFSA | TRRYYLGAVE | LSWDYMQSDL | GELPVDARFP |
| | | PRVPKSFPFN | TSVVYKKTLF | VEFTDHLFNI | AKPRPPWMGL | LGPTIQAEVY |

FIG. 17C

| | | |
|---|---|---|
| | | DTVVITLKNM ASHPVSLHAV GVSYWKASEG AEYDDQTSQR EKEDDKVFPG<br>GSHTYVWQVL KENGPMASDP LCLTYSYLSH VDLVKDLNSG LIGALLVCRE<br>GSLAKEKTQT LHKFILLFAV FDEGKSWHSE TKNSLMQDRD AASARAWPKM<br>HTVNGYVNRS LPGLIGCHRK SVYWHVIGMG TTPEVHSIFL EGHTFLVRNH<br>RQASLEISPI TFLTAQTLLM DLGQFLLFCH ISSHQHDGME AYVKVDSCPE<br>EPQLRMKNNE EAEDYDDDLT DSEMDVVRFD DDNSPSFIQI RSVAKKHPKT<br>WVHYIAAEEE DWDYAPLVLA PDDRSYKSQY LNNGPQRIGR KYKKVRFMAY<br>TDETFKTREA IQHESGILGP LLYGEVGDTL LIIFKNQASR PYNIYPHGIT<br>DVRPLYSRRL PKGVKHLKDF PILPGEIFKY KWTVTVEDGP TKSDPRCLTR<br>YYSSFVNMER DLASGLIGPL LICYKESVDQ RGNQIMSDKR NVILFSVFDE<br>NRSWYLTENI QRFLPNPAGV QLEDPEFQAS NIMHSINGYV FDSLQLSVCL<br>HEVAYWYILS IGAQTDFLSV FFSGYTFKHK MVYEDTLTLF PFSGETVFMS<br>MENPGLWILG CHNSDFRNRG MTALLKVSSC DKNTGDYYED SYEDISAYLL<br>SKNNAIEPRS FSQNPPVLKE ITRTTLQSDQ EEIDYDDTIS VEMKKEDFDI<br>YDEDENQSPR SFQKKTRHYF IAAVERLWDY GMSSSPHVLR NRAQSGSVPQ<br>FKKVVFQEFT DGSFTQPLYR GELNEHLGLL GPYIRAEVED NIMVTFRNQA<br>SRPYSFYSSL ISYEEDQRQG AEPRKNFVKP NETKTYFWKV QHHMAPTKDE<br>FDCKAWAYFS DVDLEKDVHS GLIGPLLVCH TNTLNPAHGR QVTVQEFALF<br>FTIFDETKSW YFTENMERNC RAPCNIQMED PTFKENYRFH AINGYIMDTL<br>PGLVMAQDQR IRWYLLSMGS NENIHSIHFS GHVFTVRKKE EYKMALYNLY<br>PGVFETVEML PSKAGIWRVE CLIGEHLHAG MSTLFLVYSN KCQTPLGMAS<br>GHIRDFQITA SGQYGQWAPK LARLHYSGSI NAWSTKEPFS WIKVDLLAPM<br>IIHGIKTQGA RQKFSSLYIS QFIIMYSLDG KKWQTYRGNS TGTLMVFFGN<br>VDSSGIKHNI FNPPIIARYI RLHPTHYSIR STLRMELMGC DLNSCSMPLG<br>MESKAISDAQ ITASSYFTNM FATWSPSKAR LHLQGRSNAW RPQVNNPKEW<br>LQVDFQKTMK VTGVTTQGVK SLLTSMYVKE FLISSSQDGH QWTLFFQNGK<br>VKVFQGNQDS FTPVVNSLDP PLLTRYLRIH PQSWVHQIAL RMEVLGCEAQ<br>DLY |
| 6 | rhScFVIII-BDD 4 | MQIELSTCFF LCLLRFCFSA TRRYYLGAVE LSWDYMQSDL GELPVDARFP<br>PRVPKSFPFN TSVVYKKTLF VEFTDHLFNI AKPRPPWMGL LGPTIQAEVY<br>DTVVITLKNM ASHPVSLHAV GVSYWKASEG AEYDDQTSQR EKEDDKVFPG<br>GSHTYVWQVL KENGPMASDP LCLTYSYLSH VDLVKDLNSG LIGALLVCRE<br>GSLAKEKTQT LHKFILLFAV FDEGKSWHSE TKNSLMQDRD AASARAWPKM<br>HTVNGYVNRS LPGLIGCHRK SVYWHVIGMG TTPEVHSIFL EGHTFLVRNH<br>RQASLEISPI TFLTAQTLLM DLGQFLLFCH ISSHQHDGME AYVKVDSCPE<br>EPQLRMKNNE EAEDYDDDLT DSEMDVVRFD DDNSPSFIQI RSVAKKHPKT<br>WVHYIAAEEE DWDYAPLVLA PDDRSYKSQY LNNGPQRIGR KYKKVRFMAY<br>TDETFKTREA IQHESGILGP LLYGEVGDTL LIIFKNQASR PYNIYPHGIT<br>DVRPLYSRRL PKGVKHLKDF PILPGEIFKY KWTVTVEDGP TKSDPRCLTR<br>YYSSFVNMER DLASGLIGPL LICYKESVDQ RGNQIMSDKR NVILFSVFDE<br>NRSWYLTENI QRFLPNPAGV QLEDPEFQAS NIMHSINGYV FDSLQLSVCL<br>HEVAYWYILS IGAQTDFLSV FFSGYTFKHK MVYEDTLTLF PFSGETVFMS<br>MENPGLWILG CHNSDFRNRG MTALLKVSSC DKNTGDYYED SYEDISAYLL<br>SKNNAIEPRS FSQNPPVLKR EITRTTLQSD QEEIDYDDTI SVEMKKEDFD<br>IYDEDENQSP RSFQKKTRHY FIAAVERLWD YGMSSSPHVL RNRAQSGSVP<br>QFKKVVFQEF TDGSFTQPLY RGELNEHLGL LGPYIRAEVE DNIMVTFRNQ<br>ASRPYSFYSS LISYEEDQRQ GAEPRKNFVK PNETKTYFWK VQHHMAPTKD<br>EFDCKAWAYF SDVDLEKDVH SGLIGPLLVC HTNTLNPAHG RQVTVQEFAL |

FIG. 17D

| | | | | | | |
|---|---|---|---|---|---|---|
| | | FFTIFDETKS | WYFTENMERN | CRAPCNIQME | DPTFKENYRF | HAINGYIMDT |
| | | LPGLVMAQDQ | RIRWYLLSMG | SNENIHSIHF | SGHVFTVRKK | EEYKMALYNL |
| | | YPGVFETVEM | LPSKAGIWRV | ECLIGEHLHA | GMSTLFLVYS | NKCQTPLGMA |
| | | SGHIRDFQIT | ASGQYGQWAP | KLARLHYSGS | INAWSTKEPF | SWIKVDLLAP |
| | | MIIHGIKTQG | ARQKFSSLYI | SQFIIMYSLD | GKKWQTYRGN | STGTLMVFFG |
| | | NVDSSGIKHN | IFNPPIIARY | IRLHPTHYSI | RSTLRMELMG | CDLNSCSMPL |
| | | GMESKAISDA | QITASSYFTN | MFATWSPSKA | RLHLQGRSNA | WRPQVNNPKE |
| | | WLQVDFQKTM | KVTGVTTQGV | KSLLTSMYVK | EFLISSSQDG | HQWTLFFQNG |
| | | KVKVFQGNQD | SFTPVVNSLD | PPLLTRYLRI | HPQSWVHQIA | LRMEVLGCEA |
| | | QDLY | | | | |
| 7 | rhFVIII-BDD addback | MQIELSTCFF | LCLLRFCFSA | TRRYYLGAVE | LSWDYMQSDL | GELPVDARFP |
| | | PRVPKSFPFN | TSVVYKKTLF | VEFTDHLFNI | AKPRPPWMGL | LGPTIQAEVY |
| | | DTVVITLKNM | ASHPVSLHAV | GVSYWKASEG | AEYDDQTSQR | EKEDDKVFPG |
| | | GSHTYVWQVL | KENGPMASDP | LCLTYSYLSH | VDLVKDLNSG | LIGALLVCRE |
| | | GSLAKEKTQT | LHKFILLFAV | FDEGKSWHSE | TKNSLMQDRD | AASARAWPKM |
| | | HTVNGYVNRS | LPGLIGCHRK | SVYWHVIGMG | TTPEVHSIFL | EGHTFLVRNH |
| | | RQASLEISPI | TFLTAQTLLM | DLGQFLLFCH | ISSHQHDGME | AYVKVDSCPE |
| | | EPQLRMKNNE | EAEDYDDDLT | DSEMDVVRFD | DDNSPSFIQI | RSVAKKHPKT |
| | | WVHYIAAEEE | DWDYAPLVLA | PDDRSYKSQY | LNNGPQRIGR | KYKKVRFMAY |
| | | TDETFKTREA | IQHESGILGP | LLYGEVGDTL | LIIFKNQASR | PYNIYPHGIT |
| | | DVRPLYSRRL | PKGVKHLKDF | PILPGEIFKY | KWTVTVEDGP | TKSDPRCLTR |
| | | YYSSFVNMER | DLASGLIGPL | LICYKESVDQ | RGNQIMSDKR | NVILFSVFDE |
| | | NRSWYLTENI | QRFLPNPAGV | QLEDPEFQAS | NIMHSINGYV | FDSLQLSVCL |
| | | HEVAYWYILS | IGAQTDFLSV | FFSGYTFKHK | MVYEDTLTLF | PFSGETVFMS |
| | | MENPGLWILG | CHNSDFRNRG | MTALLKVSSC | DKNTGDYYED | SYEDISAYLL |
| | | SKNNAIEPRS | FSQNATNVSN | NSNTSNDSNV | SPPVLKRHQR | EITRTTLQSD |
| | | QEEIDYDDTI | SVEMKKEDFD | IYDEDENQSP | RSFQKKTRHY | FIAAVERLWD |
| | | YGMSSSPHVL | RNRAQSGSVP | QFKKVVFQEF | TDGSFTQPLY | RGELNEHLGL |
| | | LGPYIRAEVE | DNIMVTFRNQ | ASRPYSFYSS | LISYEEDQRQ | GAEPRKNFVK |
| | | PNETKTYFWK | VQHHMAPTKD | EFDCKAWAYF | SDVDLEKDVH | SGLIGPLLVC |
| | | HTNTLNPAHG | RQVTVQEFAL | FFTIFDETKS | WYFTENMERN | CRAPCNIQME |
| | | DPTFKENYRF | HAINGYIMDT | LPGLVMAQDQ | RIRWYLLSMG | SNENIHSIHF |
| | | SGHVFTVRKK | EEYKMALYNL | YPGVFETVEM | LPSKAGIWRV | ECLIGEHLHA |
| | | GMSTLFLVYS | NKCQTPLGMA | SGHIRDFQIT | ASGQYGQWAP | KLARLHYSGS |
| | | INAWSTKEPF | SWIKVDLLAP | MIIHGIKTQG | ARQKFSSLYI | SQFIIMYSLD |
| | | GKKWQTYRGN | STGTLMVFFG | NVDSSGIKHN | IFNPPIIARY | IRLHPTHYSI |
| | | RSTLRMELMG | CDLNSCSMPL | GMESKAISDA | QITASSYFTN | MFATWSPSKA |
| | | RLHLQGRSNA | WRPQVNNPKE | WLQVDFQKTM | KVTGVTTQGV | KSLLTSMYVK |
| | | EFLISSSQDG | HQWTLFFQNG | KVKVFQGNQD | SFTPVVNSLD | PPLLTRYLRI |
| | | HPQSWVHQIA | LRMEVLGCEA | QDLY | | |

Table 5: FVIII Coding sequences expressed in ARPE-19 cells

| SEQ ID NO: | Sequence Name | Nucleotide Sequence |
|---|---|---|
| 8 | rhFVIII-BDD | ATGCAAATAG AGCTCTCCAC CTGCTTCTTT CTGTGCCTTT TGCGATTCTG 50 <br> CTTTAGTGCC ACCAGAAGAT ACTACCTGGG TGCAGTGGAA CTGTCATGGG 100 <br> ACTATATGCA AAGTGATCTC GGTGAGCTGC CTGTGGACGC AAGATTTCCT 150 |

FIG. 17E

|  |  | CCTAGAGTGC CAAAATCTTT TCCATTCAAC ACCTCAGTCG TGTACAAAAA 200 |
|  |  | GACTCTGTTT GTAGAATTCA CGGATCACCT TTTCAACATC GCTAAGCCAA 250 |
|  |  | GGCCACCCTG GATGGGTCTG CTAGGTCCTA CCATCCAGGC TGAGGTTTAT 300 |
|  |  | GATACAGTGG TCATTACACT TAAGAACATG GCTTCCCATC CTGTCAGTCT 350 |
|  |  | TCATGCTGTT GGTGTATCCT ACTGAAAGC TTCTGAGGGA GCTGAATATG 400 |
|  |  | ATGATCAGAC CAGTCAAAGG GAGAAAGAAG ATGATAAAGT CTTCCCTGGT 450 |
|  |  | GGAAGCCATA CATATGTCTG GCAGGTCCTG AAAGAGAATG GTCCAATGGC 500 |
|  |  | CTCTGACCCA CTGTGCCTTA CCTACTCATA TCTTTCTCAT GTGGACCTGG 550 |
|  |  | TAAAAGACTT GAATTCAGGC CTCATTGGAG CCCTACTAGT ATGTAGAGAA 600 |
|  |  | GGGAGTCTGG CCAAGGAAAA GACACAGACC TTGCACAAAT TTATACTACT 650 |
|  |  | TTTTGCTGTA TTTGATGAAG GAAAAGTTG GCACTCAGAA ACAAAGAACT 700 |
|  |  | CCTTGATGCA GGATAGGGAT GCTGCATCTG CTCGGGCCTG GCCTAAAATG 750 |
|  |  | CACACAGTCA ATGGTTATGT AAACAGGTCT CTGCCAGGTC TGATTGGATG 800 |
|  |  | CCACAGGAAA TCAGTCTATT GGCATGTGAT TGGAATGGGC ACCACTCCTG 850 |
|  |  | AAGTGCACTC AATATTCCTC GAAGGTCACA CATTTCTTGT GAGGAACCAT 900 |
|  |  | CGCCAGGCGT CCTTGGAAAT CTCGCCAATA ACTTTCCTTA CTGCTCAAAC 950 |
|  |  | ACTCTTGATG GACCTTGGAC AGTTTCTACT GTTTTGTCAT ATCTCTTCCC 1000 |
|  |  | ACCAACATGA TGGCATGGAA GCTTATGTCA AAGTAGACAG CTGTCCAGAG 1050 |
|  |  | GAACCCCAAC TACGAATGAA AAATAATGAA GAAGCGGAAG ACTATGATGA 1100 |
|  |  | TGATCTTACT GATTCTGAAA TGGATGTGGT CAGGTTTGAT GATGACAACT 1150 |
|  |  | CTCCTTCCTT TATCCAAATT CGCTCAGTTG CCAAGAAGCA TCCTAAAACT 1200 |
|  |  | TGGGTACATT ACATTGCTGC TGAAGAGGAG GACTGGGACT ATGCTCCCTT 1250 |
|  |  | AGTCCTCGCC CCCGATGACA GAAGTTATAA AAGTCAATAT TTGAACAATG 1300 |
|  |  | GCCCTCAGCG GATTGGTAGG AAGTACAAAA AAGTCCGATT TATGGCATAC 1350 |
|  |  | ACAGATGAAA CCTTTAAGAC TCGTGAAGCT ATTCAGCATG AATCAGGAAT 1400 |
|  |  | CTTGGGACCT TTACTTTATG GGAAGTTGG AGACACACTG TTGATTATAT 1450 |
|  |  | TTAAGAATCA AGCAAGCAGA CCATATAACA TCTACCCTCA CGGAATCACT 1500 |
|  |  | GATGTCCGTC CTTTGTATTC AAGGAGATTA CCAAAAGGTG TAAAACATTT 1550 |
|  |  | GAAGGATTTT CCAATTCTGC CAGGAGAAAT ATTCAAATAT AAATGGACAG 1600 |
|  |  | TGACTGTAGA AGATGGGCCA ACTAAATCAG ATCCTCGGTG CCTGACCCGC 1650 |
|  |  | TATTACTCTA GTTCGTTAA TATGGAGAGA GATCTAGCTT CAGGACTCAT 1700 |
|  |  | TGGCCCTCTC CTCATCTGCT ACAAAGAATC TGTAGATCAA AGAGGAAACC 1750 |
|  |  | AGATAATGTC AGACAAGAGG AATGTCATCC TGTTTTCTGT ATTTGATGAG 1800 |
|  |  | AACCGAAGCT GGTACCTCAC AGAGAATATA CAACGCTTTC TCCCCAATCC 1850 |
|  |  | AGCTGGAGTG CAGCTTGAGG ATCCAGAGTT CCAAGCCTCC AACATCATGC 1900 |
|  |  | ACAGCATCAA TGGCTATGTT TTTGATAGTT TGCAGTTGTC AGTTTGTTTG 1950 |
|  |  | CATGAGGTGG CATACTGGTA CATTCTAAGC ATTGGAGCAC AGACTGACTT 2000 |
|  |  | CCTTTCTGTC TTCTTCTCTG GATATACCTT CAAACACAAA ATGGTCTATG 2050 |
|  |  | AAGCACACT CACCCTATTC CCATTCTCAG GAGAAACTGT CTTCATGTCG 2100 |
|  |  | ATGGAAAACC CAGGTCTATG GATTCTGGGG TGCCACAACT CAGACTTTCG 2150 |
|  |  | GAACAGAGGC ATGACCGCCT TACTGAAGGT TTCTAGTTGT GACAAGAACA 2200 |
|  |  | CTGGTGATTA TTACGAGGAC AGTTATGAAG ATATTTCAGC ATACTTGCTG 2250 |
|  |  | AGTAAAAACA ATGCCATTGA ACCAAGAAGC TTCTCCCAAA ACCCACCAGT 2300 |
|  |  | CTTGAAACGC CATCAACGGG AAATAACTCG TACTACTCTT CAGTCAGATC 2350 |
|  |  | AAGAGGAAAT TGACTATGAT GATACCATAT CAGTTGAAAT GAAGAAGGAA 2400 |
|  |  | GATTTTGACA TTTATGATGA GGATGAAAAT CAGAGCCCCC GCAGCTTTCA 2450 |
|  |  | AAAGAAAACA CGACACTATT TTATTGCTGC AGTGGAGAGG CTCTGGGATT 2500 |
|  |  | ATGGGATGAG TAGCTCCCCA CATGTTCTAA GAAACAGGGC TCAGAGTGGC 2550 |
|  |  | AGTGTCCCTC AGTTCAAGAA AGTTGTTTTC CAGGAATTTA CTGATGGCTC 2600 |
|  |  | CTTTACTCAG CCCTTATACC GTGGAGAACT AAATGAACAT TTGGGACTCC 2650 |
|  |  | TGGGGCCATA TATAAGAGCA GAAGTTGAAG ATAATATCAT GGTAACTTTC 2700 |
|  |  | AGAAATCAGG CCTCTCGTCC CTATTCCTTC TATTCTAGCC TTATTTCTTA 2750 |
|  |  | TGAGGAAGAT CAGAGGCAAG GAGCAGAACC TAGAAAAAAC TTTGTCAAGC 2800 |

FIG. 17F

| | | | |
|---|---|---|---|
| | | CTAATGAAAC CAAAACTTAC TTTTGGAAAG TGCAACATCA TATGGCACCC | 2850 |
| | | ACTAAAGATG AGTTTGACTG CAAAGCCTGG GCTTATTTCT CTGATGTTGA | 2900 |
| | | CCTGGAAAAA GATGTGCACT CAGGCCTGAT TGGACCCCTT CTGGTCTGCC | 2950 |
| | | ACACTAACAC ACTGAACCCT GCTCATGGGA GACAAGTGAC AGTACAGGAA | 3000 |
| | | TTTGCTCTGT TTTTCACCAT CTTTGATGAG ACCAAAAGCT GGTACTTCAC | 3050 |
| | | TGAAAATATG GAAAGAAACT GCAGGGCTCC CTGCAATATC CAGATGGAAG | 3100 |
| | | ATCCCACTTT TAAAGAGAAT TATCGCTTCC ATGCAATCAA TGGCTACATA | 3150 |
| | | ATGGATACAC TACCTGGCTT AGTAATGGCT CAGGATCAAA GGATTCGATG | 3200 |
| | | GTATCTGCTC AGCATGGCA GCAATGAAAA CATCCATTCT ATTCATTTCA | 3250 |
| | | GTGGACATGT GTTCACTGTA CGAAAAAAG AGGAGTATAA AATGGCACTG | 3300 |
| | | TACAATCTCT ATCCAGGTGT TTTTGAGACA GTGGAAATGT TACCATCCAA | 3350 |
| | | AGCTGGAATT TGGCGGGTGG AATGCCTTAT TGGCAGCAT CTACATGCTG | 3400 |
| | | GGATGAGCAC ACTTTTTCTG GTGTACAGCA ATAAGTGTCA GACTCCCCTG | 3450 |
| | | GGAATGGCTT CTGGACACAT TAGAGATTTT CAGATTACAG CTTCAGGACA | 3500 |
| | | ATATGGACAG TGGGCCCCAA AGCTGGCCAG ACTTCATTAT TCCGGATCAA | 3550 |
| | | TCAATGCCTG GAGCACCAAG GAGCCCTTTT CTTGGATCAA GGTGGATCTG | 3600 |
| | | TTGGCACCAA TGATTATTCA CGGCATCAAG ACCCAGGGTG CCCGTCAGAA | 3650 |
| | | GTTCTCCAGC CTCTACATCT CTCAGTTTAT CATCATGTAT AGTCTTGATG | 3700 |
| | | GGAAGAAGTG GCAGACTTAT CGAGGAAATT CCACTGGAAC CTTAATGGTC | 3750 |
| | | TTCTTTGGCA ATGTGGATTC ATCTGGGATA AAACACAATA TTTTTAACCC | 3800 |
| | | TCCAATTATT GCTCGATACA TCCGTTTGCA CCCAACTCAT TATAGCATTC | 3850 |
| | | GCAGCACTCT TCGCATGGAG TTGATGGGCT GTGATTTAAA TAGTTGCAGC | 3900 |
| | | ATGCCATTGG GAATGGAGAG TAAAGCAATA TCAGATGCAC AGATTACTGC | 3950 |
| | | TTCATCCTAC TTTACCAATA TGTTTGCCAC CTGGTCTCCT TCAAAAGCTC | 4000 |
| | | GACTTCACCT CCAAGGGAGG AGTAATGCCT GGAGACCTCA GGTGAATAAT | 4050 |
| | | CCAAAAGAGT GGCTGCAAGT GGACTTCCAG AAGACAATGA AAGTCACAGG | 4100 |
| | | AGTAACTACT CAGGGAGTAA AATCTCTGCT TACCAGCATG TATGTGAAGG | 4150 |
| | | AGTTCCTCAT CTCCAGCAGT CAAGATGGCC ATCAGTGGAC TCTCTTTTTT | 4200 |
| | | CAGAATGGCA AAGTAAAGGT TTTTGAGGGA AATCAAGACT CCTTCACACC | 4250 |
| | | TGTGGTGAAC TCTCTAGACC CACCGTTACT GACTCGCTAC CTTCGAATTC | 4300 |
| | | ACCCCCAGAG TTGGGTGCAC CAGATTGCCC TGAGGATGGA GGTTCTGGGC | 4350 |
| | | TGCGAGGCAC AGGACCTCTA CTGA | 4374 |
| 9 | rhFVIII-BDD Sc1 | ATGCAAATAG AGCTCTCCAC CTGCTTCTTT CTGTGCCTTT TGCGATTCTG | |
| | | CTTTAGTGCC ACCAGAAGAT ACTACCTGGG TGCAGTGGAA CTGTCATGGG | |
| | | ACTATATGCA AAGTGATCTC GGTGAGCTGC CTGTGGACGC AAGATTTCCT | |
| | | CCTAGAGTGC CAAAATCTTT TCCATTCAAC ACCTCAGTCG TGTACAAAAA | |
| | | GACTCTGTTT GTAGAATTCA CGGATCACCT TTTCAACATC GCTAAGCCAA | |
| | | GGCCACCCTG GATGGGTCTG CTAGGTCCTA CCATCCAGGC TGAGGTTTAT | |
| | | GATACAGTGG TCATTACACT TAAGAACATG GCTTCCATC CTGTCAGTCT | |
| | | TCATGCTGTT GGTGTATCCT ACTGGAAAGC TTCTGAGGGA GCTGAATATG | |
| | | ATGATCAGAC CAGTCAAAGG GAGAAAGAAG ATGATAAAGT CTTCCCTGGT | |
| | | GGAAGCCATA CATATGTCTG GCAGGTCCTG AAAGAGAATG GTCCAATGGC | |
| | | CTCTGACCCA CTGTGCCTTA CCTACTCATA TCTTTCTCAT GTGGACCTGG | |
| | | TAAAAGACTT GAATTCAGGC CTCATTGGAG CCCTACTAGT ATGTAGAGAA | |
| | | GGGAGTCTGG CCAAGGAAAA GACACAGACC TTGCACAAAT TTATACTACT | |
| | | TTTTGCTGTA TTTGATGAAG GGAAAAGTTG GCACTCAGAA ACAAAGAACT | |
| | | CCTTGATGCA GGATAGGGAT GCTGCATCTG CTCGGGCCTG GCCTAAAATG | |
| | | CACACAGTCA ATGGTTATGT AAACAGGTCT CTGCCAGGTC TGATTGGATG | |
| | | CCACAGGAAA TCAGTCTATT GGCATGTGAT TGGAATGGGC ACCACTCCTG | |
| | | AAGTGCACTC AATATTCCTC GAAGGTCACA CATTTCTTGT GAGGAACCAT | |
| | | CGCCAGGCGT CCTTGGAAAT CTCGCCAATA ACTTTCCTTA CTGCTCAAAC | |
| | | ACTCTTGATG GACCTTGGAC AGTTTCTACT GTTTTGTCAT ATCTCTTCCC | |
| | | ACCAACATGA TGGCATGGAA GCTTATGTCA AAGTAGACAG CTGTCCAGAG | |

FIG. 17G

```
GAACCCCAAC TACGAATGAA AAATAATGAA GAAGCGGAAG ACTATGATGA
TGATCTTACT GATTCTGAAA TGGATGTGGT CAGGTTTGAT GATGACAACT
CTCCTTCCTT TATCCAAATT CGCTCAGTTG CCAAGAAGCA TCCTAAAACT
TGGGTACATT ACATTGCTGC TGAAGAGGAG GACTGGGACT ATGCTCCCTT
AGTCCTCGCC CCCGATGACA GAAGTTATAA AAGTCAATAT TTGAACAATG
GCCCTCAGCG GATTGGTAGG AAGTACAAAA AAGTCCGATT TATGGCATAC
ACAGATGAAA CCTTTAAGAC TCGTGAAGCT ATTCAGCATG AATCAGGAAT
CTTGGGACCT TTACTTTATG GGGAAGTTGG AGACACACTG TTGATTATAT
TTAAGAATCA AGCAAGCAGA CCATATAACA TCTACCCTCA CGGAATCACT
GATGTCCGTC CTTTGTATTC AAGGAGATTA CCAAAAGGTG TAAAACATTT
GAAGGATTTT CCAATTCTGC CAGGAGAAAT ATTCAAATAT AAATGGACAG
TGACTGTAGA AGATGGGCCA ACTAAATCAG ATCCTCGGTG CCTGACCCGC
TATTACTCTA GTTTCGTTAA TATGGAGAGA GATCTAGCTT CAGGACTCAT
TGGCCCTCTC CTCATCTGCT ACAAAGAATC TGTAGATCAA AGAGGAAACC
AGATAATGTC AGACAAGAGG AATGTCATCC TGTTTTCTGT ATTTGATGAG
AACCGAAGCT GGTACCTCAC AGAGAATATA CAACGCTTTC TCCCCAATCC
AGCTGGAGTG CAGCTTGAGG ATCCAGAGTT CCAAGCCTCC AACATCATGC
ACAGCATCAA TGGCTATGTT TTTGATAGTT TGCAGTTGTC AGTTTGTTTG
CATGAGGTGG CATACTGGTA CATTCTAAGC ATTGGAGCAC AGACTGACTT
CCTTTCTGTC TTCTTCTCTG GATATACCTT CAAACACAAA ATGGTCTATG
AAGCACACT CACCCTATTC CCATTCTCAG GAGAAACTGT CTTCATGTCG
ATGGAAAACC CAGGTCTATG GATTCTGGGG TGCCACAACT CAGACTTTCG
GAACAGAGGC ATGACCGCCT TACTGAAGGT TTCTAGTTGT GACAAGAACA
CTGGTGATTA TTACGAGGAC AGTTATGAAG ATATTTCAGC ATACTTGCTG
AGTAAAAACA ATGCCATTGA ACCAAGAAGC TTCTCCCAAA ACCCACCAGT
CTTGAAACAC CATCAACGGG AAATAACTCG TACTACTCTT CAGTCAGATC
AAGAGGAAAT TGACTATGAT GATACCATAT CAGTTGAAAT GAAGAAGGAA
GATTTTGACA TTTATGATGA GGATGAAAAT CAGAGCCCCC GCAGCTTTCA
AAAGAAAACA CGACACTATT TTATTGCTGC AGTGGAGAGG CTCTGGGATT
ATGGGATGAG TAGCTCCCCA CATGTTCTAA GAAACAGGGC TCAGAGTGGC
AGTGTCCCTC AGTTCAAGAA AGTTGTTTTC CAGGAATTTA CTGATGGCTC
CTTTACTCAG CCCTTATACC GTGGAGAACT AAATGAACAT TTGGGACTCC
TGGGGCCATA TATAAGAGCA GAAGTTGAAG ATAATATCAT GGTAACTTTC
AGAAATCAGG CCTCTCGTCC CTATTCCTTC TATTCTAGCC TTATTTCTTA
TGAGGAAGAT CAGAGGCAAG GAGCAGAACC TAGAAAAAAC TTTGTCAAGC
CTAATGAAAC CAAAACTTAC TTTTGGAAAG TGCAACATCA TATGGCACCC
ACTAAAGATG AGTTTGACTG CAAAGCCTGG GCTTATTTCT CTGATGTTGA
CCTGGAAAAA GATGTGCACT CAGGCCTGAT TGGACCCCTT CTGGTCTGCC
ACACTAACAC ACTGAACCCT GCTCATGGGA GACAAGTGAC AGTACAGGAA
TTTGCTCTGT TTTTCACCAT CTTTGATGAG ACCAAAAGCT GGTACTTCAC
TGAAAATATG GAAAGAAACT GCAGGGCTCC CTGCAATATC CAGATGGAAG
ATCCCACTTT TAAAGAGAAT TATCGCTTCC ATGCAATCAA TGGCTACATA
ATGGATACAC TACCTGGCTT AGTAATGGCT CAGGATCAAA GGATTCGATG
GTATCTGCTC AGCATGGGCA GCAATGAAAA CATCCATTCT ATTCATTTCA
GTGGACATGT GTTCACTGTA CGAAAAAAG AGGAGTATAA AATGGCACTG
TACAATCTCT ATCCAGGTGT TTTTGAGACA GTGGAAATGT TACCATCCAA
AGCTGGAATT TGGCGGGTGG AATGCCTTAT TGGCGAGCAT CTACATGCTG
GGATGAGCAC ACTTTTTCTG GTGTACAGCA ATAAGTGTCA GACTCCCTG
GGAATGGCTT CTGGACACAT TAGAGATTTT CAGATTACAG CTTCAGGACA
ATATGGACAG TGGGCCCCAA AGCTGGCCAG ACTTCATTAT TCCGGATCAA
TCAATGCCTG GAGCACCAAG GAGCCCTTTT CTTGGATCAA GGTGGATCTG
TTGGCACCAA TGATTATTCA CGGCATCAAG ACCCAGGGTG CCCGTCAGAA
GTTCTCCAGC CTCTACATCT CTCAGTTTAT CATCATGTAT AGTCTTGATG
```

FIG. 17H

| | | |
|---|---|---|
| | | GGAAGAAGTG GCAGACTTAT CGAGGAAATT CCACTGGAAC CTTAATGGTC<br>TTCTTTGGCA ATGTGGATTC ATCTGGGATA AAACACAATA TTTTTAACCC<br>TCCAATTATT GCTCGATACA TCCGTTTGCA CCCAACTCAT TATAGCATTC<br>GCAGCACTCT TCGCATGGAG TTGATGGGCT GTGATTTAAA TAGTTGCAGC<br>ATGCCATTGG GAATGGAGAG TAAAGCAATA TCAGATGCAC AGATTACTGC<br>TTCATCCTAC TTTACCAATA TGTTTGCCAC CTGGTCTCCT TCAAAAGCTC<br>GACTTCACCT CCAAGGGAGG AGTAATGCCT GGAGACCTCA GGTGAATAAT<br>CCAAAAGAGT GGCTGCAAGT GGACTTCCAG AAGACAATGA AAGTCACAGG<br>AGTAACTACT CAGGGAGTAA AATCTCTGCT TACCAGCATG TATGTGAAGG<br>AGTTCCTCAT CTCCAGCAGT CAAGATGGCC ATCAGTGGAC TCTCTTTTTT<br>CAGAATGGCA AAGTAAAGGT TTTTCAGGGA AATCAAGACT CCTTCACACC<br>TGTGGTGAAC TCTCTAGACC CACCGTTACT GACTCGCTAC CTTCGAATTC<br>ACCCCCAGAG TTGGGTGCAC CAGATTGCCC TGAGGATGGA GGTTCTGGGC<br>TGCGAGGCAC AGGACCTCTA CTGA |
| 10 | rhFVIII-BDD<br>Sc2 | ATGCAAATAG AGCTCTCCAC CTGCTTCTTT CTGTGCCTTT TGCGATTCTG 50<br>CTTTAGTGCC ACCAGAAGAT ACTACCTGGG TGCAGTGGAA CTGTCATGGG 100<br>ACTATATGCA AAGTGATCTC GGTGAGCTGC CTGTGGACGC AAGATTTCCT 150<br>CCTAGAGTGC CAAAATCTTT TCCATTCAAC ACCTCAGTCG TGTACAAAAA 200<br>GACTCTGTTT GTAGAATTCA CGGATCACCT TTTCAACATC GCTAAGCCAA 250<br>GGCCACCCTG GATGGGTCTG CTAGGTCCTA CCATCCAGGC TGAGGTTTAT 300<br>GATACAGTGG TCATTACACT TAAGAACATG GCTTCCCATC CTGTCAGTCT 350<br>TCATGCTGTT GGTGTATCCT ACTGGAAAGC TTCTGAGGGA GCTGAATATG 400<br>ATGATCAGAC CAGTCAAAGG GAGAAAGAAG ATGATAAAGT CTTCCCTGGT 450<br>GGAAGCCATA CATATGTCTG GCAGGTCCTG AAAGAGAATG GTCCAATGGC 500<br>CTCTGACCCA CTGTGCCTTA CCTACTCATA TCTTTCTCAT GTGGACCTGG 550<br>TAAAAGACTT GAATTCAGGC CTCATTGGAG CCCTACTAGT ATGTAGAGAA 600<br>GGGAGTCTGG CCAAGGAAAA GACACAGACC TTGCACAAAT TTATACTACT 650<br>TTTTGCTGTA TTTGATGAAG GAAAAGTTTG GCACTCAGAA ACAAAGAACT 700<br>CCTTGATGCA GGATAGGGAT GCTGCATCTG CTCGGGCCTG GCCTAAAATG 750<br>CACACAGTCA ATGGTTATGT AAACAGGTCT CTGCCAGGTC TGATTGGATG 800<br>CCACAGGAAA TCAGTCTATT GGCATGTGAT TGGAATGGGC ACCACTCCTG 850<br>AAGTGCACTC AATATTCCTC GAAGGTCACA CATTTCTTGT GAGGAACCAT 900<br>CGCCAGGCGT CCTTGGAAAT CTCGCCAATA ACTTTCCTTA CTGCTCAAAC 950<br>ACTCTTGATG GACCTTGGAC AGTTTCTACT GTTTTGTCAT ATCTCTTCCC 1000<br>ACCAACATGA TGGCATGGAA GCTTATGTCA AGTAGACAG CTGTCCAGAG 1050<br>GAACCCCAAC TACGAATGAA AATAATGAA GAAGCGGAAG ACTATGATGA 1100<br>TGATCTTACT GATTCTGAAA TGGATGTGGT CAGGTTTGAT GATGACAACT 1150<br>CTCCTTCCTT TATCCAAATT CGCTCAGTTG CCAAGAAGCA TCCTAAAACT 1200<br>TGGGTACATT ACATTGCTGC TGAAGAGGAG GACTGGGACT ATGCTCCCTT 1250<br>AGTCCTCGCC CCCGATGACA GAAGTTATAA AAGTCAATAT TTGAACAATG 1300<br>GCCCTCAGCG GATTGGTAGG AAGTACAAAA AAGTCCGATT TATGGCATAC 1350<br>ACAGATGAAA CCTTTAAGAC TCGTGAAGCT ATTCAGCATG AATCAGGAAT 1400<br>CTTGGGACCT TTACTTTATG GGGAAGTTGG AGACACACTG TTGATTATAT 1450<br>TTAAGAATCA AGCAAGCAGA CCATATAACA TCTACCCTCA CGGAATCACT 1500<br>GATGTCCGTC CTTTGTATTC AAGGAGATTA CCAAAAGGTG TAAAACATTT 1550<br>GAAGGATTTT CCAATTCTGC CAGGAGAAAT ATTCAAATAT AAATGGACAG 1600<br>TGACTGTAGA AGATGGGCCA ACTAAATCAG ATCCTCGGTG CCTGACCCGC 1650<br>TATTACTCTA GTTTCGTTAA TATGGAGAGA GATCTAGCTT CAGGACTCAT 1700<br>TGGCCCTCTC CTCATCTGCT ACAAAGAATC TGTAGATCAA AGAGGAAACC 1750<br>AGATAATGTC AGACAAGAGG AATGTCATCC TGTTTTCTGT ATTTGATGAG 1800<br>AACCGAAGCT GGTACCTCAC AGAGAATATA CAACGCTTTC TCCCCAATCC 1850<br>AGCTGGAGTG CAGCTTGAGG ATCCAGAGTT CCAAGCCTCC AACATCATGC 1900<br>ACAGCATCAA TGGCTATGTT TTTGATAGTT TGCAGTTGTC AGTTTGTTTG 1950 |

FIG. 17I

| | | | |
|---|---|---|---|
| | | CATGAGGTGG CATACTGGTA CATTCTAAGC ATTGGAGCAC AGACTGACTT 2000 | |
| | | CCTTTCTGTC TTCTTCTCTG GATATACCTT CAAACACAAA ATGGTCTATG 2050 | |
| | | AAGACACACT CACCCTATTC CCATTCTCAG GAGAAACTGT CTTCATGTCG 2100 | |
| | | ATGGAAAACC CAGGTCTATG GATTCTGGGG TGCCACAACT CAGACTTTCG 2150 | |
| | | GAACAGAGGC ATGACCGCCT TACTGAAGGT TTCTAGTTGT GACAAGAACA 2200 | |
| | | CTGGTGATTA TTACGAGGAC AGTTATGAAG ATATTTCAGC ATACTTGCTG 2250 | |
| | | AGTAAAAACA ATGCCATTGA ACCAAGAAGC TTCTCCCAAA ACCCACCAGT 2300 | |
| | | CTTGAAAGCC CATCAAGCGG AAATAACTCG TACTACTCTT CAGTCAGATC 2350 | |
| | | AAGAGGAAAT TGACTATGAT GATACCATAT CAGTTGAAAT GAAGAAGGAA 2400 | |
| | | GATTTTGACA TTTATGATGA GGATGAAAAT CAGAGCCCCC GCAGCTTTCA 2450 | |
| | | AAAGAAAACA CGACACTATT TTATTGCTGC AGTGGAGAGG CTCTGGGATT 2500 | |
| | | ATGGGATGAG TAGCTCCCCA CATGTTCTAA GAAACAGGGC TCAGAGTGGC 2550 | |
| | | AGTGTCCCTC AGTTCAAGAA AGTTGTTTTC CAGGAATTTA CTGATGGCTC 2600 | |
| | | CTTTACTCAG CCCTTATACC GTGGAGAACT AAATGAACAT TTGGGACTCC 2650 | |
| | | TGGGGCCATA TATAAGAGCA GAAGTTGAAG ATAATATCAT GGTAACTTTC 2700 | |
| | | AGAAATCAGG CCTCTCGTCC CTATTCCTTC TATTCTAGCC TTATTTCTTA 2750 | |
| | | TGAGGAAGAT CAGAGGCAAG GAGCAGAACC TAGAAAAAAC TTTGTCAAGC 2800 | |
| | | CTAATGAAAC CAAAACTTAC TTTTGGAAAG TGCAACATCA TATGGCACCC 2850 | |
| | | ACTAAAGATG AGTTTGACTG CAAAGCCTGG GCTTATTTCT CTGATGTTGA 2900 | |
| | | CCTGGAAAAA GATGTGCACT CAGGCCTGAT TGGACCCCTT CTGGTCTGCC 2950 | |
| | | ACACTAACAC ACTGAACCCT GCTCATGGGA GACAAGTGAC AGTACAGGAA 3000 | |
| | | TTTGCTCTGT TTTTCACCAT CTTTGATGAG ACCAAAAGCT GGTACTTCAC 3050 | |
| | | TGAAAATATG GAAAGAAACT GCAGGGCTCC CTGCAATATC CAGATGGAAG 3100 | |
| | | ATCCCACTTT TAAAGAGAAT TATCGCTTCC ATGCAATCAA TGGCTACATA 3150 | |
| | | ATGGATACAC TACCTGGCTT AGTAATGGCT CAGGATCAAA GGATTCGATG 3200 | |
| | | GTATCTGCTC AGCATGGGCA GCAATGAAAA CATCCATTCT ATTCATTTCA 3250 | |
| | | GTGGACATGT GTTCACTGTA CGAAAAAAAG AGGAGTATAA AATGGCACTG 3300 | |
| | | TACAATCTCT ATCCAGGTGT TTTTGAGACA GTGGAAATGT TACCATCCAA 3350 | |
| | | AGCTGGAATT TGGCGGGTGG AATGCCTTAT TGGCGAGCAT CTACATGCTG 3400 | |
| | | GGATGAGCAC ACTTTTTCTG GTGTACAGCA ATAAGTGTCA GACTCCCCTG 3450 | |
| | | GGAATGGCTT CTGGACACAT TAGAGATTTT CAGATTACAG CTTCAGGACA 3500 | |
| | | ATATGGACAG TGGGCCCCAA AGCTGGCCAG ACTTCATTAT TCCGGATCAA 3550 | |
| | | TCAATGCCTG GAGCACCAAG GAGCCCTTTT CTTGGATCAA GGTGGATCTG 3600 | |
| | | TTGGCACCAA TGATTATTCA CGGCATCAAG ACCCAGGGTG CCCGTCAGAA 3650 | |
| | | GTTCTCCAGC CTCTACATCT CTCAGTTTAT CATCATGTAT AGTCTTGATG 3700 | |
| | | GGAAGAAGTG GCAGACTTAT CGAGGAAATT CCACTGGAAC CTTAATGGTC 3750 | |
| | | TTCTTTGGCA ATGTGGATTC ATCTGGGATA AAACACAATA TTTTTAACCC 3800 | |
| | | TCCAATTATT GCTCGATACA TCCGTTTGCA CCCAACTCAT TATAGCATTC 3850 | |
| | | GCAGCACTCT TCGCATGGAG TTGATGGGCT GTGATTTAAA TAGTTGCAGC 3900 | |
| | | ATGCCATTGG GAATGGAGAG TAAAGCAATA TCAGATGCAC AGATTACTGC 3950 | |
| | | TTCATCCTAC TTTACCAATA TGTTTGCCAC CTGGTCTCCT TCAAAAGCTC 4000 | |
| | | GACTTCACCT CCAAGGGAGG AGTAATGCCT GGAGACCTCA GGTGAATAAT 4050 | |
| | | CCAAAAGAGT GGCTGCAAGT GGACTTCCAG AAGACAATGA AAGTCACAGG 4100 | |
| | | AGTAACTACT CAGGGAGTAA AATCTCTGCT TACCAGCATG TATGTGAAGG 4150 | |
| | | AGTTCCTCAT CTCCAGCAGT CAAGATGGCC ATCAGTGGAC TCTCTTTTTT 4200 | |
| | | CAGAATGGCA AAGTAAAGGT TTTTCAGGGA AATCAAGACT CCTTCACACC 4250 | |
| | | TGTGGTGAAC TCTCTAGACC CACCGTTACT GACTCGCTAC CTTCGAATTC 4300 | |
| | | ACCCCCAGAG TTGGGTGCAC CAGATTGCCC TGAGGATGGA GGTTCTGGGC 4350 | |
| | | TGCGAGGCAC AGGACCTCTA CTGA 4374 | |
| 11 | rhFVIII-BDD Sc3 | ATGCAAATAG AGCTCTCCAC CTGCTTCTTT CTGTGCCTTT TGCGATTCTG CTTTAGTGCC ACCAGAAGAT ACTACCTGGG TGCAGTGGAA CTGTCATGGG ACTATATGCA AAGTGATCTC GGTGAGCTGC CTGTGGACGC AAGATTTCCT CCTAGAGTGC CAAAATCTTT TCCATTCAAC ACCTCAGTCG TGTACAAAAA | |

FIG. 17J

```
GACTCTGTTT GTAGAATTCA CGGATCACCT TTTCAACATC GCTAAGCCAA
GGCCACCCTG GATGGGTCTG CTAGGTCCTA CCATCCAGGC TGAGGTTTAT
GATACAGTGG TCATTACACT TAAGAACATG GCTTCCCATC CTGTCAGTCT
TCATGCTGTT GGTGTATCCT ACTGGAAAGC TTCTGAGGGA GCTGAATATG
ATGATCAGAC CAGTCAAAGG GAGAAAGAAG ATGATAAAGT CTTCCCTGGT
GGAAGCCATA CATATGTCTG GCAGGTCCTG AAAGAGAATG GTCCAATGGC
CTCTGACCCA CTGTGCCTTA CCTACTCATA TCTTTCTCAT GTGGACCTGG
TAAAAGACTT GAATTCAGGC CTCATTGGAG CCCTACTAGT ATGTAGAGAA
GGGAGTCTGG CCAAGGAAAA GACACAGACC TTGCACAAAT TTATACTACT
TTTTGCTGTA TTTGATGAAG GGAAAAGTTG GCACTCAGAA ACAAAGAACT
CCTTGATGCA GGATAGGGAT GCTGCATCTG CTCGGGCCTG GCCTAAAATG
CACACAGTCA ATGGTTATGT AAACAGGTCT CTGCCAGGTC TGATTGGATG
CCACAGGAAA TCAGTCTATT GGCATGTGAT TGGAATGGGC ACCACTCCTG
AAGTGCACTC AATATTCCTC GAAGGTCACA CATTTCTTGT GAGGAACCAT
CGCCAGGCGT CCTTGGAAAT CTCGCCAATA ACTTTCCTTA CTGCTCAAAC
ACTCTTGATG GACCTTGGAC AGTTTCTACT GTTTTGTCAT ATCTCTTCCC
ACCAACATGA TGGCATGGAA GCTTATGTCA AAGTAGACAG CTGTCCAGAG
GAACCCCAAC TACGAATGAA AAATAATGAA GAAGCGGAAG ACTATGATGA
TGATCTTACT GATTCTGAAA TGGATGTGGT CAGGTTTGAT GATGACAACT
CTCCTTCCTT TATCCAAATT CGCTCAGTTG CCAAGAAGCA TCCTAAAACT
TGGGTACATT ACATTGCTGC TGAAGAGGAG GACTGGGACT ATGCTCCCTT
AGTCCTCGCC CCCGATGACA GAAGTTATAA AAGTCAATAT TTGAACAATG
GCCCTCAGCG GATTGGTAGG AAGTACAAAA AAGTCCGATT TATGGCATAC
ACAGATGAAA CCTTTAAGAC TCGTGAAGCT ATTCAGCATG AATCAGGAAT
CTTGGGACCT TTACTTTATG GGGAAGTTGG AGACACACTG TTGATTATAT
TTAAGAATCA AGCAAGCAGA CCATATAACA TCTACCCTCA CGGAATCACT
GATGTCCGTC CTTTGTATTC AAGGAGATTA CCAAAAGGTG TAAAACATTT
GAAGGATTTT CCAATTCTGC CAGGAGAAAT ATTCAAATAT AAATGGACAG
TGACTGTAGA AGATGGGCCA ACTAAATCAG ATCCTCGGTG CCTGACCCGC
TATTACTCTA GTTTCGTTAA TATGGAGAGA GATCTAGCTT CAGGACTCAT
TGGCCCTCTC CTCATCTGCT ACAAAGAATC TGTAGATCAA AGAGGAAACC
AGATAATGTC AGACAAGAGG AATGTCATCC TGTTTTCTGT ATTTGATGAG
AACCGAAGCT GGTACCTCAC AGAGAATATA CAACGCTTTC TCCCCAATCC
AGCTGGAGTG CAGCTTGAGG ATCCAGAGTT CCAAGCCTCC AACATCATGC
ACAGCATCAA TGGCTATGTT TTTGATAGTT TGCAGTTGTC AGTTTGTTTG
CATGAGGTGG CATACTGGTA CATTCTAAGC ATTGGAGCAC AGACTGACTT
CCTTTCTGTC TTCTTCTCTG GATATACCTT CAAACACAAA ATGGTCTATG
AAGACACACT CACCCTATTC CCATTCTCAG GAGAAACTGT CTTCATGTCG
ATGGAAAACC CAGGTCTATG GATTCTGGGG TGCCACAACT CAGACTTTCG
GAACAGAGGC ATGACCGCCT TACTGAAGGT TTCTAGTTGT GACAAGAACA
CTGGTGATTA TTACGAGGAC AGTTATGAAG ATATTTCAGC ATACTTGCTG
AGTAAAAACA ATGCCATTGA ACCAAGAAGC TTCTCCCAAA ACCCACCAGT
CTTGAAAGAA ATAACTCGTA CTACTCTTCA GTCAGATCAA GAGGAAATTG
ACTATGATGA TACCATATCA GTTGAAATGA AGAAGGAAGA TTTTGACATT
TATGATGAGG ATGAAAATCA GAGCCCCCGC AGCTTTCAAA AGAAAACACG
ACACTATTTT ATTGCTGCAG TGGAGAGGCT CTGGGATTAT GGGATGAGTA
GCTCCCCACA TGTTCTAAGA AACAGGGCTC AGAGTGGCAG TGTCCCTCAG
TTCAAGAAAG TTGTTTTCCA GGAATTTACT GATGGCTCCT TTACTCAGCC
CTTATACCGT GGAGAACTAA ATGAACATTT GGGACTCCTG GGGCCATATA
TAAGAGCAGA AGTTGAAGAT AATATCATGG TAACTTTCAG AAATCAGGCC
TCTCGTCCCT ATTCCTTCTA TTCTAGCCTT ATTTCTTATG AGGAAGATCA
GAGGCAAGGA GCAGAACCTA GAAAAAACTT TGTCAAGCCT AATGAAACCA
AAACTTACTT TTGGAAAGTG CAACATCATA TGGCACCCAC TAAAGATGAG
```

FIG. 17K

| | | |
|---|---|---|
| | | TTTGACTGCA AAGCCTGGGC TTATTTCTCT GATGTTGACC TGGAAAAAGA<br>TGTGCACTCA GGCCTGATTG GACCCCTTCT GGTCTGCCAC ACTAACACAC<br>TGAACCCTGC TCATGGGAGA CAAGTGACAG TACAGGAATT TGCTCTGTTT<br>TTCACCATCT TTGATGAGAC CAAAAGCTGG TACTTCACTG AAAATATGGA<br>AAGAAACTGC AGGGCTCCCT GCAATATCCA GATGGAAGAT CCCACTTTTA<br>AAGAGAATTA TCGCTTCCAT GCAATCAATG CTACATAAT GGATACACTA<br>CCTGGCTTAG TAATGGCTCA GGATCAAAGG ATTCGATGGT ATCTGCTCAG<br>CATGGGCAGC AATGAAAACA TCCATTCTAT TCATTTCAGT GGACATGTGT<br>TCACTGTACG AAAAAAAGAG GAGTATAAAA TGGCACTGTA CAATCTCTAT<br>CCAGGTGTTT TTGAGACAGT GGAAATGTTA CCATCCAAAG CTGGAATTTG<br>GCGGGTGGAA TGCCTTATTG GCGAGCATCT ACATGCTGGG ATGAGCACAC<br>TTTTTCTGGT GTACAGCAAT AAGTGTCAGA CTCCCCTGGG AATGGCTTCT<br>GGACACATTA GAGATTTTCA GATTACAGCT TCAGGACAAT ATGGACAGTG<br>GGCCCCAAAG CTGGCCAGAC TTCATTATTC CGGATCAATC AATGCCTGGA<br>GCACCAAGGA GCCCTTTTCT TGGATCAAGG TGGATCTGTT GGCACCAATG<br>ATTATTCACG GCATCAAGAC CCAGGGTGCC CGTCAGAAGT TCTCCAGCCT<br>CTACATCTCT CAGTTTATCA TCATGTATAG TCTTGATGGG AAGAAGTGGC<br>AGACTTATCG AGGAAATTCC ACTGAACCT TAATGGTCTT CTTTGGCAAT<br>GTGGATTCAT CTGGGATAAA ACACAATATT TTTAACCCTC CAATTATTGC<br>TCGATACATC CGTTTGCACC CAACTCATTA TAGCATTCGC AGCACTCTTC<br>GCATGGAGTT GATGGGCTGT GATTTAAATA GTTGCAGCAT GCCATTGGGA<br>ATGGAGAGTA AAGCAATATC AGATGCACAG ATTACTGCTT CATCCTACTT<br>TACCAATATG TTTGCCACCT GGTCTCCTTC AAAAGCTCGA CTTCACCTCC<br>AAGGGAGGAG TAATGCCTGG AGACCTCAGG TGAATAATCC AAAAGAGTGG<br>CTGCAAGTGG ACTTCCAGAA GACAATGAAA GTCACAGGAG TAACTACTCA<br>GGGAGTAAAA TCTCTGCTTA CCAGCATGTA TGTGAAGGAG TTCCTCATCT<br>CCAGCAGTCA AGATGGCCAT CAGTGGACTC TCTTTTTTCA GAATGGCAAA<br>GTAAAGGTTT TTCAGGGAAA TCAAGACTCC TTCACACCTG TGGTGAACTC<br>TCTAGACCCA CCGTTACTGA CTCGCTACCT TCGAATTCAC CCCCAGAGTT<br>GGGTGCACCA GATTGCCCTG AGGATGGAGG TTCTGGGCTG CGAGGCACAG<br>GACCTCTACT GA |
| 12 | rhFVIII-BDD<br>Sc4 | ATGCAAATAG AGCTCTCCAC CTGCTTCTTT CTGTGCCTTT TGCGATTCTG<br>CTTTAGTGCC ACCAGAAGAT ACTACCTGGG TGCAGTGGAA CTGTCATGGG<br>ACTATATGCA AAGTGATCTC GGTGAGCTGC CTGTGGACGC AAGATTTCCT<br>CCTAGAGTGC CAAAATCTTT TCCATTCAAC ACCTCAGTCG TGTACAAAAA<br>GACTCTGTTT GTAGAATTCA CGGATCACCT TTTCAACATC GCTAAGCCAA<br>GGCCACCCTG GATGGGTCTG CTAGGTCCTA CCATCCAGGC TGAGGTTTAT<br>GATACAGTGG TCATTACACT TAAGAACATG GCTTCCATC CTGTCAGTCT<br>TCATGCTGTT GGTGTATCCT ACTGGAAAGC TTCTGAGGGA GCTGAATATG<br>ATGATCAGAC CAGTCAAAGG GAGAAAGAAG ATGATAAAGT CTTCCCTGGT<br>GGAAGCCATA CATATGTCTG GCAGGTCCTG AAAGAGAATG GTCCAATGGC<br>CTCTGACCCA CTGTGCCTTA CCTACTCATA TCTTTCTCAT GTGGACCTGG<br>TAAAAGACTT GAATTCAGGC CTCATTGGAG CCCTACTAGT ATGTAGAGAA<br>GGGAGTCTGG CCAAGGAAAA GACACAGACC TTGCACAAAT TTATACTACT<br>TTTTGCTGTA TTTGATGAAG GGAAAAGTTG GCACTCAGAA ACAAAGAACT<br>CCTTGATGCA GGATAGGGAT GCTGCATCTG CTCGGGCCTG GCCTAAAATG<br>CACACAGTCA ATGGTTATGT AAACAGGTCT CTGCCAGGTC TGATTGGATG<br>CCACAGGAAA TCAGTCTATT GGCATGTGAT TGGAATGGGC ACCACTCCTG<br>AAGTGCACTC AATATTCCTC GAAGGTCACA CATTTCTTGT GAGGAACCAT<br>CGCCAGGCGT CCTTGGAAAT CTCGCCAATA ACTTTCCTTA CTGCTCAAAC<br>ACTCTTGATG GACCTTGGAC AGTTTCTACT GTTTTGTCAT ATCTCTTCCC<br>ACCAACATGA TGGCATGGAA GCTTATGTCA AAGTAGACAG CTGTCCAGAG<br>GAACCCCAAC TACGAATGAA AAATAATGAA GAAGCGGAAG ACTATGATGA |

FIG. 17L

```
TGATCTTACT GATTCTGAAA TGGATGTGGT CAGGTTTGAT GATGACAACT
CTCCTTCCTT TATCCAAATT CGCTCAGTTG CCAAGAAGCA TCCTAAAACT
TGGGTACATT ACATTGCTGC TGAAGAGGAG GACTGGGACT ATGCTCCCTT
AGTCCTCGCC CCCGATGACA GAAGTTATAA AAGTCAATAT TTGAACAATG
GCCCTCAGCG GATTGGTAGG AAGTACAAAA AAGTCCGATT TATGGCATAC
ACAGATGAAA CCTTTAAGAC TCGTGAAGCT ATTCAGCATG AATCAGGAAT
CTTGGGACCT TTACTTTATG GGGAAGTTGG AGACACACTG TTGATTATAT
TTAAGAATCA AGCAAGCAGA CCATATAACA TCTACCCTCA CGGAATCACT
GATGTCCGTC CTTTGTATTC AAGGAGATTA CCAAAAGGTG TAAAACATTT
GAAGGATTTT CCAATTCTGC CAGGAGAAAT ATTCAAATAT AAATGGACAG
TGACTGTAGA AGATGGGCCA ACTAAATCAG ATCCTCGGTG CCTGACCCGC
TATTACTCTA GTTTCGTTAA TATGGAGAGA GATCTAGCTT CAGGACTCAT
TGGCCCTCTC CTCATCTGCT ACAAAGAATC TGTAGATCAA AGAGGAAACC
AGATAATGTC AGACAAGAGG AATGTCATCC TGTTTTCTGT ATTTGATGAG
AACCGAAGCT GGTACCTCAC AGAGAATATA CAACGCTTTC TCCCCAATCC
AGCTGGAGTG CAGCTTGAGG ATCCAGAGTT CCAAGCCTCC AACATCATGC
ACAGCATCAA TGGCTATGTT TTTGATAGTT TGCAGTTGTC AGTTTGTTTG
CATGAGGTGG CATACTGGTA CATTCTAAGC ATTGGAGCAC AGACTGACTT
CCTTTCTGTC TTCTTCTCTG GATATACCTT CAAACACAAA ATGGTCTATG
AAGACACACT CACCCTATTC CCATTCTCAG GAGAAACTGT CTTCATGTCG
ATGGAAAACC CAGGTCTATG GATTCTGGGG TGCCACAACT CAGACTTTCG
GAACAGAGGC ATGACCGCCT TACTGAAGGT TTCTAGTTGT GACAAGAACA
CTGGTGATTA TTACGAGGAC AGTTATGAAG ATATTTCAGC ATACTTGCTG
AGTAAAAACA ATGCCATTGA ACCAAGAAGC TTCTCCCAAA ACCCACCAGT
CTTGAAACGC GAAATAACTC GTACTACTCT TCAGTCAGAT CAAGAGGAAA
TTGACTATGA TGATACCATA TCAGTTGAAA TGAAGAAGGA AGATTTTGAC
ATTTATGATG AGGATGAAAA TCAGAGCCCC CGCAGCTTTC AAAAGAAAAC
ACGACACTAT TTTATTGCTG CAGTGGAGAG GCTCTGGGAT TATGGGATGA
GTAGCTCCCC ACATGTTCTA AGAAACAGGG CTCAGAGTGG CAGTGTCCCT
CAGTTCAAGA AAGTTGTTTT CCAGGAATTT ACTGATGGCT CCTTTACTCA
GCCCTTATAC CGTGGAGAAC TAAATGAACA TTTGGGACTC CTGGGGCCAT
ATATAAGAGC AGAAGTTGAA GATAATATCA TGGTAACTTT CAGAAATCAG
GCCTCTCGTC CCTATTCCTT CTATTCTAGC CTTATTTCTT ATGAGGAAGA
TCAGAGGCAA GGAGCAGAAC CTAGAAAAAA CTTTGTCAAG CCTAATGAAA
CCAAAACTTA CTTTTGGAAA GTGCAACATC ATATGGCACC CACTAAAGAT
GAGTTTGACT GCAAAGCCTG GGCTTATTTC TCTGATGTTG ACCTGGAAAA
AGATGTGCAC TCAGGCCTGA TTGGACCCCT TCTGGTCTGC CACACTAACA
CACTGAACCC TGCTCATGGG AGACAAGTGA CAGTACAGGA ATTTGCTCTG
TTTTTCACCA TCTTTGATGA GACCAAAAGC TGGTACTTCA CTGAAAATAT
GGAAAGAAAC TGCAGGGCTC CCTGCAATAT CCAGATGGAA GATCCCACTT
TTAAAGAGAA TTATCGCTTC CATGCAATCA ATGGCTACAT AATGGATACA
CTACCTGGCT TAGTAATGGC TCAGGATCAA AGGATTCGAT GGTATCTGCT
CAGCATGGGC AGCAATGAAA ACATCCATTC TATTCATTTC AGTGGACATG
TGTTCACTGT ACGAAAAAAA GAGGAGTATA AAATGGCACT GTACAATCTC
TATCCAGGTG TTTTTGAGAC AGTGGAAATG TTACCATCCA AAGCTGGAAT
TTGGCGGGTG GAATGCCTTA TTGGCGAGCA TCTACATGCT GGGATGAGCA
CACTTTTTCT GGTGTACAGC AATAAGTGTC AGACTCCCCT GGGAATGGCT
TCTGGACACA TTAGAGATTT TCAGATTACA GCTTCAGGAC AATATGGACA
GTGGGCCCCA AAGCTGGCCA GACTTCATTA TTCCGGATCA ATCAATGCCT
GGAGCACCAA GGAGCCCTTT TCTTGGATCA AGGTGGATCT GTTGGCACCA
ATGATTATTC ACGGCATCAA GACCCAGGGT GCCCGTCAGA AGTTCTCCAG
CCTCTACATC TCTCAGTTTA TCATCATGTA TAGTCTTGAT GGGAAGAAGT
GGCAGACTTA TCGAGGAAAT TCCACTGGAA CCTTAATGGT CTTCTTTGGC
```

FIG. 17M

| | | | |
|---|---|---|---|
| | | AATGTGGATT CATCTGGGAT AAAACACAAT ATTTTTAACC CTCCAATTAT | |
| | | TGCTCGATAC ATCCGTTTGC ACCCAACTCA TTATAGCATT CGCAGCACTC | |
| | | TTCGCATGGA GTTGATGGGC TGTGATTTAA ATAGTTGCAG CATGCCATTG | |
| | | GGAATGGAGA GTAAAGCAAT ATCAGATGCA CAGATTACTG CTTCATCCTA | |
| | | CTTTACCAAT ATGTTGCCA CCTGGTCTCC TTCAAAAGCT CGACTTCACC | |
| | | TCCAAGGGAG GAGTAATGCC TGGAGACCTC AGGTGAATAA TCCAAAAGAG | |
| | | TGGCTGCAAG TGGACTTCCA GAAGACAATG AAAGTCACAG GAGTAACTAC | |
| | | TCAGGGAGTA AAATCTCTGC TTACCAGCAT GTATGTGAAG GAGTTCCTCA | |
| | | TCTCCAGCAG TCAAGATGGC CATCAGTGGA CTCTCTTTTT TCAGAATGGC | |
| | | AAAGTAAAGG TTTTTCAGGG AAATCAAGAC TCCTTCACAC CTGTGGTGAA | |
| | | CTCTCTAGAC CCACCGTTAC TGACTCGCTA CCTTCGAATT CACCCCCAGA | |
| | | GTTGGGTGCA CCAGATTGCC CTGAGGATGG AGGTTCTGGG CTGCGAGGCA | |
| | | CAGGACCTCT ACTGA | |
| 13 | rhFVIII-BDD CO2 | ATGCAGATCG AGCTGTCTAC CTGCTTCTTC CTGTGCCTGC TGCGGTTCTG | 50 |
| | | CTTCAGCGCC ACCAGAAGAT ATTACCTGGG CGCCGTGGAA CTGAGCTGGG | 100 |
| | | ACTACATGCA GTCTGACCTG GGAGAGCTGC CCGTGGACGC TAGATTTCCT | 150 |
| | | CCAAGAGTGC CCAAGAGCTT CCCCTTCAAC ACCTCCGTGG TGTACAAGAA | 200 |
| | | AACCCTGTTC GTGGAATTCA CCGACCACCT GTTCAATATC GCCAAGCCTC | 250 |
| | | GGCCTCCTTG GATGGGACTG CTGGGACCTA CAATTCAGGC CGAGGTGTAC | 300 |
| | | GACACCGTGG TCATCACCCT GAAGAACATG GCCAGCCATC CTGTGTCTCT | 350 |
| | | GCACGCCGTG GGAGTGTCTT ACTGGAAGGC TTCTGAGGGC GCCGAGTACG | 400 |
| | | ACGATCAGAC AAGCCAGAGA GAGAAGAGG ACGACAAGGT TTTCCCTGGC | 450 |
| | | GGCAGCCACA CCTATGTCTG GCAGGTCCTG AAGAAAACG GCCCTATGGC | 500 |
| | | CTCCGATCCT CTGTGCCTGA CATACAGCTA CCTGAGCCAC GTGGACCTGG | 550 |
| | | TCAAGGACCT GAATTCTGGC CTGATCGGAG CCCTGCTCGT GTGTAGAGAA | 600 |
| | | GGCAGCCTGG CCAAAGAGAA AACCCAGACA CTGCACAAGT TCATCCTGCT | 650 |
| | | GTTCGCCGTG TTCGACGAGG CAAGAGCTG GCACAGCGAG ACAAAGAACA | 700 |
| | | GCCTGATGCA GGACAGGGAT GCCGCCTCTG CTAGAGCTTG GCCTAAGATG | 750 |
| | | CACACCGTGA ACGGCTACGT GAACAGAAGC CTGCCTGGAC TGATCGGCTG | 800 |
| | | CCACAGAAAG TCCGTGTACT GGCACGTGAT GGCCATGGGC ACAACACCTG | 850 |
| | | AGGTGCACAG CATCTTTCTG GAAGGACACA CCTTCCTCGT GCGGAACCAT | 900 |
| | | AGACAGGCCA GCTGGAAAT CAGCCCTATC ACCTTCCTGA CCGCTCAGAC | 950 |
| | | CCTGCTGATG GATCTGGGCC AGTTTCTGCT GTTCTGCCAC ATCAGCTCCC | 1000 |
| | | ACCAGCACGA TGGCATGGAA GCCTACGTGA AGGTGGACAG CTGCCCCGAA | 1050 |
| | | GAACCCCAGC TGCGGATGAA GAACAACGAG GAAGCCGAGG ACTACGACGA | 1100 |
| | | CGACCTGACC GACTCTGAGA TGGACGTCGT CAGATTCGAC GACGATAACA | 1150 |
| | | GCCCCAGCTT CATCCAGATC AGAAGCGTGG CCAAGAAGCA CCCCAAGACC | 1200 |
| | | TGGGTGCACT ATATCGCCGC CGAGGAAGAG GACTGGGATT ACGCTCCTCT | 1250 |
| | | GGTGCTGGCC CCTGACGACA GAAGCTACAA GAGCCAGTAC CTGAACAACG | 1300 |
| | | GCCCTCAGCG GATCGGCCGG AAGTATAAGA AAGTGCGGTT CATGGCCTAC | 1350 |
| | | ACCGACGAGA CATTCAAGAC CAGAGAGGCC ATCCAGCACG AGAGCGGAAT | 1400 |
| | | TCTGGGCCCT CTGCTGTATG GCGAAGTGGG CGATACACTG CTGATCATCT | 1450 |
| | | TCAAGAACCA GGCCAGCAGA CCCTACAACA TCTACCCTCA CGGCATCACC | 1500 |
| | | GATGTGCGGC CCCTGTATTC TAGAAGGCTG CCCAAGGGCG TGAAGCACCT | 1550 |
| | | GAAGGACTTC CCTATCCTGC CTGGCGAGAT CTTCAAGTAC AAGTGGACCG | 1600 |
| | | TGACCGTGGA AGATGGCCCC ACCAAGAGCG ACCCTAGATG TCTGACACGG | 1650 |
| | | TACTACAGCA GCTTCGTGAA CATGGAACGC GACCTGGCCA GCGGCCTGAT | 1700 |
| | | TGGACCTCTG CTGATCTGCT ACAAAGAAAG CGTGGACCAG CGGGGCAACC | 1750 |
| | | AGATCATGAG CGACAAGCGG AACGTGATCC TGTTTAGCGT GTTCGATGAG | 1800 |
| | | AACCGGTCCT GGTATCTGAC CGAGAACATC CAGCGGTTTC TGCCCAATCC | 1850 |
| | | TGCTGGCGTG CAGCTGGAAG ATCCTGAGTT CCAGGCCTCC AACATCATGC | 1900 |
| | | ACTCCATCAA TGGCTATGTG TTCGACAGCC TGCAGCTGAG CGTGTGCCTG | 1950 |
| | | CACGAAGTGG CCTACTGGTA CATCCTGAGC ATTGGCGCCC AGACCGACTT | 2000 |

FIG. 17N

| | | | |
|---|---|---|---|
| | | CCTGTCCGTG TTCTTTAGCG GCTACACCTT CAAGCACAAG ATGGTGTACG 2050 | |
| | | AGGATACCCT GACACTGTTC CCATTCAGCG GCGAGACAGT GTTCATGAGC 2100 | |
| | | ATGGAAAACC CCGGCCTGTG GATCCTGGGC TGTCACAACA GCGACTTCCG 2150 | |
| | | GAACAGAGGC ATGACAGCCC TGCTGAAGGT GTCCAGCTGC GACAAGAACA 2200 | |
| | | CCGGCGACTA CTACGAGGAC AGCTATGAGG ACATCAGCGC CTACCTGCTG 2250 | |
| | | AGCAAGAACA ATGCCATCGA GCCTCGGAGC TTCAGCCAGA ATCCTCCTGT 2300 | |
| | | GCTGAAGCGG CACCAGCGCG AGATCACCAG AACAACCCTG CAGAGCGACC 2350 | |
| | | AAGAGGAAAT CGATTACGAC GACACCATCA GCGTCGAGAT GAAGAAAGAA 2400 | |
| | | GATTTCGACA TCTACGACGA GGACGAGAAT CAGAGCCCCA GAAGCTTTCA 2450 | |
| | | GAAAAAGACC CGGCACTACT TCATTGCCGC CGTCGAGAGA CTGTGGGACT 2500 | |
| | | ACGGCATGTC TAGCAGCCCT CACGTGCTGA GAAATAGAGC CCAGAGCGGC 2550 | |
| | | AGCGTGCCCC AGTTCAAGAA AGTGGTGTTC CAAGAGTTCA CCGACGGCAG 2600 | |
| | | CTTCACCCAG CCACTGTATA GAGGCGAGCT GAACGAGCAT CTGGGCCTGC 2650 | |
| | | TGGGCCCTTA TATCAGAGCC GAAGTGGAAG ATAACATCAT GGTCACCTTC 2700 | |
| | | CGGAATCAGG CCTCTCGGCC CTACAGCTTC TACAGCTCCC TGATCAGCTA 2750 | |
| | | CGAAGAGGAC CAGAGACAGG GCGCTGAGCC CAGAAAGAAC TTCGTGAAGC 2800 | |
| | | CCAACGAGAC TAAGACCTAC TTTTGGAAGG TGCAGCACCA CATGGCCCCT 2850 | |
| | | ACAAAGGACG AGTTCGACTG CAAGGCCTGG GCCTACTTTT CCGATGTGGA 2900 | |
| | | TCTGGAAAAG GACGTGCACA GCGGGCTCAT CGGACCACTG CTTGTGTGCC 2950 | |
| | | ACACCAACAC ACTGAACCCC GCTCACGGCA GACAAGTGAC AGTGCAAGAG 3000 | |
| | | TTCGCCCTGT TCTTCACCAT CTTCGACGAA ACAAAGAGCT GGTACTTCAC 3050 | |
| | | CGAGAATATG GAACGGAACT GCAGAGCCCC TTGCAACATC CAGATGGAAG 3100 | |
| | | ATCCCACCTT CAAAGAGAAC TACCGGTTCC ACGCCATCAA CGGCTACATC 3150 | |
| | | ATGGACACAC TGCCCGGCCT GGTTATGGCT CAGGATCAGA GAATCCGGTG 3200 | |
| | | GTATCTGCTG TCCATGGGCT CCAACGAGAA TATCCACAGC ATCCACTTCA 3250 | |
| | | GCGGCCACGT GTTCACCGTG CGGAAAAAAG AAGAGTACAA AATGGCCCTG 3300 | |
| | | TACAATCTGT ACCCTGGGGT GTTCGAAACC GTGGAAATGC TGCCTTCCAA 3350 | |
| | | GGCCGGCATT TGGAGAGTGG AATGTCTGAT TGGAGAGCAC CTCCACGCCG 3400 | |
| | | GAATGAGCAC CCTGTTTCTG GTGTACAGCA ACAAGTGTCA GACCCCTCTC 3450 | |
| | | GGCATGGCCT CTGGACACAT CAGAGACTTC CAGATCACCG CCTCTGGCCA 3500 | |
| | | GTACGGACAG TGGGCTCCTA AACTGGCTCG GCTGCACTAC AGCGGCAGCA 3550 | |
| | | TCAATGCCTG GTCCACCAAA GAGCCCTTCA GCTGGATCAA GGTGGACCTG 3600 | |
| | | CTGGCTCCCA TGATCATCCA CGGAATCAAG ACCCAGGGCG CCAGACAGAA 3650 | |
| | | GTTCAGCAGC CTGTACATCA GCCAGTTCAT CATCATGTAC AGCCTGGACG 3700 | |
| | | GCAAGAAGTG GCAGACCTAC AGAGGCAACA GCACCGGCAC ACTCATGGTT 3750 | |
| | | TTCTTCGGCA ACGTGGACTC CAGCGGCATT AAGCACAACA TCTTCAACCC 3800 | |
| | | TCCAATCATT GCCCGGTACA TCCGGCTGCA CCCCACACAC TACAGCATCC 3850 | |
| | | GGTCTACCCT GAGAATGGAA CTGATGGGCT GCGACCTGAA CAGCTGCAGC 3900 | |
| | | ATGCCCCTCG GAATGGAAAG CAAGGCCATC AGCGACGCCC AGATCACAGC 3950 | |
| | | CAGCAGCTAC TTCACCAACA TGTTCGCCAC TTGGAGCCCC TCCAAGGCTA 4000 | |
| | | GACTGCATCT GCAGGGCAGA AGCAACGCTT GGAGGCCCCA AGTGAACAAC 4050 | |
| | | CCCAAAGAGT GGCTGCAGGT CGACTTTCAA AAGACCATGA AAGTGACCGG 4100 | |
| | | CGTGACCACA CAGGGCGTCA AGTCTCTGCT GACCTCTATG TACGTGAAAG 4150 | |
| | | AGTTCCTGAT CTCCAGCAGC CAGGACGGCC ATCAGTGGAC CCTGTTTTTC 4200 | |
| | | CAGAACGGCA AAGTGAAAGT GTTCCAGGGC AATCAGGACA GCTTCACACC 4250 | |
| | | CGTGGTCAAC TCCCTGGATC CTCCACTGCT GACCAGATAC CTGCGGATTC 4300 | |
| | | ACCCTCAGTC TTGGGTGCAC CAGATCGCTC TGCGGATGGA AGTGCTGGGC 4350 | |
| | | TGTGAAGCTC AGGACCTCTA CTGA 4374 | |
| 14 | rhFVIII-BDD CO3 | ATGCAGATCG AGCTGAGCAC CTGCTTCTTC CTGTGCCTGC TGCGCTTCTG 50 | |
| | | CTTCAGCGCC ACCCGCCGCT ACTACCTGGG CGCCGTGGAG CTGAGCTGGG 100 | |
| | | ACTACATGCA GAGCGACCTG GGCGAGCTGC CCGTGGACGC CCGCTTCCCC 150 | |
| | | CCCCGCGTGC CCAAGAGCTT CCCCTTCAAC ACCAGCGTGG TGTACAAGAA 200 | |
| | | GACCCTGTTC GTGGAGTTCA CCGACCACCT GTTCAACATC GCCAAGCCCC 250 | |

FIG. 17O

|  |  | GCCCCCCCTG GATGGGCCTG CTGGGCCCCA CCATCCAGGC CGAGGTGTAC 300 |
|---|---|---|

```
GCCCCCCCTG GATGGGCCTG CTGGGCCCCA CCATCCAGGC CGAGGTGTAC 300
GACACCGTGG TGATCACCCT GAAGAACATG GCCAGCCACC CCGTGAGCCT 350
GCACGCCGTG GGCGTGAGCT ACTGGAAGGC CAGCGAGGGC GCCGAGTACG 400
ACGACCAGAC CAGCCAGCGC GAGAAGGAGG ACGACAAGGT GTTCCCCGGC 450
GGCAGCCACA CCTACGTGTG GCAGGTGCTG AAGGAGAACG GCCCCATGGC 500
CAGCGACCCC CTGTGCCTGA CCTACAGCTA CCTGAGCCAC GTGGACCTGG 550
TGAAGGACCT GAACAGCGGC CTGATCGGCG CCCTGCTGGT GTGCCGCGAG 600
GGCAGCCTGG CCAAGGAGAA GACCCAGACC CTGCACAAGT TCATCCTGCT 650
GTTCGCCGTG TTCGACGAGG CAAGAGCTG GCACAGCGAG ACCAAGAACA 700
GCCTGATGCA GGACCGCGAC GCCGCCAGCG CCCGCGCCTG GCCCAAGATG 750
CACACCGTGA ACGGCTACGT GAACCGCAGC CTGCCCGGCC TGATCGGCTG 800
CCACCGCAAG AGCGTGTACT GGCACGTGAT CGGCATGGGC ACCACCCCCG 850
AGGTGCACAG CATCTTCCTG GAGGGCCACA CCTTCCTGGT GCGCAACCAC 900
CGCCAGGCCA GCCTGGAGAT CAGCCCCATC ACCTTCCTGA CCGCCAGAC 950
CCTGCTGATG GACCTGGGCC AGTTCCTGCT GTTCTGCCAC ATCAGCAGCC 1000
ACCAGCACGA CGGCATGGAG GCCTACGTGA AGGTGGACAG CTGCCCCGAG 1050
GAGCCCAGC TGCGCATGAA GAACAACGAG GAGGCCGAGG ACTACGACGA 1100
CGACCTGACC GACAGCGAGA TGGACGTGGT GCGCTTCGAC GACGACAACA 1150
GCCCCAGCTT CATCCAGATC CGCAGCGTGG CCAAGAAGCA CCCCAAGACC 1200
TGGGTGCACT ACATCGCCGC CGAGGAGGAG GACTGGGACT ACGCCCCCT 1250
GGTGCTGGCC CCCGACGACC GCAGCTACAA GAGCCAGTAC CTGAACAACG 1300
GCCCCCAGCG CATCGGCCGC AAGTACAAGA AGGTGCGCTT CATGGCCTAC 1350
ACCGACGAGA CCTTCAAGAC CCGCGAGGCC ATCCAGCACG AGAGCGGCAT 1400
CCTGGGCCCC CTGCTGTACG GCGAGGTGGG CGACACCCTG CTGATCATCT 1450
TCAAGAACCA GGCCAGCCGC CCCTACAACA TCTACCCCCA CGGCATCACC 1500
GACGTGCGCC CCCTGTACAG CCGCCGCCTG CCCAAGGGCG TGAAGCACCT 1550
GAAGGACTTC CCCATCCTGC CCGGCGAGAT CTTCAAGTAC AAGTGGACCG 1600
TGACCGTGGA GGACGGCCCC ACCAAGAGCG ACCCCGCTG CCTGACCCGC 1650
TACTACAGCA GCTTCGTGAA CATGGAGCGC GACCTGGCCA GCGGCCTGAT 1700
CGGCCCCCTG CTGATCTGCT ACAAGGAGAG CGTGGACCAG CGCGGCAACC 1750
AGATCATGAG CGACAAGCGC AACGTGATCC TGTTCAGCGT GTTCGACGAG 1800
AACCGCAGCT GGTACCTGAC CGAGAACATC CAGCGCTTCC TGCCCAACCC 1850
CGCCGGCGTG CAGCTGGAGG ACCCCGAGTT CCAGGCCAGC AACATCATGC 1900
ACAGCATCAA CGGCTACGTG TTCGACAGCC TGCAGCTGAG CGTGTGCCTG 1950
CACGAGGTGG CCTACTGGTA CATCCTGAGC ATCGGCGCCC AGACCGACTT 2000
CCTGAGCGTG TTCTTCAGCG GCTACACCTT CAAGCACAAG ATGGTGTACG 2050
AGGACACCCT GACCCTGTTC CCCTTCAGCG GCGAGACCGT GTTCATGAGC 2100
ATGGAGAACC CCGGCCTGTG GATCCTGGGC TGCCACAACA GCGACTTCCG 2150
CAACCGCGGC ATGACCGCCC TGCTGAAGGT GAGCAGCTGC GACAAGAACA 2200
CCGGCGACTA CTACGAGGAC AGCTACGAGG ACATCAGCGC CTACCTGCTG 2250
AGCAAGAACA ACGCCATCGA GCCCCGCAGC TTCAGCCAGA ACCCCCCGT 2300
GCTGAAGCGC CACCAGCGCG AGATCACCCG CACCACCCTG CAGAGCGACC 2350
AGGAGGAGAT CGACTACGAC GACACCATCA GCGTGGAGAT GAAGAAGGAG 2400
GACTTCGACA TCTACGACGA GGACGAGAAC CAGAGCCCCC GCAGCTTCCA 2450
GAAGAAGACC CGCCACTACT TCATCGCCGC CGTGGAGCGC CTGTGGGACT 2500
ACGGCATGAG CAGCAGCCCC CACGTGCTGC GCAACCGCGC CCAGAGCGGC 2550
AGCGTGCCCC AGTTCAAGAA GGTGGTGTTC CAGGAGTTCA CCGACGGCAG 2600
CTTCACCCAG CCCCTGTACC GCGGCGAGCT GAACGAGCAC CTGGGCCTGC 2650
TGGGCCCCTA CATCCGCGCC GAGGTGGAGG ACAACATCAT GGTGACCTTC 2700
CGCAACCAGG CCAGCCGCCC CTACAGCTTC TACAGCAGCC TGATCAGCTA 2750
CGAGGAGGAC CAGCGCCAGG GCGCCGAGCC CCGCAAGAAC TTCGTGAAGC 2800
CAACGAGAC CAAGACCTAC TTCTGGAAGG TGCAGCACCA CATGGCCCCC 2850
ACCAAGGACG AGTTCGACTG CAAGGCCTGG GCCTACTTCA GCGACGTGGA 2900
```

FIG. 17P

| | | | |
|---|---|---|---|
| | | CCTGGAGAAG GACGTGCACA GCGGCCTGAT CGGCCCCCTG CTGGTGTGCC | 2950 |
| | | ACACCAACAC CCTGAACCCC GCCCACGGCC GCCAGGTGAC CGTGCAGGAG | 3000 |
| | | TTCGCCCTGT TCTTCACCAT CTTCGACGAG ACCAAGAGCT GGTACTTCAC | 3050 |
| | | CGAGAACATG GAGCGCAACT GCCGCGCCCC CTGCAACATC CAGATGGAGG | 3100 |
| | | ACCCCACCTT CAAGGAGAAC TACCGCTTCC ACGCCATCAA CGGCTACATC | 3150 |
| | | ATGGACACCC TGCCCGGCCT GGTGATGGCC CAGGACCAGC GCATCCGCTG | 3200 |
| | | GTACCTGCTG AGCATGGGCA GCAACGAGAA CATCCACAGC ATCCACTTCA | 3250 |
| | | GCGGCCACGT GTTCACCGTG CGCAAGAAGG AGGAGTACAA GATGGCCCTG | 3300 |
| | | TACAACCTGT ACCCCGGCGT GTTCGAGACC GTGGAGATGC TGCCCAGCAA | 3350 |
| | | GGCCGGCATC TGGCGCGTGG AGTGCCTGAT CGGCGAGCAC CTGCACGCCG | 3400 |
| | | GCATGAGCAC CCTGTTCCTG GTGTACAGCA ACAAGTGCCA GACCCCCCTG | 3450 |
| | | GGCATGGCCA GCGGCCACAT CCGCGACTTC CAGATCACCG CCAGCGGCCA | 3500 |
| | | GTACGGCCAG TGGGCCCCCA AGCTGGCCCG CCTGCACTAC AGCGGCAGCA | 3550 |
| | | TCAACGCCTG GAGCACCAAG GAGCCCTTCA GCTGGATCAA GGTGGACCTG | 3600 |
| | | CTGGCCCCCA TGATCATCCA CGGCATCAAG ACCCAGGGCG CCCGCCAGAA | 3650 |
| | | GTTCAGCAGC CTGTACATCA GCCAGTTCAT CATCATGTAC AGCCTGGACG | 3700 |
| | | GCAAGAAGTG GCAGACCTAC CGCGGCAACA GCACCGGCAC CCTGATGGTG | 3750 |
| | | TTCTTCGGCA ACGTGGACAG CAGCGGCATC AAGCACAACA TCTTCAACCC | 3800 |
| | | CCCCATCATC GCCCGCTACA TCCGCCTGCA CCCCACCCAC TACAGCATCC | 3850 |
| | | GCAGCACCCT GCGCATGGAG CTGATGGGCT GCGACCTGAA CAGCTGCAGC | 3900 |
| | | ATGCCCCTGG GCATGGAGAG CAAGGCCATC AGCGACGCCC AGATCACCGC | 3950 |
| | | CAGCAGCTAC TTCACCAACA TGTTCGCCAC CTGGAGCCCC AGCAAGGCCC | 4000 |
| | | GCCTGCACCT GCAGGGCCGC AGCAACGCCT GGCGCCCCCA GGTGAACAAC | 4050 |
| | | CCCAAGGAGT GGCTGCAGGT GGACTTCCAG AAGACCATGA AGGTGACCGG | 4100 |
| | | CGTGACCACC CAGGGCGTGA AGAGCCTGCT GACCAGCATG TACGTGAAGG | 4150 |
| | | AGTTCCTGAT CAGCAGCAGC CAGGACGGCC ACCAGTGGAC CCTGTTCTTC | 4200 |
| | | CAGAACGGCA AGGTGAAGGT GTTCCAGGGC AACCAGGACA GCTTCACCCC | 4250 |
| | | CGTGGTGAAC AGCCTGGACC CCCCCCTGCT GACCCGCTAC CTGCGCATCC | 4300 |
| | | ACCCCCAGAC CTGGGTGCAC CAGATCGCCC TGCGCATGGA GGTGCTGGGC | 4350 |
| | | TGCGAGGCCC AGGACCTGTA CTGA | 4374 |
| 15 | rhFVIII-BDD CO6 | ATGCAGATTG AGCTGAGCAC CTGTTTCTTC CTGTGCCTGC TGAGATTTTG | 50 |
| | | CTTCTCAGCT ACCCGCAGGT ACTACCTGGG AGCCGTTGAG CTGTCCTGGG | 100 |
| | | ATTACATGCA GTCAGATCTG GGGGAGCTGC CTGTGGACGC TCGGTTTCCC | 150 |
| | | CCCAGAGTGC CAAAGTCCTT TCCCTTCAAC ACCAGCGTGG TGTACAAAAA | 200 |
| | | GACACTTTTT GTTGAATTTA CTGACCACTT GTTCAACATC GCCAAGCCAC | 250 |
| | | GACCCCCATG GATGGGCCTG CTGGGGCCAA CCATTCAGGC AGAGGTTTAC | 300 |
| | | GACACAGTCG TGATCACACT GAAGAACATG GCCTCCCATC CAGTGTCTCT | 350 |
| | | GCACGCCGTC GGTGTGTCCT ACTGGAAAGC ATCCGAGGGC GCCGAGTATG | 400 |
| | | ACGACCAGAC CAGCCAGAGA GAGAAGAGG ACGACAAAGT GTTCCCTGGA | 450 |
| | | GGCAGCCACA CCTACGTGTG GCAGGTGTTG AAGGAAATG GCCCATGGC | 500 |
| | | CAGTGACCCT TTGTGTCTGA CTTACTCATA CCTGTCTCAT GTGGATCTAG | 550 |
| | | TCAAGGACCT GAATTCTGGA CTGATTGGGG CACTGCTTGT GTGCCGCGAA | 600 |
| | | GGCAGCCTGG CCAAAGAAAA GACACAGACC CTTCACAAGT TCATCCTGCT | 650 |
| | | GTTCGCCGTG TTCGACGAAG GCAAATCCTG GCACTCAGAA ACCAAAAACT | 700 |
| | | CACTGATGCA GGACCGGGAT GCCGCCTCTG CCCGCGCATG GCCAAAAATG | 750 |
| | | CACACCGTCA ACGGCTATGT CAATAGAAGT TTGCCCGGCC TCATTGGATG | 800 |
| | | TCACAGGAAA AGCGTCTATT GGCATGTAAT CGGGATGGGA ACCACACCTG | 850 |
| | | AGGTCCACAG CATATTTCTG GAAGGCCACA CATTTCTGGT GAGAAATCAT | 900 |
| | | CGCCAGGCTT CCCTGGAAAT TTCCCCCATC ACCTTCTTGA CCGCCAGAC | 950 |
| | | ACTGCTCATG GATCTTGGGC AGTTTCTGCT GTTTTGTCAT ATTTCTTCTC | 1000 |
| | | ACCAACACGA CGGAATGGAG GCCTACGTTA AGGTCGATAG TTGCCCTGAA | 1050 |
| | | GAACCTCAGC TGAGGATGAA GAACAACGAG GAAGCCGAGG ACTACGATGA | 1100 |
| | | CGATTTGACC GATTCCGAAA TGGACGTGGT GCGCTTTGAT GATGACAATT | 1150 |

FIG. 17Q

```
CTCCATCCTT CATTCAGATT AGATCCGTCG CCAAGAAGCA CCCCAAGACC 1200
TGGGTGCACT ACATTGCAGC CGAGGAGGAG GATTGGGACT ACGCCCCCCT 1250
GGTGCTGGCA CCCGACGACC GAAGCTACAA ATCTCAGTAC CTGAACAATG 1300
GTCCACAACG GATCGGCAGG AAGTACAAGA AAGTGCGGTT CATGGCCTAT 1350
ACAGACGAAA CCTTCAAAAC CAGGGAGGCT ATCCAGCACG AGTCTGGGAT 1400
TCTGGGACCA CTCCTGTACG GCGAAGTGGG CGACACCTTG TTAATTATCT 1450
TCAAGAACCA GGCTAGTAGA CCTTATAACA TTTATCCCCA CGGCATTACC 1500
GATGTGCGGC CTCTCTACTC TAGGCGGCTT CCAAAGGGGG TGAAACACCT 1550
GAAGGACTTT CCCATCCTCC CTGGCGAAAT CTTTAAGTAT AAGTGGACAG 1600
TGACCGTGGA GGATGGACCA ACCAAGAGCG ACCCCAGGTG CCTGACACGC 1650
TATTATTCAA GCTTCGTGAA TATGGAAAGG GACCTCGCAT CTGGCTTGAT 1700
CGGCCCTCTG CTGATATGTT ACAAGGAAAG CGTCGATCAG AGAGGAAATC 1750
AGATCATGTC AGACAAAAGG AATGTGATCC TGTTCTCCGT CTTCGATGAA 1800
AACAGGAGCT GGTATCTGAC AGAGAACATC CAGAGATTCC TGCCAAATCC 1850
CGCCGGCGTC CAGCTGGAGG ACCCGGAGTT TCAGGCATCT AACATCATGC 1900
ATTCCATTAA TGGTTACGTG TTCGACTCCC TGCAGCTGAG CGTGTGCCTC 1950
CACGAGGTGG CCTACTGGTA CATCTTGAGC ATCGGCGCCC AGACCGACTT 2000
TCTGAGCGTC TTTTTCTCCG GGTATACTTT CAAACATAAG ATGGTGTACG 2050
AAGATACTCT GACGCTGTTC CCTTTCTCTG GGGAGACTGT GTTTATGTCT 2100
ATGGAGAACC CTGGACTGTG GATTCTCGGA TGCCACAACA GTGACTTTCG 2150
TAATAGAGGG ATGACTGCAC TGCTGAAGGT GTCCAGCTGT GATAAAAATA 2200
CTGGCGACTA CTACGAAGAT AGCTATGAGG ATATCTCAGC ATACCTGCTG 2250
AGCAAGAATA ACGCCATCGA GCCCCGAAGC TTCTCACAGA ATCCCCCTGT 2300
CCTCAAGAGG CACCAGCGAG AGATCACAAG GACCACACTC CAGTCCGACC 2350
AGGAGGAGAT TGACTACGAT GACACGATTT CTGTGGAGAT GAAAAAAGAG 2400
GACTTTGACA TCTACGATGA GGATGAAAAC CAGAGCCCTA GGTCGTTCCA 2450
GAAGAAAACA AGGCACTACT TCATTGCCGC CGTGGAGAGA CTGTGGGACT 2500
ACGGAATGAG TAGTTCCCCA CACGTGTTGC GGAACAGAGC CCAGAGTGGG 2550
TCCGTCCCAC AGTTCAAGAA GGTTGTTTTC CAGGAGTTCA CAGATGGCTC 2600
CTTCACTCAG CCACTGTATC GCGGCGAGCT GAATGAGCAC TTGGGCTTAT 2650
TGGGCCCCTA CATTCGCGCA GAAGTCGAAG ATAATATTAT GGTGACCTTC 2700
CGCAACCAGG CCAGCCGGCC TTACTCATTC TACTCCTCTC TCATCTCTTA 2750
TGAGGAGGAT CAGCGCCAGG GCGCCGAACC CCGGAAGAAC TTTGTGAAGC 2800
CCAATGAAAC CAAAACTTAC TTTTGGAAGG TGCAGCACCA TATGGCGCCG 2850
ACGAAAGACG AATTTGACTG CAAAGCCTGG GCCTACTTCA GCGACGTCGA 2900
CTTGGAGAAG GACGTCCACA GCGGCCTGAT TGCCCTTTG TTGGTCTGCC 2950
ATACCAATAC ACTCAACCCT GCCCACGGGA GGCAGGTGAC CGTGCAGGAG 3000
TTTGCCTTGT TCTTCACCAT CTTCGACGAA ACCAAGAGCT GGTACTTCAC 3050
AGAGAACATG GAGAGGAACT GCAGAGCACC CTGTAACATC CAGATGGAGG 3100
ACCCTACTTT CAAGGAAAAT TACAGGTTCC ATGCCATTAA TGGCTACATC 3150
ATGGATACCC TCCCCGGGCT TGTGATGGCT CAGGACCAGC GCATCCGCTG 3200
GTACCTGCTC TCAATGGGCT CCAACGAGAA CATTCATAGC ATCCACTTTA 3250
GTGGCCACGT GTTTACCGTG CGCAAGAAGG AGGAGTACAA GATGGCACTG 3300
TACAACCTGT ACCCTGGCGT GTTTGAGACA GTGGAGATGC TGCCATCCAA 3350
GGCCGGCATC TGGCGCGTGG AGTGCCTCAT TGGGGAGCAC CTCCATGCTG 3400
GCATGTCTAC ACTGTTCCTG GTGTACAGCA ACAAGTGTCA GACTCCACTC 3450
GGAATGGCCT CCGGGCATAT CCGCGATTTT CAGATCACGG CCTCTGGCCA 3500
GTATGGCCAA TGGGCTCCCA AGCTGGCCAG GCTGCACTAC AGTGGAGTA 3550
TCAACGCTTG GAGCACCAAG GAGCCTTTCT CCTGGATCAA GGTGGACCTG 3600
CTTGCCCCCA TGATTATTCA CGGCATTAAG ACACAGGGGG CCAGGCAGAA 3650
ATTCTCCTCC CTGTACATCT CCCAGTTCAT CATCATGTAC AGTCTGGACG 3700
GCAAAAAGTG GCAGACCTAC CGCGGGAACA GTACCGGGAC ATTGATGGTG 3750
TTCTTCGGGA ACGTGGACTC TAGCGGCATT AAACACAACA TTTTCAACCC 3800
```

FIG. 17R

| | | | |
|---|---|---|---|
| | | CCCCATCATT GCTAGGTATA TCAGGCTCCA TCCCACCCAC TATAGCATCA 3850 | |
| | | GGTCCACTCT GCGGATGGAG CTGATGGGCT GCGACCTTAA TTCATGCAGC 3900 | |
| | | ATGCCGCTGG GCATGGAGTC AAAGGCCATC TCCGACGCCC AAATCACCGC 3950 | |
| | | CTCCAGCTAC TTCACCAATA TGTTCGCCAC CTGGAGCCCC AGCAAGGCCC 4000 | |
| | | GGCTGCACCT GCAGGGCCGC AGCAACGCCT GGCGGCCTCA GGTGAACAAC 4050 | |
| | | CCCAAGGAGT GGCTGCAGGT GGACTTCCAG AAAACCATGA AGGTGACTGG 4100 | |
| | | GGTCACCACC CAGGGAGTCA AGAGCCTGCT GACCAGCATG TATGTGAAGG 4150 | |
| | | AGTTCTTGAT CAGCTCGTCA CAGGATGGCC ACCAGTGGAC TTTGTTCTTT 4200 | |
| | | CAGAACGGTA AGGTGAAAGT GTTCCAGGGA ACCAAGATT CCTTTACACC 4250 | |
| | | AGTGGTCAAC TCTCTGGATC CTCCCCTGCT GACACGGTAC CTGCGGATCC 4300 | |
| | | ATCCCCAGTC ATGGGTGCAC CAGATTGCTC TGCGCATGGA GGTGCTTGGC 4350 | |
| | | TGCGAGGCCC AGGACCTGTA CTGA 4374 | |
| 16 | rhFVIII-BDD CO6 sc2 | ATGCAGATTG AGCTGAGCAC CTGTTTCTTC CTGTGCCTGC TGAGATTTTG 50 | |
| | | CTTCTCAGCT ACCCGCAGGT ACTACCTGGG AGCCGTTGAG CTGTCCTGGG 100 | |
| | | ATTACATGCA GTCAGATCTG GGGGAGCTGC CTGTGGACGC TCGGTTTCCC 150 | |
| | | CCCAGAGTGC AAAGTCCTT TCCCTTCAAC ACCAGCGTGG TGTACAAAAA 200 | |
| | | GACACTTTTT GTTGAATTTA CTGACCACTT GTTCAACATC GCCAAGCCAC 250 | |
| | | GACCCCCATG GATGGGCCTG CTGGGGCCAA CCATTCAGGC AGAGGTTTAC 300 | |
| | | GACACAGTCG TGATCACACT GAAGAACATG GCCTCCCATC CAGTGTCTCT 350 | |
| | | GCACGCCGTC GGTGTGTCCT ACTGGAAAGC ATCCGAGGGC GCCGAGTATG 400 | |
| | | ACGACCAGAC CAGCCAGAGA GAGAAAGAGG ACGACAAAGT GTTCCCTGGA 450 | |
| | | GGCAGCCACA CCTACGTGTG GCAGGTGTTG AAGGAAAATG GGCCCATGGC 500 | |
| | | CAGTGACCCT TTGTGTCTGA CTTACTCATA CCTGTCTCAT GTGGATCTAG 550 | |
| | | TCAAGGACCT GAATTCTGGA CTGATTGGGG CACTGCTTGT GTGCCGCGAA 600 | |
| | | GGCAGCCTGG CCAAAGAAAA GACACAGACC CTTCACAAGT TCATCCTGCT 650 | |
| | | GTTCGCCGTG TTCGACGAAG GCAAATCCTG GCACTCAGAA ACCAAAAACT 700 | |
| | | CACTGATGCA GGACCGGGAT GCCGCCTCTG CCCGCGCATG GCCAAAAATG 750 | |
| | | CACACCGTCA ACGGCTATGT CAATAGAAGT TTGCCCGGCC TCATTGGATG 800 | |
| | | TCACAGGAAA AGCGTCTATT GGCATGTAAT CGGGATGGGA ACCACACCTG 850 | |
| | | AGGTCCACAG CATATTTCTG GAAGGCCACA CATTTCTGGT GAGAAATCAT 900 | |
| | | CGCCAGGCTT CCCTGGAAAT TTCCCCCATC ACCTTCTTGA CCGCCCAGAC 950 | |
| | | ACTGCTCATG GATCTTGGGC AGTTTCTGCT GTTTTGTCAT ATTTCTTCTC 1000 | |
| | | ACCAACACGA CGGAATGGAG GCCTACGTTA AGGTCGATAG TTGCCCTGAA 1050 | |
| | | GAACCTCAGC TGAGGATGAA GAACAACGAG GAAGCCGAGG ACTACGATGA 1100 | |
| | | CGATTTGACC GATTCCGAAA TGGACGTGGT GCGCTTTGAT GATGACAATT 1150 | |
| | | CTCCATCCTT CATTCAGATT AGATCCGTCG CCAAGAAGCA CCCCAAGACC 1200 | |
| | | TGGGTGCACT ACATTGCAGC CGAGGAGGAG GATTGGGACT ACGCCCCCCT 1250 | |
| | | GGTGCTGGCA CCCGACGACC GAAGCTACAA ATCTCAGTAC CTGAACAATG 1300 | |
| | | GTCCACAACG GATCGGCAGG AAGTACAAGA AAGTGCGGTT CATGGCCTAT 1350 | |
| | | ACAGACGAAA CCTTCAAAAC CAGGGAGGCT ATCCAGCACG AGTCTGGGAT 1400 | |
| | | TCTGGGACCA CTCCTGTACG GCGAAGTGGG CGACACCTTG TTAATTATCT 1450 | |
| | | TCAAGAACCA GGCTAGTAGA CCTTATAACA TTTATCCCCA CGGCATTACC 1500 | |
| | | GATGTGCGGC CTCTCTACTC TAGGCGGCTT CCAAAGGGGG TGAAACACCT 1550 | |
| | | GAAGGACTTT CCCATCCTCC CTGGCGAAAT CTTTAAGTAT AAGTGGACAG 1600 | |
| | | TGACCGTGGA GGATGGACCA ACCAAGAGCG ACCCCAGGTG CCTGACACGC 1650 | |
| | | TATTATTCAA GCTTCGTGAA TATGGAAAGG GACCTCGCAT CTGGCTTGAT 1700 | |
| | | CGGCCCTCTG CTGATATGTT ACAAGGAAAG CGTCGATCAG AGAGGAAATC 1750 | |
| | | AGATCATGTC AGACAAAAGG AATGTGATCC TGTTCTCCGT CTTCGATGAA 1800 | |
| | | AACAGGAGCT GGTATCTGAC AGAGAACATC CAGAGATTCC TGCCAAATCC 1850 | |
| | | CGCCGGCGTC CAGCTGGAGG ACCCGGAGTT TCAGGCATCT AACATCATGC 1900 | |
| | | ATTCCATTAA TGGTTACGTG TTCGACTCCC TGCAGCTGAG CGTGTGCCTC 1950 | |
| | | CACGAGGTGG CCTACTGGTA CATCTTGAGC ATCGGCGCCC AGACCGACTT 2000 | |
| | | TCTGAGCGTC TTTTTCTCCG GGTATACTTT CAAACATAAG ATGGTGTACG 2050 | |

FIG. 17S

| | | | |
|---|---|---|---|
| | | AAGATACTCT GACGCTGTTC CCTTTCTCTG GGGAGACTGT GTTTATGTCT 2100 | |
| | | ATGGAGAACC CTGGACTGTG GATTCTCGGA TGCCACAACA GTGACTTTCG 2150 | |
| | | TAATAGAGGG ATGACTGCAC TGCTGAAGGT GTCCAGCTGT GATAAAAATA 2200 | |
| | | CTGGCGACTA CTACGAAGAT AGCTATGAGG ATATCTCAGC ATACCTGCTG 2250 | |
| | | AGCAAGAATA ACGCCATCGA GCCCCGAAGC TTCTCACAGA ATCCCCCTGT 2300 | |
| | | CCTCAAGGCC CACCAGGCGG AGATCACAAG GACCACACTC CAGTCCGACC 2350 | |
| | | AGGAGGAGAT TGACTACGAT GACACGATTT CTGTGGAGAT GAAAAAAGAG 2400 | |
| | | GACTTTGACA TCTACGATGA GGATGAAAAC CAGAGCCCTA GGTCGTTCCA 2450 | |
| | | GAAGAAAACA AGGCACTACT TCATTGCCGC CGTGGAGAGA CTGTGGGACT 2500 | |
| | | ACGGAATGAG TAGTTCCCCA CACGTGTTGC GGAACAGAGC CCAGAGTGGG 2550 | |
| | | TCCGTCCCAC AGTTCAAGAA GGTTGTTTTC CAGGAGTTCA CAGATGGCTC 2600 | |
| | | CTTCACTCAG CCACTGTATC GCGGCGAGCT GAATGAGCAC TTGGGCTTAT 2650 | |
| | | TGGGCCCCTA CATTCGCGCA GAAGTCGAAG ATAATATTAT GGTGACCTTC 2700 | |
| | | CGCAACCAGG CCAGCCGGCC TTACTCATTC TACTCCTCTC TCATCTCTTA 2750 | |
| | | TGAGGAGGAT CAGCGCCAGG GCGCCGAACC CCGGAAGAAC TTTGTGAAGC 2800 | |
| | | CCAATGAAAC CAAAACTTAC TTTTGGAAGG TGCAGCACCA TATGGCGCCA 2850 | |
| | | ACGAAAGACG AATTTGACTG CAAAGCCTGG GCCTACTTCA GCGACGTCGA 2900 | |
| | | CTTGGAGAAG GACGTCCACA GCGGCCTGAT TGGCCCTTTG TTGGTCTGCC 2950 | |
| | | ATACCAATAC ACTCAACCCT GCCCACGGGA GGCAGGTGAC CGTGCAGGAG 3000 | |
| | | TTTGCCTTGT TCTTCACCAT CTTCGACGAA ACCAAGAGCT GGTACTTCAC 3050 | |
| | | AGAGAACATG GAGAGGAACT GCAGAGCACC CTGTAACATC CAGATGGAGG 3100 | |
| | | ACCCTACTTT CAAGGAAAAT TACAGGTTCC ATGCCATTAA TGGCTACATC 3150 | |
| | | ATGGATACCC TCCCCGGGCT TGTGATGGCT CAGGACCAGC GCATCCGCTG 3200 | |
| | | GTACCTGCTC TCAATGGGCT CCAACGAGAA CATTCATAGC ATCCACTTTA 3250 | |
| | | GTGGCCACGT GTTTACCGTG CGCAAGAAGG AGGAGTACAA GATGGCACTG 3300 | |
| | | TACAACCTGT ACCCTGGCGT GTTTGAGACA GTGGAGATGC TGCCATCCAA 3350 | |
| | | GGCCGGCATC TGGCGCGTGG AGTGCCTCAT TGGGGAGCAC CTCCATGCTG 3400 | |
| | | GCATGTCTAC ACTGTTCCTG GTGTACAGCA ACAAGTGTCA GACTCCACTC 3450 | |
| | | GGAATGGCCT CCGGGCATAT CCGCGATTTT CAGATCACGG CCTCTGGCCA 3500 | |
| | | GTATGGCCAA TGGGCTCCCA AGCTGGCCAG GCTGCACTAC AGTGGGAGTA 3550 | |
| | | TCAACGCTTG GAGCACCAAG GAGCCTTTCT CCTGGATCAA GGTGGACCTG 3600 | |
| | | CTTGCCCCCA TGATTATTCA CGGCATTAAG ACACAGGGGG CCAGGCAGAA 3650 | |
| | | ATTCTCCTCC CTGTACATCT CCCAGTTCAT CATCATGTAC AGTCTGGACG 3700 | |
| | | GCAAAAAGTG GCAGACCTAC CGCGGGAACA GTACCGGGAC ATTGATGGTG 3750 | |
| | | TTCTTCGGGA ACGTGGACTC TAGCGGCATT AAACACAACA TTTTCAACCC 3800 | |
| | | CCCCATCATT GCTAGGTATA TCAGGCTCCA TCCCACCCAC TATAGCATCA 3850 | |
| | | GGTCCACTCT GCGGATGGAG CTGATGGGCT GCGACCTTAA TTCATGCAGC 3900 | |
| | | ATGCCGCTGG GCATGGAGTC AAAGGCCATC TCCGACGCCC AAATCACCGC 3950 | |
| | | CTCCAGCTAC TTCACCAATA TGTTCGCCAC CTGGAGCCCC AGCAAGGCCC 4000 | |
| | | GGCTGCACCT GCAGGGCCGC AGCAACGCCT GGCGGCCTCA GGTGAACAAC 4050 | |
| | | CCCAAGGAGT GGCTGCAGGT GGACTTCCAG AAAACCATGA AGGTGACTGG 4100 | |
| | | GGTCACCACC CAGGGAGTCA AGAGCCTGCT GACCAGCATG TATGTGAAGG 4150 | |
| | | AGTTCTTGAT CAGCTCGTCA CAGGATGGCC ACCAGTGGAC TTTGTTCTTT 4200 | |
| | | CAGAACGGTA AGGTGAAAGT GTTCCAGGGA AACCAAGATT CCTTTACACC 4250 | |
| | | AGTGGTCAAC TCTCTGGATC CTCCCCTGCT GACACGGTAC CTGCGGATCC 4300 | |
| | | ATCCCCAGTC ATGGGTGCAC CAGATTGCTC TGCGCATGGA GGTGCTTGGC 4350 | |
| | | TGCGAGGCCC AGGACCTGTA CTGA                          4374 | |
| 17 | rhScFVIII-BDD Addback (AHQA) | ATGCAGATTG AGCTGAGCAC CTGTTTCTTC CTGTGCCTGC TGAGATTTTG 50 | |
| | | CTTCTCAGCT ACCCGCAGGT ACTACCTGGG AGCCGTTGAG CTGTCCTGGG 100 | |
| | | ATTACATGCA GTCAGATCTG GGGGAGCTGC CTGTGGACGC TCGGTTTCCC 150 | |
| | | CCCAGAGTGC CAAAGTCCTT TCCCTTCAAC ACCAGCGTGG TGTACAAAAA 200 | |
| | | GACACTTTTT GTTGAATTTA CTGACCACTT GTTCAACATC GCCAAGCCAC 250 | |
| | | GACCCCCATG GATGGGCCTG CTGGGGCCAA CCATTCAGGC AGAGGTTTAC 300 | |

FIG. 17T

```
         GACACAGTCG TGATCACACT GAAGAACATG GCCTCCCATC CAGTGTCTCT 350
         GCACGCCGTC GGTGTGTCCT ACTGGAAAGC ATCCGAGGGC GCCGAGTATG 400
         ACGACCAGAC CAGCCAGAGA GAGAAGAGG ACGACAAAGT GTTCCCTGGA 450
         GGCAGCCACA CCTACGTGTG GCAGGTGTTG AAGGAAAATG GCCCATGGC 500
         CAGTGACCCT TTGTGTCTGA CTTACTCATA CCTGTCTCAT GTGGATCTAG 550
         TCAAGGACCT GAATTCTGGA CTGATTGGGG CACTGCTTGT GTGCCGCGAA 600
         GGCAGCCTGG CCAAAGAAAA GACACAGACC CTTCACAAGT TCATCCTGCT 650
         GTTCGCCGTG TTCGACGAAG GCAAATCCTG GCACTCAGAA ACCAAAAACT 700
         CACTGATGCA GGACCGGGAT GCCGCCTCTG CCCGCGCATG GCCAAAAATG 750
         CACACCGTCA ACGGCTATGT CAATAGAAGT TTGCCCGGCC TCATTGGATG 800
         TCACAGGAAA AGCGTCTATT GGCATGTAAT CGGGATGGGA ACCACACCTG 850
         AGGTCCACAG CATATTTCTG GAAGGCCACA CATTTCTGGT GAGAAATCAT 900
         CGCCAGGCTT CCCTGGAAAT TTCCCCCATC ACCTTCTTGA CCGCCCAGAC 950
         ACTGCTCATG GATCTTGGGC AGTTTCTGCT GTTTTGTCAT ATTTCTTCTC 1000
         ACCAACACGA CGGAATGGAG GCCTACGTTA AGGTCGATAG TTGCCCTGAA 1050
         GAACCTCAGC TGAGGATGAA GAACAACGAG GAAGCCGAGG ACTACGATGA 1100
         CGATTTGACC GATTCCGAAA TGGACGTGGT GCGCTTTGAT GATGACAATT 1150
         CTCCATCCTT CATTCAGATT AGATCCGTCG CCAAGAAGCA CCCCAAGACC 1200
         TGGGTGCACT ACATTGCAGC CGAGGAGGAG GATTGGGACT ACGCCCCCT 1250
         GGTGCTGGCA CCCGACGACC GAAGCTACAA ATCTCAGTAC CTGAACAATG 1300
         GTCCACAACG GATCGGCAGG AAGTACAAGA AAGTGCGGTT CATGGCCTAT 1350
         ACAGACGAAA CCTTCAAAAC CAGGGAGGCT ATCCAGCACG AGTCTGGGAT 1400
         TCTGGGACCA CTCCTGTACG GCGAAGTGGG CGACACCTTG TTAATTATCT 1450
         TCAAGAACCA GGCTAGTAGA CCTTATAACA TTTATCCCCA CGGCATTACC 1500
         GATGTGCGGC CTCTCTACTC TAGGCGGCTT CCAAAGGGGG TGAAACACCT 1550
         GAAGGACTTT CCCATCCTCC CTGGCGAAAT CTTTAAGTAT AAGTGGACAG 1600
         TGACCGTGGA GGATGGACCA ACCAAGAGCG ACCCCAGGTG CCTGACACGC 1650
         TATTATTCAA GCTTCGTGAA TATGGAAAGG GACCTCGCAT CTGGCTTGAT 1700
         CGGCCCTCTG CTGATATGTT ACAAGGAAGA CGTCGATCAG AGAGGAAATC 1750
         AGATCATGTC AGACAAAAGG AATGTGATCC TGTTCTCCGT CTTCGATGAA 1800
         AACAGGAGCT GGTATCTGAC AGAGAACATC CAGAGATTCC TGCCAAATCC 1850
         CGCCGGCGTC CAGCTGGAGG ACCCGGAGTT TCAGGCATCT AACATCATGC 1900
         ATTCCATTAA TGGTTACGTG TTCGACTCCC TGCAGCTGAG CGTGTGCCTC 1950
         CACGAGGTGG CCTACTGGTA CATCTTGAGC ATCGGCGCCC AGACCGACTT 2000
         TCTGAGCGTC TTTTTCTCCG GGTATACTTT CAAACATAAG ATGGTGTACG 2050
         AAGATACTCT GACGCTGTTC CCTTTCTCTG GGGAGACTGT GTTTATGTCT 2100
         ATGGAGAACC CTGGACTGTG GATTCTCGGA TGCCACAACA GTGACTTTCG 2150
         TAATAGAGGG ATGACTGCAC TGCTGAAGGT GTCCAGCTGT GATAAAAATA 2200
         CTGGCGACTA CTACGAAGAT AGCTATGAGG ATATCTCAGC ATACCTGCTG 2250
         AGCAAGAATA ACGCCATCGA GCCCCGAAGC TTCTCACAGA ATGCCACCAA 2300
         CGTGAGCAAC AACAGCAACA CCAGCAACGA CAGCAACGTG AGCCCCCTG 2350
         TCCTCAAGGC CCACCAGGCG GAGATCACAA GGACCACACT CCAGTCCGAC 2400
         CAGGAGGAGA TTGACTACGA TGACACGATT TCTGTGGAGA TGAAAAAAGA 2450
         GGACTTTGAC ATCTACGATG AGGATGAAAA CCAGAGCCCT AGGTCGTTCC 2500
         AGAAGAAAAC AAGGCACTAC TTCATTGCCG CCGTGGAGAG ACTGTGGGAC 2550
         TACGGAATGA GTAGTTCCCC ACACGTGTTG CGGAACAGAG CCCAGAGTGG 2600
         GTCCGTCCCA CAGTTCAAGA AGGTTGTTTT CCAGGAGTTC ACAGATGGCT 2650
         CCTTCACTCA GCCACTGTAT CGCGGCGAGC TGAATGAGCA CTTGGGCTTA 2700
         TTGGGCCCCT ACATTCGCGC AGAAGTCGAA GATAATATTA TGGTGACCTT 2750
         CCGCAACCAG GCCAGCCGGC CTTACTCATT CTACTCCTCT CTCATCTCTT 2800
         ATGAGGAGGA TCAGCGCCAG GGCGCCGAAC CCCGGAAGAA CTTTGTGAAG 2850
         CCCAATGAAA CCAAAACTTA CTTTTGGAAG GTGCAGCACC ATATGGCGCC 2900
         GACGAAAGAC GAATTTGACT GCAAAGCCTG GGCCTACTTC AGCGACGTCG 2950
```

FIG. 17U

|  |  | ACTTGGAGAA GGACGTCCAC AGCGGCCTGA TTGGCCCTTT GTTGGTCTGC 3000<br>CATACCAATA CACTCAACCC TGCCCACGGG AGGCAGGTGA CCGTGCAGGA 3050<br>GTTTGCCTTG TTCTTCACCA TCTTCGACGA AACCAAGAGC TGGTACTTCA 3100<br>CAGAGAACAT GGAGAGGAAC TGCAGAGCAC CCTGTAACAT CCAGATGGAG 3150<br>GACCCTACTT TCAAGGAAAA TTACAGGTTC CATGCCATTA ATGGCTACAT 3200<br>CATGGATACC CTCCCCGGGC TTGTGATGGC TCAGGACCAG CGCATCCGCT 3250<br>GGTACCTGCT CTCAATGGGC TCCAACGAGA ACATTCATAG CATCCACTTT 3300<br>AGTGGCCACG TGTTTACCGT GCGCAAGAAG GAGGAGTACA AGATGGCACT 3350<br>GTACAACCTG TACCCTGGCG TGTTTGAGAC AGTGGAGATG CTGCCATCCA 3400<br>AGGCCGGCAT CTGGCGCGTG GAGTGCCTCA TTGGGGAGCA CCTCCATGCT 3450<br>GGCATGTCTA CACTGTTCCT GGTGTACAGC AACAAGTGTC AGACTCCACT 3500<br>CGGAATGGCC TCCGGGCATA TCCGCGATTT TCAGATCACG GCCTCTGGCC 3550<br>AGTATGGCCA ATGGGCTCCC AAGCTGGCCA GGCTGCACTA CAGTGGGAGT 3600<br>ATCAACGCTT GGAGCACCAA GGAGCCTTTC TCCTGGATCA AGGTGGACCT 3650<br>GCTTGCCCCC ATGATTATTC ACGGCATTAA GACACAGGGG GCCAGGCAGA 3700<br>AATTCTCCTC CCTGTACATC TCCCAGTTCA TCATCATGTA CAGTCTGGAC 3750<br>GGCAAAAAGT GGCAGACCTA CCGCGGGAAC AGTACCGGGA CATTGATGGT 3800<br>GTTCTTCGGG AACGTGGACT CTAGCGGCAT TAAACACAAC ATTTTCAACC 3850<br>CCCCCATCAT TGCTAGGTAT ATCAGGCTCC ATCCCACCCA CTATAGCATC 3900<br>AGGTCCACTC TGCGGATGGA GCTGATGGGC TGCGACCTTA ATTCATGCAG 3950<br>CATGCCGCTG GGCATGGAGT CAAAGGCCAT CTCCGACGCC CAAATCACCG 4000<br>CCTCCAGCTA CTTCACCAAT ATGTTCGCCA CCTGGAGCCC CAGCAAGGCC 4050<br>CGGCTGCACC TGCAGGGCCG CAGCAACGCC TGGCGGCCTC AGGTGAACAA 4100<br>CCCCAAGGAG TGGCTGCAGG TGGACTTCCA GAAAACCATG AAGGTGACTG 4150<br>GGGTCACCAC CCAGGGAGTC AAGAGCCTGC TGACCAGCAT GTATGTGAAG 4200<br>GAGTTCTTGA TCAGCTCGTC ACAGGATGGC CACCAGTGGA CTTTGTTCTT 4250<br>TCAGAACGGT AAGGTGAAAG TGTTCCAGGG AAACCAAGAT TCCTTTACAC 4300<br>CAGTGGTCAA CTCTCTGGAT CCTCCCCTGC TGACACGGTA CCTGCGGATC 4350<br>CATCCCCAGT CATGGGTGCA CCAGATTGCT CTGCGCATGG AGGTGCTTGG 4400<br>CTGCGAGGCC CAGGACCTGT ACTAA                                4425 |

Table 6: FIX coding sequences expressed in ARPE-19 cells

| SEQ ID NO. | Sequence Name | Nucleotide Sequence |
|---|---|---|
| 18 | rhFIX Padua | ATGCAGCGCG TGAACATGAT CATGGCAGAA TCACCAGGCC TCATCACCAT 50<br>CTGCCTTTTA GGATATCTAC TCAGTGCTGA ATGTACAGTT TTTCTTGATC 100<br>ATGAAAACGC CAACAAAATT CTGAATCGGC CAAAGAGGTA TAATTCAGGT 150<br>AAATTGGAAG AGTTTGTTCA AGGGAACCTT GAGAGAGAAT GTATGGAAGA 200<br>AAAGTGTAGT TTTGAAGAAG CACGAGAAGT TTTTGAAAAC ACTGAAAGAA 250<br>CAACTGAATT TTGGAAGCAG TATGTTGATG GAGATCAGTG TGAGTCCAAT 300<br>CCATGTTTAA ATGGCGGCAG TTGCAAGGAT GACATTAATT CCTATGAATG 350<br>TTGGTGTCCC TTTGATTTG AAGGAAAGAA CTGTGAATTA GATGTAACAT 400<br>GTAACATTAA GAATGGCAGA TGCGAGCAGT TTTGTAAAAA TAGTGCTGAT 450<br>AACAAGGTGG TTTGCTCCTG TACTGAGGGA TATCGACTTG CAGAAAACCA 500<br>GAAGTCCTGT GAACCAGCAG TGCCATTTCC ATGTGGAAGA GTTTCTGTTT 550<br>CACAAACTTC TAAGCTCACC CGTGCTGAGA CTGTTTTTCC TGATGTGGAC 600<br>TATGTAAATT CTACTGAAGC TGAAACCATT TTGGATAACA TCACTCAAAG 650<br>CACCCAATCA TTTAATGACT TCACTCGGGT TGTTGGTGGA GAAGATGCCA 700<br>AACCAGGTCA ATTCCCTTGG CAGGTTGTTT TGAATGGTAA AGTTGATGCA 750<br>TTCTGTGGAG GCTCTATCGT TAATGAAAAA TGGATTGTAA CTGCTGCCCA 800<br>CTGTGTTGAA ACTGGTGTTA AAATTACAGT TGTCGCAGGT GAACATAATA 850 |

FIG. 17V

| | | | |
|---|---|---|---|
| | | TTGAGGAGAC AGAACATACA GAGCAAAAGC GAAATGTGAT TCGAATTATT | 900 |
| | | CCTCACCACA ACTACAATGC AGCTATTAAT AAGTACAACC ATGACATTGC | 950 |
| | | CCTTCTGGAA CTGGACGAAC CCTTAGTGCT AAACAGCTAC GTTACACCTA | 1000 |
| | | TTTGCATTGC TGACAAGGAA TACACGAACA TCTTCCTCAA ATTTGGATCT | 1050 |
| | | GGCTATGTAA GTGGCTGGGG AAGAGTCTTC CACAAAGGGA GATCAGCTTT | 1100 |
| | | AGTTCTTCAG TACCTTAGAG TTCCACTTGT TGACCGAGCC ACATGTCTTC | 1150 |
| | | TGTCTACAAA GTTCACCATC TATAACAACA TGTTCTGTGC TGGCTTCCAT | 1200 |
| | | GAAGGAGGTA GAGATTCATG TCAAGGAGAT AGTGGGGGAC CCCATGTTAC | 1250 |
| | | TGAAGTGGAA GGGACCAGTT TCTTAACTGG AATTATTAGC TGGGGTGAAG | 1300 |
| | | AGTGTGCAAT GAAAGGCAAA TATGGAATAT ATACCAAGGT ATCCCGGTAT | 1350 |
| | | GTCAACTGGA TTAAGGAAAA AACAAAGCTC ACTTAA | 1386 |
| 19 | rhFIX Padua CO2 | ATGCAGCGCG TGAACATGAT TATGGCCGAG TCTCCCGGCC TGATCACCAT | 50 |
| | | CTGTCTGCTG GGCTATCTGC TGAGCGCCGA GTGCACCGTG TTTCTGGATC | 100 |
| | | ACGAGAACGC CAACAAGATC CTGAACAGAC CCAAGCGGTA CAACAGCGGC | 150 |
| | | AAGCTGGAAG AGTTCGTGCA GGGCAACCTG AACGCGAGT GCATGGAAGA | 200 |
| | | GAAGTGCAGC TTCGAAGAGG CCAGAGAGGT GTTCGAGAAC ACCGAGAGAA | 250 |
| | | CCACCGAGTT CTGGAAGCAG TACGTGGACG GCGATCAGTG CGAGAGCAAC | 300 |
| | | CCTTGTCTGA ATGGCGGCAG CTGCAAGGAC GACATCAACA GCTACGAGTG | 350 |
| | | CTGGTGCCCC TTCGGCTTCG AGGGCAAGAA TTGCGAGCTG GACGTGACCT | 400 |
| | | GCAACATCAA GAACGGCAGA TGCGAGCAGT TCTGCAAGAA CAGCGCCGAC | 450 |
| | | AACAAGGTCG TGTGCTCCTG CACAGAGGGC TACAGACTGG CCGAGAACCA | 500 |
| | | GAAGTCTTGC GAGCCCGCTG TGCCCTTTCC ATGTGGCAGA GTGTCTGTGT | 550 |
| | | CCCAGACCAG CAAGCTGACC AGAGCCGAGA CAGTGTTCCC CGACGTGGAC | 600 |
| | | TACGTGAACA GCACCGAGGC CGAGACAATC CTGGACAACA TCACCCAGAG | 650 |
| | | CACCCAGTCC TTCAACGACT TCACCAGAGT CGTCGGCGGC GAGGATGCTA | 700 |
| | | AGCCTGGACA GTTCCTTGG CAAGTGGTGC TGAACGGCAA GGTGGACGCT | 750 |
| | | TTTTGTGGCG GCTCCATCGT GAACGAGAAG TGGATCGTGA CCGCCGCTCA | 800 |
| | | CTGTGTGGAA ACCGGCGTGA AGATTACAGT GGTGGCCGGC GAGCACAACA | 850 |
| | | TCGAGGAAAC AGAGCACACC GAGCAGAAAC GGAACGTGAT CAGAATCATC | 900 |
| | | CCTCACCACA ACTACAACGC CGCCATCAAC AAGTACAACC ACGATATCGC | 950 |
| | | CCTGCTGGAA CTGGACGAGC CCCTGGTCCT GAACTCTTAC GTGACCCCTA | 1000 |
| | | TCTGTATCGC CGACAAAGAG TACACCAACA TCTTTCTGAA GTTCGGCAGC | 1050 |
| | | GGCTACGTGT CCGGCTGGGG AAGAGTTTTC CACAAGGGCA GATCAGCCCT | 1100 |
| | | GGTGCTGCAG TACCTGAGAG TGCCCCTGGT GGATAGAGCC ACATGCCTGC | 1150 |
| | | TGAGCACCAA GTTCACCATC TACAACAACA TGTTCTGCGC CGGCTTCCAC | 1200 |
| | | GAAGGCGGCA GAGATTCTTG TCAAGGCGAT TCTGGCGGCC CTCACGTGAC | 1250 |
| | | AGAGGTTGAG GGCACAAGCT TTCTGACCGG CATCATCAGC TGGGGCGAAG | 1300 |
| | | AGTGTGCCAT GAAGGGGAAG TACGGCATCT ACACCAAGGT GTCCAGATAC | 1350 |
| | | GTGAACTGGA TCAAAGAAAA GACCAAGCTC ACCTGA | 1386 |
| 20 | rHFIX Padua CO3 | ATGCAGCGCG TGAACATGAT CATGGCCGAG AGCCCCGGCC TGATCACCAT | 50 |
| | | CTGCCTGCTG GGCTACCTGC TGAGCGCCGA GTGCACCGTG TTCCTGGACC | 100 |
| | | ACGAGAACGC CAACAAGATC CTGAACCGCC CCAAGCGCTA CAACAGCGGC | 150 |
| | | AAGCTGGAGG AGTTCGTGCA GGGCAACCTG GAGCGCGAGT GCATGGAGGA | 200 |
| | | GAAGTGCAGC TTCGAGGAGG CCCGCGAGGT GTTCGAGAAC ACCGAGCGCA | 250 |
| | | CCACCGAGTT CTGGAAGCAG TACGTGGACG GCGACCAGTG CGAGAGCAAC | 300 |
| | | CCCTGCCTGA ACGGCGGCAG CTGCAAGGAC GACATCAACA GCTACGAGTG | 350 |
| | | CTGGTGCCCC TTCGGCTTCG AGGGCAAGAA CTGCGAGCTG GACGTGACCT | 400 |
| | | GCAACATCAA GAACGGCCGC TGCGAGCAGT TCTGCAAGAA CAGCGCCGAC | 450 |
| | | AACAAGGTGG TGTGCAGCTG CACCGAGGGC TACCGCCTGG CCGAGAACCA | 500 |
| | | GAAGAGCTGC GAGCCCGCCG TGCCCTTCCC CTGCGGCCGC GTGAGCGTGA | 550 |
| | | GCCAGACCAG CAAGCTGACC CGCGCCGAGA CTGTGTTCCC CGACGTGGAC | 600 |
| | | TACGTGAACA GCACCGAGGC CGAAACGATC CTGGACAACA TCACCCAGAG | 650 |
| | | CACCCAGAGC TTCAACGACT TCACCCGCGT GGTGGGCGGC GAGGACGCCA | 700 |

FIG. 17W

| | | | |
|---|---|---|---|
| | | AGCCCGGCCA GTTCCCCTGG CAGGTGGTGC TGAACGGCAA GGTGGACGCC | 750 |
| | | TTCTGCGGCG GCAGCATCGT GAACGAGAAG TGGATCGTGA CCGCCGCCCA | 800 |
| | | CTGCGTGGAA ACCGGCGTGA AGATCACCGT GGTGGCCGGC GAGCACAACA | 850 |
| | | TCGAGGAAAC CGAGCACACC GAGCAGAAGC GCAACGTGAT CCGCATCATC | 900 |
| | | CCCCACCACA ACTACAACGC CGCCATCAAC AAGTACAACC ACGACATCGC | 950 |
| | | CCTGCTGGAG CTGGACGAGC CCCTGGTGCT GAACAGCTAC GTGACCCCCA | 1000 |
| | | TCTGCATCGC CGACAAGGAG TACACCAACA TCTTCCTGAA GTTCGGCAGC | 1050 |
| | | GGCTACGTGA GCGGCTGGGG CCGCGTGTTC CACAAGGGCC GCAGCGCCCT | 1100 |
| | | GGTGCTGCAG TACCTGCGCG TGCCCCTGGT GGACCGCGCC ACCTGCCTGC | 1150 |
| | | TGAGCACCAA GTTCACCATC TACAACAACA TGTTCTGCGC CGGCTTCCAC | 1200 |
| | | GAGGGCGGCC GCGACAGCTG CCAGGGCGAC AGCGGCGGCC CCACGTGAC | 1250 |
| | | CGAGGTGGAG GGCACCAGCT TCCTGACCGG CATCATCAGC TGGGGCGAGG | 1300 |
| | | AGTGCGCCAT GAAGGGCAAG TACGGCATCT ACACCAAGGT GAGCCGCTAC | 1350 |
| | | GTGAACTGGA TCAAGGAGAA AACCAAGCTG ACCTAA | 1386 |
| 21 | rhFIX Padua CO5 | ATGCAGCGGG TGAACATGAT CATGGCCGAG AGCCCCGGGC TGATCACCAT | 50 |
| | | CTGTCTGCTG GGGTACCTGC TGTCCGCCGA GTGCACCGTG TTCCTGGACC | 100 |
| | | ACGAGAACGC CAACAAGATC CTGAATCGCC CAAGAGATA CAATTCCGGA | 150 |
| | | AAGCTGGAAG AGTTTGTGCA GGGCAACCTG GAGAGAGAGT GCATGGAAGA | 200 |
| | | GAAGTGCTCC TTCGAGGAGG CCCGGGAGGT GTTCGAGAAT ACTGAACGGA | 250 |
| | | CAACAGAGTT CTGGAAGCAG TATGTGGACG GCGACCAGTG TGAGAGCAAC | 300 |
| | | CCCTGTCTGA ACGGCGGGAG CTGCAAGGAC GACATTAATT CCTACGAATG | 350 |
| | | CTGGTGCCCA TTCGGCTTCG AGGGCAAGAA CTGCGAGCTG GACGTGACCT | 400 |
| | | GCAACATCAA GAACGGCCGC TGCGAGCAGT TTTGCAAGAA CTCCGCCGAC | 450 |
| | | AACAAGGTGG TGTGTTCTTG CACCGAGGGC TACCGCCTGG CCGAAAACCA | 500 |
| | | GAAGAGCTGT GAGCCTGCCG TGCCCTTCCC CTGCGGCCGG GTGTCTGTGT | 550 |
| | | CCCAGACCTC CAAGCTGACC AGAGCCGAAA CCGTGTTTCC AGATGTGGAC | 600 |
| | | TACGTGAATA GCACCGAGGC CGAGACTATC CTCGACAACA TCACCCAGTC | 650 |
| | | CACCCAGAGC TTTAACGACT TCACCCGCGT GGTGGGCGGC GAGGACGCCA | 700 |
| | | AGCCCGGCCA GTTCCCCTGG CAGGTGGTGC TCAACGGAAA GGTGGACGCC | 750 |
| | | TTCTGCGGAG GCAGCATCGT GAATGAAAAG TGGATCGTGA CAGCCGCCCA | 800 |
| | | CTGCGTGGAA ACAGGGGTGA AGATCACCGT GGTGGCTGGA GAGCACAACA | 850 |
| | | TCGAGGAGAC AGAGCACACC GAACAGAAGA GGAATGTGAT CAGGATCATC | 900 |
| | | CCCCACCACA ACTATAATGC CGCCATCAAC AAGTACAACC ACGACATCGC | 950 |
| | | CCTGCTGGAG CTGGATGAGC CCCTGGTGCT CAACAGCTAC GTGACCCCCA | 1000 |
| | | TCTGCATCGC TGACAAGGAG TACACCAACA TCTTCCTGAA GTTCGGCTCC | 1050 |
| | | GGCTACGTGT CTGGCTGGGG CCGCGTGTTC CACAAGGGAA GAAGCGCCCT | 1100 |
| | | CGTGCTGCAG TACCTGCGGG TGCCACTGGT GGACAGGGCC ACCTGCCTGC | 1150 |
| | | TGAGCACTAA GTTCACCATT TACAACAACA TGTTCTGCGC CGGCTTCCAC | 1200 |
| | | GAGGGCGGCA GGGACTCCTG CCAGGGCGAC AGCGGCGGCC CCATGTGAC | 1250 |
| | | CGAGGTGGAG GGCACCTCCT TTCTGACTGG CATTATCTCC TGGGGCGAGG | 1300 |
| | | AGTGCGCCAT GAAGGGGAAG TATGGCATCT ACACCAAGGT GTCCCGCTAC | 1350 |
| | | GTGAACTGGA TTAAGGAGAA AACCAAGCTG ACCTGA | 1386 |

Table 7: Expression Vector Sequences

| SEQ ID NO. | Component | Nucleotide Sequence |
|---|---|---|
| 22 | 5' ITR | TTAACCCTAG AAAGATAGTC TGCGTAAAAT TGACGCATGC ATTCTTGAAA TATTGCTCTC TCTTTCTAAA TAGCGCGAAT CCGTCGCTGT GCATTTAGGA CATCTCAGTC GCCGCTTGGA GCTCCCGTGA GGCGTGCTTG TCAATGCGGT |

FIG. 17X

| | | |
|---|---|---|
| | | AAGTGTCACT GATTTTGAAC TATAACGACC GCGTGAGTCA AAATGACGCA TGATTATCTT TTACGTGACT TTTAAGATTT AACTCATACG ATAATTATAT TGTTATTTCA TGTTCTACTT ACGTGATAAC TTATTATATA TATATTTTCT TGTTATAGAT ATC |
| 23 | CAG Promoter | CTCGACATTG ATTATTGACT AGTTATTAAT AGTAATCAAT TACGGGGTCA TTAGTTCATA GCCCATATAT GGAGTTCCGC GTTACATAAC TTACGGTAAA TGGCCCGCCT GGCTGACCGC CCAACGACCC CCGCCCATTG ACGTCAATAA TGACGTATGT TCCCATAGTA ACGCCAATAG GGACTTTCCA TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT AAATGGCCCG CCTGGCATTA TGCCCAGTAC ATGACCTTAT GGGACTTTCC TACTTGGCAG TACATCTACG TATTAGTCAT CGCTATTACC ATGGTCGAGG TGAGCCCCAC GTTCTGCTTC ACTCTCCCCA TCTCCCCCCC CTCCCCACCC CCAATTTTGT ATTTATTTAT TTTTTAATTA TTTTGTGCAG CGATGGGGGC GGGGGGGGGG GGGGGGCGCG CGCCAGGCGG GGCGGGGCGG GGCGAGGGGC GGGGCGGGGC GAGGCGGAGA GGTGCGGCGG CAGCCAATCA GAGCGGCGCG CTCCGAAAGT TTCCTTTTAT GGCGAGGCGG CGGCGGCGGC GGCCCTATAA AAAGCGAAGC GCGCGGCGGG CGGGAGTCGC TGCGCGCTGC CTTCGCCCCG TGCCCCGCTC CGCCGCCGCC TCGCGCCGCC CGCCCCGGCT CTGACTGACC GCGTTACTCC CACAGGTGAG CGGGCGGGAC GGCCCTTCTC CTCCGGGCTG TAATTAGCGC TTGGTTTAAT GACGGCTTGT TTCTTTTCTG TGGCTGCGTG AAAGCCTTGA GGGGCTCCGG GAGGGCCCTT TGTGCGGGGG GAGCGGCTCG GGGGGTGCGT GCGTGTGTGT GTGCGTGGGG AGCGCCGCGT GCGGCTCCGC GCTGCCCGGC GGCTGTGAGC GCTGCGGGCG CGGCGCGGGG CTTTGTGCGC TCCGCAGTGT GCGCGAGGGG AGCGCGGCCG GGGGCGGTGC CCCGCGGTGC GGGGGGGGCT GCGAGGGGAA CAAAGGCTGC GTGCGGGGTG TGTGCGTGGG GGGGTGAGCA GGGGGTGTGG GCGCGTCGGT CGGGCTGCAA CCCCCCCTGC ACCCCCCTCC CCGAGTTGCT GAGCACGGCC CGGCTTCGGG TGCGGGGCTC CGTACGGGGC GTGGCGCGGG GCTCGCCGTG CCGGGCGGGG GGTGGCGGCA GGTGGGGGTG CCGGGCGGGG CGGGGCCGCC TCGGGCCGGG GAGGGCTCGG GGGAGGGGCG CGGCGGCCCC CGGAGCGCCG GCGGCTGTCG AGGCGCGGCG AGCCGCAGCC ATTGCCTTTT ATGGTAATCG TGCGAGAGGG CGCAGGGACT TCCTTTGTCC CAAATCTGTG CGGAGCCGAA ATCTGGGAGG CGCCGCCGCA CCCCCTCTAG CGGGCGCGGG GCGAAGCGGT GCGGCGCCGG CAGGAAGGAA ATGGGCGGGG AGGGCCTTCG TGCGTCGCCG CGCCGCCGTC CCCTTCTCCC TCTCCAGCCT CGGGGCTGTC CGCGGGGGGA CGGCTGCCTT CGGGGGGGAC GGGGCAGGGC GGGGTTCGGC TTCTGGCGTG TGACCGGCGG CTCTAGAGCC TCTGCTAACC ATGTTCATGC CTTCTTCTTT TTCCTACAGC TCCTGGGCAA CGTGCTGGTT ATTGTGCTGT CTCATCATTT TGGCAAAGAA TTG |
| 24 | rBG pA | TCCTCAGGTG CAGGCTGCCT ATCAGAAGGT GGTGGCTGGT GTGGCCAATG CCCTGGCTCA CAAATACCAC TGAGATCTTT TTCCCTCTGC CAAAAATTAT GGGGACATCA TGAAGCCCCT TGAGCATCTG ACTTCTGGCT AATAAAGGAA ATTTATTTTC ATTGCAATAG TGTGTTGGAA TTTTTTGTGT CTCTCACTCG GAAGGACATA TGGGAGGGCA AATCATTTAA AACATCAGAA TGAGTATTTG GTTTAGAGTT TGGCAACATA TGCCCATATG CTGGCTGCCA TGAACAAAGG TTGGCTATAA AGAGGTCATC AGTATATGAA ACAGCCCCCT GCTGTCCATT CCTTATTCCA TAGAAAAGCC TTGACTTGAG GTTAGATTTT TTTTATATTT TGTTTTGTGT TATTTTTTTC TTTAACATCC CTAAAATTTT CCTTACATGT TTTACTAGCC AGATTTTTCC TCCTCTCCTG ACTACTCCCA GTCATAGCTG TCCCTCTTCT CTTATGGAGA TC |
| 25 | 3' ITR | TTAACCCTAG AAAGATAATC ATATTGTGAC GTACGTTAAA GATAATCATG CGTAAAATTG ACGCATGTGT TTTATCGGTC TGTATATCGA GGTTTATTTA TTAATTTGAA TAGATATTAA GTTTTATTAT ATTTACACTT ACATACTAAT |

FIG. 17Y

| | | |
|---|---|---|
| | | AATAAATTCA ACAAACAATT TATTTATGTT TATTTATTTA TTAAAAAAAA |
| | | ACAAAAACTC AAAATTTCTT CTATAAAGTA ACAAA |
| 26 | Vector | TTAACCCTAG AAAGATAGTC TGCGTAAAAT TGACGCATGC ATTCTTGAAA |
| | | TATTGCTCTC TCTTTCTAAA TAGCGCGAAT CCGTCGCTGT GCATTTAGGA |
| | | CATCTCAGTC GCCGCTTGGA GCTCCCGTGA GGCGTGCTTG TCAATGCGGT |
| | | AAGTGTCACT GATTTTGAAC TATAACGACC GCGTGAGTCA AAATGACGCA |
| | | TGATTATCTT TTACGTGACT TTTAAGATTT AACTCATACG ATAATTATAT |
| | | TGTTATTTCA TGTTCTACTT ACGTGATAAC TTATTATATA TATATTTTCT |
| | | TGTTATAGAT ATCATCAACT TTGTATAGAA AAGTTGCTCG ACATTGATTA |
| | | TTGACTAGTT ATTAATAGTA ATCAATTACG GGGTCATTAG TTCATAGCCC |
| | | ATATATGGAG TTCCGCGTTA CATAACTTAC GGTAAATGGC CCGCCTGGCT |
| | | GACCGCCCAA CGACCCCCGC CCATTGACGT CAATAATGAC GTATGTTCCC |
| | | ATAGTAACGC CAATAGGGAC TTTCCATTGA CGTCAATGGG TGGAGTATTT |
| | | ACGGTAAACT GCCCACTTGG CAGTACATCA AGTGTATCAT ATGCCAAGTA |
| | | CGCCCCCTAT TGACGTCAAT GACGGTAAAT GGCCCGCCTG GCATTATGCC |
| | | CAGTACATGA CCTTATGGGA CTTTCCTACT TGGCAGTACA TCTACGTATT |
| | | AGTCATCGCT ATTACCATGG TCGAGGTGAG CCCCACGTTC TGCTTCACTC |
| | | TCCCCATCTC CCCCCCCTCC CCACCCCCAA TTTTGTATTT ATTTATTTTT |
| | | TAATTATTTT GTGCAGCGAT GGGGGCGGGG GGGGGGGGGG GGCGCGCGCC |
| | | AGGCGGGGCG GGGCGGGGCG AGGGGCGGGG CGGGGCGAGG CGGAGAGGTG |
| | | CGGCGGCAGC CAATCAGAGC GGCGCGCTCC GAAAGTTTCC TTTTATGGCG |
| | | AGGCGGCGGC GGCGGCGGCC CTATAAAAAG CGAAGCGCGC GGCGGGCGGG |
| | | AGTCGCTGCG CGCTGCCTTC GCCCCGTGCC CCGCTCCGCC GCCGCCTCGC |
| | | GCCGCCCGCC CCGGCTCTGA CTGACCGCGT TACTCCCACA GGTGAGCGGG |
| | | CGGGACGGCC CTTCTCCTCC GGGCTGTAAT TAGCGCTTGG TTTAATGACG |
| | | GCTTGTTTCT TTTCTGTGGC TGCGTGAAAG CCTTGAGGGG CTCCGGGAGG |
| | | GCCCTTTGTG CGGGGGGAGC GGCTCGGGGG GTGCGTGCGT GTGTGTGTGC |
| | | GTGGGGAGCG CCGCGTGCGG CTCCGCGCTG CCCGGCGGCT GTGAGCGCTG |
| | | CGGGCGCGGC GCGGGGCTTT GTGCGCTCCG CAGTGTGCGC GAGGGGAGCG |
| | | CGGCCGGGGG CGGTGCCCCG CGGTGCGGGG GGGGCTGCGA GGGGAACAAA |
| | | GGCTGCGTGC GGGGTGTGTG CGTGGGGGGG TGAGCAGGGG GTGTGGGCGC |
| | | GTCGGTCGGG CTGCAACCCC CCCTGCACCC CCCTCCCCGA GTTGCTGAGC |
| | | ACGGCCCGGC TTCGGGTGCG GGGCTCCGTA CGGGGCGTGG CGCGGGGCTC |
| | | GCCGTGCCGG GCGGGGGGTG GCGGCAGGTG GGGGTGCCGG GCGGGGCGGG |
| | | GCCGCCTCGG GCCGGGGAGG GCTCGGGGGA GGGGCGCGGC GGCCCCGGGA |
| | | GCGCCGGCGG CTGTCGAGGC GCGGCGAGCC GCAGCCATTG CCTTTTATGG |
| | | TAATCGTGCG AGAGGGCGCA GGGACTTCCT TTGTCCCAAA TCTGTGCGGA |
| | | GCCGAAATCT GGGAGGCGCC GCCGCACCCC CTCTAGCGGG CGCGGGGCGA |
| | | AGCGGTGCGG CGCCGGCAGG AAGGAAATGG GCGGGAGGG CCTTCGTGCG |
| | | TCGCCGCGCC GCCGTCCCCT TCTCCCTCTC CAGCCTCGGG GCTGTCCGCG |
| | | GGGGGACGGC TGCCTTCGGG GGGGACGGGG CAGGGCGGGG TTCGGCTTCT |
| | | GGCGTGTGAC CGGCGGCTCT AGAGCCTCTG CTAACCATGT TCATGCCTTC |
| | | TTCTTTTTCC TACAGCTCCT GGGCAACGTG CTGGTTATTG TGCTGTCTCA |
| | | TCATTTTGGC AAAGAATTGC AAGTTTGTAC AAAAAAGCAG GCTGCCACCG |
| | | AATTCGCGGC CGCTAAACCC AGCTTTCTTG TACAAAGTGG CAACTTTATT |
| | | ATACATAGTT GATCCTCAGG TGCAGGCTGC CTATCAGAAG GTGGTGGCTG |
| | | GTGTGGCCAA TGCCCTGGCT CACAAATACC ACTGAGATCT TTTTCCCTCT |
| | | GCCAAAAATT ATGGGACAT CATGAAGCCC CTTGAGCATC TGACTTCTGG |
| | | CTAATAAAGG AAATTTATTT TCATTGCAAT AGTGTGTTGG AATTTTTTGT |
| | | GTCTCTCACT CGGAAGGACA TATGGGAGGG CAAATCATTT AAAACATCAG |
| | | AATGAGTATT TGGTTTAGAG TTTGGCAACA TATGCCCATA TGCTGGCTGC |
| | | CATGAACAAA GGTTGGCTAT AAAGAGGTCA TCAGTATATG AAACAGCCCC |
| | | CTGCTGTCCA TTCCTTATTC CATAGAAAAG CCTTGACTTG AGGTTAGATT |

FIG. 17Z

```
TTTTTTATAT TTTGTTTTGT GTTATTTTTT TCTTTAACAT CCCTAAAATT
TTCCTTACAT GTTTTACTAG CCAGATTTTT CCTCCTCTCC TGACTACTCC
CAGTCATAGC TGTCCCTCTT CTCTTATGGA GATCCCTCGA CCTGCAGCCC
AAGCTTGGAT CCCTCGAGTT AATTAACGAG AGCATAATAT TGATATGTGC
CAAAGTTGTT TCTGACTGAC TAATAAGTAT AATTTGTTTC TATTATGTAT
AGGTTAAGCT AATTACTTAT TTTATAATAC AACATGACTG TTTTTAAAGT
ACAAAATAAG TTTATTTTTG TAAAGAGAG AATGTTTAAA AGTTTTGTTA
CTTTATAGAA GAAATTTTGA GTTTTTGTTT TTTTTTAATA AATAAATAAA
CATAAATAAA TTGTTTGTTG AATTTATTAT TAGTATGTAA GTGTAAATAT
AATAAAACTT AATATCTATT CAAATTAATA AATAAACCTC GATATACAGA
CCGATAAAAC ACATGCGTCA ATTTTACGCA TGATTATCTT TAACGTACGT
CACAATATGA TTATCTTTCT AGGGTTAAAT AATAGTTTCT AATTTTTTTA
TTATTCAGCC TGCTGTCGTG AATACCGAGC TCCAATTCGC CCTATAGTGA
GTCGTATTAC AATTCACTGG CCGTCGTTTT ACAACGTCGT GACTGGGAAA
ACCCTGGCGT TACCCAACTT AATCGCCTTG CAGCACATCC CCCTTTCGCC
AGCTGGCGTA ATAGCGAAGA GGCCCGCACC GATCGCCCTT CCCAACAGTT
GCGCAGCCTG AATGGCGAAT GGGACGCGCC CTGTAGCGGC GCATTAAGCG
CGGCGGGTGT GGTGGTTACG CGCAGCGTGA CCGCTACACT TGCCAGCGCC
CTAGCGCCCG CTCCTTTCGC TTTCTTCCCT TCCTTTCTCG CCACGTTCGC
CGGCTTTCCC CGTCAAGCTC TAAATCGGGG CTCCCTTTA GGGTTCCGAT
TTAGTGCTTT ACGGCACCTC GACCCCAAAA AACTTGATTA GGGTGATGGT
TCACGTAGTG GGCCATCGCC CTGATAGACG GTTTTTCGCC CTTTGACGTT
GGAGTCCACG TTCTTTAATA GTGGACTCTT GTTCCAAACT GGAACAACAC
TCAACCCTAT CTCGGTCTAT TCTTTTGATT TATAAGGGAT TTTGCCGATT
TCGGCCTATT GGTTAAAAAA TGAGCTGATT TAACAAAAAT TTAACGCGAA
TTTTAACAAA ATATTAACGC TTACAATTTA GGTGGCACTT TTCGGGGAAA
TGTGCGCGGA ACCCCTATTT GTTTATTTTT CTAAATACAT TCAAATATGT
ATCCGCTCAT GAGACAATAA CCCTGATAAA TGCTTCAATA ATATTGAAAA
AGGAAGAGTA TGAGTATTCA ACATTTCCGT GTCGCCCTTA TTCCCTTTTT
TGCGGCATTT TGCCTTCCTG TTTTTGCTCA CCCAGAAACG CTGGTGAAAG
TAAAAGATGC TGAAGATCAG TTGGGTGCAC GAGTGGGTTA CATCGAACTG
GATCTCAACA GCGGTAAGAT CCTTGAGAGT TTTCGCCCCG AAGAACGTTT
TCCAATGATG AGCACTTTTA AAGTTCTGCT ATGTGGCGCG GTATTATCCC
GTATTGACGC CGGGCAAGAG CAACTCGGTC GCCGCATACA CTATTCTCAG
AATGACTTGG TTGAGTACTC ACCAGTCACA GAAAAGCATC TTACGGATGG
CATGACAGTA AGAGAATTAT GCAGTGCTGC CATAACCATG AGTGATAACA
CTGCGGCCAA CTTACTTCTG ACAACGATCG GAGGACCGAA GGAGCTAACC
GCTTTTTTGC ACAACATGGG GGATCATGTA ACTCGCCTTG ATCGTTGGGA
ACCGGAGCTG AATGAAGCCA TACCAAACGA CGAGCGTGAC ACCACGATGC
CTGTAGCAAT GGCAACAACG TTGCGCAAAC TATTAACTGG CGAACTACTT
ACTCTAGCTT CCCGGCAACA ATTAATAGAC TGGATGGAGG CGGATAAAGT
TGCAGGACCA CTTCTGCGCT CGGCCCTTCC GGCTGGCTGG TTTATTGCTG
ATAAATCTGG AGCCGGTGAG CGTGGGTCTC GCGGTATCAT TGCAGCACTG
GGGCCAGATG GTAAGCCCTC CCGTATCGTA GTTATCTACA CGACGGGGAG
TCAGGCAACT ATGGATGAAC GAAATAGACA GATCGCTGAG ATAGGTGCCT
CACTGATTAA GCATTGGTAA CTGTCAGACC AAGTTTACTC ATATATACTT
TAGATTGATT TAAAACTTCA TTTTTAATTT AAAAGGATCT AGGTGAAGAT
CCTTTTTGAT AATCTCATGA CCAAAATCCC TTAACGTGAG TTTTCGTTCC
ACTGAGCGTC AGACCCCGTA GAAAAGATCA AAGGATCTTC TTGAGATCCT
TTTTTTCTGC GCGTAATCTG CTGCTTGCAA ACAAAAAAAC CACCGCTACC
AGCGGTGGTT TGTTTGCCGG ATCAAGAGCT ACCAACTCTT TTTCCGAAGG
TAACTGGCTT CAGCAGAGCG CAGATACCAA ATACTGTTCT TCTAGTGTAG
CCGTAGTTAG GCCACCACTT CAAGAACTCT GTAGCACCGC CTACATACCT
```

FIG. 17AA

| | | |
|---|---|---|
| | | CGCTCTGCTA ATCCTGTTAC CAGTGGCTGC TGCCAGTGGC GATAAGTCGT |
| | | GTCTTACCGG GTTGGACTCA AGACGATAGT TACCGGATAA GGCGCAGCGG |
| | | TCGGGCTGAA CGGGGGGTTC GTGCACACAG CCCAGCTTGG AGCGAACGAC |
| | | CTACACCGAA CTGAGATACC TACAGCGTGA GCTATGAGAA AGCGCCACGC |
| | | TTCCCGAAGA GAGAAAGGCG GACAGGTATC CGGTAAGCGG CAGGGTCGGA |
| | | ACAGGAGAGC GCACGAGGGA GCTTCCAGGG GGAAACGCCT GGTATCTTTA |
| | | TAGTCCTGTC GGGTTTCGCC ACCTCTGACT TGAGCGTCGA TTTTTGTGAT |
| | | GCTCGTCAGG GGGGCGGAGC CTATGGAAAA ACGCCAGCAA CGCGGCCTTT |
| | | TTACGGTTCC TGGCCTTTTG CTGGCCTTTT GCTCACATGT TCTTTCCTGC |
| | | GTTATCCCCT GATTCTGTGG ATAACCGTAT TACCGCCTTT GAGTGAGCTG |
| | | ATACCGCTCG CCGCAGCCGA ACGACCGAGC GCAGCGAGTC AGTGAGCGAG |
| | | GAAGCGGAAG AGCGCCCAAT ACGCAAACCG CCTCTCCCCG CGCGTTGGCC |
| | | GATTCATTAA TGCAGCTGGC ACGACAGGTT TCCCGACTGG AAAGCGGGCA |
| | | GTGAGCGCAA CGCAATTAAT GTGAGTTAGC TCACTCATTA GGCACCCCAG |
| | | GCTTTACACT TTATGCTTCC GGCTCGTATG TTGTGTGGAA TTGTGAGCGG |
| | | ATAACAATTT CACACAGGAA ACAGCTATGA CCATGATTAC GCCAAGCTCG |
| | | AAATTAACCC TCACTAAAGG GAACAAAAGC TGGTACCTCG CGCGACTTGG |
| | | TTTGCCATTC TTTAGCGCGC GTCGCGTCAC ACAGCTTGGC CACAATGTGG |
| | | TTTTTGTCAA ACGAAGATTC TATGACGTGT TTAAAGTTTA GGTCGAGTAA |
| | | AGCGCAAATC TTTT |
| 27 | Transcription Unit for rhScFVIIIBDD CO6 | CTCGACATTG ATTATTGACT AGTTATTAAT AGTAATCAAT TACGGGGTCA |
| | | TTAGTTCATA GCCCATATAT GGAGTTCCGC GTTACATAAC TTACGGTAAA |
| | | TGGCCCGCCT GGCTGACCGC CCAACGACCC CCGCCCATTG ACGTCAATAA |
| | | TGACGTATGT TCCCATAGTA ACGCCAATAG GGACTTTCCA TTGACGTCAA |
| | | TGGGTGGAGT ATTTACGGTA AACTGCCCAC TTGGCAGTAC ATCAAGTGTA |
| | | TCATATGCCA AGTACGCCCC CTATTGACGT CAATGACGGT AAATGGCCCG |
| | | CCTGGCATTA TGCCCAGTAC ATGACCTTAT GGGACTTTCC TACTTGGCAG |
| | | TACATCTACG TATTAGTCAT CGCTATTACC ATGGTCGAGG TGAGCCCCAC |
| | | GTTCTGCTTC ACTCTCCCCA TCTCCCCCCC CTCCCCACCC CCAATTTTGT |
| | | ATTTATTTAT TTTTTAATTA TTTTGTGCAG CGATGGGGGC GGGGGGGGGG |
| | | GGGGGGCGCG CGCCAGGCGG GGCGGGGCGG GGCGAGGGGC GGGGCGGGGC |
| | | GAGGCGGAGA GGTGCGGCGG CAGCCAATCA GAGCGGCGCG CTCCGAAAGT |
| | | TTCCTTTTAT GGCGAGGCGG CGGCGGCGGC GGCCCTATAA AAAGCGAAGC |
| | | GCGCGGCGGG CGGGAGTCGC TGCGCGCTGC CTTCGCCCCG TGCCCCGCTC |
| | | CGCCGCCGCC TCGCGCCGCC CGCCCCGGCT CTGACTGACC GCGTTACTCC |
| | | CACAGGTGAG CGGGCGGGAC GGCCCTTCTC CTCCGGGCTG TAATTAGCGC |
| | | TTGGTTTAAT GACGGCTTGT TTCTTTTCTG TGGCTGCGTG AAAGCCTTGA |
| | | GGGGCTCCGG GAGGGCCCTT TGTGCGGGGG GAGCGGCTCG GGGGGTGCGT |
| | | GCGTGTGTGT GTGCGTGGGG AGCGCCGCGT GCGGCTCCGC GCTGCCCGGC |
| | | GGCTGTGAGC GCTGCGGGCG CGGCGCGGGG CTTTGTGCGC TCCGCAGTGT |
| | | GCGCGAGGGG AGCGCGGCCG GGGCGGTGC CCCGCGGTGC GGGGGGGGCT |
| | | GCGAGGGGAA CAAAGGCTGC GTGCGGGGTG TGTGCGTGGG GGGGTGAGCA |
| | | GGGGGTGTGG GCGCGTCGGT CGGGCTGCAA CCCCCCCTGC ACCCCCCTCC |
| | | CCGAGTTGCT GAGCACGGCC CGGCTTCGGG TGCGGGGCTC CGTACGGGGC |
| | | GTGGCGCGGG GCTCGCCGTG CCGGGCGGGG GGTGGCGGCA GGTGGGGGTG |
| | | CCGGGCGGGG CGGGGCCGCC TCGGGCCGGG GAGGGCTCGG GGAGGGGCG |
| | | CGGCGGCCCC CGGAGCGCCG GCGGCTGTCG AGGCGCGGCG AGCCGCAGCC |
| | | ATTGCCTTTT ATGGTAATCG TGCGAGAGGG CGCAGGGACT CCTTTGTCC |
| | | CAAATCTGTG CGGAGCCGAA ATCTGGGAGG CGCCGCCGCA CCCCCTCTAG |
| | | CGGGCGCGGG GCGAAGCGGT GCGGCGCCGG CAGGAAGGAA ATGGGCGGGG |
| | | AGGGCCTTCG TGCGTCGCCG CGCCGCCGTC CCCTTCTCCC TCTCCAGCCT |
| | | CGGGGCTGTC CGCGGGGGA CGGCTGCCTT CGGGGGGAC GGGGCAGGGC |
| | | GGGGTTCGGC TTCTGGCGTG TGACCGGCGG CTCTAGAGCC TCTGCTAACC |

FIG. 17BB

| | | |
|---|---|---|
| | | ATGTTCATGC CTTCTTCTTT TTCCTACAGC TCCTGGGCAA CGTGCTGGTT<br>ATTGTGCTGT CTCATCATTT TGGCAAAGAA TTGCAAGTTT GTACAAAAAA<br>GCAGGCTGCC ACCATGCAGA TTGAGCTGAG CACCTGTTTC TTCCTGTGCC<br>TGCTGAGATT TTGCTTCTCA GCTACCCGCA GGTACTACCT GGGAGCCGTT<br>GAGCTGTCCT GGGATTACAT GCAGTCAGAT CTGGGGGAGC TGCCTGTGGA<br>CGCTCGGTTT CCCCCCAGAG TGCCAAAGTC CTTTCCCTTC AACACCAGCG<br>TGGTGTACAA AAAGACACTT TTTGTTGAAT TTACTGACCA CTTGTTCAAC<br>ATCGCCAAGC CACGACCCCC ATGGATGGGC CTGCTGGGGC CAACCATTCA<br>GGCAGAGGTT TACGACACAG TCGTGATCAC ACTGAAGAAC ATGGCCTCCC<br>ATCCAGTGTC TCTGCACGCC GTCGGTGTGT CCTACTGGAA AGCATCCGAG<br>GGCGCCGAGT ATGACGACCA GACCAGCCAG AGAGAGAAAG AGGACGACAA<br>AGTGTTCCCT GGAGGCAGCC ACACCTACGT GTGGCAGGTG TTGAAGGAAA<br>ATGGGCCCAT GGCCAGTGAC CCTTTGTGTC TGACTTACTC ATACCTGTCT<br>CATGTGGATC TAGTCAAGGA CCTGAATTCT GGACTGATTG GGCACTGCT<br>TGTGTGCCGC GAAGGCAGCC TGGCCAAAGA AAAGACACAG ACCCTTCACA<br>AGTTCATCCT GCTGTTCGCC GTGTTCGACG AAGGCAAATC CTGGCACTCA<br>GAAACCAAAA ACTCACTGAT GCAGGACCGG GATGCCGCCT CTGCCCGCGC<br>ATGGCCAAAA ATGCACACCG TCAACGGCTA TGTCAATAGA AGTTTGCCCG<br>GCCTCATTGG ATGTCACAGG AAAAGCGTCT ATTGGCATGT AATCGGGATG<br>GGAACCACAC CTGAGGTCCA CAGCATATTT CTGGAAGGCC ACACATTTCT<br>GGTGAGAAAT CATCGCCAGG CTTCCCTGGA AATTTCCCCC ATCACCTTCT<br>TGACCGCCCA GACACTGCTC ATGGATCTTG GGCAGTTTCT GCTGTTTTGT<br>CATATTTCTT CTCACCAACA CGACGGAATG GAGGCCTACG TTAAGGTCGA<br>TAGTTGCCCT GAAGAACCTC AGCTGAGGAT GAAGAACAAC GAGGAAGCCG<br>AGGACTACGA TGACGATTTG ACCGATTCCG AAATGACGT GGTGCGCTTT<br>GATGATGACA ATTCTCCATC CTTCATTCAG ATTAGATCCG TCGCCAAGAA<br>GCACCCCAAG ACCTGGGTGC ACTACATTGC AGCCGAGGAG GAGGATTGGG<br>ACTACGCCCC CCTGGTGCTG GCACCCGACG ACCGAAGCTA CAAATCTCAG<br>TACCTGAACA ATGGTCCACA ACGGATCGGC AGGAAGTACA AGAAAGTGCG<br>GTTCATGGCC TATACAGACG AAACCTTCAA AACCAGGGAG GCTATCCAGC<br>ACGAGTCTGG GATTCTGGA CCACTCCTGT ACGGCGAAGT GGGCGACACC<br>TTGTTAATTA TCTTCAAGAA CCAGGCTAGT AGACCTTATA ACATTTATCC<br>CCACGGCATT ACCGATGTGC GGCCTCTCTA CTCTAGGCGG CTTCCAAAGG<br>GGGTGAAACA CCTGAAGGAC TTTCCCATCC TCCCTGGCGA AATCTTTAAG<br>TATAAGTGGA CAGTGACCGT GGAGGATGGA CCAACCAAGA GCGACCCCAG<br>GTGCCTGACA CGCTATTATT CAAGCTTCGT GAATATGGAA AGGGACCTCG<br>CATCTGGCTT GATCGGCCCT CTGCTGATAT GTTACAAGGA AAGCGTCGAT<br>CAGAGAGGAA ATCAGATCAT GTCAGACAAA AGGAATGTGA TCCTGTTCTC<br>CGTCTTCGAT GAAAACAGGA GCTGGTATCT GACAGAGAAC ATCCAGAGAT<br>TCCTGCCAAA TCCCGCCGGC GTCCAGCTGG AGGACCCGGA GTTTCAGGCA<br>TCTAACATCA TGCATTCCAT TAATGGTTAC GTGTTCGACT CCCTGCAGCT<br>GAGCGTGTGC CTCCACGAGG TGGCCTACTG GTACATCTTG AGCATCGGCG<br>CCCAGACCGA CTTTCTGAGC GTCTTTTTCT CCGGGTATAC TTTCAAACAT<br>AAGATGGTGT ACGAAGATAC TCTGACGCTG TTCCCTTTCT CTGGGGAGAC<br>TGTGTTTATG TCTATGGAGA ACCCTGGACT GTGGATTCTC GGATGCCACA<br>ACAGTGACTT TCGTAATAGA GGGATGACTG CACTGCTGAA GGTGTCCAGC<br>TGTGATAAAA ATACTGGCGA CTACTACGAA GATAGCTATG AGGATATCTC<br>AGCATACCTG CTGAGCAAGA ATAACGCCAT CGAGCCCGA AGCTTCTCAC<br>AGAATCCCCC TGTCCTCAAG GCCCACCAGG CGGAGATCAC AAGGACCACA<br>CTCCAGTCCG ACCAGGAGGA GATTGACTAC GATGACACGA TTTCTGTGGA<br>GATGAAAAAA GAGGACTTTG ACATCTACGA TGAGGATGAA AACCAGAGCC<br>CTAGGTCGTT CCAGAAGAAA ACAAGGCACT ACTTCATTGC CGCCGTGGAG<br>AGACTGTGGG ACTACGGAAT GAGTAGTTCC CCACACGTGT TGCGGAACAG |

FIG. 17CC

| | | |
|---|---|---|
| | | AGCCCAGAGT GGGTCCGTCC CACAGTTCAA GAAGGTTGTT TTCCAGGAGT |
| | | TCACAGATGG CTCCTTCACT CAGCCACTGT ATCGCGGCGA GCTGAATGAG |
| | | CACTTGGGCT TATTGGGCCC CTACATTCGC GCAGAAGTCG AAGATAATAT |
| | | TATGGTGACC TTCCGCAACC AGGCCAGCCG GCCTTACTCA TTCTACTCCT |
| | | CTCTCATCTC TTATGAGGAG GATCAGCGCC AGGGCGCCGA ACCCCGGAAG |
| | | AACTTTGTGA AGCCCAATGA AACCAAAACT TACTTTTGGA AGGTGCAGCA |
| | | CCATATGGCG CCGACGAAAG ACGAATTTGA CTGCAAAGCC TGGGCCTACT |
| | | TCAGCGACGT CGACTTGGAG AAGGACGTCC ACAGCGGCCT GATTGGCCCT |
| | | TTGTTGGTCT GCCATACCAA TACACTCAAC CCTGCCCACG GGAGGCAGGT |
| | | GACCGTGCAG GAGTTTGCCT TGTTCTTCAC CATCTTCGAC GAAACCAAGA |
| | | GCTGGTACTT CACAGAGAAC ATGGAGAGGA ACTGCAGAGC ACCCTGTAAC |
| | | ATCCAGATGG AGGACCCTAC TTTCAAGGAA AATTACAGGT TCCATGCCAT |
| | | TAATGGCTAC ATCATGGATA CCCTCCCCGG GCTTGTGATG GCTCAGGACC |
| | | AGCGCATCCG CTGGTACCTG CTCTCAATGG GCTCCAACGA GAACATTCAT |
| | | AGCATCCACT TTAGTGGCCA CGTGTTTACC GTGCGCAAGA AGGAGGAGTA |
| | | CAAGATGGCA CTGTACAACC TGTACCCTGG CGTGTTTGAG ACAGTGGAGA |
| | | TGCTGCCATC CAAGGCCGGC ATCTGGCGCG TGGAGTGCCT CATTGGGGAG |
| | | CACCTCCATG CTGGCATGTC TACACTGTTC CTGGTGTACA GCAACAAGTG |
| | | TCAGACTCCA CTCGGAATGG CCTCCGGGCA TATCCGCGAT TTTCAGATCA |
| | | CGGCCTCTGG CCAGTATGGC AATGGGCTC CCAAGCTGGC CAGGCTGCAC |
| | | TACAGTGGGA GTATCAACGC TTGGAGCACC AAGGAGCCTT CTCCTGGAT |
| | | CAAGGTGGAC CTGCTTGCCC CCATGATTAT TCACGGCATT AAGACACAGG |
| | | GGGCCAGGCA GAAATTCTCC TCCCTGTACA TCTCCCAGTT CATCATCATG |
| | | TACAGTCTGG ACGGCAAAAA GTGGCAGACC TACCGCGGGA ACAGTACCGG |
| | | GACATTGATG GTGTTCTTCG GAACGTGGA CTCTAGCGGC ATTAAACACA |
| | | ACATTTTCAA CCCCCCCATC ATTGCTAGGT ATATCAGGCT CCATCCCACC |
| | | CACTATAGCA TCAGGTCCAC TCTGCGGATG GAGCTGATGG GCTGCGACCT |
| | | TAATTCATGC AGCATGCCGC TGGGCATGGA GTCAAAGGCC ATCTCCGACG |
| | | CCCAAATCAC CGCCTCCAGC TACTTCACCA ATATGTTCGC CACCTGGAGC |
| | | CCCAGCAAGG CCCGGCTGCA CCTGCAGGGC CGCAGCAACG CCTGGCGGCC |
| | | TCAGGTGAAC AACCCCAAGG AGTGGCTGCA GGTGGACTTC CAGAAAACCA |
| | | TGAAGGTGAC TGGGGTCACC ACCCAGGGAG TCAAGAGCCT GCTGACCAGC |
| | | ATGTATGTGA AGGAGTTCTT GATCAGCTCG TCACAGGATG GCCACCAGTG |
| | | GACTTTGTTC TTTCAGAACG GTAAGGTGAA AGTGTTCCAG GGAAACCAAG |
| | | ATTCCTTTAC ACCAGTGGTC AACTCTCTGG ATCCTCCCCT GCTGACACGG |
| | | TACCTGCGGA TCCATCCCCA GTCATGGGTG CACCAGATTG CTCTGCGCAT |
| | | GGAGGTGCTT GGCTGCGAGG CCCAGGACCT GTACTGAAAT TCGCGGCCGC |
| | | TAAACCCAGC TTTCTTGTAC AAAGTGGCAA CTTTATTATA CATAGTTGAT |
| | | CCTCAGGTGC AGGCTGCCTA TCAGAAGGTG GTGGCTGGTG TGGCCAATGC |
| | | CCTGGCTCAC AAATACCACT GAGATCTTTT TCCCTCTGCC AAAAATTATG |
| | | GGGACATCAT GAAGCCCCTT GAGCATCTGA CTTCTGGCTA ATAAAGGAAA |
| | | TTTATTTTCA TTGCAATAGT GTGTTGGAAT TTTTTGTGTC TCTCACTCGG |
| | | AAGGACATAT GGGAGGGCAA ATCATTTAAA ACATCAGAAT GAGTATTTGG |
| | | TTTAGAGTTT GGCAACATAT GCCCATATGC TGGCTGCCAT GAACAAAGGT |
| | | TGGCTATAAA GAGGTCATCA GTATATGAAA CAGCCCCCTG CTGTCCATTC |
| | | CTTATTCCAT AGAAAAGCCT TGACTTGAGG TTAGATTTTT TTTATATTTT |
| | | GTTTTGTGTT ATTTTTTTCT TTAACATCCC TAAAATTTTC CTTACATGTT |
| | | TTACTAGCCA GATTTTTCCT CCTCTCCTGA CTACTCCCAG TCATAGCTGT |
| | | CCCTCTTCTC TTATGGAGAT C |
| 28 | Transcription Unit for rhFIX Padua CO2 | CTCGACATTG ATTATTGACT AGTTATTAAT AGTAATCAAT TACGGGGTCA |
| | | TTAGTTCATA GCCCATATAT GGAGTTCCGC GTTACATAAC TTACGGTAAA |
| | | TGGCCCGCCT GGCTGACCGC CCAACGACCC CCGCCCATTG ACGTCAATAA |
| | | TGACGTATGT TCCCATAGTA ACGCCAATAG GGACTTTCCA TTGACGTCAA |

FIG. 17DD

```
TGGGTGGAGT ATTTACGGTA AACTGCCCAC TTGGCAGTAC ATCAAGTGTA
TCATATGCCA AGTACGCCCC CTATTGACGT CAATGACGGT AAATGGCCCG
CCTGGCATTA TGCCCAGTAC ATGACCTTAT GGGACTTTCC TACTTGGCAG
TACATCTACG TATTAGTCAT CGCTATTACC ATGGTCGAGG TGAGCCCCAC
GTTCTGCTTC ACTCTCCCCA TCTCCCCCCC CTCCCCACCC CCAATTTTGT
ATTTATTTAT TTTTTAATTA TTTTGTGCAG CGATGGGGGC GGGGGGGGGG
GGGGGGCGCG CGCCAGGCGG GGCGGGGCGG GGCGAGGGGC GGGGCGGGGC
GAGGCGGAGA GGTGCGGCGG CAGCCAATCA GAGCGGCGCG CTCCGAAAGT
TTCCTTTTAT GGCGAGGCGG CGGCGGCGGC GGCCCTATAA AAAGCGAAGC
GCGCGGCGGG CGGGAGTCGC TGCGCGCTGC CTTCGCCCCG TGCCCCGCTC
CGCCGCCGCC TCGCGCCGCC CGCCCCGGCT CTGACTGACC GCGTTACTCC
CACAGGTGAG CGGGCGGGAC GGCCCTTCTC CTCCGGGCTG TAATTAGCGC
TTGGTTTAAT GACGGCTTGT TTCTTTTCTG TGGCTGCGTG AAAGCCTTGA
GGGGCTCCGG GAGGGCCCTT TGTGCGGGGG GAGCGGCTCG GGGGGTGCGT
GCGTGTGTGT GTGCGTGGGG AGCGCCGCGT GCGGCTCCGC GCTGCCCGGC
GGCTGTGAGC GCTGCGGGCG CGGCGCGGGG CTTTGTGCGC TCCGCAGTGT
GCGCGAGGGG AGCGCGGCCG GGGGCGGTGC CCCGCGGTGC GGGGGGGGCT
GCGAGGGGAA CAAAGGCTGC GTGCGGGGTG TGTGCGTGGG GGGGTGAGCA
GGGGGTGTGG GCGCGTCGGT CGGGCTGCAA CCCCCCCTGC ACCCCCCTCC
CCGAGTTGCT GAGCACGGCC CGGCTTCGGG TGCGGGGCTC CGTACGGGGC
GTGGCGCGGG GCTCGCCGTG CCGGGCGGGG GGTGGCGGCA GGTGGGGGTG
CCGGGCGGGG CGGGGCCGCC TCGGGCCGGG GAGGGCTCGG GGGAGGGGCG
CGGCGGCCCC CGGAGCGCCG GCGGCTGTCG AGGCGCGGCG AGCCGCAGCC
ATTGCCTTTT ATGGTAATCG TGCGAGAGGG CGCAGGGACT TCCTTTGTCC
CAAATCTGTG CGGAGCCGAA ATCTGGGAGG CGCCGCCGCA CCCCCTCTAG
CGGGCGCGGG GCGAAGCGGT GCGGCGCCGG CAGGAAGGAA ATGGGCGGGG
AGGGCTTCG TGCGTCGCCG CGCCGCCGTC CCCTTCTCCC TCTCCAGCCT
CGGGGCTGTC CGCGGGGGGA CGGCTGCCTT CGGGGGGGAC GGGGCAGGGC
GGGGTTCGGC TTCTGGCGTG TGACCGGCGG CTCTAGAGCC TCTGCTAACC
ATGTTCATGC CTTCTTCTTT TTCCTACAGC TCCTGGGCAA CGTGCTGGTT
ATTGTGCTGT CTCATCATTT TGGCAAAGAA TTGCAAGTTT GTACAAAAAA
GCAGGCTGCC ACCATGCAGC GCGTGAACAT GATTATGGCC GAGTCTCCCG
GCCTGATCAC CATCTGTCTG CTGGGCTATC TGCTGAGCGC CGAGTGCACC
GTGTTTCTGG ATCACGAGAA CGCCAACAAG ATCCTGAACA GACCCAAGCG
GTACAACAGC GGCAAGCTGG AAGAGTTCGT GCAGGGCAAC CTGGAACGCG
AGTGCATGGA AGAGAAGTGC AGCTTCGAAG AGGCCAGAGA GGTGTTCGAG
AACACCGAGA GAACCACCGA GTTCTGGAAG CAGTACGTGG ACGGCGATCA
GTGCGAGAGC AACCCTTGTC TGAATGGCGG CAGCTGCAAG GACGACATCA
ACAGCTACGA GTGCTGGTGC CCCTTCGGCT TCGAGGGCAA GAATTGCGAG
CTGGACGTGA CCTGCAACAT CAAGAACGGC AGATGCGAGC AGTTCTGCAA
GAACAGCGCC GACAACAAGG TCGTGTGCTC CTGCACAGAG GGCTACAGAC
TGGCCGAGAA CCAGAAGTCT TGCGAGCCCG CTGTGCCCTT TCCATGTGGC
AGAGTGTCTG TGTCCCAGAC CAGCAAGCTG ACCAGAGCCG AGACAGTGTT
CCCCGACGTG GACTACGTGA ACAGCACCGA GGCCGAGACA ATCCTGGACA
ACATCACCCA GAGCACCCAG TCCTTCAACG ACTTCACCAG AGTCGTCGGC
GGCGAGGATG CTAAGCCTGG ACAGTTTCCT TGGCAAGTGG TGCTGAACGG
CAAGGTGGAC GCTTTTTGTG GCGGCTCCAT CGTGAACGAG AAGTGGATCG
TGACCGCCGC TCACTGTGTG GAAACCGGCG TGAAGATTAC AGTGGTGGCC
GGCGAGCACA ACATCGAGGA AACAGAGCAC ACCGAGCAGA ACGGAACGT
GATCAGAATC ATCCCTCACC ACAACTACAA CGCCGCCATC AACAAGTACA
ACCACGATAT CGCCCTGCTG GAACTGGACG AGCCCCTGGT CCTGAACTCT
TACGTGACCC CTATCTGTAT CGCCGACAAA GAGTACACCA ACATCTTTCT
GAAGTTCGGC AGCGGCTACG TGTCCGGCTG GGGAAGAGTT TTCCACAAGG
```

FIG. 17EE

|  |  | GCAGATCAGC CCTGGTGCTG CAGTACCTGA GAGTGCCCCT GGTGGATAGA<br>GCCACATGCC TGCTGAGCAC CAAGTTCACC ATCTACAACA ACATGTTCTG<br>CGCCGGCTTC CACGAAGGCG GCAGAGATTC TTGTCAAGGC GATTCTGGCG<br>GCCCTCACGT GACAGAGGTT GAGGGCACAA GCTTTCTGAC CGGCATCATC<br>AGCTGGGGCG AAGAGTGTGC CATGAAGGGG AAGTACGGCA TCTACACCAA<br>GGTGTCCAGA TACGTGAACT GGATCAAAGA AAAGACCAAG CTCACCTGAA<br>ATTCGCGGCC GCTAAACCCA GCTTTCTTGT ACAAAGTGGC AACTTTATTA<br>TACATAGTTG ATCCTCAGGT GCAGGCTGCC TATCAGAAGG TGGTGGCTGG<br>TGTGGCCAAT GCCCTGGCTC ACAAATACCA CTGAGATCTT TTTCCCTCTG<br>CCAAAAATTA TGGGGACATC ATGAAGCCCC TTGAGCATCT GACTTCTGGC<br>TAATAAAGGA AATTTATTTT CATTGCAATA GTGTGTTGGA ATTTTTTGTG<br>TCTCTCACTC GGAAGGACAT ATGGGAGGGC AAATCATTTA AACATCAGA<br>ATGAGTATTT GGTTTAGAGT TTGGCAACAT ATGCCCATAT GCTGGCTGCC<br>ATGAACAAAG GTTGGCTATA AAGAGGTCAT CAGTATATGA AACAGCCCCC<br>TGCTGTCCAT TCCTTATTCC ATAGAAAAGC CTTGACTTGA GGTTAGATTT<br>TTTTTATATT TTGTTTTGTG TTATTTTTTT CTTTAACATC CCTAAAATTT<br>TCCTTACATG TTTTACTAGC CAGATTTTTC CTCCTCTCCT GACTACTCCC<br>AGTCATAGCT GTCCCTCTTC TCTTATGGAG ATC |

Table 8: Additional Amino Acid Sequences

| SEQ ID NO. | Protein Name | Amino Acid Sequence |
|---|---|---|
| 29 | Interleukin-2 | MYRMQLLSCI ALSLALVTNS APTSSSTKKT QLQLEHLLLD LQMILNGINN 50<br>YKNPKLTRML TFKFYMPKKA TELKHLQCLE EELKPLEEVL NLAQSKNFHL 100<br>RPRDLISNIN VIVLELKGSE TTFMCEYADE TATIVEFLNR WITFCQSIIS 150<br>TLT 153 |
| 30 | Parathyroid hormone, Truncated | MIPAKDMAKV MIVMLAICFL TKSDGKSVKK RSVSEIQLMH NLGKHLNSME 50<br>RVEWLRKKLQ DVHNF 65 |
| 31 | Parathyroid hormone | MIPAKDMAKV MIVMLAICFL TKSDGKSVKK RSVSEIQLMH NLGKHLNSME 50<br>RVEWLRKKLQ DVHNFVALGA PLAPRDAGSQ RPRKKEDNVL VESHEKSLGE 100<br>ADKADVNVLT KAKSQ 115 |
| 32 | Von Willebrand Factor, Truncated 1 | MIPARFAGVL LALALILPGT LCSLSCRPP MVKLVCPADN LRAEGLECTK 49<br>TCQNYDLECM SMGCVSGCLC PPGMVRHENR CVALERCPCF HQGKEYAPGE 99<br>TVKIGCNTCV CRDRKWNCTD HVCDATCSTI GMAHYLTFDG LKYLFPGECQ 149<br>YVLVQDYCGS NPGTFRILVG NKGCSHPSVK CKKRVTILVE GGEIELFDGE 199<br>VNVKRPMKDE THFEVVESGR YIILLLGKAL SVVWDRHLSI SVVLKQTYQE 249<br>KVCGLCGNFD GIQNNDLTSS NLQVEEDPVD FGNSWKVSSQ CADTRKVPLD 299<br>SSPATCHNNI MKQTMVDSSC RILTSDVFQD CNKLVDPEPY LDVCIYDTCS 349<br>CESIGDCACF CDTIAAYAHV CAQHGKVVTW RTATLCPQSC EERNLRENGY 399<br>ECEWRYNSCA PACQVTCQHP EPLACPVQCV EGCHAHCPPG KILDELLQTC 449<br>VDPEDCPVCE VAGRRFASGK KVTLNPSDPE HCQICHCDVV NLTCEACQEP 499<br>GGLVVPP 506 |
| 33 | Von Willebrand Factor, Truncated 2 | MIPARFAGVL LALALILPGT LCAEGTRGRS STARCSLFGS DFVNTFDGSM 50<br>YSFAGYCSYL LAGGCQKRSF SIIGDFQNGK RVSLSVYLGE FFDIHLFVNG 100<br>TVTQGDQRVS MPYASKGLYL ETEAGYYKLS GEAYGFVARI DGSGNFQVLL 150<br>SDRYFNKTCG LCGNFNIFAE DDFMTQEGTL TSDPYDFANS WALSSGEQWC 200<br>ERASPPSSSC NISSGEMQKG LWEQCQLLKS TSVFARCHPL VDPEPFVALC 250<br>EKTLCECAGG LECACPALLE YARTCAQEGM VLYGWTDHSA CSPVCPAGME 300 |

FIG. 17FF

| | | | |
|---|---|---|---|
| | | YRQCVSPCAR TCQSLHINEM CQERCVDGCS CPEGQLLDEG LCVESTECPC 350<br>VHSGKRYPPG TSLSRDCNTC ICRNSQWICS NEECPGECLV TGQSHFKSFD 400<br>NRYFTFSGIC QYLLARDCQD HSFSIVIETV QCADDRDAVC TRSVTVRLPG 450<br>LHNSLVKLKH GAGVAMDGQD VQLPLLKGDL RIQHTVTASV RLSYGEDLQM 500<br>DWDGRGRLLV KLSPVYAGKT CGLCGNYNGN QGDDFLTPSG LAEPRVEDFG 550<br>NAWKLHGDCQ DLQKQHSDPC ALNPRMTRFS EEACAVLTSP TFEACHRAVS 600<br>PLPYLRNCRY DVCSCSDGRE CLCGALASYA AACAGRGVRV AWREPGRCEL 650<br>NCPKGQVYLQ CGTPCNLTCR SLSYPDEECN EACLEGCFCP PGLYMDERGD 700<br>CVPKAQCPCY YDGEIFQPED IFSDHHTMCY CEDGFMHCTM SGVPGSLLPD 750<br>AVLSSPLSHR SKRSLSCRPP MVKLVCPADN LRAEGLECTK TCQNYDLECM 800<br>SMGCVSGCLC PPGMVRHENR CVALERCPCF HQGKEYAPGE TVKIGCNTCV 850<br>CRDRKWNCTD HVCDATCSTI GMAHYLTFDG LKYLFPGECQ YVLVQDYCGS 900<br>NPGTFRILVG NKGCSHPSVK CKKRVTILVE GGEIELFDGE VNVKRPMKDE 950<br>THFEVVESGR YIILLLGKAL SVVWDRHLSI SVVLKQTYQE KVCGLCGNFD 1000<br>GIQNNDLTSS NLQVEEDPVD FGNSWKVSSQ CADTRKVPLD SSPATCHNNI 1050<br>MKQTMVDSSC RILTSDVFQD CNKLVDPEPY LDVCIYDTCS CESIGDCACF 1100<br>CDTIAAYAHV CAQHGKVVTW RTATLCPQSC EERNLRENGY ECEWRYNSCA 1150<br>PACQVTCQHP EPLACPVQCV EGCHAHCPPG KILDELLQTC VDPEDCPVCE 1200<br>VAGRRFASGK KVTLNPSDPE HCQICHCDVV NLTCEACQEP GGLVVPP 1247 |
| 34 | Fc | EPKSCDKTHT CPPCPAPELL GGPSVFLFPP KPKDTLMISR TPEVTCVVVD 50<br>VSHEDPEVKF NWYVDGVEVH NAKTKPREEQ YNSTYRVVSV LTVLHQDWLN 100<br>GKEYKCKVSN KALPAPIEKT ISKAKGQPRE PQVYTLPPSR DELTKNQVSL 150<br>TCLVKGFYPS DIAVEWESNG QPENNYKTTP PVLDSDGSFF LYSKLTVDKS 200<br>RWQQGNVFSC SVMHEALHNH YTQKSLSLSP GK 232 |
| 35 | Albumin | DAHKSEVAHR FKDLGEENFK ALVLIAFAQY LQQCPFEDHV KLVNEVTEFA 50<br>KTCVADESAE NCDKSLHTLF GDKLCTVATL RETYGEMADC CAKQEPERNE 100<br>CFLQHKDDNP NLPRLVRPEV DVMCTAFHDN EETFLKKYLY EIARRHPYFY 150<br>APELLFFAKR YKAAFTECCQ AADKAACLLP KLDELRDEGK ASSAKQRLKC 200<br>ASLQKFGERA FKAWAVARLS QRFPKAEFAE VSKLVTDLTK VHTECCHGDL 250<br>LECADDRADL AKYICENQDS ISSKLKECCE KPLLEKSHCI AEVENDEMPA 300<br>DLPSLAADFV ESKDVCKNYA EAKDVFLGMF LYEYARRHPD YSVVLLLRLA 350<br>KTYETTLEKC CAAADPHECY AKVFDEFKPL VEEPQNLIKQ NCELFEQLGE 400<br>YKFQNALLVR YTKKVPQVST PTLVEVSRNL GKVGSKCCKH PEAKRMPCAE 450<br>DYLSVVLNQL CVLHEKTPVS DRVTKCCTES LVNRRPCFSA LEVDETYVPK 500<br>EFNAETFTFH ADICTLSEKE RQIKKQTALV ELVKHKPKAT KEQLKAVMDD 550<br>FAAFVEKCCK ADDKETCFAE EGKKLVAASQ AALGL 585 |
| 36 | FIX-Padua | MQRVNMIMAE SPGLITICLL GYLLSAECTV FLDHENANKI LNRPKRYNSG<br>KLEEFVQGNL ERECMEEKCS FEEAREVFEN TERTTEFWKQ YVDGDQCESN<br>PCLNGGSCKD DINSYECWCP FGFEGKNCEL DVTCNIKNGR CEQFCKNSAD<br>NKVVCSCTEG YRLAENQKSC EPAVFPCGR VSVSQTSKLT RAETVFPDVD<br>YVNSTEAETI LDNITQSTQS FNDFTRVVGG EDAKPGQFPW QVVLNGKVDA<br>FCGGSIVNEK WIVTAAHCVE TGVKITVVAG EHNIEETEHT EQKRNVIRII<br>PHHNYNAAIN KYNHDIALLE LDEPLVLNSY VTPICIADKE YTNIFLKFGS<br>GYVSGWGRVF HKGRSALVLQ YLRVPLVDRA TCLLSTKFTI YNNMFCAGFH<br>EGGRDSCQGD SGGPHVTEVE GTSFLTGIIS WGEECAMKGK YGIYTKVSRY<br>VNWIKEKTKL T |

SEQUENCE LISTING

<160> NUMBER OF SEQ ID NOS: 36

<210> SEQ ID NO 1
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(19)
<223> OTHER INFORMATION: /note="Signal sequence"

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His

-continued

```
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
                355                 360                 365
Leu Thr Asp Ser Glu Met Asp Val Val Arg Phe Asp Asp Asn Ser
        370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                    405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Val Arg Phe Met
                435                 440                 445
Ala Tyr Thr Asp Glu Thr Phe Lys Thr Arg Glu Ala Ile Gln His Glu
                450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                    485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
                530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                    565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
                610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                    645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
                690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                    725                 730                 735
Tyr Tyr Glu Asp Ser Tyr Glu Asp Ile Ser Ala Tyr Leu Leu Ser Lys
                740                 745                 750
```

```
Asn Asn Ala Ile Glu Pro Arg Ser Phe Ser Gln Asn Pro Val Leu
        755                 760                 765

Lys Arg His Gln Arg Glu Ile Thr Arg Thr Thr Leu Gln Ser Asp Gln
        770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
        930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Leu Tyr Asn Leu Tyr Pro Gly Val Phe Glu Thr Val Glu Met
        1100                1105                1110

Leu Pro Ser Lys Ala Gly Ile Trp Arg Val Glu Cys Leu Ile Gly
        1115                1120                1125

Glu His Leu His Ala Gly Met Ser Thr Leu Phe Leu Val Tyr Ser
        1130                1135                1140

Asn Lys Cys Gln Thr Pro Leu Gly Met Ala Ser Gly His Ile Arg
        1145                1150                1155
```

```
Asp Phe Gln Ile Thr Ala Ser Gly Gln Tyr Gly Gln Trp Ala Pro
    1160            1165            1170

Lys Leu Ala Arg Leu His Tyr Ser Gly Ser Ile Asn Ala Trp Ser
    1175            1180            1185

Thr Lys Glu Pro Phe Ser Trp Ile Lys Val Asp Leu Leu Ala Pro
    1190            1195            1200

Met Ile Ile His Gly Ile Lys Thr Gln Gly Ala Arg Gln Lys Phe
    1205            1210            1215

Ser Ser Leu Tyr Ile Ser Gln Phe Ile Ile Met Tyr Ser Leu Asp
    1220            1225            1230

Gly Lys Lys Trp Gln Thr Tyr Arg Gly Asn Ser Thr Gly Thr Leu
    1235            1240            1245

Met Val Phe Phe Gly Asn Val Asp Ser Ser Gly Ile Lys His Asn
    1250            1255            1260

Ile Phe Asn Pro Pro Ile Ile Ala Arg Tyr Ile Arg Leu His Pro
    1265            1270            1275

Thr His Tyr Ser Ile Arg Ser Thr Leu Arg Met Glu Leu Met Gly
    1280            1285            1290

Cys Asp Leu Asn Ser Cys Ser Met Pro Leu Gly Met Glu Ser Lys
    1295            1300            1305

Ala Ile Ser Asp Ala Gln Ile Thr Ala Ser Ser Tyr Phe Thr Asn
    1310            1315            1320

Met Phe Ala Thr Trp Ser Pro Ser Lys Ala Arg Leu His Leu Gln
    1325            1330            1335

Gly Arg Ser Asn Ala Trp Arg Pro Gln Val Asn Asn Pro Lys Glu
    1340            1345            1350

Trp Leu Gln Val Asp Phe Gln Lys Thr Met Lys Val Thr Gly Val
    1355            1360            1365

Thr Thr Gln Gly Val Lys Ser Leu Leu Thr Ser Met Tyr Val Lys
    1370            1375            1380

Glu Phe Leu Ile Ser Ser Ser Gln Asp Gly His Gln Trp Thr Leu
    1385            1390            1395

Phe Phe Gln Asn Gly Lys Val Lys Val Phe Gln Gly Asn Gln Asp
    1400            1405            1410

Ser Phe Thr Pro Val Val Asn Ser Leu Asp Pro Pro Leu Leu Thr
    1415            1420            1425

Arg Tyr Leu Arg Ile His Pro Gln Ser Trp Val His Gln Ile Ala
    1430            1435            1440

Leu Arg Met Glu Val Leu Gly Cys Glu Ala Gln Asp Leu Tyr
    1445            1450            1455

<210> SEQ ID NO 2
<211> LENGTH: 461
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(28)
<223> OTHER INFORMATION: /note="Signal sequence"

<400> SEQUENCE: 2

Met Gln Arg Val Asn Met Ile Met Ala Glu Ser Pro Gly Leu Ile Thr
1               5                   10                  15
```

-continued

```
Ile Cys Leu Leu Gly Tyr Leu Leu Ser Ala Glu Cys Thr Val Phe Leu
            20                  25                  30
Asp His Glu Asn Ala Asn Lys Ile Leu Asn Arg Pro Lys Arg Tyr Asn
        35                  40                  45
Ser Gly Lys Leu Glu Glu Phe Val Gln Gly Asn Leu Glu Arg Glu Cys
    50                  55                  60
Met Glu Glu Lys Cys Ser Phe Glu Glu Ala Arg Glu Val Phe Glu Asn
65                  70                  75                  80
Thr Glu Arg Thr Thr Glu Phe Trp Lys Gln Tyr Val Asp Gly Asp Gln
                85                  90                  95
Cys Glu Ser Asn Pro Cys Leu Asn Gly Gly Ser Cys Lys Asp Asp Ile
            100                 105                 110
Asn Ser Tyr Glu Cys Trp Cys Pro Phe Gly Phe Glu Gly Lys Asn Cys
        115                 120                 125
Glu Leu Asp Val Thr Cys Asn Ile Lys Asn Gly Arg Cys Glu Gln Phe
    130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
    210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
    290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Leu
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
```

```
                435                 440                 445
Arg Tyr Val Asn Trp Ile Lys Glu Lys Thr Lys Leu Thr
    450                 455                 460

<210> SEQ ID NO 3
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(19)
<223> OTHER INFORMATION: /note="Signal sequence"

<400> SEQUENCE: 3

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
```

-continued

```
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Ala Glu Asp Tyr Asp Asp Asp
                355                 360                 365
Leu Thr Asp Ser Glu Met Asp Val Val Arg Phe Asp Asp Asn Ser
370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
                530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
                690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
```

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Val Leu
            755                 760                 765

Lys His His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
            850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
     1010                1015                1020

Cys Arg Ala Pro Cys Asn Ile Gln Met Glu Asp Pro Thr Phe Lys
     1025                1030                1035

Glu Asn Tyr Arg Phe His Ala Ile Asn Gly Tyr Ile Met Asp Thr
     1040                1045                1050

Leu Pro Gly Leu Val Met Ala Gln Asp Gln Arg Ile Arg Trp Tyr
     1055                1060                1065

Leu Leu Ser Met Gly Ser Asn Glu Asn Ile His Ser Ile His Phe
     1070                1075                1080

Ser Gly His Val Phe Thr Val Arg Lys Lys Glu Glu Tyr Lys Met
     1085                1090                1095

Ala Leu Tyr Asn Leu Tyr Pro Gly Val Phe Glu Thr Val Glu Met
     1100                1105                1110

Leu Pro Ser Lys Ala Gly Ile Trp Arg Val Glu Cys Leu Ile Gly
     1115                1120                1125

Glu His Leu His Ala Gly Met Ser Thr Leu Phe Leu Val Tyr Ser
     1130                1135                1140
```

Asn Lys Cys Gln Thr Pro Leu Gly Met Ala Ser Gly His Ile Arg
1145                1150                1155

Asp Phe Gln Ile Thr Ala Ser Gly Gln Tyr Gly Gln Trp Ala Pro
1160                1165                1170

Lys Leu Ala Arg Leu His Tyr Ser Gly Ser Ile Asn Ala Trp Ser
1175                1180                1185

Thr Lys Glu Pro Phe Ser Trp Ile Lys Val Asp Leu Leu Ala Pro
1190                1195                1200

Met Ile Ile His Gly Ile Lys Thr Gln Gly Ala Arg Gln Lys Phe
1205                1210                1215

Ser Ser Leu Tyr Ile Ser Gln Phe Ile Ile Met Tyr Ser Leu Asp
1220                1225                1230

Gly Lys Lys Trp Gln Thr Tyr Arg Gly Asn Ser Thr Gly Thr Leu
1235                1240                1245

Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Leu Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr
1445                1450                1455

<210> SEQ ID NO 4
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(19)
<223> OTHER INFORMATION: /note="Signal sequence"

<400> SEQUENCE: 4

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
                35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
```

-continued

```
                420             425             430
Asn Gly Pro Gln Arg Ile Gly Arg Lys Tyr Lys Lys Val Arg Phe Met
            435             440             445
Ala Tyr Thr Asp Glu Thr Phe Lys Thr Arg Glu Ala Ile Gln His Glu
        450             455             460
Ser Gly Ile Leu Gly Pro Leu Leu Tyr Gly Glu Val Gly Asp Thr Leu
465             470             475             480
Leu Ile Ile Phe Lys Asn Gln Ala Ser Arg Pro Tyr Asn Ile Tyr Pro
                485             490             495
His Gly Ile Thr Asp Val Arg Pro Leu Tyr Ser Arg Arg Leu Pro Lys
            500             505             510
Gly Val Lys His Leu Lys Asp Phe Pro Ile Leu Pro Gly Glu Ile Phe
        515             520             525
Lys Tyr Lys Trp Thr Val Thr Val Glu Asp Gly Pro Thr Lys Ser Asp
530             535             540
Pro Arg Cys Leu Thr Arg Tyr Tyr Ser Ser Phe Val Asn Met Glu Arg
545             550             555             560
Asp Leu Ala Ser Gly Leu Ile Gly Pro Leu Leu Ile Cys Tyr Lys Glu
                565             570             575
Ser Val Asp Gln Arg Gly Asn Gln Ile Met Ser Asp Lys Arg Asn Val
            580             585             590
Ile Leu Phe Ser Val Phe Asp Glu Asn Arg Ser Trp Tyr Leu Thr Glu
        595             600             605
Asn Ile Gln Arg Phe Leu Pro Asn Pro Ala Gly Val Gln Leu Glu Asp
            610             615             620
Pro Glu Phe Gln Ala Ser Asn Ile Met His Ser Ile Asn Gly Tyr Val
625             630             635             640
Phe Asp Ser Leu Gln Leu Ser Val Cys Leu His Glu Val Ala Tyr Trp
                645             650             655
Tyr Ile Leu Ser Ile Gly Ala Gln Thr Asp Phe Leu Ser Val Phe Phe
            660             665             670
Ser Gly Tyr Thr Phe Lys His Lys Met Val Tyr Glu Asp Thr Leu Thr
        675             680             685
Leu Phe Pro Phe Ser Gly Glu Thr Val Phe Met Ser Met Glu Asn Pro
        690             695             700
Gly Leu Trp Ile Leu Gly Cys His Asn Ser Asp Phe Arg Asn Arg Gly
705             710             715             720
Met Thr Ala Leu Leu Lys Val Ser Ser Cys Asp Lys Asn Thr Gly Asp
            725             730             735
Tyr Tyr Glu Asp Ser Tyr Glu Asp Ile Ser Ala Tyr Leu Leu Ser Lys
        740             745             750
Asn Asn Ala Ile Glu Pro Arg Ser Phe Ser Gln Asn Pro Pro Val Leu
            755             760             765
Lys Ala His Gln Ala Glu Ile Thr Arg Thr Thr Leu Gln Ser Asp Gln
        770             775             780
Glu Glu Ile Asp Tyr Asp Asp Thr Ile Ser Val Glu Met Lys Lys Glu
785             790             795             800
Asp Phe Asp Ile Tyr Asp Glu Asp Glu Asn Gln Ser Pro Arg Ser Phe
                805             810             815
Gln Lys Lys Thr Arg His Tyr Phe Ile Ala Ala Val Glu Arg Leu Trp
            820             825             830
Asp Tyr Gly Met Ser Ser Ser Pro His Val Leu Arg Asn Arg Ala Gln
        835             840             845
```

```
Ser Gly Ser Val Pro Gln Phe Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245
```

```
Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455
```

<210> SEQ ID NO 5
<211> LENGTH: 1453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(19)
<223> OTHER INFORMATION: /note="Signal sequence"

<400> SEQUENCE: 5

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110
```

```
His Pro Val Ser Leu His Ala Val Gly Val Ser Tyr Trp Lys Ala Ser
            115                 120                 125
Glu Gly Ala Glu Tyr Asp Asp Gln Thr Ser Gln Arg Glu Lys Glu Asp
        130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
        195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
        275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
        355                 360                 365
Leu Thr Asp Ser Glu Met Asp Val Val Arg Phe Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
```

```
            530                 535                 540
Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Glu Ile Thr Arg Thr Thr Leu Gln Ser Asp Gln Glu Glu Ile Asp
    770                 775                 780

Tyr Asp Asp Thr Ile Ser Val Glu Met Lys Lys Glu Asp Phe Asp Ile
785                 790                 795                 800

Tyr Asp Glu Asp Glu Asn Gln Ser Pro Arg Ser Phe Gln Lys Lys Thr
                805                 810                 815

Arg His Tyr Phe Ile Ala Ala Val Glu Arg Leu Trp Asp Tyr Gly Met
            820                 825                 830

Ser Ser Ser Pro His Val Leu Arg Asn Arg Ala Gln Ser Gly Ser Val
        835                 840                 845

Pro Gln Phe Lys Lys Val Val Phe Gln Glu Phe Thr Asp Gly Ser Phe
    850                 855                 860

Thr Gln Pro Leu Tyr Arg Gly Glu Leu Asn Glu His Leu Gly Leu Leu
865                 870                 875                 880

Gly Pro Tyr Ile Arg Ala Glu Val Glu Asp Asn Ile Met Val Thr Phe
                885                 890                 895

Arg Asn Gln Ala Ser Arg Pro Tyr Ser Phe Tyr Ser Ser Leu Ile Ser
            900                 905                 910

Tyr Glu Glu Asp Gln Arg Gln Gly Ala Glu Pro Arg Lys Asn Phe Val
        915                 920                 925

Lys Pro Asn Glu Thr Lys Thr Tyr Phe Trp Lys Val Gln His His Met
    930                 935                 940

Ala Pro Thr Lys Asp Glu Phe Asp Cys Lys Ala Trp Ala Tyr Phe Ser
945                 950                 955                 960
```

```
Asp Val Asp Leu Glu Lys Asp Val His Ser Gly Leu Ile Gly Pro Leu
            965                 970                 975

Leu Val Cys His Thr Asn Thr Leu Asn Pro Ala His Gly Arg Gln Val
            980                 985                 990

Thr Val Gln Glu Phe Ala Leu Phe Phe Thr Ile Phe Asp Glu Thr Lys
            995                 1000                1005

Ser Trp Tyr Phe Thr Glu Asn Met Glu Arg Asn Cys Arg Ala Pro
        1010                1015                1020

Cys Asn Ile Gln Met Glu Asp Pro Thr Phe Lys Glu Asn Tyr Arg
        1025                1030                1035

Phe His Ala Ile Asn Gly Tyr Ile Met Asp Thr Leu Pro Gly Leu
        1040                1045                1050

Val Met Ala Gln Asp Gln Arg Ile Arg Trp Tyr Leu Leu Ser Met
        1055                1060                1065

Gly Ser Asn Glu Asn Ile His Ser Ile His Phe Ser Gly His Val
        1070                1075                1080

Phe Thr Val Arg Lys Lys Glu Glu Tyr Lys Met Ala Leu Tyr Asn
        1085                1090                1095

Leu Tyr Pro Gly Val Phe Glu Thr Val Glu Met Leu Pro Ser Lys
        1100                1105                1110

Ala Gly Ile Trp Arg Val Glu Cys Leu Ile Gly Glu His Leu His
        1115                1120                1125

Ala Gly Met Ser Thr Leu Phe Leu Val Tyr Ser Asn Lys Cys Gln
        1130                1135                1140

Thr Pro Leu Gly Met Ala Ser Gly His Ile Arg Asp Phe Gln Ile
        1145                1150                1155

Thr Ala Ser Gly Gln Tyr Gly Gln Trp Ala Pro Lys Leu Ala Arg
        1160                1165                1170

Leu His Tyr Ser Gly Ser Ile Asn Ala Trp Ser Thr Lys Glu Pro
        1175                1180                1185

Phe Ser Trp Ile Lys Val Asp Leu Leu Ala Pro Met Ile Ile His
        1190                1195                1200

Gly Ile Lys Thr Gln Gly Ala Arg Gln Lys Phe Ser Ser Leu Tyr
        1205                1210                1215

Ile Ser Gln Phe Ile Ile Met Tyr Ser Leu Asp Gly Lys Lys Trp
        1220                1225                1230

Gln Thr Tyr Arg Gly Asn Ser Thr Gly Thr Leu Met Val Phe Phe
        1235                1240                1245

Gly Asn Val Asp Ser Ser Gly Ile Lys His Asn Ile Phe Asn Pro
        1250                1255                1260

Pro Ile Ile Ala Arg Tyr Ile Arg Leu His Pro Thr His Tyr Ser
        1265                1270                1275

Ile Arg Ser Thr Leu Arg Met Glu Leu Met Gly Cys Asp Leu Asn
        1280                1285                1290

Ser Cys Ser Met Pro Leu Gly Met Glu Ser Lys Ala Ile Ser Asp
        1295                1300                1305

Ala Gln Ile Thr Ala Ser Ser Tyr Phe Thr Asn Met Phe Ala Thr
        1310                1315                1320

Trp Ser Pro Ser Lys Ala Arg Leu His Leu Gln Gly Arg Ser Asn
        1325                1330                1335

Ala Trp Arg Pro Gln Val Asn Asn Pro Lys Glu Trp Leu Gln Val
        1340                1345                1350
```

-continued

```
Asp Phe Gln Lys Thr Met Lys Val Thr Gly Val Thr Thr Gln Gly
    1355                1360                1365

Val Lys Ser Leu Leu Thr Ser Met Tyr Val Lys Glu Phe Leu Ile
    1370                1375                1380

Ser Ser Ser Gln Asp Gly His Gln Trp Thr Leu Phe Phe Gln Asn
    1385                1390                1395

Gly Lys Val Lys Val Phe Gln Gly Asn Gln Asp Ser Phe Thr Pro
    1400                1405                1410

Val Val Asn Ser Leu Asp Pro Pro Leu Leu Thr Arg Tyr Leu Arg
    1415                1420                1425

Ile His Pro Gln Ser Trp Val His Gln Ile Ala Leu Arg Met Glu
    1430                1435                1440

Val Leu Gly Cys Glu Ala Gln Asp Leu Tyr
    1445                1450

<210> SEQ ID NO 6
<211> LENGTH: 1454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(19)
<223> OTHER INFORMATION: /note="Signal sequence"

<400> SEQUENCE: 6

Met Gln Ile Glu Leu Ser Thr Cys Phe Phe Leu Cys Leu Leu Arg Phe
  1               5                  10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
               100                 105                 110

His Pro Val Ser Leu His Ala Val Gly Val Ser Tyr Trp Lys Ala Ser
           115                 120                 125

Glu Gly Ala Glu Tyr Asp Asp Gln Thr Ser Gln Arg Glu Lys Glu Asp
       130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220
```

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
        260                 265                 270

Tyr Trp His Val Ile Gly Met Gly Thr Thr Pro Glu Val His Ser Ile
    275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
```

-continued

```
                    645                 650                 655
Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Pro Pro Val Leu
                755                 760                 765

Lys Arg Glu Ile Thr Arg Thr Thr Leu Gln Ser Asp Gln Glu Glu Ile
            770                 775                 780

Asp Tyr Asp Asp Thr Ile Ser Val Glu Met Lys Lys Glu Asp Phe Asp
785                 790                 795                 800

Ile Tyr Asp Glu Asp Glu Asn Gln Ser Pro Arg Ser Phe Gln Lys Lys
                805                 810                 815

Thr Arg His Tyr Phe Ile Ala Ala Val Glu Arg Leu Trp Asp Tyr Gly
                820                 825                 830

Met Ser Ser Ser Pro His Val Leu Arg Asn Arg Ala Gln Ser Gly Ser
                835                 840                 845

Val Pro Gln Phe Lys Lys Val Val Phe Gln Glu Phe Thr Asp Gly Ser
850                 855                 860

Phe Thr Gln Pro Leu Tyr Arg Gly Glu Leu Asn Glu His Leu Gly Leu
865                 870                 875                 880

Leu Gly Pro Tyr Ile Arg Ala Glu Val Glu Asp Asn Ile Met Val Thr
                885                 890                 895

Phe Arg Asn Gln Ala Ser Arg Pro Tyr Ser Phe Tyr Ser Ser Leu Ile
                900                 905                 910

Ser Tyr Glu Glu Asp Gln Arg Gln Gly Ala Glu Pro Arg Lys Asn Phe
            915                 920                 925

Val Lys Pro Asn Glu Thr Lys Thr Tyr Phe Trp Lys Val Gln His His
            930                 935                 940

Met Ala Pro Thr Lys Asp Glu Phe Asp Cys Lys Ala Trp Ala Tyr Phe
945                 950                 955                 960

Ser Asp Val Asp Leu Glu Lys Asp Val His Ser Gly Leu Ile Gly Pro
                965                 970                 975

Leu Leu Val Cys His Thr Asn Thr Leu Asn Pro Ala His Gly Arg Gln
                980                 985                 990

Val Thr Val Gln Glu Phe Ala Leu Phe Phe Thr Ile Phe Asp Glu Thr
                995                 1000                1005

Lys Ser Trp Tyr Phe Thr Glu Asn Met Glu Arg Asn Cys Arg Ala
            1010                1015                1020

Pro Cys Asn Ile Gln Met Glu Asp Pro Thr Phe Lys Glu Asn Tyr
            1025                1030                1035

Arg Phe His Ala Ile Asn Gly Tyr Ile Met Asp Thr Leu Pro Gly
            1040                1045                1050

Leu Val Met Ala Gln Asp Gln Arg Ile Arg Trp Tyr Leu Leu Ser
            1055                1060                1065
```

```
Met Gly Ser Asn Glu Asn Ile His Ser Ile His Phe Ser Gly His
    1070                1075                1080

Val Phe Thr Val Arg Lys Lys Glu Glu Tyr Lys Met Ala Leu Tyr
    1085                1090                1095

Asn Leu Tyr Pro Gly Val Phe Glu Thr Val Glu Met Leu Pro Ser
    1100                1105                1110

Lys Ala Gly Ile Trp Arg Val Glu Cys Leu Ile Gly Glu His Leu
    1115                1120                1125

His Ala Gly Met Ser Thr Leu Phe Leu Val Tyr Ser Asn Lys Cys
    1130                1135                1140

Gln Thr Pro Leu Gly Met Ala Ser Gly His Ile Arg Asp Phe Gln
    1145                1150                1155

Ile Thr Ala Ser Gly Gln Tyr Gly Gln Trp Ala Pro Lys Leu Ala
    1160                1165                1170

Arg Leu His Tyr Ser Gly Ser Ile Asn Ala Trp Ser Thr Lys Glu
    1175                1180                1185

Pro Phe Ser Trp Ile Lys Val Asp Leu Leu Ala Pro Met Ile Ile
    1190                1195                1200

His Gly Ile Lys Thr Gln Gly Ala Arg Gln Lys Phe Ser Ser Leu
    1205                1210                1215

Tyr Ile Ser Gln Phe Ile Ile Met Tyr Ser Leu Asp Gly Lys Lys
    1220                1225                1230

Trp Gln Thr Tyr Arg Gly Asn Ser Thr Gly Thr Leu Met Val Phe
    1235                1240                1245

Phe Gly Asn Val Asp Ser Ser Gly Ile Lys His Asn Ile Phe Asn
    1250                1255                1260

Pro Pro Ile Ile Ala Arg Tyr Ile Arg Leu His Pro Thr His Tyr
    1265                1270                1275

Ser Ile Arg Ser Thr Leu Arg Met Glu Leu Met Gly Cys Asp Leu
    1280                1285                1290

Asn Ser Cys Ser Met Pro Leu Gly Met Glu Ser Lys Ala Ile Ser
    1295                1300                1305

Asp Ala Gln Ile Thr Ala Ser Ser Tyr Phe Thr Asn Met Phe Ala
    1310                1315                1320

Thr Trp Ser Pro Ser Lys Ala Arg Leu His Leu Gln Gly Arg Ser
    1325                1330                1335

Asn Ala Trp Arg Pro Gln Val Asn Asn Pro Lys Glu Trp Leu Gln
    1340                1345                1350

Val Asp Phe Gln Lys Thr Met Lys Val Thr Gly Val Thr Thr Gln
    1355                1360                1365

Gly Val Lys Ser Leu Leu Thr Ser Met Tyr Val Lys Glu Phe Leu
    1370                1375                1380

Ile Ser Ser Ser Gln Asp Gly His Gln Trp Thr Leu Phe Phe Gln
    1385                1390                1395

Asn Gly Lys Val Lys Val Phe Gln Gly Asn Gln Asp Ser Phe Thr
    1400                1405                1410

Pro Val Val Asn Ser Leu Asp Pro Pro Leu Leu Thr Arg Tyr Leu
    1415                1420                1425

Arg Ile His Pro Gln Ser Trp Val His Gln Ile Ala Leu Arg Met
    1430                1435                1440

Glu Val Leu Gly Cys Glu Ala Gln Asp Leu Tyr
    1445                1450
```

<210> SEQ ID NO 7
<211> LENGTH: 1474
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: SITE
<222> LOCATION: (1)..(19)
<223> OTHER INFORMATION: /note="Signal sequence"

<400> SEQUENCE: 7

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335
```

```
Asp Gly Met Glu Ala Tyr Val Lys Val Asp Ser Cys Pro Glu Pro
            340                 345                 350

Gln Leu Arg Met Lys Asn Asn Glu Glu Ala Glu Asp Tyr Asp Asp
            355                 360                 365

Leu Thr Asp Ser Glu Met Asp Val Val Arg Phe Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ala Thr Asn Val
```

```
                755                 760                 765
Ser Asn Asn Ser Asn Thr Ser Asn Asp Ser Asn Val Ser Pro Val
770                 775                 780

Leu Lys Arg His Gln Arg Glu Ile Thr Arg Thr Thr Leu Gln Ser Asp
785                 790                 795                 800

Gln Glu Glu Ile Asp Tyr Asp Asp Thr Ile Ser Val Glu Met Lys Lys
                805                 810                 815

Glu Asp Phe Asp Ile Tyr Asp Glu Asp Glu Asn Gln Ser Pro Arg Ser
        820                 825                 830

Phe Gln Lys Lys Thr Arg His Tyr Phe Ile Ala Ala Val Glu Arg Leu
835                 840                 845

Trp Asp Tyr Gly Met Ser Ser Pro His Val Leu Arg Asn Arg Ala
850                 855                 860

Gln Ser Gly Ser Val Pro Gln Phe Lys Lys Val Val Phe Gln Glu Phe
865                 870                 875                 880

Thr Asp Gly Ser Phe Thr Gln Pro Leu Tyr Arg Gly Glu Leu Asn Glu
                885                 890                 895

His Leu Gly Leu Leu Gly Pro Tyr Ile Arg Ala Glu Val Glu Asp Asn
            900                 905                 910

Ile Met Val Thr Phe Arg Asn Gln Ala Ser Arg Pro Tyr Ser Phe Tyr
        915                 920                 925

Ser Ser Leu Ile Ser Tyr Glu Glu Asp Gln Arg Gln Gly Ala Glu Pro
930                 935                 940

Arg Lys Asn Phe Val Lys Pro Asn Glu Thr Lys Thr Tyr Phe Trp Lys
945                 950                 955                 960

Val Gln His His Met Ala Pro Thr Lys Asp Glu Phe Asp Cys Lys Ala
                965                 970                 975

Trp Ala Tyr Phe Ser Asp Val Asp Leu Glu Lys Asp Val His Ser Gly
            980                 985                 990

Leu Ile Gly Pro Leu Leu Val Cys His Thr Asn Thr Leu Asn Pro Ala
        995                 1000                1005

His Gly Arg Gln Val Thr Val Gln Glu Phe Ala Leu Phe Phe Thr
    1010                1015                1020

Ile Phe Asp Glu Thr Lys Ser Trp Tyr Phe Thr Glu Asn Met Glu
    1025                1030                1035

Arg Asn Cys Arg Ala Pro Cys Asn Ile Gln Met Glu Asp Pro Thr
    1040                1045                1050

Phe Lys Glu Asn Tyr Arg Phe His Ala Ile Asn Gly Tyr Ile Met
    1055                1060                1065

Asp Thr Leu Pro Gly Leu Val Met Ala Gln Asp Gln Arg Ile Arg
    1070                1075                1080

Trp Tyr Leu Leu Ser Met Gly Ser Asn Glu Asn Ile His Ser Ile
    1085                1090                1095

His Phe Ser Gly His Val Phe Thr Val Arg Lys Lys Glu Glu Tyr
    1100                1105                1110

Lys Met Ala Leu Tyr Asn Leu Tyr Pro Gly Val Phe Glu Thr Val
    1115                1120                1125

Glu Met Leu Pro Ser Lys Ala Gly Ile Trp Arg Val Glu Cys Leu
    1130                1135                1140

Ile Gly Glu His Leu His Ala Gly Met Ser Thr Leu Phe Leu Val
    1145                1150                1155

Tyr Ser Asn Lys Cys Gln Thr Pro Leu Gly Met Ala Ser Gly His
    1160                1165                1170
```

Ile Arg Asp Phe Gln Ile Thr Ala Ser Gly Gln Tyr Gly Gln Trp
    1175              1180                1185

Ala Pro Lys Leu Ala Arg Leu His Tyr Ser Gly Ser Ile Asn Ala
    1190              1195                1200

Trp Ser Thr Lys Glu Pro Phe Ser Trp Ile Lys Val Asp Leu Leu
    1205              1210                1215

Ala Pro Met Ile Ile His Gly Ile Lys Thr Gln Gly Ala Arg Gln
    1220              1225                1230

Lys Phe Ser Ser Leu Tyr Ile Ser Gln Phe Ile Ile Met Tyr Ser
    1235              1240                1245

Leu Asp Gly Lys Lys Trp Gln Thr Tyr Arg Gly Asn Ser Thr Gly
    1250              1255                1260

Thr Leu Met Val Phe Phe Gly Asn Val Asp Ser Ser Gly Ile Lys
    1265              1270                1275

His Asn Ile Phe Asn Pro Pro Ile Ile Ala Arg Tyr Ile Arg Leu
    1280              1285                1290

His Pro Thr His Tyr Ser Ile Arg Ser Thr Leu Arg Met Glu Leu
    1295              1300                1305

Met Gly Cys Asp Leu Asn Ser Cys Ser Met Pro Leu Gly Met Glu
    1310              1315                1320

Ser Lys Ala Ile Ser Asp Ala Gln Ile Thr Ala Ser Ser Tyr Phe
    1325              1330                1335

Thr Asn Met Phe Ala Thr Trp Ser Pro Ser Lys Ala Arg Leu His
    1340              1345                1350

Leu Gln Gly Arg Ser Asn Ala Trp Arg Pro Gln Val Asn Asn Pro
    1355              1360                1365

Lys Glu Trp Leu Gln Val Asp Phe Gln Lys Thr Met Lys Val Thr
    1370              1375                1380

Gly Val Thr Thr Gln Gly Val Lys Ser Leu Leu Thr Ser Met Tyr
    1385              1390                1395

Val Lys Glu Phe Leu Ile Ser Ser Ser Gln Asp Gly His Gln Trp
    1400              1405                1410

Thr Leu Phe Phe Gln Asn Gly Lys Val Lys Val Phe Gln Gly Asn
    1415              1420                1425

Gln Asp Ser Phe Thr Pro Val Val Asn Ser Leu Asp Pro Pro Leu
    1430              1435                1440

Leu Thr Arg Tyr Leu Arg Ile His Pro Gln Ser Trp Val His Gln
    1445              1450                1455

Ile Ala Leu Arg Met Glu Val Leu Gly Cys Glu Ala Gln Asp Leu
    1460              1465                1470

Tyr

<210> SEQ ID NO 8
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
atgcaaatag agctctccac ctgcttcttt ctgtgccttt tgcgattctg ctttagtgcc      60
accagaagat actacctggg tgcagtggaa ctgtcatggg actatatgca aagtgatctc     120

```
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgt tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggataggggat   720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccta caaacacaaaa  2040
atggtctatg aagacacact caccctattc ccattctcag agaaactgt cttcatgtcg    2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
```

-continued

```
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat ggacccctt    2940 ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct caagggagg    4020 agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctctttttt    4200
cagaatggca aagtaaaggt ttttcaggga aatcaagact ccttcacacc tgtggtgaac    4260
tctctagacc caccgttact gactcgctac cttcgaattc accccagag ttgggtgcac    4320 cagattgccc tgaggatgga ggttctgggc tgcgaggcac aggacctcta ctga          4374
```

<210> SEQ ID NO 9
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
```

```
ggtgagctgc ctgtggacgc aagatttcct cctagagtgc aaaatctttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgt tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aataatgaa    1080 gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa agtcaatat ttgaacaatg gccctcagcg gattggtagg    1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg atatacctt caaacacaaa    2040 atggtctatg aagacacact cacccctattc ccattctcag agaaactgt cttcatgtcg   2100 atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga ccaagaagc    2280 ttctcccaaa acccaccagt cttgaaacac catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
```

```
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc taatgaaaac caaaacttac    2820 tttttggaaag tgcaacatca tatggcaccc actaaagatg agtttgactg caaagcctgg    2880
gcttatttct ctgatgttga cctggaaaaa gatgtgcact caggcctgat ggaccccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactcccctg gaatggcctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctctttttt    4200
cagaatggca aagtaaaggt tttttcaggga aatcaagact ccttcacacc tgtggtgaac    4260
tctctagacc caccgttact gactcgctac cttcgaattc accccccagag ttgggtgcac    4320 cagattgccc tgaggatgga ggttctgggc tgcgaggcac aggacctcta ctga    4374
```

<210> SEQ ID NO 10
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 10

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
```

```
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgt tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa    1020
gcttatgtca agtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgaccccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg atataccttt caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaaa acccaccagt cttgaaagcc catcaagcgg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
```

```
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820 tttttggaaag tgcaacatca tatggcaccc actaaagatg agtttgactg caaagcctgg    2880
gcttatttct ctgatgttga cctggaaaaa gatgtgcact caggcctgat ggaccccctt    2940
ctggtctgcc acactaacac actgaaccct gctcatggga acaagtgac agtacaggaa     3000 tttgctctgt ttttcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg gaagaagtg gcagacttat    3720 cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctcttttt    4200 cagaatggca aagtaaaggt ttttcaggga aatcaagact ccttcacacc tgtggtgaac    4260
tctctagacc caccgttact gactcgctac cttcgaattc acccccagag ttgggtgcac    4320
cagattgccc tgaggatgga ggttctgggc tgcgaggcac aggacctcta ctga          4374
```

<210> SEQ ID NO 11
<211> LENGTH: 4362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

```
atgcaaatag agctctccac ctgcttcttt ctgtgccttt tgcgattctg ctttagtgcc      60
accagaagat actacctggg tgcagtggaa ctgtcatggg actatatgca aagtgatctc    120
```

-continued

```
ggtgagctgc ctgtggacgc aagatttcct cctagagtgc caaaatctttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgt tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa agtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacatttt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg atataccttt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga ccaagaagc   2280
ttctcccaaa acccaccagt cttgaaagaa ataactcgta ctactcttca gtcagatcaa   2340
gaggaaattg actatgatga taccatatca gttgaaatga gaaggaaga ttttgacatt   2400
tatgatgagg atgaaaatca gagccccgc agctttcaaa agaaaacacg acactatttt   2460
attgctgcag tggagaggct ctgggattat gggatgagta gctccccaca tgttctaaga   2520
```

```
aacagggctc agagtggcag tgtccctcag ttcaagaaag ttgttttcca ggaatttact   2580
gatggctcct ttactcagcc cttataccgt ggagaactaa atgaacattt gggactcctg   2640
gggccatata taagagcaga agttgaagat aatatcatgg taactttcag aaatcaggcc   2700
tctcgtccct attccttcta ttctagcctt atttcttatg aggaagatca gaggcaagga   2760
gcagaaccta gaaaaaactt tgtcaagcct aatgaaacca aaacttactt ttggaaagtg   2820
caacatcata tggcacccac taaagatgag tttgactgca aagcctgggc ttatttctct   2880
gatgttgacc tggaaaaaga tgtgcactca ggcctgattg accccttct ggtctgccac    2940 actaacacac tgaaccctgc tcatgggaga caagtgacag tacaggaatt tgctctgttt   3000
ttcaccatct tgatgagac caaaagctgg tacttcactg aaaatatgga agaaactgc     3060 agggctccct gcaatatcca gatggaagat cccactttta aagagaatta tcgcttccat   3120
gcaatcaatg ctacataat ggatacacta cctggcttag taatggctca ggatcaaagg   3180
attcgatggt atctgctcag catgggcagc aatgaaaaca tccattctat tcatttcagt   3240
ggacatgtgt tcactgtacg aaaaaaagag gagtataaaa tggcactgta caatctctat   3300
ccaggtgttt ttgagacagt ggaaatgtta ccatccaaag ctggaatttg gcgggtggaa   3360
tgccttattg gcgagcatct acatgctggg atgagcacac ttttctggt gtacagcaat    3420 aagtgtcaga ctccccctggg aatggcttct ggacacatta gagattttca gattacagct   3480
tcaggacaat atggacagtg ggccccaaag ctggccagac ttcattattc cggatcaatc   3540
aatgcctgga gcaccaagga gccctttttct tggatcaagg tggatctgtt ggcaccaatg  3600
attattcacg gcatcaagac ccagggtgcc cgtcagaagt tctccagcct ctacatctct   3660
cagtttatca tcatgtatag tcttgatggg aagaagtggc agacttatcg aggaaattcc   3720
actggaacct taatggtctt cttttggcaat gtggattcat ctgggataaa acacaatatt   3780
tttaaccctc caattattgc tcgatacatc cgtttgcacc caactcatta tagcattcgc   3840
agcactcttc gcatggagtt gatgggctgt gatttaaata gttgcagcat gccattggga   3900
atggagagta aagcaatatc agatgcacag attactgctt catcctactt taccaatatg   3960
tttgccacct ggtctccttc aaaagctcga cttcacctcc aagggaggag taatgcctgg   4020
agacctcagg tgaataatcc aaaagagtgg ctgcaagtgg acttccagaa gacaatgaaa   4080
gtcacaggag taactactca gggagtaaaa tctctgctta ccagcatgta tgtgaaggag   4140
ttcctcatct ccagcagtca agatggccat cagtggactc tctttttca gaatggcaaa    4200 gtaaaggttt tcagggaaa tcaagactcc ttcacacctg tggtgaactc tctagaccca    4260
ccgttactga ctcgctacct tcgaattcac ccccagagtt gggtgcacca gattgccctg   4320
aggatggagg ttctgggctg cgaggcacag gacctctact ga                      4362
```

<210> SEQ ID NO 12
<211> LENGTH: 4365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
```

```
ggtgagctgc ctgtggacgc aagatttcct cctagagtgc caaaatcttt tccattcaac      180
acctcagtcg tgtacaaaaa gactctgttt gtagaattca cggatcacct tttcaacatc      240
gctaagccaa ggccaccctg gatgggtctg ctaggtccta ccatccaggc tgaggtttat      300
gatacagtgt tcattacact taagaacatg gcttcccatc ctgtcagtct tcatgctgtt      360
ggtgtatcct actggaaagc ttctgaggga gctgaatatg atgatcagac cagtcaaagg      420
gagaaagaag atgataaagt cttccctggt ggaagccata catatgtctg gcaggtcctg      480
aaagagaatg gtccaatggc ctctgaccca ctgtgcctta cctactcata tctttctcat      540
gtggacctgg taaaagactt gaattcaggc ctcattggag ccctactagt atgtagagaa      600
gggagtctgg ccaaggaaaa gacacagacc ttgcacaaat ttatactact ttttgctgta      660
tttgatgaag ggaaaagttg gcactcagaa acaaagaact ccttgatgca ggatagggat      720
gctgcatctg ctcgggcctg gcctaaaatg cacacagtca atggttatgt aaacaggtct      780
ctgccaggtc tgattggatg ccacaggaaa tcagtctatt ggcatgtgat tggaatgggc      840
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca agtagacag ctgtccagag gaaccccaac tacgaatgaa aaataatgaa      1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctccctt agtcctcgcc     1260
cccgatgaca gaagttataa aagtcaatat ttgaacaatg gccctcagcg gattggtagg     1320
aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg gatataccct caaacacaaa     2040
atggtctatg aagacacact caccctattc ccattctcag agaaactgt cttcatgtcg      2100 atggaaaacc caggtctatg gattctgggg tgccacaact cagactttcg gaacagaggc     2160
atgaccgcct tactgaaggt ttctagttgt gacaagaaca ctggtgatta ttacgaggac     2220
agttatgaag atatttcagc atacttgctg agtaaaaaca atgccattga accaagaagc     2280
ttctcccaaa acccaccagt cttgaaacgc gaaataactc gtactactct tcagtcagat     2340
caagaggaaa ttgactatga tgataccata tcagttgaaa tgaagaagga agattttgac     2400
atttatgatg aggatgaaaa tcagagcccc cgcagctttc aaaagaaaac acgacactat     2460
tttattgctg cagtggagag gctctgggat tatgggatga gtagctcccc acatgttcta     2520
```

```
agaaacaggg ctcagagtgg cagtgtccct cagttcaaga aagttgtttt ccaggaattt    2580
actgatggct cctttactca gcccttatac cgtggagaac taaatgaaca tttgggactc    2640
ctggggccat atataagagc agaagttgaa gataatatca tggtaacttt cagaaatcag    2700
gcctctcgtc cctattcctt ctattctagc cttatttctt atgaggaaga tcagaggcaa    2760
ggagcagaac ctagaaaaaa ctttgtcaag cctaatgaaa ccaaaactta cttttggaaa    2820
gtgcaacatc atatggcacc cactaaagat gagtttgact gcaaagcctg gcttatttc     2880 tctgatgttg acctggaaaa agatgtgcac tcaggcctga ttggaccct tctggtctgc     2940 cacactaaca cactgaaccc tgctcatggg agacaagtga cagtacagga atttgctctg    3000
tttttcacca tctttgatga gaccaaaagc tggtacttca ctgaaaatat ggaaagaaac    3060
tgcagggctc cctgcaatat ccagatggaa gatcccactt ttaaagagaa ttatcgcttc    3120
catgcaatca atggctacat aatggataca ctacctggct tagtaatggc tcaggatcaa    3180
aggattcgat ggtatctgct cagcatgggc agcaatgaaa acatccattc tattcatttc    3240
agtggacatg tgttcactgt acgaaaaaaa gaggagtata aaatggcact gtacaatctc    3300
tatccaggtt tttttgagac agtggaaatg ttaccatcca aagctggaat ttggcgggtg    3360
gaatgcctta ttggcgagca tctacatgct gggatgagca cacttttctt ggtgtacagc    3420
aataagtgtc agactcccct gggaatggct tctggacaca ttagagattt tcagattaca    3480
gcttcaggac aatatggaca gtgggcccca aagctggcca gacttcatta ttccggatca    3540
atcaatgcct ggagcaccaa ggagcccttt tcttggatca aggtggatct gttggcacca    3600
atgattattc acggcatcaa gacccagggt gcccgtcaga agttctccag cctctacatc    3660
tctcagttta tcatcatgta tagtcttgat gggaagaagt ggcagactta tcgaggaaat    3720
tccactggaa ccttaatggt cttctttggc aatgtggatt catctgggat aaaacacaat    3780
atttttaacc ctccaattat tgctcgatac atccgtttgc acccaactca ttatagcatt    3840
cgcagcactc ttcgcatgga gttgatgggc tgtgatttaa atagttgcag catgccattg    3900
ggaatggaga gtaaagcaat atcagatgca cagattactg cttcatccta ctttaccaat    3960
atgtttgcca cctggtctcc ttcaaaagct cgacttcacc tccaagggag gagtaatgcc    4020
tggagacctc aggtgaataa tccaaaagag tggctgcaag tggacttcca gaagacaatg    4080
aaagtcacag gagtaactac tcagggagta aaatctctgc ttaccagcat gtatgtgaag    4140
gagttcctca tctccagcag tcaagatggc catcagtgga ctctctttt tcagaatggc    4200 aaagtaaagg ttttttcaggg aaatcaagac tccttcacac ctgtggtgaa ctctctagac    4260
ccaccgttac tgactcgcta ccttcgaatt cacccccaga gttgggtgca ccagattgcc    4320
ctgaggatgg aggttctggg ctgcgaggca caggacctct actga                    4365
```

<210> SEQ ID NO 13
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

```
atgcagatcg agctgtctac ctgcttcttc ctgtgcctgc tgcggttctg cttcagcgcc      60
accagaagat attacctggg cgccgtggaa ctgagctggg actacatgca gtctgacctg     120
```

-continued

| | |
|---|---|
| ggagagctgc ccgtggacgc tagatttcct ccaagagtgc ccaagagctt ccccttcaac | 180 |
| acctccgtgg tgtacaagaa aaccctgttc gtggaattca ccgaccacct gttcaatatc | 240 |
| gccaagcctc ggcctccttg gatgggactg ctgggaccta caattcaggc cgaggtgtac | 300 |
| gacaccgtgt tcatcaccct gaagaacatg gccagccatc ctgtgtctct gcacgccgtg | 360 |
| ggagtgtctt actggaaggc ttctgagggc gccgagtacg acgatcagac aagccagaga | 420 |
| gagaaagagg acgacaaggt tttccctggc ggcagccaca cctatgtctg gcaggtcctg | 480 |
| aaagaaaacg gccctatggc ctccgatcct ctgtgcctga catacagcta cctgagccac | 540 |
| gtggacctgg tcaaggacct gaattctggc ctgatcggag ccctgctcgt gtgtagagaa | 600 |
| ggcagcctgg ccaaagagaa aacccagaca ctgcacaagt tcatcctgct gttcgccgtg | 660 |
| ttcgacgagg gcaagagctg gcacagcgag acaaagaaca gcctgatgca ggacagggat | 720 |
| gccgcctctg ctagagcttg gcctaagatg cacaccgtga acggctacgt gaacagaagc | 780 |
| ctgcctggac tgatcggctg ccacagaaag tccgtgtact ggcacgtgat cggcatgggc | 840 |
| acaacacctg aggtgcacag catctttctg gaaggacaca ccttcctcgt gcggaaccat | 900 |
| agacaggcca gcctggaaat cagccctatc accttcctga ccgctcagac cctgctgatg | 960 |
| gatctgggcc agtttctgct gttctgccac atcagctccc accagcacga tggcatggaa | 1020 |
| gcctacgtga aggtggacag ctgccccgaa gaacccagcc tgcggatgaa gaacaacgag | 1080 |
| gaagccgagg actacgacga cgacctgacc gactctgaga tggacgtcgt cagattcgac | 1140 |
| gacgataaca gccccagctt catccagatc agaagcgtgg ccaagaagca ccccaagacc | 1200 |
| tgggtgcact atatcgccgc cgaggaagag gactgggatt acgctcctct ggtgctggcc | 1260 |
| cctgacgaca gaagctacaa gagccagtac ctgaacaacg ccctcagcg atcggccgg | 1320 |
| aagtataaga aagtgcggtt catggcctac accgacgaga cattcaagac cagagaggcc | 1380 |
| atccagcacg agagcggaat tctgggccct ctgctgtatg gcgaagtggg cgatacactg | 1440 |
| ctgatcatct tcaagaacca ggccagcaga ccctacaaca tctaccctca cggcatcacc | 1500 |
| gatgtgcggc ccctgtattc tagaaggctg cccaagggcg tgaagcacct gaaggacttc | 1560 |
| cctatcctgc ctggcgagat cttcaagtac aagtggaccg tgaccgtgga agatggcccc | 1620 |
| accaagagcg accctagatg tctgacacgg tactacagca gcttcgtgaa catggaacgc | 1680 |
| gacctggcca gcggcctgat tggacctctg ctgatctgct acaaagaaag cgtggaccag | 1740 |
| cggggcaacc agatcatgag cgacaagcgg aacgtgatcc tgtttagcgt gttcgatgag | 1800 |
| aaccggtcct ggtatctgac cgagaacatc cagcggtttc tgcccaatcc tgctggcgtg | 1860 |
| cagctggaag atcctgagtt ccaggcctcc aacatcatgc actccatcaa tggctatgtg | 1920 |
| ttcgacagcc tgcagctgag cgtgtgcctg cacgaagtgg cctactggta catcctgagc | 1980 |
| attggcgccc agaccgactt cctgtccgtg ttctttagcg gctacacctt caagcacaag | 2040 |
| atggtgtacg aggataccct gacactgttc ccattcagcg gcgagacagt gttcatgagc | 2100 |
| atggaaaacc ccggcctgtg gatcctgggc tgtcacaaca gcgacttccg gaacagaggc | 2160 |
| atgacagccc tgctgaaggt gtccagctgc gacaagaaca ccggcgacta ctacgaggac | 2220 |
| agctatgagg acatcagcgc ctacctgctg agcaagaaca tgccatcga gcctcggagc | 2280 |
| ttcagccaga tcctcctgt gctgaagcgg caccagcgcg agatcaccag aacaaccctg | 2340 |
| cagagcgacc aagaggaaat cgattacgac gacaccatca gcgtcgagat gaagaaagaa | 2400 |
| gatttcgaca tctacgacga ggacgagaat cagagcccca aagctttca gaaaaagacc | 2460 |
| cggcactact tcattgccgc cgtcgagaga ctgtgggact acggcatgtc tagcagccct | 2520 |

```
cacgtgctga gaaatagagc ccagagcggc agcgtgcccc agttcaagaa agtggtgttc      2580
caagagttca ccgacggcag cttcacccag ccactgtata gaggcgagct gaacgagcat      2640
ctgggcctgc tgggccctta tatcagagcc gaagtggaag ataacatcat ggtcaccttc      2700
cggaatcagg cctctcggcc ctacagcttc tacagctccc tgatcagcta cgaagaggac      2760
cagagacagg gcgctgagcc cagaaagaac ttcgtgaagc ccaacgagac taagacctac      2820 tttggaagg tgcagcacca catggcccct acaaaggacg agttcgactg caaggcctgg      2880
gcctactttt ccgatgtgga tctggaaaag gacgtgcaca gcgggctcat cggaccactg      2940
cttgtgtgcc acaccaacac actgaacccc gctcacggca gacaagtgac agtgcaagag      3000
ttcgccctgt tcttcaccat cttcgacgaa acaaagagct ggtacttcac cgagaatatg      3060
gaacggaact gcagagcccc ttgcaacatc cagatgaag atcccacctt caaagagaac      3120
taccggttcc acgccatcaa cggctacatc atggacacac tgcccggcct ggttatggct      3180
caggatcaga gaatccggtg gtatctgctg tccatgggct ccaacgagaa tatccacagc      3240
atccacttca gcggccacgt gttcaccgtg cggaaaaaag aagagtacaa aatggccctg      3300
tacaatctgt accctggggt gttcgaaacc gtggaaatgc tgccttccaa ggccggcatt      3360
tggagagtgg aatgtctgat tggagagcac ctccacgccg gaatgagcac cctgtttctg      3420
gtgtacagca caagtgtca gacccctctc ggcatggcct ctggacacat cagagacttc      3480
cagatcaccg cctctggcca gtacggacag tgggctccta aactggctcg gctgcactac      3540
agcggcagca tcaatgcctg gtccaccaaa gagcccttca gctggatcaa ggtgaccctg      3600
ctggctccca tgatcatcca cggaatcaag acccagggcg ccagacagaa gttcagcagc      3660
ctgtacatca gccagttcat catcatgtac agcctggacg gcaagaagtg gcagacctac      3720
agaggcaaca gcaccggcac actcatggtg ttcttcggca acgtggactc cagcggcatt      3780
aagcacaaca tcttcaaccc tccaatcatt gcccggtaca tccggctgca ccccacacac      3840
tacagcatcc ggtctaccct gagaatggaa ctgatgggct gcgacctgaa cagctgcagc      3900
atgcccctcg gaatggaaag caaggccatc agcgacgccc agatcacagc cagcagctac      3960
ttcaccaaca tgttcgccac ttggagcccc tccaaggcta gactgcatct gcagggcaga      4020
agcaacgctt ggaggcccca agtgaacaac cccaaagagt ggctgcaggt cgactttcaa      4080
aagaccatga aagtgaccgg cgtgaccaca cagggcgtca agtctctgct gacctctatg      4140
tacgtgaaag agttcctgat ctccagcagc caggacggcc atcagtggac cctgttttc      4200 cagaacggca aagtgaaagt gttccaggc aatcaggaca gcttcacacc cgtggtcaac      4260
tccctggatc ctccactgct gaccagatac ctgcggattc accctcagtc ttgggtgcac      4320
cagatcgctc tgcggatgga agtgctgggc tgtgaagctc aggacctcta ctga            4374
```

<210> SEQ ID NO 14
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
atgcagatcg agctgagcac ctgcttcttc ctgtgcctgc tgcgcttctg cttcagcgcc        60
acccgccgct actacctggg cgccgtggag ctgagctggg actacatgca gagcgacctg       120
```

-continued

| | |
|---|---|
| ggcgagctgc cgtggacgc cgcttcccc cccgcgtgc ccaagagctt cccttcaac | 180 |
| accagcgtgg tgtacaagaa gaccctgttc gtggagttca ccgaccacct gttcaacatc | 240 |
| gccaagcccc gccccctg gatgggcctg ctgggcccca ccatccaggc cgaggtgtac | 300 |
| gacaccgtgg tgatcaccct gaagaacatg gccagccacc ccgtgagcct gcacgccgtg | 360 |
| ggcgtgagct actggaaggc cagcgagggc gccgagtacg acgaccagac cagccagcgc | 420 |
| gagaaggagg acgacaaggt gttccccggc ggcagccaca cctacgtgtg gcaggtgctg | 480 |
| aaggagaacg gccccatggc cagcgacccc ctgtgcctga cctacagcta cctgagccac | 540 |
| gtggacctgg tgaaggacct gaacagcggc ctgatcggcg ccctgctggt gtgccgcgag | 600 |
| ggcagcctgg ccaaggagaa gacccagacc ctgcacaagt tcatcctgct gttcgccgtg | 660 |
| ttcgacgagg gcaagagctg gcacagcgag accaagaaca gcctgatgca ggaccgcgac | 720 |
| gccgccagcg cccgcgcctg gcccaagatg cacaccgtga acggctacgt gaaccgcagc | 780 |
| ctgcccggcc tgatcggctg ccaccgcaag agcgtgtact ggcacgtgat cggcatgggc | 840 |
| accacccccg aggtgcacag catcttcctg gagggccaca ccttcctggt gcgcaaccac | 900 |
| cgccaggcca gcctggagat cagccccatc accttcctga ccgcccagac cctgctgatg | 960 |
| gacctgggcc agttcctgct gttctgccac atcagcagcc accagcacga cggcatggag | 1020 |
| gcctacgtga aggtggacag ctgccccgag gagccccagc tgcgcatgaa gaacaacgag | 1080 |
| gaggccgagg actacgacga cgacctgacc gacagcgaga tggacgtggt gcgcttcgac | 1140 |
| gacgacaaca gccccagctt catccagatc cgcagcgtgg ccaagaagca ccccaagacc | 1200 |
| tgggtgcact acatcgccgc cgaggaggag gactgggact acgcccccct ggtgctggcc | 1260 |
| cccgacgacc gcagctacaa gagccagtac ctgaacaacg gccccagcg catcggccgc | 1320 |
| aagtacaaga aggtgcgctt catggcctac accgacgaga ccttcaagac ccgcgaggcc | 1380 |
| atccagcacg agagcggcat cctgggcccc ctgctgtacg gcgaggtggg cgacaccctg | 1440 |
| ctgatcatct tcaagaacca ggccagccgc ccctacaaca tctacccca cggcatcacc | 1500 |
| gacgtgcgcc ccctgtacag ccgccgcctg cccaagggcg tgaagcacct gaaggacttc | 1560 |
| cccatcctgc ccggcgagat cttcaagtac aagtggaccg tgaccgtgga ggacggcccc | 1620 |
| accaagagcg acccccgctg cctgacccgc tactacagca gcttcgtgaa catggagcgc | 1680 |
| gacctggcca gcgcctgat cggccccctg ctgatctgct acaaggagag cgtggaccag | 1740 |
| cgcggcaacc agatcatgag cgacaagcgc aacgtgatcc tgttcagcgt gttcgacgag | 1800 |
| aaccgcagct ggtacctgac cgagaacatc agcgcttcc tgcccaaccc cgccggcgtg | 1860 |
| cagctggagg accccgagtt ccaggccagc aacatcatgc acagcatcaa cggctacgtg | 1920 |
| ttcgacagcc tgcagctgag cgtgtgcctg cacgaggtgg cctactggta catcctgagc | 1980 |
| atcggcgccc agaccgactt cctgagcgtg ttcttcagcg gctacacctt caagcacaag | 2040 |
| atggtgtacg aggacaccct gaccctgttc cccttcagcg gcgagaccgt gttcatgagc | 2100 |
| atggagaacc ccgcctgtg gatcctgggc tgccacaaca gcgacttccg caaccgcggc | 2160 |
| atgaccgccc tgctgaaggt gagcagctgc gacaagaaca ccggcgacta ctacgaggac | 2220 |
| agctacgagg acatcagcgc ctacctgctg agcaagaaca acgccatcga gccccgcagc | 2280 |
| ttcagccaga acccccccgt gctgaagcgc caccagcgcg agatcacccg caccaccctg | 2340 |
| cagagcgacc aggaggagat cgactacgac gacaccatca gcgtggagat gaagaaggag | 2400 |
| gacttcgaca tctacgacga ggacgagaac cagagccccc gcagcttcca gaagaagacc | 2460 |
| cgccactact tcatcgccgc cgtggagcgc ctgtgggact acggcatgag cagcagcccc | 2520 |

```
cacgtgctgc gcaaccgcgc ccagagcggc agcgtgcccc agttcaagaa ggtggtgttc      2580
caggagttca ccgacggcag cttcacccag cccctgtacc gcggcgagct gaacgagcac      2640
ctgggcctgc tgggcccta catccgcgcc gaggtggagg acaacatcat ggtgaccttc       2700
cgcaaccagg ccagccgccc ctacagcttc tacagcagcc tgatcagcta cgaggaggac      2760
cagcgccagg gcgccgagcc ccgcaagaac ttcgtgaagc ccaacgagac caagacctac      2820
ttctggaagg tgcagcacca catggccccc accaaggacg agttcgactg caaggcctgg      2880
gcctacttca gcgacgtgga cctggagaag gacgtgcaca gcggcctgat cggcccctg      2940 ctggtgtgcc acaccaacac cctgaacccc gcccacggcc gccaggtgac cgtgcaggag      3000
ttcgccctgt tcttcaccat cttcgacgag accaagagct ggtacttcac cgagaacatg      3060
gagcgcaact gccgcgcccc ctgcaacatc cagatggagg accccacctt caaggagaac      3120
taccgcttcc acgccatcaa cggctacatc atggacaccc tgcccggcct ggtgatggcc      3180
caggaccagc gcatccgctg gtacctgctg agcatgggca gcaacgagaa catccacagc      3240
atccacttca gcggccacgt gttcaccgtg cgcaagaagg aggagtacaa gatggccctg      3300
tacaacctgt accccggcgt gttcgagacc gtggagatgc tgcccagcaa ggccggcatc      3360
tggcgcgtgg agtgcctgat cggcgagcac ctgcacgccg gcatgagcac cctgttcctg      3420
gtgtacagca acaagtgcca gaccccctg ggcatggcca gcggccacat ccgcgacttc       3480
cagatcaccg ccagcggcca gtacggccag tgggccccca gctggccccg cctgcactac      3540
agcggcagca tcaacgcctg gagcaccaag gagcccttca gctggatcaa ggtgaccctg      3600 ctggcccca tgatcatcca cggcatcaag acccagggcg cccgccagaa gttcagcagc      3660
ctgtacatca gccagttcat catcatgtac agcctggacg gcaagaagtg gcagacctac      3720
cgcggcaaca gcaccggcac cctgatggtg ttcttcggca acgtggacag cagcggcatc      3780
aagcacaaca tcttcaaccc ccccatcatc gcccgctaca tccgcctgca ccccacccac      3840
tacagcatcc gcagcaccct gcgcatggag ctgatgggct gcgacctgaa cagctgcagc      3900 atgccctgg gcatggagag caaggccatc agcgacgccc agatcaccgc cagcagctac      3960
ttcaccaaca tgttcgccac ctggagcccc agcaaggccc gcctgcacct gcagggccgc      4020
agcaacgcct ggcgccccca ggtgaacaac cccaaggagt ggctgcaggt ggacttccag      4080
aagaccatga aggtgaccgg cgtgaccacc caggcgtga agagcctgct gaccagcatg       4140
tacgtgaagg agttcctgat cagcagcagc caggacggcc accagtggac cctgttcttc      4200
cagaacggca aggtgaaggt gttccagggc aaccaggaca gcttccaccc cgtggtgaac      4260
agcctggacc cccccctgct gacccgctac ctgcgcatcc accccagag ctgggtgcac       4320 cagatcgccc tgcgcatgga ggtgctgggc tgcgaggccc aggacctgta ctga            4374
```

<210> SEQ ID NO 15
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

```
atgcagattg agctgagcac ctgtttcttc ctgtgcctgc tgagattttg cttctcagct      60
acccgcaggt actacctggg agccgttgag ctgtcctggg attacatgca gtcagatctg      120
```

```
ggggagctgc ctgtggacgc tcggtttccc cccagagtgc caaagtcctt tcccttcaac    180
accagcgtgg tgtacaaaaa gacactttt gttgaattta ctgaccactt gttcaacatc    240
gccaagccac gaccccatg atgggcctg ctggggccaa ccattcaggc agaggtttac     300
gacacagtcg tgatcacact gaagaacatg gcctcccatc cagtgtctct gcacgccgtc    360
ggtgtgtcct actggaaagc atccgagggc gccgagtatg acgaccagac cagccagaga    420
gagaaagagg acgacaaagt gttccctgga ggcagccaca cctacgtgtg caggtgttg    480
aaggaaaatg ggcccatggc cagtgaccct ttgtgtctga cttactcata cctgtctcat    540
gtggatctag tcaaggacct gaattctgga ctgattgggg cactgcttgt gtgccgcgaa    600
ggcagcctgg ccaaagaaaa gacacagacc cttcacaagt tcatcctgct gttcgccgtg    660
ttcgacgaag gcaaatcctg gcactcagaa accaaaaact cactgatgca ggaccgggat    720
gccgcctctg cccgcgcatg gccaaaaatg cacaccgtca acggctatgt caatagaagt    780
ttgcccggcc tcattggatg tcacaggaaa agcgtctatt ggcatgtaat cgggatggga    840
accacacctg aggtccacag catatttctg gaaggccaca catttctggt gagaaatcat    900
cgccaggctt ccctggaaat ttcccccatc accttcttga ccgcccagac actgctcatg    960
gatcttgggc agtttctgct gttttgtcat atttcttctc accaacacga cggaatggag   1020
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgccccct ggtgctggca   1260
cccgacgacc gaagctacaa atctcagtac ctgaacaatg gtccacaacg atcggcagg   1320
aagtacaaga aagtgcggtt catggcctat acagacgaaa ccttcaaaac cagggaggct   1380
atccagcacg agtctgggat tctgggacca ctcctgtacg gcgaagtggg cgacaccttg   1440
ttaattatct tcaagaacca ggctagtaga cctataacaa tttatcccca cggcattacc   1500
gatgtgcggc ctctctactc taggcggctt ccaaggggg tgaaacacct gaaggacttt    1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc ttttctccg gtatactttt caaacataag   2040
atggtgtacg aagatactct gacgctgttc cctttctctg gggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc ataccctgct agcaagaata cgccatcga gcccgaagc   2280
ttctcacaga atcccctgt cctcaagagg caccagcgag agatcacaag gaccacactc   2340
cagtccgacc aggaggagat tgactacgat gacacgattt ctgtggagat gaaaaagag   2400
gactttgaca tctacgatga ggatgaaaac cagagcccta gtcgttcca gaagaaaaca   2460
aggcactact tcattgccgc cgtggagaga ctgtgggact acggaatgag tagttcccca   2520
```

```
cacgtgttgc ggaacagagc ccagagtggg tccgtcccac agttcaagaa ggttgttttc    2580
caggagttca cagatggctc cttcactcag ccactgtatc gcggcgagct gaatgagcac    2640
ttgggcttat tgggccccta cattcgcgca gaagtcgaag ataatattat ggtgaccttc    2700
cgcaaccagg ccagccggcc ttactcattc tactcctctc tcatctctta tgaggaggat    2760
cagcgccagg gcgccgaacc ccggaagaac tttgtgaagc ccaatgaaac caaaacttac    2820
ttttggaagg tgcagcacca tatggcgccg acgaaagacg aatttgactg caaagcctgg    2880
gcctacttca gcgacgtcga cttggagaag gacgtccaca gcggcctgat tggccctttg    2940
ttggtctgcc ataccaatac actcaaccct gcccacggga ggcaggtgac cgtgcaggag    3000
tttgccttgt tcttcaccat cttcgacgaa accaagagct ggtacttcac agagaacatg    3060
gagaggaact gcagagcacc ctgtaacatc cagatggagg accctacttt caaggaaaat    3120
tacaggttcc atgccattaa tggctacatc atggataccc tccccgggct tgtgatggct    3180
caggaccagc gcatccgctg gtacctgctc tcaatgggct ccaacgagaa cattcatagc    3240
atccacttta gtggccacgt gtttaccgtg cgcaagaagg aggagtacaa gatggcactg    3300
tacaacctgt accctggcgt gtttgagaca gtggagatgc tgccatccaa ggccggcatc    3360
tggcgcgtgg agtgcctcat tggggagcac ctccatgctg gcatgtctac actgttcctg    3420
gtgtacagca caagtgtca gactccactc ggaatggcct ccgggcatat ccgcgatttt    3480
cagatcacgg cctctggcca gtatggccaa tgggctccca agctggccag gctgcactac    3540 agtggggagta tcaacgcttg gagcaccaag gagcctttct cctggatcaa ggtgacctg    3600 cttgccccca tgattattca cggcattaag acacagggggg ccaggcagaa attctcctcc    3660
ctgtacatct cccagttcat catcatgtac agtctggacg gcaaaaagtg gcagacctac    3720
cgcgggaaca gtaccgggac attgatggtg ttcttcggga acgtggactc tagcggcatt    3780
aaacacaaca ttttcaaccc ccccatcatt gctaggtata tcaggctcca tcccacccac    3840
tatagcatca ggtccactct gcggatggag ctgatgggct gcgaccttaa ttcatgcagc    3900
atgccgctgg gcatggagtc aaaggccatc tccgacgccc aaatcaccgc ctccagctac    3960
ttcaccaata tgttcgccac ctggagcccc agcaaggccc ggctgcacct gcagggccgc    4020
agcaacgcct ggcggcctca ggtgaacaac cccaaggagt ggctgcaggt ggacttccag    4080
aaaaccatga aggtgactgg ggtcaccacc cagggagtca gagcctgct gaccagcatg    4140 tatgtgaagg agttcttgat cagctcgtca caggatggcc accagtggac tttgttcttt    4200
cagaacggta aggtgaaagt gttccaggga aaccaagatt cctttacacc agtggtcaac    4260
tctctggatc ctccccctgct gacacggtac ctgcggatcc atccccagtc atgggtgcac    4320
cagattgctc tgcgcatgga ggtgcttggc tgcgaggccc aggacctgta ctga          4374
```

<210> SEQ ID NO 16
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

```
atgcagattg agctgagcac ctgtttcttc ctgtgcctgc tgagattttg cttctcagct      60
acccgcaggt actacctggg agccgttgag ctgtcctggg attacatgca gtcagatctg     120
```

```
ggggagctgc ctgtggacgc tcggtttccc cccagagtgc caaagtcctt tcccttcaac      180
accagcgtgg tgtacaaaaa gacactttt gttgaattta ctgaccactt gttcaacatc       240
gccaagccac gaccccatg gatgggcctg ctggggccaa ccattcaggc agaggtttac       300
gacacagtcg tgatcacact gaagaacatg gcctcccatc cagtgtctct gcacgccgtc     360
ggtgtgtcct actggaaagc atccgagggc gccgagtatg acgaccagac cagccagaga     420
gagaaagagg acgacaaagt gttccctgga ggcagccaca cctacgtgtg gcaggtgttg     480
aaggaaaatg ggcccatggc cagtgaccct tgtgtctga cttactcata cctgtctcat      540
gtggatctag tcaaggacct gaattctgga ctgattgggg cactgcttgt gtgccgcgaa     600
ggcagcctgg ccaaagaaaa gacacagacc cttcacaagt tcatcctgct gttcgccgtg     660
ttcgacgaag gcaaatcctg gcactcagaa accaaaaact cactgatgca ggaccgggat     720
gccgcctctg cccgcgcatg gccaaaaatg cacaccgtca acggctatgt caatagaagt     780
ttgcccggcc tcattggatg tcacaggaaa agcgtctatt ggcatgtaat cgggatggga     840
accacacctg aggtccacag catatttctg gaaggccaca catttctggt gagaaatcat     900
cgccaggctt ccctggaaat ttccccatc accttcttga ccgcccagac actgctcatg      960
gatcttgggc agtttctgct gttttgtcat atttcttctc accaacacga cggaatggag     1020
gcctacgtta aggtcgatag ttgccctgaa gaacctcagc tgaggatgaa gaacaacgag     1080
gaagccgagg actacgatga cgatttgacc gattccgaaa tggacgtggt gcgctttgat     1140
gatgacaatt ctccatcctt cattcagatt agatccgtcg ccaagaagca ccccaagacc     1200
tgggtgcact acattgcagc cgaggaggag gattgggact acgccccct ggtgctggca     1260 cccgacgacc gaagctacaa atctcagtac ctgaacaatg gtccacaacg gatcggcagg     1320
aagtacaaga aagtgcggtt catggcctat acagacgaaa ccttcaaaac cagggaggct     1380
atccagcacg agtctgggat tctgggacca ctcctgtacg gcgaagtggg cgacaccttg     1440
ttaattatct tcaagaacca ggctagtaga ccttataaca tttatcccca cggcattacc     1500
gatgtgcggc ctctctactc taggcggctt ccaaaggggg tgaaacacct gaaggacttt     1560
cccatcctcc ctggcgaaat ctttaagtat aagtggacag tgaccgtgga ggatggacca     1620
accaagagcg accccaggtg cctgacacgc tattattcaa gcttcgtgaa tatggaaagg     1680
gacctcgcat ctggcttgat cggccctctg ctgatatgtt acaaggaaag cgtcgatcag     1740
agaggaaatc agatcatgtc agacaaaagg aatgtgatcc tgttctccgt cttcgatgaa     1800
aacaggagct ggtatctgac agagaacatc cagagattcc tgccaaatcc cgccggcgtc     1860
cagctggagg acccggagtt tcaggcatct aacatcatgc attccattaa tggttacgtg     1920
ttcgactccc tgcagctgag cgtgtgcctc cacgaggtgg cctactggta catcttgagc     1980
atcggcgccc agaccgactt tctgagcgtc ttttctccg gtatactttt caaacataag     2040
atggtgtacg aagatactct gacgctgttc cctttctctg gggagactgt gtttatgtct     2100
atggagaacc ctggactgtg gattctcgga tgccacaaca gtgactttcg taatagaggg     2160
atgactgcac tgctgaaggt gtccagctgt gataaaaata ctggcgacta ctacgaagat     2220
agctatgagg atatctcagc ataccctgctg agcaagaata cgccatcga gcccgaagc      2280 ttctcacaga atcccctgt cctcaaggcc caccaggcgg agatcacaag gaccacactc      2340
cagtccgacc aggaggagat tgactacgat gacacgattt ctgtggagat gaaaaagag     2400 gactttgaca tctacgatga ggatgaaaac cagagcccta ggtcgttcca gaagaaaaca     2460
aggcactact tcattgccgc cgtggagaga ctgtgggact acggaatgag tagttcccca     2520
```

```
cacgtgttgc ggaacagagc ccagagtggg tccgtcccac agttcaagaa ggttgttttc    2580
caggagttca cagatggctc cttcactcag ccactgtatc gcggcgagct gaatgagcac    2640
ttgggcttat tgggcccta cattcgcgca gaagtcgaag ataatattat ggtgaccttc    2700
cgcaaccagg ccagccggcc ttactcattc tactcctctc tcatctctta tgaggaggat    2760
cagcgccagg gcgccgaacc ccggaagaac tttgtgaagc ccaatgaaac caaaacttac    2820
ttttggaagt gcagcacca tatggcgccg acgaaagacg aatttgactg caaagcctgg    2880
gcctacttca gcgacgtcga cttggagaag gacgtccaca gcggcctgat tggcccttg    2940 ttggtctgcc ataccaatac actcaaccct gcccacggga ggcaggtgac cgtgcaggag    3000
tttgccttgt tcttcaccat cttcgacgaa accaagagct ggtacttcac agagaacatg    3060
gagaggaact gcagagcacc ctgtaacatc cagatggagg accctacttt caaggaaaat    3120
tacaggttcc atgccattaa tggctacatc atggataccc tccccgggct tgtgatggct    3180
caggaccagc gcatccgctg gtacctgctc tcaatgggct ccaacgagaa cattcatagc    3240 atccactta gtggccacgt gtttaccgtg cgcaagaagg aggagtacaa gatggcactg    3300
tacaacctgt accctggcgt gtttgagaca gtggagatgc tgccatccaa ggccggcatc    3360
tggcgcgtgg agtgcctcat tggggagcac ctccatgctg gcatgtctac actgttcctg    3420
gtgtacagca caagtgtca gactccactc ggaatggcct ccgggcatat ccgcgatttt    3480
cagatcacgg cctctggcca gtatggccaa tgggctccca agctggccag gctgcactac    3540 agtggggagta tcaacgcttg gagcaccaag gagccttctc cctggatcaa ggtgacctg    3600 cttgccccca tgattattca cggcattaag acacaggggg ccaggcagaa attctcctcc    3660
ctgtacatct cccagttcat catcatgtac agtctggacg gcaaaaagtg gcagacctac    3720
cgcgggaaca gtaccgggac attgatggtg ttcttcggga acgtggactc tagcggcatt    3780
aaacacaaca ttttcaaccc ccccatcatt gctaggtata tcaggctcca tcccaccac    3840 tatagcatca ggtccactct gcggatggag ctgatggggct gcgaccttaa ttcatgcagc    3900
atgccgctgg gcatggagtc aaaaggccatc tccgacgccc aaatcaccgc ctccagctac    3960
ttcaccaata tgttcgccac ctggagcccc agcaaggccc ggctgcacct gcagggccgc    4020
agcaacgcct ggcggcctca ggtgaacaac cccaaggagt ggctgcaggt ggacttccag    4080
aaaaccatga aggtgactgg ggtcaccacc cagggagtca agagcctgct gaccagcatg    4140
tatgtgaagg agttcttgat cagctcgtca caggatggcc accagtggac tttgttcttt    4200
cagaacggta aggtgaaagt gttccaggga accaagatt cctttacacc agtggtcaac    4260
tctctggatc ctcccctgct gacacggtac ctgcggatcc atccccagtc atgggtgcac    4320
cagattgctc tgcgcatgga ggtgcttggc tgcgaggccc aggacctgta ctga          4374
```

<210> SEQ ID NO 17
<211> LENGTH: 4425
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
atgcagattg agctgagcac ctgtttcttc ctgtgcctgc tgagattttg cttctcagct      60
acccgcaggt actacctggg agccgttgag ctgtcctggg attacatgca gtcagatctg     120
```

```
ggggagctgc ctgtggacgc tcggtttccc cccagagtgc caaagtcctt tcccttcaac    180
accagcgtgg tgtacaaaaa gacactttt gttgaattta ctgaccactt gttcaacatc      240
gccaagccac gacccccatg gatgggcctg ctggggccaa ccattcaggc agaggtttac    300
gacacagtcg tgatcacact gaagaacatg gcctcccatc cagtgtctct gcacgccgtc    360
ggtgtgtcct actggaaagc atccgagggc gccgagtatg acgaccagac cagccagaga    420
gagaaagagg acgacaaagt gttccctgga ggcagccaca cctacgtgtg gcaggtgttg    480
aaggaaaatg ggcccatggc cagtgaccct ttgtgtctga cttactcata cctgtctcat    540
gtggatctag tcaaggacct gaattctgga ctgattgggg cactgcttgt gtgccgcgaa    600
ggcagcctgg ccaaagaaaa gacacagacc cttcacaagt tcatcctgct gttcgccgtg    660
ttcgacgaag gcaaatcctg gcactcagaa accaaaaact cactgatgca ggaccgggat    720
gccgcctctg cccgcgcatg gccaaaaatg cacaccgtca acggctatgt caatagaagt    780
ttgcccggcc tcattggatg tcacaggaaa gcgtctatt ggcatgtaat cgggatggga     840
accacacctg aggtccacag catatttctg gaaggccaca catttctggt gagaaatcat    900
cgccaggctt ccctggaaat ttcccccatc accttcttga ccgcccagac actgctcatg    960
gatcttgggc agtttctgct gttttgtcat atttcttctc accaacacga cggaatggaa   1020
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgcccccct ggtgctggca   1260
cccgacgacc gaagctacaa atctcagtac ctgaacaatg gtccacaacg gatcggcagg   1320
aagtacaaga aagtgcggtt catggcctat acagacgaaa ccttcaaaac cagggaggct   1380
atccagcacg agtctgggat ctgggaccac tcctgtacg gcgaagtggg cgacaccttg    1440
ttaattatct tcaagaacca ggctagtaga cctataacaa tttatcccca cggcattacc   1500
gatgtgcggc ctctctactc taggcggctt ccaaggggg tgaaacacct gaaggacttt     1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc tttttctccg ggtatacttt caaacataag   2040
atggtgtacg aagatactct gacgctgttc ccttttctctg gggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc ataccctgct agcaagaata cgccatcga gccccgaagc    2280
ttctcacaga atgccaccaa cgtgagcaac aacagcaaca ccagcaacga cagcaacgtg   2340
agcccccctg tcctcaaggc ccaccaggcg gagatcacaa ggaccacact ccagtccgac   2400
caggaggaga ttgactacga tgacacgatt tctgtggaga tgaaaaaaga ggactttgac   2460
atctacgatg aggatgaaaa ccagagccct aggtcgttcc agaagaaaac aaggcactac   2520
```

```
ttcattgccg ccgtggagag actgtgggac tacggaatga gtagttcccc acacgtgttg    2580
cggaacagag cccagagtgg gtccgtccca cagttcaaga aggttgtttt ccaggagttc    2640
acagatggct ccttcactca gccactgtat cgcggcgagc tgaatgagca cttgggctta    2700
ttgggcccct acattcgcgc agaagtcgaa gataatatta tggtgacctt ccgcaaccag    2760
gccagccggc cttactcatt ctactcctct ctcatctctt atgaggagga tcagcgccag    2820
ggcgccgaac cccggaagaa ctttgtgaag cccaatgaaa ccaaaactta cttttggaag    2880
gtgcagcacc atatggcgcc gacgaaagac gaatttgact gcaaagcctg ggcctacttc    2940
agcgacgtcg acttggagaa ggacgtccac agcggcctga ttggccctt gttggtctgc    3000 cataccaata cactcaaccc tgcccacggg aggcaggtga ccgtgcagga gtttgccttg    3060
ttcttcacca tcttcgacga aaccaagagc tggtacttca cagagaacat ggagaggaac    3120
tgcagagcac cctgtaacat ccagatggag gaccctactt tcaaggaaaa ttacaggttc    3180
catgccatta atggctacat catggatacc ctcccccggg ttgtgatggc tcaggaccag    3240
cgcatccgct ggtacctgct ctcaatgggc tccaacgaga acattcatag catccacttt    3300
agtggccacg tgtttaccgt gcgcaagaag gaggagtaca agatggcact gtacaacctg    3360
taccctggcg tgtttgagac agtggagatg ctgccatcca aggccggcat ctggcgcgtg    3420
gagtgcctca ttggggagca cctccatgct ggcatgtcta cactgttcct ggtgtacagc    3480
aacaagtgtc agactccact cggaatggcc tccgggcata tccgcgattt tcagatcacg    3540
gcctctggcc agtatggcca atgggctccc aagctggcca ggctgcacta cagtgggagt    3600
atcaacgctt ggagcaccaa ggagcctttc tcctggatca aggtggacct gcttgccccc    3660
atgattattc acggcattaa gacacagggg gccaggcaga aattctcctc cctgtacatc    3720
tcccagttca tcatcatgta cagtctggac ggcaaaaagt ggcagaccta ccgcgggaac    3780
agtaccggga cattgatggt gttcttcggg aacgtggact ctagcggcat taaacacaac    3840
attttcaacc ccccatcat tgctaggtat atcaggctcc atcccaccca ctatagcatc    3900
aggtccactc tgcggatgga gctgatgggc tgcgaccta attcatgcag catgccgctg    3960
ggcatggagt caaaggccat ctccgacgcc caaatcaccg cctccagcta cttcaccaat    4020
atgttcgcca cctggagccc cagcaaggcc cggctgcacc tgcagggccg cagcaacgcc    4080
tggcggcctc aggtgaacaa ccccaaggag tggctgcagg tggacttcca gaaaaccatg    4140
aaggtgactg gggtcaccac ccagggagtc aagagcctgc tgaccagcat gtatgtgaag    4200
gagttcttga tcagctcgtc acaggatggc caccagtgga ctttgttctt tcagaacggt    4260
aaggtgaaag tgttccaggg aaaccaagat tcctttacac cagtggtcaa ctctctggat    4320
cctcccctgc tgacacggta cctgcggatc catcccagt catgggtgca ccagattgct    4380
ctgcgcatgg aggtgcttgg ctgcgaggcc caggacctgt actaa                    4425
```

<210> SEQ ID NO 18
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
atgcagcgcg tgaacatgat catggcagaa tcaccaggcc tcatcaccat ctgccttta      60

| | |
|---|---|
| ggatatctac tcagtgctga atgtacagtt tttcttgatc atgaaaacgc aacaaaatt | 120 |
| ctgaatcggc aaagaggta taattcaggt aaattggaag agtttgttca agggaaccctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |
| ctggacgaac ccttagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga gatcagcttt agttcttcag taccttagag ttccacttgt tgaccgagcc | 1140 |
| acatgtcttc tgtctacaaa gttcaccatc tataacaaca tgttctgtgc tggcttccat | 1200 |
| gaaggaggta gagattcatg tcaaggagat agtggggac cccatgttac tgaagtggaa | 1260 |
| gggaccagtt tcttaactgg aattattagc tggggtgaag agtgtgcaat gaaaggcaaa | 1320 |
| tatggaatat ataccaaggt atcccggtat gtcaactgga ttaaggaaaa aacaaagctc | 1380 |
| acttaa | 1386 |

<210> SEQ ID NO 19
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

| | |
|---|---|
| atgcagcgcg tgaacatgat tatggccgag tctcccggcc tgatcaccat ctgtctgctg | 60 |
| ggctatctgc tgagcgccga gtgcaccgtg tttctggatc acgagaacgc caacaagatc | 120 |
| ctgaacagac ccaagcggta caacagcggc aagctggaag agttcgtgca gggcaacctg | 180 |
| gaacgcgagt gcatggaaga agtgcagc ttcgaagagg ccagagaggt gttcgagaac | 240 |
| accgagagaa ccaccgagtt ctggaagcag tacgtggacg gcgatcagtg cgagagcaac | 300 |
| ccttgtctga atggcggcag ctgcaaggac gacatcaaca gctacgagtg ctggtgcccc | 360 |
| ttcggcttcg agggcaagaa ttgcgagctg gacgtgacct gcaacatcaa gaacggcaga | 420 |
| tgcgagcagt tctgcaagaa cagcgccgac aacaaggtcg tgtgctcctg cacagagggc | 480 |
| tacagactgg ccgagaacca gaagtcttgc gagcccgctg tgccctttcc atgtggcaga | 540 |
| gtgtctgtgt cccagaccag caagctgacc agagccgaga cagtgttccc cgacgtggac | 600 |
| tacgtgaaca gcaccgaggc cgagacaatc ctggacaaca tcacccagag cacccagtcc | 660 |

```
ttcaacgact tcaccagagt cgtcggcggc gaggatgcta agcctggaca gtttccttgg        720
caagtggtgc tgaacggcaa ggtggacgct ttttgtggcg gctccatcgt gaacgagaag        780
tggatcgtga ccgccgctca ctgtgtggaa accggcgtga agattacagt ggtggccggc        840
gagcacaaca tcgaggaaac agagcacacc gagcagaaac ggaacgtgat cagaatcatc        900
cctcaccaca actacaacgc cgccatcaac aagtacaacc acgatatcgc cctgctggaa        960
ctggacgagc ccctggtcct gaactcttac gtgaccccta tctgtatcgc cgacaaagag       1020
tacaccaaca tctttctgaa gttcggcagc ggctacgtgt ccggctgggg aagagttttc       1080
cacaagggca gatcagccct ggtgctgcag tacctgagag tgccccctggt ggatagagcc       1140 acatgcctgc tgagcaccaa gttcaccatc tacaacaaca tgttctgcgc cggcttccac       1200
gaaggcggca gagattcttg tcaaggcgat tctggcggcc ctcacgtgac agaggttgag       1260
ggcacaagct ttctgaccgg catcatcagc tggggcgaag agtgtgccat gaaggggaag       1320
tacggcatct acaccaaggt gtccagatac gtgaactgga tcaaagaaaa gaccaagctc       1380
acctga                                                                 1386
```

<210> SEQ ID NO 20
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20

```
atgcagcgcg tgaacatgat catggccgag agccccggcc tgatcaccat ctgcctgctg         60
ggctacctgc tgagcgccga gtgcaccgtg ttcctggacc acgagaacgc caacaagatc        120
ctgaaccgcc ccaagcgcta caacagcggc aagctggagg agttcgtgca gggcaacctg        180
gagcgcgagt gcatggagga agtgcagc ttcgaggagg cccgcgaggt gttcgagaac         240
accgagcgca ccaccgagtt ctggaagcag tacgtggacg cgaccagtg cgagagcaac         300 ccctgcctga acgcggcag ctgcaaggac gacatcaaca gctacgagtg ctggtgcccc         360
ttcggcttcg agggcaagaa ctgcgagctg gacgtgacct gcaacatcaa gaacggccgc        420
tgcgagcagt tctgcaagaa cagcgccgac aacaaggtgg tgtgcagctg caccgagggc        480
taccgcctgg ccgagaacca gaagagctgc gagcccgccg tgcccttccc ctgcggccgc        540
gtgagcgtga gccagaccag caagctgacc cgcgccgaga ctgtgttccc cgacgtggac        600
tacgtgaaca gcaccgaggc cgaaacgatc ctggacaaca tcacccagag cacccagagc        660
ttcaacgact caccccgcgt ggtgggcggc gaggacgcca agcccggcca gttcccctgg        720
caggtggtgc tgaacggcaa ggtggacgcc ttctgcggcg gcagcatcgt gaacgagaag        780
tggatcgtga ccgccgccca ctgcgtggaa accggcgtga agatcaccgt ggtggccggc        840
gagcacaaca tcgaggaaac cgagcacacc gagcagaagc gcaacgtgat ccgcatcatc        900
ccccaccaca actacaacgc cgccatcaac aagtacaacc acgacatcgc cctgctggag        960
ctggacgagc ccctggtgct gaacagctac gtgaccccca tctgcatcgc cgacaaggag       1020
tacaccaaca tcttcctgaa gttcggcagc ggctacgtga cggctggggg ccgcgtgttc       1080
cacaagggcc gcagcgccct ggtgctgcag tacctgcgcg tgccccctggt ggaccgcgcc       1140 acctgcctgc tgagcaccaa gttcaccatc tacaacaaca tgttctgcgc cggcttccac       1200
```

```
gagggcggcc gcgacagctg ccagggcgac agcggcggcc cccacgtgac cgaggtggag   1260
ggcaccagct tcctgaccgg catcatcagc tggggcgagg agtgcgccat gaagggcaag   1320
tacggcatct acaccaaggt gagccgctac gtgaactgga tcaaggagaa aaccaagctg   1380
acctaa                                                              1386
```

<210> SEQ ID NO 21
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 21

```
atgcagcggg tgaacatgat catggccgag agccccgggc tgatcaccat ctgtctgctg     60
gggtacctgc tgtccgccga gtgcaccgtg ttcctggacc acgagaacgc caacaagatc    120
ctgaatcgcc ccaagagata caattccgga aagctggaag agtttgtgca gggcaacctg    180
gagagagagt gcatggaaga gaagtgctcc ttcgaggagg cccgggaggt gttcgagaat    240
actgaacgga caacagagtt ctggaagcag tatgtggacg gcgaccagtg tgagagcaac    300
ccctgtctga cggcgggag ctgcaaggac gacattaatt cctacgaatg ctggtgccca    360
ttcggcttcg agggcaagaa ctgcgagctg gacgtgacct gcaacatcaa gaacggccgc    420
tgcgagcagt tttgcaagaa ctccgccgac aacaaggtgg tgtgttcttg caccgagggc    480
taccgcctgg ccgaaaaacca gaagagctgt gagcctgccg tgcccttccc ctgcggccgg    540
gtgtctgtgt cccagacctc caagctgacc agagccgaaa ccgtgtttcc agatgtggac    600
tacgtgaata gcaccgaggc cgagactatc ctcgacaaca tcacccagtc cacccagagc    660
tttaacgact tcacccgcgt ggtgggcggc gaggacgcca agcccggcca gttcccctgg    720
caggtggtgc tcaacggaaa ggtggacgcc ttctgcggag gcagcatcgt gaatgaaaag    780
tggatcgtga cagccgccca ctgcgtggaa acaggggtga agatcaccgt ggtggctgga    840
gagcacaaca tcgaggagac agagcacacc gaacagaaga ggaatgtgat caggatcatc    900
ccccaccaca ctataatgc cgccatcaac aagtacaacc acgacatcgc cctgctggag    960
ctggatgagc ccctggtgct caacagctac gtgacccca tctgcatcgc tgacaaggag   1020
tacaccaaca tcttcctgaa gttcggctcc ggctacgtgt ctggctgggg ccgcgtgttc    1080
cacaagggaa gaagcgccct cgtgctgcag tacctgcggg tgccactggt ggacagggcc    1140
acctgcctgc tgagcactaa gttcaccatt tacaacaaca tgttctgcgc cggcttccac    1200
gagggcggca gggactcctg ccagggcgac agcggcggcc ccatgtgac cgaggtggag    1260 ggcacctcct ttctgactgg cattatctcc tggggcgagg agtgcgccat gaaggggaag    1320
tatggcatct acaccaaggt gtcccgctac gtgaactgga ttaaggagaa aaccaagctg    1380
acctga                                                              1386
```

<210> SEQ ID NO 22
<211> LENGTH: 313
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 22

```
ttaaccctag aaagatagtc tgcgtaaaat tgacgcatgc attcttgaaa tattgctctc      60
tctttctaaa tagcgcgaat ccgtcgctgt gcatttagga catctcagtc gccgcttgga     120
gctcccgtga ggcgtgcttg tcaatgcggt aagtgtcact gattttgaac tataacgacc     180
gcgtgagtca aaatgacgca tgattatctt ttacgtgact tttaagattt aactcatacg     240
ataattatat tgttatttca tgttctactt acgtgataac ttattatata tatattttct     300
tgttatagat atc                                                        313
```

```
<210> SEQ ID NO 23
<211> LENGTH: 1733
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
```

```
ctcgacattg attattgact agttattaat agtaatcaat tacgggtca ttagttcata      60 gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtcgagg tgagccccac gttctgcttc actctcccca     420
tctccccccc ctccccaccc ccaattttgt atttatttat tttttaatta ttttgtgcag     480 cgatggggc ggggggggg gggggcgcg cgccaggcgg ggcggggcgg ggcgagggc        540 ggggcggggc gaggcggaga ggtgcggcgg cagccaatca gagcggcgcg ctccgaaagt     600
ttccttttat ggcgaggcgg cggcggcggc ggccctataa aaagcgaagc gcgcggcggg     660
cgggagtcgc tgcgcgctgc cttcgccccg tgccccgctc cgccgccgcc tcgcgccgcc     720
cgccccggct ctgactgacc gcgttactcc cacaggtgag cgggcgggac ggcccttctc     780
ctccgggctg taattagcgc ttggtttaat gacggcttgt ttcttttctg tggctgcgtg     840
aaagccttga gggctccgg gagggccctt tgtgcggggg gagcggctcg ggggtgcgt      900 gcgtgtgtgt gtgcgtgggg agcgccgcgt gcggctccgc gctgcccggc ggctgtgagc    960
gctgcgggcg cggcgcgggg ctttgtgcgc tccgcagtgt gcgcgagggg agcgcggccg   1020
ggggcggtgc cccgcggtgc gggggggct gcgaggggaa caaaggctgc gtgcgggtg    1080 tgtgcgtggg gggtgagca gggggtgtgg gcgcgtcggt cgggctgcaa ccccccctgc    1140
acccccctcc ccgagttgct gagcacggcc cggcttcggg tgcggggctc cgtacggggc   1200
gtggcgcggg gctcgccgtg ccggcgggg ggtggcggca ggtgggggtg ccggcgggg    1260 cggggccgcc tcgggccggg gagggctcgg ggaggggcg cggcggcccc cggagcgccg    1320
gcggctgtcg aggcgcggcg agccgcagcc attgcctttt atggtaatcg tgcgagaggg   1380
cgcagggact tcctttgtcc caaatctgtg cggagccgaa atctgggagg cgccgccgca   1440
ccccctctag cgggcgcggg gcgaagcggt gcggcgccgg caggaaggaa atgggcgggg   1500
agggccttcg tgcgtcgccg cgccgccgtc cccttctccc tctccagcct cggggctgtc   1560
cgcgggggga cggctgcctt cgggggggac ggggcagggc ggggttcggc ttctggcgtg   1620
```

| | |
|---|---|
| tgaccggcgg ctctagagcc tctgctaacc atgttcatgc cttcttcttt ttcctacagc | 1680 |
| tcctgggcaa cgtgctggtt attgtgctgt ctcatcattt tggcaaagaa ttg | 1733 |

<210> SEQ ID NO 24
<211> LENGTH: 522
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24

| | |
|---|---|
| tcctcaggtg caggctgcct atcagaaggt ggtggctggt gtggccaatg ccctggctca | 60 |
| caaataccac tgagatcttt ttccctctgc caaaaattat ggggacatca tgaagcccct | 120 |
| tgagcatctg acttctggct aataaaggaa atttattttc attgcaatag tgtgttggaa | 180 |
| ttttttgtgt ctctcactcg gaaggacata tgggagggca aatcatttaa aacatcagaa | 240 |
| tgagtatttg gtttagagtt tggcaacata tgcccatatg ctggctgcca tgaacaaagg | 300 |
| ttggctataa agaggtcatc agtatatgaa acagcccct gctgtccatt ccttattcca | 360 |
| tagaaaagcc ttgacttgag gttagatttt ttttatattt tgttttgtgt tattttttc | 420 |
| tttaacatcc ctaaaatttt ccttacatgt tttactagcc agattttcc tcctctcctg | 480 |
| actactccca gtcatagctg tccctcttct cttatggaga tc | 522 |

<210> SEQ ID NO 25
<211> LENGTH: 235
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

| | |
|---|---|
| ttaaccctag aaagataatc atattgtgac gtacgttaaa gataatcatg cgtaaaattg | 60 |
| acgcatgtgt tttatcggtc tgtatatcga ggtttattta ttaatttgaa tagatattaa | 120 |
| gttttattat atttacactt acatactaat aataaattca acaaacaatt tatttatgtt | 180 |
| tatttattta ttaaaaaaaa acaaaaactc aaaatttctt ctataaagta acaaa | 235 |

<210> SEQ ID NO 26
<211> LENGTH: 6164
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26

| | |
|---|---|
| ttaaccctag aaagatagtc tgcgtaaaat tgacgcatgc attcttgaaa tattgctctc | 60 |
| tctttctaaa tagcgcgaat ccgtcgctgt gcatttagga catctcagtc gccgcttgga | 120 |
| gctcccgtga ggcgtgcttg tcaatgcggt aagtgtcact gattttgaac tataacgacc | 180 |
| gcgtgagtca aaatgacgca tgattatctt ttacgtgact tttaagattt aactcatacg | 240 |
| ataattatat tgttatttca tgttctactt acgtgataac ttattatata tatattttct | 300 |
| tgttatagat atcatcaact ttgtatagaa aagttgctcg acattgatta ttgactagtt | 360 |
| attaatagta atcaattacg gggtcattag ttcatagccc atatatggag ttccgcgtta | 420 |

```
cataacttac ggtaaatggc ccgcctggct gaccgcccaa cgaccccgc ccattgacgt      480 caataatgac gtatgttccc atagtaacgc caatagggac tttccattga cgtcaatggg      540
tggagtattt acggtaaact gcccacttgg cagtacatca agtgtatcat atgccaagta      600 cgcccctat tgacgtcaat gacggtaaat ggcccgcctg gcattatgcc cagtacatga      660
ccttatggga ctttcctact tggcagtaca tctacgtatt agtcatcgct attaccatgg      720
tcgaggtgag ccccacgttc tgcttcactc tccccatctc ccccccctcc caccccaa       780 ttttgtattt atttattttt taattatttt gtgcagcgat ggggcgggg ggggggggg       840 ggcgcgcgcc aggcggggcg gggcggggcg agggcgggg cggggcgagg cggagaggtg      900
cggcggcagc caatcagagc ggcgcgctcc gaaagtttcc ttttatggcg aggcggcggc      960
ggcggcggcc ctataaaaag cgaagcgcgc ggcgggcggg agtcgctgcg cgctgccttc     1020
gccccgtgcc ccgctccgcc gccgcctcgc gccgcccgcc ccggctctga ctgaccgcgt     1080
tactcccaca ggtgagcggg cgggacggcc cttctcctcc gggctgtaat tagcgcttgg     1140
tttaatgacg gcttgtttct ttctgtggc tgcgtgaaag ccttgagggg ctccgggagg     1200 gcccttgtg cggggggagc ggctcggggg gtgcgtgcgt gtgtgtgtgc gtggggagcg     1260
ccgcgtgcgg ctccgcgctg cccggcggct gtgagcgctg cggcgcggc gcgggctttt    1320 gtgcgctccg cagtgtgcgc gaggggagcg cggccggggg cggtgccccg cggtgcggg      1380 ggggctgcga ggggaacaaa ggctgcgtgc ggggtgtgtg cgtggggggg tgagcagggg     1440
gtgtgggcgc gtcggtcggg ctgcaacccc ccctgcaccc ccctccccga gttgctgagc     1500
acggcccggc ttcgggtgcg gggctccgta cggggcgtgg cgcggggctc gccgtgccgg     1560
gcggggggtg gcggcaggtg ggggtgccgg gcggggcggg gccgcctcgg gccggggagg     1620
gctcggggga ggggcgcggc ggccccccgga gcgccggcgg ctgtcgaggc gcggcgagcc     1680
gcagccattg cctttatgg taatcgtgcg agagggcgca gggacttcct ttgtcccaaa      1740
tctgtgcgga gccgaaatct gggaggcgcc gccgcacccc ctctagcggg cgcggggcga     1800
agcggtgcgg cgccggcagg aaggaaatgg gcggggaggg ccttcgtgcg tcgccgcgcc     1860
gccgtcccct tctccctctc cagcctcggg gctgtccgcg gggggacggc tgccttcggg     1920
ggggacgggg cagggcgggg ttcggcttct ggcgtgtgac cggcggctct agagcctctg     1980
ctaaccatgt tcatgccttc ttctttttcc tacagctcct gggcaacgtg ctggttattg     2040
tgctgtctca tcattttggc aaagaattgc aagtttgtac aaaaaagcag gctgccaccg     2100
aattcgcggc cgctaaaccc agctttcttg tacaaagtgg caactttatt atacatagtt     2160
gatcctcagg tgcaggctgc ctatcagaag gtggtggctg gtgtggccaa tgccctggct     2220
cacaaatacc actgagatct ttttccctct gccaaaaatt atgggacat catgaagccc     2280 cttgagcatc tgacttctgg ctaataaagg aaatttattt tcattgcaat agtgtgttgg     2340 aatttttttgt gtctctcact cggaaggaca tatgggaggg caaatcattt aaaacatcag     2400
aatgagtatt tggtttagag tttggcaaca tatgcccata tgctggctgc catgaacaaa     2460
ggttggctat aaagaggtca tcagtatatg aaacagcccc ctgctgtcca ttccttattc     2520
catagaaaag ccttgacttg aggttagatt ttttttatat tttgttttgt gttattttt     2580 tctttaacat ccctaaaatt ttccttacat gttttactag ccagatttt cctcctctcc     2640 tgactactcc cagtcatagc tgtccctctt ctcttatgga gatccctcga cctgcagccc     2700
aagcttggat ccctcgagtt aattaacgag agcataatat tgatatgtgc caaagttgtt     2760
```

```
tctgactgac taataagtat aatttgtttc tattatgtat aggttaagct aattacttat    2820
tttataatac aacatgactg tttttaaagt acaaaataag tttattttttg taaaagagag    2880 aatgtttaaa agttttgtta ctttatagaa gaaattttga gttttttgttt ttttttaata    2940 aataaataaa cataaataaa ttgtttgttg aatttattat tagtatgtaa gtgtaaatat    3000
aataaaactt aatatctatt caaattaata aataaacctc gatatacaga ccgataaaac    3060
acatgcgtca attttacgca tgattatctt taacgtacgt cacaatatga ttatcttttct    3120 agggttaaat aatagtttct aattttttta ttattcagcc tgctgtcgtg aataccgagc    3180
tccaattcgc cctatagtga gtcgtattac aattcactgg ccgtcgtttt acaacgtcgt    3240
gactgggaaa accctggcgt tacccaactt aatcgccttg cagcacatcc ccctttcgcc    3300
agctggcgta atagcgaaga ggcccgcacc gatcgccctt cccaacagtt gcgcagcctg    3360
aatggcgaat gggacgcgcc ctgtagcggc gcattaagcg cggcgggtgt ggtggttacg    3420
cgcagcgtga ccgctacact tgccagcgcc ctagcgcccg ctcctttcgc tttcttccct    3480
tcctttctcg ccacgttcgc cggctttccc cgtcaagctc taaatcgggg gctcccttta    3540
gggttccgat ttagtgcttt acggcacctc gaccccaaaa aacttgatta gggtgatggt    3600
tcacgtagtg ggccatcgcc ctgatagacg ttttttcgcc ctttgacgtt ggagtccacg    3660
ttctttaata gtggactctt gttccaaact ggaacaacac tcaaccctat ctcggtctat    3720
tcttttgatt tataagggat tttgccgatt tcggcctatt ggttaaaaaa tgagctgatt    3780
taacaaaaat ttaacgcgaa ttttaacaaa atattaacgc ttacaattta ggtggcactt    3840
ttcggggaaa tgtgcgcgga accccctattt gtttattttt ctaaatacat tcaaatatgt    3900
atccgctcat gagacaataa ccctgataaa tgcttcaata atattgaaaa aggaagagta    3960
tgagtattca acatttccgt gtcgccctta ttcccttttt tgcggcattt tgccttcctg    4020 ttttttgctca cccagaaacg ctggtgaaag taaaagatgc tgaagatcag ttgggtgcac    4080
gagtgggtta catcgaactg gatctcaaca gcggtaagat ccttgagagt tttcgccccg    4140
aagaacgttt tccaatgatg agcactttta aagttctgct atgtggcgcg gtattatccc    4200
gtattgacgc cgggcaagag caactcggtc gccgcataca ctattctcag aatgacttgg    4260
ttgagtactc accagtcaca gaaaagcatc ttacggatgg catgacagta agagaattat    4320
gcagtgctgc cataaccatg agtgataaca ctgcggccaa cttacttctg acaacgatcg    4380
gaggaccgaa ggagctaacc gcttttttgc acaacatggg ggatcatgta actcgccttg    4440
atcgttggga accggagctg aatgaagcca taccaaacga cgagcgtgac accacgatgc    4500
ctgtagcaat ggcaacaacg ttgcgcaaac tattaactgg cgaactactt actctagctt    4560
cccggcaaca attaatagac tggatggagg cggataaagt tgcaggacca cttctgcgct    4620
cggcccttcc ggctggctgg tttattgctg ataaatctgg agccggtgag cgtgggtctc    4680
gcggtatcat tgcagcactg gggccagatg gtaagccctc ccgtatcgta gttatctaca    4740
cgacggggag tcaggcaact atggatgaac gaaatagaca gatcgctgag ataggtgcct    4800
cactgattaa gcattggtaa ctgtcagacc aagtttactc atatatactt tagattgatt    4860
taaaacttca ttttttaattt aaaaggatct aggtgaagat cctttttgat aatctcatga    4920
ccaaaatccc ttaacgtgag ttttcgttcc actgagcgtc agaccccgta gaaaagatca    4980
aaggatcttc ttgagatcct ttttttctgc gcgtaatctg ctgcttgcaa acaaaaaaac    5040
caccgctacc agcggtggtt tgtttgccgg atcaagagct accaactctt tttccgaagg    5100
taactggctt cagcagagcg cagataccaa atactgttct tctagtgtag ccgtagttag    5160
```

```
gccaccactt caagaactct gtagcaccgc ctacatacct cgctctgcta atcctgttac    5220
cagtggctgc tgccagtggc gataagtcgt gtcttaccgg gttggactca agacgatagt    5280
taccggataa ggcgcagcgg tcgggctgaa cggggggttc gtgcacacag cccagcttgg    5340
agcgaacgac ctacaccgaa ctgagatacc tacagcgtga gctatgagaa agcgccacgc    5400
ttcccgaaga gagaaaggcg gacaggtatc cggtaagcgg cagggtcgga acaggagagc    5460
gcacgaggga gcttccaggg ggaaacgcct ggtatcttta tagtcctgtc gggtttcgcc    5520
acctctgact tgagcgtcga ttttgtgat gctcgtcagg ggggcggagc ctatggaaaa    5580
acgccagcaa cgcggccttt ttacggttcc tggccttttg ctggcctttt gctcacatgt    5640
tctttcctgc gttatcccct gattctgtgg ataaccgtat taccgccttt gagtgagctg    5700
ataccgctcg ccgcagccga acgaccgagc gcagcgagtc agtgagcgag gaagcggaag    5760
agcgcccaat acgcaaaccg cctctccccg cgcgttggcc gattcattaa tgcagctggc    5820
acgacaggtt tcccgactgg aaagcgggca gtgagcgcaa cgcaattaat gtgagttagc    5880
tcactcatta ggcacccag gctttacact ttatgcttcc ggctcgtatg ttgtgtggaa    5940
ttgtgagcgg ataacaattt cacacaggaa acagctatga ccatgattac gccaagctcg    6000
aaattaaccc tcactaaagg gaacaaaagc tggtacctcg cgcgacttgg tttgccattc    6060
tttagcgcgc gtcgcgtcac acagcttggc cacaatgtgg tttttgtcaa acgaagattc    6120
tatgacgtgt ttaaagttta ggtcgagtaa agcgcaaatc tttt          6164
```

<210> SEQ ID NO 27
<211> LENGTH: 6721
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

```
ctcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtcgagg tgagccccac gttctgcttc actctcccca     420 tctcccccc ctccccaccc ccaattttgt atttattat ttttaatta ttttgtgcag     480 cgatggggc ggggggggg gggggcgcg cgccaggcgg ggcggggcgg ggcgaggggc     540 ggggcgggc gaggcggaga ggtgcggcgg cagccaatca gagcggcgcg ctccgaaagt     600 ttcctttat ggcgaggcgg cggcggcggc ggccctataa aaagcgaagc gcgcggcggg     660
cgggagtcgc tgcgcgctgc cttcgccccg tgccccgctc cgccgccgcc tcgcgccgcc     720
cgccccggct ctgactgacc gcgttactcc cacaggtgag cgggcgggac ggcccttctc     780
ctccgggctg taattagcgc ttggtttaat gacggcttgt ttcttttctg tggctgcgtg     840
aaagccttga ggggctccgg gagggccctt tgtgcggggg gagcggctcg ggggtgcgt     900 gcgtgtgtgt gtgcgtgggg agcgccgcgt gcggctccgc gctgcccggc ggctgtgagc     960
```

-continued

```
gctgcgggcg cggcgcgggg ctttgtgcgc tccgcagtgt gcgcgagggg agcgcggccg      1020
ggggcggtgc cccgcggtgc gggggggggct gcgagggaa caaaggctgc gtgcggggtg      1080
tgtgcgtggg ggggtgagca gggggtgtgg gcgcgtcggt cgggctgcaa ccccccctgc      1140 accccccctcc ccgagttgct gagcacggcc cggcttcggg tgcggggctc cgtacggggc     1200
gtggcgcggg gctcgccgtg ccgggcgggg ggtggcggca ggtgggggtg ccgggcgggg      1260
cggggccgcc tcgggccggg gagggctcgg gggaggggcg cggcggcccc cggagcgccg      1320
gcggctgtcg aggcgcggcg agccgcagcc attgcctttt atggtaatcg tgcgagaggg      1380
cgcagggact tcctttgtcc caaatctgtg cggagccgaa atctgggagg cgccgccgca      1440
ccccctctag cgggcgcggg gcgaagcggt gcggcgccgg caggaaggaa atgggcgggg      1500
agggccttcg tgcgtcgccg cgccgccgtc cccttctccc tctccagcct cggggctgtc      1560
cgcgggggga cggctgcctt cggggggggac ggggcagggc ggggttcggc ttctggcgtg     1620
tgaccggcgg ctctagagcc tctgctaacc atgttcatgc cttcttcttt ttcctacagc      1680
tcctgggcaa cgtgctggtt attgtgctgt ctcatcattt tggcaaagaa ttgcaagttt      1740
gtacaaaaaa gcaggctgcc accatgcaga ttgagctgag cacctgtttc ttcctgtgcc      1800
tgctgagatt ttgcttctca gctacccgca ggtactacct gggagccgtt gagctgtcct      1860
gggattacat gcagtcagat ctgggggagc tgcctgtgga cgctcggttt cccccccagag     1920 tgccaaagtc ctttcccttc aacaccgcg tggtgtacaa aaagacactt tttgttgaat       1980
ttactgacca cttgttcaac atcgccaagc acgaccccc atggatgggc ctgctggggc       2040
caaccattca ggcagaggtt tacgacacag tcgtgatcac actgaagaac atggcctccc      2100
atccagtgtc tctgcacgcc gtcggtgtgt cctactggaa agcatccgag ggcgccgagt      2160
atgacgacca gaccagccag agagagaaag aggacgacaa agtgttccct ggaggcagcc      2220
acacctacgt gtggcaggtg ttgaaggaaa atgggcccat ggccagtgac cctttgtgtc      2280
tgacttactc ataccgtgtct catgtggatc tagtcaagga cctgaattct ggactgattg     2340
gggcactgct tgtgtgccgc gaaggcagcc tggccaaaga aaagacacag accccttcaca    2400 agttcatcct gctgttcgcc gtgttcgacg aaggcaaatc ctggcactca gaaaccaaaa      2460
actcactgat gcaggaccgg gatgccgcct ctgcccgcgc atggccaaaa atgcacaccg      2520
tcaacggcta tgtcaataga gtttgcccg gcctcattgg atgtcacagg aaaagcgtct      2580
attggcatgt aatcgggatg ggaaccacac ctgaggtcca cagcatattt ctggaaggcc      2640
acacatttct ggtgagaaat catcgccagg cttccctgga aatttccccc atcaccttct      2700
tgaccgccca gacactgctc atggatcttg gcagtttct gctgttttgt catatttctt       2760
ctcaccaaca cgacggaatg gaggcctacg ttaaggtcga tagttgccct gaagaacctc     2820
agctgaggat gaagaacaac gaggaagccg aggactacga tgacgatttg accgattccg      2880
aaatggacgt ggtgcgcttt gatgatgaca attctccatc cttcattcag attagatccg      2940
tcgccaagaa gcaccccaag acctgggtgc actacattgc agccgaggag gaggattggg     3000
actacgcccc cctggtgctg gcacccgacg accgaagcta caaatctcag tacctgaaca      3060
atggtccaca acggatcggc aggaagtaca agaaagtgcg gttcatggcc tatacagacg      3120
aaaccttcaa aaccagggag gctatccagc acgagtctgg gattctggga ccactcctgt     3180
acggcgaagt gggcgacacc ttgttaatta tcttcaagaa ccaggctagt agaccttata      3240
acatttatcc ccacgcatt accgatgtgc ggcctctcta ctctaggcgg cttccaaggg      3300
gggtgaaaca cctgaaggac tttcccatcc tccctggcga aatctttaag tataagtgga     3360
```

-continued

```
cagtgaccgt ggaggatgga ccaaccaaga gcgaccccag gtgcctgaca cgctattatt    3420
caagcttcgt gaatatggaa agggacctcg catctggctt gatcggccct ctgctgatat    3480
gttacaagga aagcgtcgat cagagaggaa atcagatcat gtcagacaaa aggaatgtga    3540
tcctgttctc cgtcttcgat gaaaacagga gctggtatct gacagagaac atccagagat    3600
tcctgccaaa tcccgccggc gtccagctgg aggacccgga gtttcaggca tctaacatca    3660
tgcattccat taatggttac gtgttcgact ccctgcagct gagcgtgtgc ctccacgagg    3720
tggcctactg gtacatcttg agcatcggcg cccagaccga cttcctgagc gtcttttct     3780
```
*(line 3780 continued reading)* ctttctgagc gtcttttct
```
ccgggtatac tttcaaacat aagatggtgt acgaagatac tctgacgctg ttccctttct    3840
ctggggagac tgtgtttatg tctatggaga ccctggact gtggattctc ggatgccaca     3900
```

```
acagtgactt tcgtaataga gggatgactg cactgctgaa ggtgtccagc tgtgataaaa    3960
atactggcga ctactacgaa gatagctatg aggatatctc agcatacctg ctgagcaaga    4020
ataacgccat cgagccccga agcttctcac agaatccccc tgtcctcaag gcccaccagg    4080
cggagatcac aaggaccaca ctccagtccg accaggagga gattgactac gatgacacga    4140
tttctgtgga gatgaaaaaa gaggactttg acatctacga tgaggatgaa aaccagagcc    4200
ctaggtcgtt ccagaagaaa acaaggcact acttcattgc cgccgtggag agactgtggg    4260
actacggaat gagtagttcc ccacacgtgt tgcggaacag agcccagagt gggtccgtcc    4320
cacagttcaa gaaggttgtt ttccaggagt tcacagatgg ctccttcact cagccactgt    4380
atcgcggcga gctgaatgag cacttgggct tattgggccc ctacattcgc gcagaagtcg    4440
aagataatat tatggtgacc ttccgcaacc aggccagccg gccttactca ttctactcct    4500
ctctcatctc ttatgaggag gatcagcgcc agggcgccga accccggaag aactttgtga    4560
agcccaatga aaccaaaact tacttttgga aggtgcagca ccatatggcg ccgacgaaag    4620
acgaatttga ctgcaaagcc tgggcctact tcagcgacgt cgactggag aaggacgtcc     4680
```
```
acagcggcct gattggccct tgttggtct gccataccaa tacactcaac cctgcccacg     4740
ggaggcaggt gaccgtgcag gagttttgcct tgttcttcac catcttcgac gaaaccaaga    4800
gctggtactt cacagagaac atggagagga actgcagagc accctgtaac atccagatgg    4860
aggaccctac tttcaaggaa aattacaggt tccatgccat taatggctac atcatggata    4920
ccctccccgg gcttgtgatg gctcaggacc agcgcatccg ctggtacctg ctctcaatgg    4980
gctccaacga gaacattcat agcatccact ttagtggcca cgtgtttacc gtgcgcaaga    5040
aggaggagta caagatggca ctgtacaacc tgtaccctgg cgtgtttgag acagtggaga    5100
tgctgccatc caaggccggc atctggcgcg tggagtgcct cattggggag cacctccatg    5160
ctggcatgtc tacactgttc ctggtgtaca gcaacaagtg tcagactcca ctcggaatgg    5220
cctccgggca tatccgcgat tttcagatca cggcctctgg ccagtatggc caatgggctc    5280
ccaagctggc caggctgcac tacagtggga gtatcaacgc ttggagcacc aaggagcctt    5340
tctcctggat caaggtggac ctgcttgccc ccatgattat tcacggcatt aagacacagg    5400
gggccaggca gaaattctcc tccctgtaca tctcccagtt catcatcatg tacagtctgg    5460
acggcaaaaa gtggcagacc taccgcggga acagtaccgg gacattgatg gtgttcttcg    5520
ggaacgtgga ctctagcggc attaaacaca acattttcaa ccccccatc attgctaggt     5580 atatcaggct ccatcccacc cactatagca tcaggtccac tctgcggatg gagctgatgg    5640
gctgcgacct taattcatgc agcatgccgc tgggcatgga gtcaaggcc atctccgacg      5700
```

| | |
|---|---|
| cccaaatcac cgcctccagc tacttcacca atatgttcgc cacctggagc cccagcaagg | 5760 |
| cccggctgca cctgcagggc cgcagcaacg cctggcggcc tcaggtgaac aaccccaagg | 5820 |
| agtggctgca ggtggacttc cagaaaacca tgaaggtgac tggggtcacc acccagggag | 5880 |
| tcaagagcct gctgaccagc atgtatgtga aggagttctt gatcagctcg tcacaggatg | 5940 |
| gccaccagtg gactttgttc tttcagaacg gtaaggtgaa agtgttccag ggaaaccaag | 6000 |
| attcctttac accagtggtc aactctctgg atcctcccct gctgacacgg tacctgcgga | 6060 |
| tccatcccca gtcatgggtg caccagattg ctctgcgcat ggaggtgctt ggctgcgagg | 6120 |
| cccaggacct gtactgaaat cgcggccgc taaacccagc tttcttgtac aaagtggcaa | 6180 |
| ctttattata catagttgat cctcaggtgc aggctgccta tcagaaggtg gtggctggtg | 6240 |
| tggccaatgc cctggctcac aaataccact gagatctttt tccctctgcc aaaaattatg | 6300 |
| gggacatcat gaagcccctt gagcatctga cttctggcta taaaggaaa tttattttca | 6360 |
| ttgcaatagt gtgttggaat ttttttgtgtc tctcactcgg aaggacatat gggagggcaa | 6420 |
| atcatttaaa acatcagaat gagtatttgg tttagagttt ggcaacatat gcccatatgc | 6480 |
| tggctgccat gaacaaaggt tggctataaa gaggtcatca gtatatgaaa cagcccctg | 6540 |
| ctgtccattc cttattccat agaaaagcct tgacttgagg ttagattttt tttatatttt | 6600 |
| gttttgtgtt attttttttct ttaacatccc taaaatttc cttacatgtt ttactagcca | 6660 |
| gatttttcct cctctcctga ctactcccag tcatagctgt ccctcttctc ttatggagat | 6720 |
| c | 6721 |

<210> SEQ ID NO 28
<211> LENGTH: 3733
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

| | |
|---|---|
| ctcgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtcgagg tgagccccac gttctgcttc actctcccca | 420 |
| tctcccccc ctccccaccc ccaattttgt atttatttat tttttaatta ttttgtgcag | 480 |
| cgatggggc ggggggggg ggggggcgcg cgccaggcgg ggcggggcgg ggcgagggc | 540 |
| ggggcgggc gaggcggaga ggtgcggcgg cagccaatca gagcggcgcg ctccgaaagt | 600 |
| ttcctttat ggcgaggcgg cggcggcggc ggccctataa aaagcgaagc gcgcggcggg | 660 |
| cgggagtcgc tgcgcgctgc cttcgccccg tgccccgctc cgccgccgcc tcgcgccgcc | 720 |
| cgccccggct ctgactgacc gcgttactcc cacaggtgag cgggcgggac ggcccttctc | 780 |
| ctccgggctg taattagcgc ttggtttaat gacggcttgt ttcttttctg tggctgcgtg | 840 |
| aaagccttga gggctccgg gagggccctt tgtgcggggg gagcggctcg ggggtgcgt | 900 |
| gcgtgtgtgt gtgcgtgggg agcgccgcgt gcggctccgc gctgcccggc ggctgtgagc | 960 |

-continued

```
gctgcgggcg cggcgcgggg ctttgtgcgc tccgcagtgt gcgcgagggg agcgcggccg   1020
ggggcggtgc cccgcggtgc ggggggggct gcgaggggaa caaaggctgc gtgcggggtg   1080
tgtgcgtggg ggggtgagca ggggtgtgg gcgcgtcggt cggctgcaa cccccctgc     1140
accccctcc ccgagttgct gagcacggcc cggcttcggg tgcggggctc cgtacggggc   1200
gtggcgcggg gctcgccgtg ccgggcgggg ggtggcggca ggtgggggtg ccgggcgggg   1260
cggggccgcc tcgggccggg gagggctcgg gggaggggcg cggcggcccc cggagcgccg   1320
gcggctgtcg aggcgcggcg agccgcagcc attgcctttt atggtaatcg tgcgagaggg   1380
cgcagggact tcctttgtcc caaatctgtg cggagccgaa atctgggagg cgccgccgca   1440
ccccctctag cgggcgcggg gcgaagcggt gcggcgccgg caggaaggaa atgggcgggg   1500
agggccttcg tgcgtcgccg cgccgccgtc cccttctccc tctccagcct cggggctgtc   1560
cgcgggggga cggctgcctt cgggggggac ggggcagggc ggggttcggc ttctggcgtg   1620
tgaccggcg ctctagagcc tctgctaacc atgttcatgc cttcttcttt ttcctacagc    1680
tcctgggcaa cgtgctggtt attgtgctgt ctcatcattt tggcaaagaa ttgcaagttt   1740
gtacaaaaaa gcaggctgcc accatgcagc gcgtgaacat gattatggcc gagtctcccg   1800
gcctgatcac catctgtctg ctgggctatc tgctgagcgc cgagtgcacc gtgtttctgg   1860
atcacgagaa cgccaacaag atcctgaaca gacccaagcg gtacaacagc ggcaagctgg   1920
aagagttcgt gcagggcaac ctggaacgcg agtgcatgga agagaagtgc agcttcgaag   1980
aggccagaga ggtgttcgag aacaccagaa gaaccaccga gttctggaag cagtacgtgg   2040
acggcgatca gtgcgagagc aacccttgtc tgaatggcgg cagctgcaag gacgacatca   2100
acagctacga gtgctggtgc cccttcggct tcgagggcaa gaattgcgag ctggacgtga   2160
cctgcaacat caagaacggc agatgcgagc agttctgcaa gaacagcgcc gacaacaagg   2220
tcgtgtgctc ctgcacagag ggctacgacg tggccgagaa ccagaagtct tgcgagcccg   2280
ctgtgccctt tccatgtggc agagtgtctg tgtcccagac cagcaagctg accagagccg   2340
agacagtgtt ccccgacgtg gactacgtga acagcaccga ggccgagaca atcctggaca   2400
acatcaccca gagcacccag tccttcaacg acttcaccag agtcgtcggc ggcgaggatg   2460
ctaagcctgg acagtttcct tggcaagtgg tgctgaacgg caaggtggac gcttttgtg    2520
gcggctccat cgtgaacgag aagtggatcg tgaccgccgc tcactgtgtg gaaaccggcg   2580
tgaagattac agtggtggcc ggcgagcaca acatcgagga acagagcac accgagcaga   2640
aacggaacgt gatcagaatc atccctcacc acaactacaa cgccgccatc aacaagtaca   2700
accacgatat cgccctgctg gaactggacg agcccctggt cctgaactct tacgtgaccc   2760
ctatctgtat cgccgacaaa gagtacacca acatctttct gaagttcggc agcggctacg   2820
tgtccggctg gggaagagtt ttccacaagg gcagatcagc cctggtgctg cagtacctga   2880
gagtgccct ggtggataga ccacatgcc tgctgagcac caagttcacc atctacaaca    2940
acatgttctg cgccggcttc cacgaaggcg gcagagattc ttgtcaaggc gattctggcg   3000
gccctcacgt gacagaggtt gagggcacaa gctttctgac cggcatcatc agctgggggcg   3060
aagagtgtgc catgaagggg aagtacgca tctacaccaa ggtgtccaga tacgtgaact   3120
ggatcaaaga aaagaccaag ctcacctgaa attcgcggcc gctaaaccca gctttcttgt   3180
acaaagtggc aactttatta tacatagttg atcctcaggt gcaggctgcc tatcagaagg   3240
tggtggctgg tgtggccaat gccctggctc acaaatacca ctgagatctt tttccctctg   3300
```

```
ccaaaaatta tggggacatc atgaagcccc ttgagcatct gacttctggc taataaagga   3360
aatttatttt cattgcaata gtgtgttgga attttttgtg tctctcactc ggaaggacat   3420
atgggagggc aaatcattta aaacatcaga atgagtattt ggtttagagt ttggcaacat   3480
atgcccatat gctggctgcc atgaacaaag gttggctata aagaggtcat cagtatatga   3540
aacagccccc tgctgtccat tccttattcc atagaaaagc cttgacttga ggttagattt   3600 ttttatatt ttgttttgtg ttatttttt ctttaacatc cctaaaattt tccttacatg   3660
ttttactagc cagattttc ctcctctcct gactactccc agtcatagct gtccctcttc   3720
tcttatggag atc                                                     3733
```

```
<210> SEQ ID NO 29
<211> LENGTH: 153
<212> TYPE: PRT
<213> ORGANISM: Homo sapiens
<220> FEATURE:
<221> NAME/KEY: SITE
<222> LOCATION: (1)..(20)
<223> OTHER INFORMATION: /note="Signal sequence"

<400> SEQUENCE: 29

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 30
<211> LENGTH: 65
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(25)
<223> OTHER INFORMATION: /note="Signal sequence"

<400> SEQUENCE: 30

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30
```

-continued

Val Ser Glu Ile Gln Leu Met His Asn Leu Gly Lys His Leu Asn Ser
          35                  40                  45

Met Glu Arg Val Glu Trp Leu Arg Lys Lys Leu Gln Asp Val His Asn
 50                  55                  60

Phe
65

<210> SEQ ID NO 31
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(25)
<223> OTHER INFORMATION: /note="Signal sequence"

<400> SEQUENCE: 31

Met Ile Pro Ala Lys Asp Met Ala Lys Val Met Ile Val Met Leu Ala
 1               5                  10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
          35                  40                  45

Met Glu Arg Val Glu Trp Leu Arg Lys Lys Leu Gln Asp Val His Asn
 50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
               100                 105                 110

Lys Ser Gln
       115

<210> SEQ ID NO 32
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(22)
<223> OTHER INFORMATION: /note="Signal sequence"

<400> SEQUENCE: 32

Met Ile Pro Ala Arg Phe Ala Gly Val Leu Leu Ala Leu Ala Leu Ile
 1               5                  10                  15

Leu Pro Gly Thr Leu Cys Ser Leu Ser Cys Arg Pro Met Val Lys
                20                  25                  30

Leu Val Cys Pro Ala Asp Asn Leu Arg Ala Glu Gly Leu Glu Cys Thr
                35                  40                  45

Lys Thr Cys Gln Asn Tyr Asp Leu Glu Cys Met Ser Met Gly Cys Val
 50                  55                  60

Ser Gly Cys Leu Cys Pro Pro Gly Met Val Arg His Glu Asn Arg Cys

```
                65                  70                  75                  80
Val Ala Leu Glu Arg Cys Pro Cys Phe His Gln Gly Lys Glu Tyr Ala
                        85                  90                  95
Pro Gly Glu Thr Val Lys Ile Gly Cys Asn Thr Cys Val Cys Arg Asp
                    100                 105                 110
Arg Lys Trp Asn Cys Thr Asp His Val Cys Asp Ala Thr Cys Ser Thr
                115                 120                 125
Ile Gly Met Ala His Tyr Leu Thr Phe Asp Gly Leu Lys Tyr Leu Phe
            130                 135                 140
Pro Gly Glu Cys Gln Tyr Val Leu Val Gln Asp Tyr Cys Gly Ser Asn
145                 150                 155                 160
Pro Gly Thr Phe Arg Ile Leu Val Gly Asn Lys Gly Cys Ser His Pro
                        165                 170                 175
Ser Val Lys Cys Lys Lys Arg Val Thr Ile Leu Val Glu Gly Gly Glu
                    180                 185                 190
Ile Glu Leu Phe Asp Gly Glu Val Asn Val Lys Arg Pro Met Lys Asp
                195                 200                 205
Glu Thr His Phe Glu Val Val Glu Ser Gly Arg Tyr Ile Ile Leu Leu
            210                 215                 220
Leu Gly Lys Ala Leu Ser Val Val Trp Asp Arg His Leu Ser Ile Ser
225                 230                 235                 240
Val Val Leu Lys Gln Thr Tyr Gln Glu Lys Val Cys Gly Leu Cys Gly
                        245                 250                 255
Asn Phe Asp Gly Ile Gln Asn Asn Asp Leu Thr Ser Ser Asn Leu Gln
                    260                 265                 270
Val Glu Glu Asp Pro Val Asp Phe Gly Asn Ser Trp Lys Val Ser Ser
                275                 280                 285
Gln Cys Ala Asp Thr Arg Lys Val Pro Leu Asp Ser Ser Pro Ala Thr
            290                 295                 300
Cys His Asn Asn Ile Met Lys Gln Thr Met Val Asp Ser Ser Cys Arg
305                 310                 315                 320
Ile Leu Thr Ser Asp Val Phe Gln Asp Cys Asn Lys Leu Val Asp Pro
                        325                 330                 335
Glu Pro Tyr Leu Asp Val Cys Ile Tyr Asp Thr Cys Ser Cys Glu Ser
                    340                 345                 350
Ile Gly Asp Cys Ala Cys Phe Cys Asp Thr Ile Ala Ala Tyr Ala His
                355                 360                 365
Val Cys Ala Gln His Gly Lys Val Val Thr Trp Arg Thr Ala Thr Leu
            370                 375                 380
Cys Pro Gln Ser Cys Glu Glu Arg Asn Leu Arg Glu Asn Gly Tyr Glu
385                 390                 395                 400
Cys Glu Trp Arg Tyr Asn Ser Cys Ala Pro Ala Cys Gln Val Thr Cys
                        405                 410                 415
Gln His Pro Glu Pro Leu Ala Cys Pro Val Gln Cys Val Glu Gly Cys
                    420                 425                 430
His Ala His Cys Pro Pro Gly Lys Ile Leu Asp Glu Leu Leu Gln Thr
                435                 440                 445
Cys Val Asp Pro Glu Asp Cys Pro Val Cys Glu Val Ala Gly Arg Arg
            450                 455                 460
Phe Ala Ser Gly Lys Lys Val Thr Leu Asn Pro Ser Asp Pro Glu His
465                 470                 475                 480
Cys Gln Ile Cys His Cys Asp Val Val Asn Leu Thr Cys Glu Ala Cys
                        485                 490                 495
```

```
Gln Glu Pro Gly Gly Leu Val Val Pro Pro
            500                 505

<210> SEQ ID NO 33
<211> LENGTH: 1247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(22)
<223> OTHER INFORMATION: /note="Signal sequence"

<400> SEQUENCE: 33

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320
```

-continued

```
Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
            370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
            450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735
```

```
His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
            850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
```

```
                    1145                1150                1155

His Pro Glu Pro Leu Ala Cys Pro Val Gln Cys Val Glu Gly Cys
        1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro
    1235                1240                1245

<210> SEQ ID NO 34
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 35
```

```
<211> LENGTH: 585
<212> TYPE: PRT
<213> ORGANISM: Homo sapiens

<400> SEQUENCE: 35

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
```

```
                385                 390                 395                 400
Tyr Lys Phe Gln Asn Ala Leu Leu Val Arg Tyr Thr Lys Lys Val Pro
                    405                 410                 415
Gln Val Ser Thr Pro Thr Leu Val Glu Val Ser Arg Asn Leu Gly Lys
                    420                 425                 430
Val Gly Ser Lys Cys Cys Lys His Pro Glu Ala Lys Arg Met Pro Cys
                    435                 440                 445
Ala Glu Asp Tyr Leu Ser Val Val Leu Asn Gln Leu Cys Val Leu His
                    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                    485                 490                 495
Tyr Val Pro Lys Glu Phe Asn Ala Glu Thr Phe Thr Phe His Ala Asp
                    500                 505                 510
Ile Cys Thr Leu Ser Glu Lys Glu Arg Gln Ile Lys Lys Gln Thr Ala
                    515                 520                 525
Leu Val Glu Leu Val Lys His Lys Pro Lys Ala Thr Lys Glu Gln Leu
                    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                    565                 570                 575
Ala Ala Ser Gln Ala Ala Leu Gly Leu
                    580                 585

<210> SEQ ID NO 36
<211> LENGTH: 415
<212> TYPE: PRT
<213> ORGANISM: Homo sapiens

<400> SEQUENCE: 36

Tyr Asn Ser Gly Lys Leu Glu Glu Phe Val Gln Gly Asn Leu Glu Arg
1               5                   10                  15
Glu Cys Met Glu Glu Lys Cys Ser Phe Glu Glu Ala Arg Glu Val Phe
                20                  25                  30
Glu Asn Thr Glu Arg Thr Thr Glu Phe Trp Lys Gln Tyr Val Asp Gly
                35                  40                  45
Asp Gln Cys Glu Ser Asn Pro Cys Leu Asn Gly Gly Ser Cys Lys Asp
            50                  55                  60
Asp Ile Asn Ser Tyr Glu Cys Trp Cys Pro Phe Gly Phe Glu Gly Lys
65                  70                  75                  80
Asn Cys Glu Leu Asp Val Thr Cys Asn Ile Lys Asn Gly Arg Cys Glu
                85                  90                  95
Gln Phe Cys Lys Asn Ser Ala Asp Asn Lys Val Val Cys Ser Cys Thr
                    100                 105                 110
Glu Gly Tyr Arg Leu Ala Glu Asn Gln Lys Ser Cys Glu Pro Ala Val
                115                 120                 125
Pro Phe Pro Cys Gly Arg Val Ser Val Ser Gln Thr Ser Lys Leu Thr
            130                 135                 140
Arg Ala Glu Thr Val Phe Pro Asp Val Asp Tyr Val Asn Ser Thr Glu
145                 150                 155                 160
Ala Glu Thr Ile Leu Asp Asn Ile Thr Gln Ser Thr Gln Ser Phe Asn
                165                 170                 175
```

```
Asp Phe Thr Arg Val Val Gly Gly Glu Asp Ala Lys Pro Gly Gln Phe
            180             185             190

Pro Trp Gln Val Val Leu Asn Gly Lys Val Asp Ala Phe Cys Gly Gly
        195             200             205

Ser Ile Val Asn Glu Lys Trp Ile Val Thr Ala Ala His Cys Val Glu
        210             215             220

Thr Gly Val Lys Ile Thr Val Val Ala Gly Glu His Asn Ile Glu Glu
225             230             235             240

Thr Glu His Thr Glu Gln Lys Arg Asn Val Ile Arg Ile Ile Pro His
                245             250             255

His Asn Tyr Asn Ala Ala Ile Asn Lys Tyr Asn His Asp Ile Ala Leu
            260             265             270

Leu Glu Leu Asp Glu Pro Leu Val Leu Asn Ser Tyr Val Thr Pro Ile
        275             280             285

Cys Ile Ala Asp Lys Glu Tyr Thr Asn Ile Phe Leu Lys Phe Gly Ser
    290             295             300

Gly Tyr Val Ser Gly Trp Gly Arg Val Phe His Lys Gly Arg Ser Ala
305             310             315             320

Leu Val Leu Gln Tyr Leu Arg Val Pro Leu Val Asp Arg Ala Thr Cys
            325             330             335

Leu Arg Ser Thr Lys Phe Thr Ile Tyr Asn Asn Met Phe Cys Ala Gly
            340             345             350

Phe His Glu Gly Gly Arg Asp Ser Cys Gln Gly Asp Ser Gly Gly Pro
            355             360             365

His Val Thr Glu Val Glu Gly Thr Ser Phe Leu Thr Gly Ile Ile Ser
    370             375             380

Trp Gly Glu Glu Cys Ala Met Lys Gly Lys Tyr Gly Ile Tyr Thr Lys
385             390             395             400

Val Ser Arg Tyr Val Asn Trp Ile Lys Glu Lys Thr Lys Leu Thr
                405             410             415
```

IMPLANTABLE PARTICLES AND RELATED METHODS

CLAIM OF PRIORITY

This application is a U.S. National Phase Application under 35 U.S.C. § 371 of International Application No. PCT/US2019/024371, filed Mar. 27, 2019, which claims priority to U.S. Provisional Application No. 62/652,880, filed Apr. 4, 2018; U.S. Application No. 62/737,838, filed Sep. 27, 2018; and U.S. Application No. 62/812,568, filed Mar. 1, 2019. The disclosure of each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 26, 2018, is named 52225-7022WO_SL.txt and is 205,145 bytes in size.

BACKGROUND

The function of implanted particles comprising engineered cells depends on numerous factors including the ability to provide a product and the biological immune response pathway of the recipient (Anderson et al., *Semin Immunol* (2008) 20:86-100; Langer, *Adv Mater* (2009) 21:3235-3236). The performance of such particles after implant will depend to a large extent on their biocompatibility, including the degree to which they are afibrotic, e.g., are able to avoid or mitigate the foreign-body response. Several publications have reported that the foreign body response (FBR) to implanted hydrogel capsules in rodents and non-human primates can be significantly reduced by using spherical capsules that have a size of at least 1 mm in diameter, e.g., millicapsules (Veiseh, O., et al, *Nature Materials* 14:643-652 (2015); WO2014/153126; WO2016/187225) and/or that are prepared using hydrogel-forming polymers that are chemically modified with certain compounds that mitigate the FBR (Vegas, A., et al., *Nature Medicine* 22(3):306-311 (2016), Vegas, A., et al., *Nature Biotechnology* 34(3):345-352 (2016); WO 2012/167223; WO 2017/075631).

SUMMARY

Described herein are particles comprising a first compartment, a second compartment, and a compound of Formula (I) (e.g., as described herein), as well as compositions and methods of making and using the same. In some embodiments, the particle comprises a cell (e.g., a cell described herein). In some embodiments, the cell produces a therapeutic agent useful, e.g., for the treatment of a disease, disorder or condition in a subject, e.g., a blood clotting disorder or a lysosomal storage disease. In some embodiments, the particle is capable of modulating the immune response (e.g., FBR) or the effect of an immune response (e.g., FBR) in a subject.

In one aspect, the present disclosure features a particle comprising a) a first compartment; b) a second compartment; and c) a compound of Formula (I):

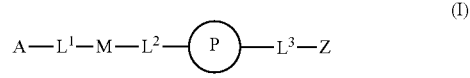

(I)

or a pharmaceutically acceptable salt thereof, wherein the variables A, $L^1$, M, $L^2$, P, $L^3$, and Z, as well as related subvariables, are defined herein. In some embodiments, the first compartment is surrounded by the second compartment. In some embodiments, the second compartment forms a barrier around the first compartment. In some embodiments, the first compartment comprises a compound of Formula (I). In some embodiments, the second compartment comprises a compound of Formula (I). In some embodiments, each of the first and second compartments independently comprise a compound of Formula (I). In some embodiments, a compound of Formula (I) is disposed on the exterior surface of the particle.

In some embodiments, the compound of Formula (I) or a pharmaceutically acceptable salt thereof (e.g., Formulas (I-a), (I-b), (I-c), (I-d), (I-e), (I-f), (II), (II-a), (III), (III-a), (III-b), (III-c), or (III-d)) is a compound described herein. In some embodiments, the compound of Formula (I) is one of the compounds shown in Table 2 herein.

In some embodiments, at least one of the compartments in the particle comprises a polymer. In some embodiments, both the first compartment and the second compartment of the particle comprise a polymer (e.g., a polysaccharide, e.g., alginate). In some embodiments, the first compartment and the second compartment of the particle comprise the same polymer. In some embodiments, the first compartment and the second compartment of the particle comprise a different polymer.

In some embodiments, the polymer is a polysaccharide or other hydrogel-forming polymer (e.g., alginate, hyaluronate or chondroitin). In some embodiments, the polymer is an alginate. In some embodiments, the particle comprises an alginate that is chemically modified with a compound of Formula (I). In some embodiments, the chemically modified alginate has a low molecular weight (e.g., approximate molecular weight of <75 kD). In some embodiments, the particle comprises a mixture of chemically modified alginate and unmodified alginate. In some embodiments, the particle is a hydrogel capsule. In some embodiments, the particle is a millicapsule or a microcapsule (e.g., a hydrogel millicapsule or a hydrogel microcapsule). In some embodiments, the particle is spherical. In some embodiments, the total volume (as defined herein) of the second compartment is greater than (e.g. >1.5×, 2×, 3×, or 5×) the volume of the first compartment. In some embodiments, the differential volume (as defined herein) of the second compartment is less than (e.g. <1.5×, 2×, 3×, or 5×) the volume of the first compartment. In some embodiments, the total volume of the second compartment is about 1%, 2%, 5%, 7.5%, 10%, 15%, 20%, 25%, 30%, 35%, 40%, 45%, 50%, 55%, 60%, 65%, or 75% greater than the volume of the first compartment. In some embodiments, the differential volume of the first compartment is greater than (e.g., >1.5×, 2×, 3×, or 5×) the volume of the second compartment. In some embodiments, the total volume of the first compartment is about 1%, 2%, 5%, 7.5%, 10%, 15%, 20%, 25%, 30%, 35%, 40%, 45%, 50%, 55%, 60%, 65%, or 75% greater than the volume of the second compartment.

In some embodiments, the particle has a largest linear dimension (LLD), e.g., diameter, of between about 20 nanometers to about 10 millimeters. In some embodiments, the largest linear dimension (LLD), e.g., diameter, of the particle is between about 500 nanometers to about 10 millimeters, between about 1 millimeter to 10 millimeters, between about 1 millimeter to 5 millimeters, between about 1 millimeter to 4 millimeters, between about 1 millimeter to 3 millimeters, between about 1 millimeter to 2 millimeters, or between about 1.5 millimeters to 2 millimeters or about 1.5 millimeters.

In some embodiments, the average distance between the outer boundary of the second (outer) compartment and the interface is between about 1 nanometers and 1 millimeter, e.g., between about 100 nanometers and 1 millimeter, between about 500 nanometers and about 1 millimeter, or between about 500 nanometers and 500 micrometers.

In some embodiments, the particle comprises a cell. In some embodiments, the first compartment comprises a cell and/or the second compartment comprises a cell. In some embodiments, the first compartment and the second compartment both comprise the same type of cell or different types of cells. In some embodiments, the first compartment comprises a cell and the second compartment does not comprise a cell. A particle described herein may comprise a plurality of cells. The cell or plurality of cells may be present in the particle as single cells, cell clusters (e.g., as spheroids), or attached to a microcarrier. In some embodiments, the particle is formed from a polymer solution and comprises at least any of 5, 10, 15, 20, 30, 40, 50, 75, 100, 150, 200, 250 or 400 million cells/ml of the polymer solution or any number between these values. In some embodiments, the particle comprises an epithelial cell, endothelial cell, fibroblast cell, mesenchymal stem cell, keratinocyte cell or an islet cell or a cell derived from any of the foregoing cell types. In some embodiments, the particle comprises a retinal pigment epithelial (RPE cell) or a mesenchymal stem cell (MSC). In some embodiments, the particle comprises an engineered cell (e.g., an engineered RPE cell or an engineered MSC).

In some embodiments, the particle comprises a cell that expresses a therapeutic agent, such as a nucleic acid (e.g., a nucleotide, DNA, or RNA), a polypeptide, a lipid, a sugar (e.g., a monosaccharide, disaccharide, oligosaccharide, or polysaccharide), or a small molecule. In some embodiments, the therapeutic agent is a replacement therapy or a replacement protein, e.g., useful for the treatment of a blood clotting disorder or a lysosomal storage disease in a subject. In some embodiments, the therapeutic agent is a polypeptide, e.g., a Factor VIII protein or variant thereof of a Factor IX protein or variant thereof.

In another aspect, the present disclosure features a preparation of a plurality of particles, wherein one or more of the particles in the plurality comprises: a) a first compartment; b) a second compartment; and c) a compound of Formula (I) as described herein. In some embodiments, each particle in the plurality comprises the first and second compartments and a compound of Formula (I). In some embodiments, at least 75%, 80%, 85%, 90%, 95%, 99%, or more of the particles in the plurality are spherical particles. In some embodiments, the preparation is a pharmaceutically acceptable preparation.

In another aspect, the present disclosure features a method of making a particle described herein. In some embodiments, the first compartment of the particle is formed at the same time as the second compartment of the particle. In some embodiments, the method comprises use of an electrostatic droplet generator equipped with a coaxial needle to form multiple droplets from first and second polymer solutions that comprise a hydrogel forming polymer or a mixture of hydrogel forming polymers. In some embodiments, the polymer or mixture of polymers is modified with a compound of Formula (I). In some embodiments, the polymer is an alginate. In some embodiments, the method further comprises contacting the droplets with a cross-linking solution comprising multivalent cations to cross-link each droplet into a particle (e.g., a hydrogel capsule with an inner compartment and an outer compartment). In some embodiments, the cross-linking solution comprises a cross-linking agent, a buffer, and an osmolarity-adjusting agent. In some embodiments, the cross-linking solution further comprises a surfactant.

In another aspect, the present disclosure features a method of implanting a particle described herein into a subject. In another aspect, the present disclosure features a method of providing a substance (e.g., a therapeutic agent, e.g., a polypeptide) to a subject comprising administering to the subject a particle described herein, wherein the particle comprises, or has the ability to produce, the substance. In another aspect, the present disclosure features a method of treating a subject in need of a substance (e.g., a therapeutic agent, e.g., a polypeptide) comprising administering to the subject a particle described herein, wherein the particle comprises, or has the ability to produce, the substance. In some embodiments, the administering step comprises implanting in the subject a pharmaceutically acceptable preparation comprising a plurality of particles, each of which comprises, or has the ability to produce, the substance. In some embodiments, the subject is a mammal (e.g., a human).

In another aspect, the present disclosure features a method of evaluating a particle described herein. In some embodiments, the method comprises providing a particle described herein and evaluating a structural or functional parameter of the particle. In some embodiments, the method comprises evaluating the particle or a plurality of particles described herein for one or more of: a) structural integrity; b) cell viability; c) the production of a therapeutic agent (e.g., a polypeptide); d) the uptake of a nutrient or oxygen; e) the production of a waste product; and f) fibrosis. In some embodiments, the evaluation is performed at least 1, 5, 10, 20, 30, 60, 90 or 120 days after formation of the particle or administration of the particle to a subject. In some embodiments, the subject is a mammal (e.g., a human).

The details of one or more embodiments of the disclosure are set forth herein. Other features, objects, and advantages of the disclosure will be apparent from the Detailed Description, the Figures, the Examples, and the Claims.

BRIEF DESCRIPTION OF THE DRAWINGS

FIGS. 2A-2B shows exemplary amino acid sequences encoded by exemplary engineered cells, with FIG. 2A showing the amino acid sequence (SEQ ID NO:1) of a Factor VIII-BDD protein encoded by an exemplary engineered cell and FIG. 2B showing the amino acid sequence (SEQ ID NO:2) of a human wild-type Factor IX protein.

FIG. 3 is a graph comparing quality of single-compartment and two-compartment hydrogel capsules as a function of equivalent cell loading (million cells/ml alginate), where ml alginate is the sum of alginate used to make the first (inner) compartment and second (outer) compartment of the two-compartment capsules.

FIG. 4A is a graph showing the mean second (outer) compartment thickness for particles (about 1.5 millimeter (mm) diameter) produced by varying flow rates of the polymer solutions used to form the first (inner) compartment and second (outer) compartments. FIG. 4B is a table of first (inner) compartment and second (outer) compartment volume percentages and the resulting compartment thicknesses achieved.

FIGS. 7A-7F illustrate the effect on fibrosis in vivo of varying the level of chemical modification on the alginate comprising the second (outer) compartment of exemplary particles (i.e., two-compartment hydrogel millicapsules). FIGS. 7A-7E are brightfield images of particles retrieved from C57/BL6 mice 1 week after implantation. Particles containing the engineered RPE cells within the first (inner) compartment had second (outer) compartments composed of: (i) low, medium or high levels of a compound of Formula (I) conjugated to an alginate, (ii) an unmodified alginate, or (iii) empty capsules composed of medium levels of a compound of Formula (I) conjugated to an alginate. FIG. 7F is a graph comparing the mean initial fracture of particles prior to implantation in a mouse model (initial, black bars) and after retrieval following 7 days implantation in C57/BL6 mice (retrieval, gray bars).

FIGS. 8A-8E are images comparing various hydrogel millicapsules and their effect on the fibrotic response. Schematics are shown of the millicapsules retrieved from C57/BL6 mice after a 2-week implantation. FIG. 8A: empty capsules comprising no cells. FIG. 8B: one-compartment capsules with 5000 cells/capsule; FIG. 8C: two-compartment capsules with 5000 cells/particle: FIG. 8D: two-compartment capsules with 2500 cells/capsule; FIG. 8E: two-compartment capsules with 2500 cells/capsule and a thicker second (outer) compartment.

FIGS. 9A-9K are immunofluorescent staining images comparing the level of macrophage adhesion in vivo on exemplary particles (i.e., two-compartment hydrogel millicapsules) with varying (low, medium, or high) amounts of chemically modified alginate in the second (outer) compartment at 1, 2, and 4 weeks post-implantation in C57/BL6 mice. A positive control (SLG20: unmodified medium MW alginate) and a negative control (empty capsule) were included in these experiments.

FIGS. 10A-10E are brightfield images indicating the level of fibrotic response on exemplary particles (i.e., two-compartment hydrogel millicapsules) 2 weeks post-implantation in C57/BL6 mice. The particles comprised varying (medium, medium high, high, or double high) amounts of chemically modified alginate in the second (outer) compartment. A negative control (empty) capsule with a medium amount of chemically modified alginate in the second (outer) compartment was also included.

FIG. 11 is a graph comparing the mean initial fracture of particles prior to implantation in a mouse model (initial, black bars) and after retrieval following 2 weeks of implantation in C57/BL6 mice (retrieval, gray bars). The particles comprise varying (medium, medium high, high, or double high) amounts of chemically modified alginate in the second (outer) compartment. A negative control (empty) capsule with a medium amount of chemically modified alginate in the second (outer) compartment was included.

FIGS. 12A-12C are brightfield images indicating the level of fibrotic response in vivo on exemplary particles (i.e., two-compartment hydrogel millicapsules) with either varying (medium or high) amounts of chemically modified alginate in the second (outer) compartment, or non-conjugated afibrotic small molecules (e.g., a compound of Formula (I)) in the second (outer) compartment ("amine added back" capsules), 2 weeks post-implantation in C57/BL6 mice.

FIGS. 13A-13F are immunofluorescent staining images comparing the level of macrophage adhesion in vivo on exemplary particles (i.e., two-compartment hydrogel millicapsules) with differing second (outer) compartments. The second (outer) compartments were prepared from either 70:30 or 60:40 ratio blends of chemically modified low-molecular weight (CM-LMW) alginate to unmodified high-molecular weight (U-HMW) alginate, and also with varying (medium, medium high, or high) amounts of chemically modified alginate in the second (outer) compartment.

FIGS. 14A-14D are brightfield images of encapsulated HEK293F cells in one-compartment or two-compartment hydrogel millicapsules that were cultured for 1 week after encapsulation. FIGS. 14A-14B correspond to images of one-compartment or two-compartment capsules. FIGS. 14C-14D correspond to images of the culture surface to identify cells not contained in the capsules following a 1-week incubation at 37° C.

FIG. 15A shows cell numbers in capsules prepared with different cell loading concentration prior to implant into the IP space mice (Initial) and upon retrieval five days after implant (Retrieval). FIGS. 15B and 15C show FIX levels in plasma and IP fluid produced by the implanted capsules, respectively.

FIG. 16A shows FIX levels in IP fluid of mice implanted with the capsules. FIG. 16B are brightfield images of the capsules prepared with 646 M/ml cells at the pre-implantation (initial) and retrieval time points.

FIGS. 17A-17FF shows in Tables 4-8 exemplary amino acid sequences and coding sequences for therapeutic polypeptides and nucleotide sequences within an exemplary expression vector useful for engineering RPE cells.

DETAILED DESCRIPTION

Figure 1:
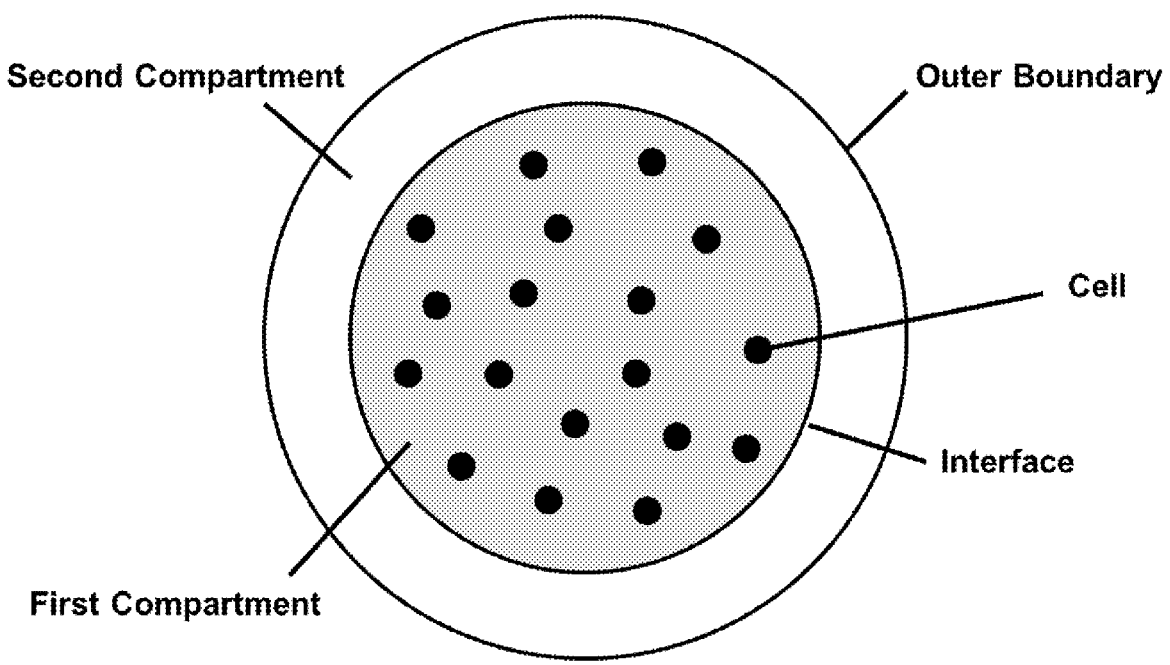
FIG. 1 illustrates an exemplary spherical particle of the disclosure, with lines indicating: a first, inner compartment and cells encapsulated therein; a second, outer compartment with an outer boundary; and the interface between the first and second compartments.

The present disclosure features a particle comprising a first compartment, a second compartment, and a compound of Formula (I) (e.g., as described herein), as well as compositions and methods of making and using the same. In some embodiments, the particles and compositions thereof are useful for the prevention or treatment of a disease, disorder, or condition. In some embodiments, particles configured as hydrogel millicapsules comprising a first hydrogel compartment and a second hydrogel compartment and a compound of Formula (I) exhibit advantageous properties, e.g., they are more afibrotic than similar millicapsules lacking a compound of Formula (I) but comprised of the same type of polymer, and substantially the same size, and can hold a greater number of cells with minimal detrimental effect on capsule quality compared with millicapsules containing a single compartment. In some embodiments, the particles described herein comprise a cell (e.g., an engineered cell) that produces a therapeutic agent (e.g., a polypeptide) suitable for treating a disease, disorder, or condition in a subject.

Abbreviations and Definitions

Throughout the detailed description and examples of the disclosure the following abbreviations will be used.
CM-Alg chemically modified alginate
CM-LMW-Alg chemically modified, low molecular weight alginate
CM-LMW-Alg-101 low molecular weight alginate, chemically modified with Compound 101 shown in Table 2
CM-HMW-Alg chemically modified, high molecular weight alginate
CM-HMW-Alg-101 high molecular weight alginate, chemically modified with Compound 101 shown in Table 2
CM-MMW-Alg chemically modified, medium molecular weight alginate
CM-MMW-Alg-101 medium molecular weight alginate, chemically modified with Compound 101 shown in Table 2
HMW-Alg high molecular weight alginate
MMW-Alg medium molecular weight alginate
U-Alg unmodified alginate
U-HMW-Alg unmodified high molecular weight alginate
U-LMW-Alg unmodified low molecular weight alginate
U-MMW-Alg unmodified medium molecular weight alginate
70:30 CM-Alg:U-Alg 70:30 mixture (V:V) of a chemically modified alginate and an unmodified alginate So that the disclosure may be more readily understood, certain technical and scientific terms used herein are specifically defined below. Unless specifically defined elsewhere in this document, all other technical and scientific terms used herein have the meaning commonly understood by one of ordinary skill in the art to which this disclosure belongs.

As used herein, including the appended claims, the singular forms of words such as "a," "an," and "the," include their corresponding plural references unless the context clearly dictates otherwise.

"About", when used herein to modify a numerically defined parameter (e.g., a physical description of a hydrogel capsule such as diameter, sphericity, number of cells in a particle, the number of particles in a preparation), means that the parameter may vary by as much as 15% above or below the stated numerical value for that parameter. For example, a hydrogel capsule defined as having a diameter of about 1.5 millimeters (mm) and encapsulating about 5 million (M) cells may have a diameter of 1.275 to 1.725 mm and may encapsulate about 4.25 M to 5.75 M cells. In some embodiments, about means that the parameter may vary by as much as 10% above or below the stated numerical value for that parameter.

"Acquire" or "acquiring", as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., fluorescence microscope to acquire fluorescence microscopy data.

"Administer", "administering", or "administration", as used herein, refer to implanting, absorbing, ingesting, injecting, or otherwise introducing an entity described herein (e.g., a particle comprising a first compartment, a second compartment, and a compound of Formula (I) (including particles encapsulating cells, e.g., engineered RPE cells), or a composition comprising said particles), or providing the same to a subject.

"Afibrotic", as used herein, refers to a compound or material that mitigates the foreign body response (FBR). For example, the amount of FBR in a biological tissue that is induced by implant into that tissue of a particle (e.g., a hydrogel capsule) comprising an afibrotic compound (e.g., a compound of Formula (I), e.g., a compound listed in Table 2) is lower than the FBR induced by implantation of an afibrotic-null reference particle, i.e., a particle that lacks the afibrotic compound or material, but is of substantially the same composition (e.g., same cell type(s)) and structure (e.g., size, shape, no. of compartments, same encapsulating polymers, etc.). In an embodiment, the degree of the FBR is assessed by the immunological response in the tissue containing the implanted particle (e.g., hydrogel capsule), which may include, for example, protein adsorption, macrophages, multinucleated foreign body giant cells, fibroblasts, and angiogenesis, using assays known in the art, e.g., as described in WO 2017/075630, or using one or more of the assays/methods described Vegas, A., et al., *Nature Biotechnol* (supra), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68 or F4/80), myfibroblasts (alpha-muscle actin, SMA) or general cellular deposition, quantification of 79 RNA sequences of known inflammation factors and immune cell markers, or FACS analysis for macrophage and neutrophil cells on retrieved particles (e.g., capsules) after a set time period (e.g., 14 days) in the intraperitoneal space of a suitable test subject, e.g., an immunocompetent mouse. In an embodiment, the FBR is assessed by measuring the levels in the tissue containing the implant of one or more biomarkers of immune response, e.g., cathepsin, TNF-α, IL-13, IL-6, G-CSF, GM-CSF, IL-4, CCL2, or CCL4. In some embodiments, the FBR induced by a particle described herein (e.g., a two-compartment hydrogel capsule comprising an afibrotic compound disposed in and/or on the surface of the outer compartment), is at least about 80%, about 85%, about 90%, about 95%, about 99%, or about 100% lower than the FBR induced by an FBR-null reference particle, e.g., a particle that is substantially identical to the claimed particle except for lacking the afibrotic compound or material but is otherwise substantially identical to the claimed particle. In some embodiments, the FBR (e.g., FBR biomarker level(s)) induced by an implanted particle is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Cell," as used herein, refers to an engineered cell or a cell that is not engineered. In an embodiment, a cell is an immortalized cell.

"Conservatively modified variants" or "conservative substitution", as used herein, refers to a variant of a reference peptide or polypeptide that is identical to the reference molecule, except for having one or more conservative amino acid substitutions in its amino acid sequence. In an embodiment, a conservatively modified variant consists of an amino acid sequence that is at least 70%, 80%, 85%, 90%, 95%, 97%, 98% or 99% identical to the reference amino acid sequence. A conservative amino acid substitution refers to substitution of an amino acid with an amino acid having similar characteristics (e.g., charge, side-chain size, hydrophobicity/hydrophilicity, backbone conformation and rigidity, etc.) and which has minimal impact on the biological activity of the resulting substituted peptide or polypeptide. Conservative substitution tables of functionally similar amino acids are well known in the art, and exemplary substitutions grouped by functional features are set forth in Table 1 below.

TABLE 1

Exemplary conservative amino acid substitution groups.

| Feature | Conservative Amino Group |
|---|---|
| Charge/Polarity | His, Arg, Lys |
|  | Asp, Glu |
|  | Cys, Thr, Ser, Gly, Asn, Gln, Tyr |
|  | Ala, Pro, Met, Leu, Ile, Val, Phe, Trp |
| Hydrophobicity | Asp, Glu, Asn, Gln, Arg, Lys |
|  | Cys, Ser, Thr, Pro, Gly, His, Tyr |
|  | Ala, Met, Ile Leu, Val, Phe, Trp |
| Structural/Surface Exposure | Asp, Glu, Asn, Aln, His, Arg, Lys |
|  | Cys, Ser, Tyr, Pro, Ala, Gly, Trp, Tyr |
|  | Met, Ile, Leu, Val, Phe |
| Secondary Structure Propensity | Ala, Glu, Aln, His, Lys, Met, Leu, Arg |
|  | Cys, Thr, Ile, Val, Phe, Tyr, Trp |
|  | Ser, Gly, Pro, Asp, Asn |

TABLE 1-continued

Exemplary conservative amino acid substitution groups.

| Feature | Conservative Amino Group |
|---|---|
| Evolutionary Conservation | Asp, Glu |
|  | His, Lys, Arg |
|  | Asn, Gln |
|  | Ser, Thr |
|  | Leu, Ile, Val |
|  | Phe, Tyr, Trp |
|  | Ala, Gly |
|  | Met, Cys |

"Consists essentially of", and variations such as "consist essentially of" or "consisting essentially of" as used throughout the specification and claims, indicate the inclusion of any recited elements or group of elements, and the optional inclusion of other elements, of similar or different nature than the recited elements, that do not materially change the basic or novel properties of the specified molecule, composition, particle, or method. As a non-limiting example, a therapeutic protein that consists essentially of a recited amino acid sequence may also include one or more amino acids, including substitutions in the recited amino acid sequence, of one or more amino acid residues, which do not materially affect the relevant biological activity of the therapeutic protein, respectively. As another non-limiting example, a polypeptide that consists essentially of a recited amino acid sequence may contain one or more covalently attached moieties (e.g., a radioactive or fluorescent label) that do not materially change the relevant biological activity of the polypeptide.

"Derived from", as used herein with respect to a cell or cells, refers to a cell or cells obtained from tissue, a cell line, or other cells, which optionally are then cultured, passaged, immortalized, differentiated and/or induced, to produce the derived cell(s).

"Differential volume," as used herein, refers to a volume of one compartment within a particle that excludes the space occupied by another compartment(s). For example, the differential volume of the second compartment in a 2-compartment particle refers to a volume within the second (e.g., outer) compartment that excludes space occupied by the first compartment.

"Effective amount" as used herein refers to an amount of a composition of particles (e.g., a particle composition) or a particle component, e.g, a cell, e.g., an engineered cell, or an agent, e.g., a therapeutic agent, produced by a cell, e.g., an engineered cell, sufficient to elicit a biological response, e.g., to treat a disease, disorder, or condition. In some embodiments, the term "effective amount" refers to the amount of a particle component, e.g., number of cells in the particle, the concentration or density of an afibrotic compound disposed on the particle surface and/or in the outer compartment. As will be appreciated by those of ordinary skill in this art, the effective amount may vary depending on such factors as the desired biological endpoint, the pharmacokinetics of the therapeutic agent, composition or particle, the condition being treated, the mode of administration, and the age and health of the subject. An effective amount encompasses therapeutic and prophylactic treatment. For example, to mitigate the FBR induced by a particle, an afibrotic-effective amount of a compound of Formula (I) may reduce the fibrosis or stop the growth or spread of fibrotic tissue on or near the implanted particle. An afibrotic-effective amount of a particle, composition or component thereof (e.g., an afibrotic compound, e.g., an afibrotic polymer) may be determined by any technique known in the art or described herein.

An "endogenous nucleic acid" as used herein, is a nucleic acid that occurs naturally in a subject cell.

An "endogenous polypeptide," as used herein, is a polypeptide that occurs naturally in a subject cell.

"Engineered cell," as used herein, is a cell (e.g., an RPE cell) having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide. In an embodiment, an engineered cell comprises an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a chromosomal or extra-chromosomal nucleic acid sequence, which comprises a sequence that encodes a polypeptide, or which is expressed as a polypeptide. In an embodiment, the exogenous nucleic acid sequence comprises a first chromosomal or extra-chromosomal exogenous nucleic acid sequence that modulates the conformation or expression of a second nucleic acid sequence, wherein the second amino acid sequence can be exogenous or endogenous. For example, an engineered cell can comprise an exogenous nucleic acid that controls the expression of an endogenous sequence. In an embodiment, an engineered cell comprises a polypeptide present at a level or distribution which differs from the level found in a similar cell that has not been engineered. In an embodiment, an engineered cell comprises an RPE cell engineered to provide an RNA or a polypeptide. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell (e.g., an RPE cell) comprises an exogenous nucleic acid sequence that comprises a chromosomal or extra-chromosomal nucleic acid sequence comprising a sequence that encodes a polypeptide, or which is expressed as a polypeptide. In an embodiment, an engineered cell (e.g., an RPE cell) comprises an exogenous nucleic acid sequence that modulates the conformation or expression of an endogenous sequence.

"An "exogenous nucleic acid," as used herein, is a nucleic acid that does not occur naturally in a subject cell.

An "exogenous polypeptide," as used herein, is polypeptide that does not occur naturally in a subject cell.

"Factor VII protein" or "FVII protein" as used herein, means a polypeptide that comprises the amino acid sequence of a naturally-occurring factor VII protein or variant thereof that has a FVII biological activity, e.g., promoting blood clotting, as determined by an art-recognized assay, unless otherwise specified. Naturally-occurring FVII exists as a single chain zymogen, a zymogen-like two-chain polypeptide and a fully activated two-chain form (FVIIa). In some embodiments, reference to FVII includes single-chain and two-chain forms thereof, including zymogen-like and FVIIa. FVII proteins that may be produced by a particle described herein (e.g., a two-compartment hydrogel capsule containing engineered RPE cells), include wild-type primate (e.g., human), porcine, canine, and murine proteins, as well as variants of such wild-type proteins, including fragments, mutants, variants with one or more amino acid substitutions and/or deletions. In some embodiments, a variant FVII protein is capable of being activated to the fully activated two-chain form (Factor VIIa) that has at least 50%, 75%, 90% or more (including >100%) of the activity of wild-type Factor VIIa. Variants of FVII and FVIIa are known, e.g., marzeptacog alfa (activated) (MarzAA) and the variants described in European Patent No. 1373493, U.S. Pat. Nos. 7,771,996, 9,476,037 and US published application No. US20080058255.

FVII biological activity may be quantified by an art recognized assay, unless otherwise specified. For example, FVII biological activity in a sample of a biological fluid, e.g., plasma, may be quantified by (i) measuring the amount of Factor Xa produced in a system comprising TF embedded in a lipid membrane and Factor X. (Persson et al., *J. Biol. Chem.* 272:19919-19924, 1997); (ii) measuring Factor X hydrolysis in an aqueous system; (iii) measuring its physical binding to tissue factor (TF) using an instrument based on surface plasmon resonance (Persson, *FEBS Letts.* 413:359-363, 1997); or (iv) measuring hydrolysis of a synthetic substrate; and/or (v) measuring generation of thrombin in a TF-independent in vitro system. In an embodiment, FVII activity is assessed by a commercially available chromogenic assay (BIOPHEN FVII, HYPHEN BioMed Neuville sur Oise, France), in which the biological sample containing FVII is mixed with thromboplastin calcium, Factor X and SXa-11 (a chromogenic substrate specific for Factor Xa.

"Factor VIII protein" or "FVIII protein" as used herein, means a polypeptide that comprises the amino acid sequence of a naturally occurring factor VIII polypeptide or variant thereof that has an FVIII biological activity, e.g., coagulation activity, as determined by an art-recognized assay, unless otherwise specified. FVIII proteins that may be expressed by a particle described herein, e.g., a two-compartment hydrogel capsule containing engineered RPE cells, include wild-type primate (e.g., human), porcine, canine, and murine proteins, as well as variants of such wild-type proteins, including fragments, mutants, variants with one or more amino acid substitutions and/or deletions, B-domain deletion (BDD) variants, single chain variants and fusions of any of the foregoing wild-type or variants with a half-life extending polypeptide. In an embodiment, the cells are engineered to encode a precursor factor VIII polypeptide (e.g., with the signal sequence) with a full or partial deletion of the B domain. In an embodiment, the cells are engineered to encode a single chain factor VIII polypeptide. A variant FVIII protein preferably has at least 50%, 75%, 90% or more (including >100%) of the coagulation activity of the corresponding wild-type factor VIII. Assays for measuring the coagulation activity of FVIII proteins include the one stage or two stage coagulation assay (Rizza et al., 1982, Coagulation assay of FVIII:C and FIXa in Bloom ed. The Hemophelias. NY Churchill Livingston 1992) or the chromogenic substrate FVIII:C assay (Rosen, S. 1984. *Scand J Haematol* 33:139-145, suppl.)

A number of FVIII-BDD variants are known, and include, e.g., variants with the full or partial B-domain deletions disclosed in any of the following U.S. Pat. No. 4,868,112 (e.g., col. 2, line 2 to col. 19, line 21 and table 2); U.S. Pat. No. 5,112,950 (e.g., col. 2, lines 55-68, FIG. 2, and example 1); U.S. Pat. No. 5,171,844 (e.g., col. 4, line1 22 to col. 5, line 36); U.S. Pat. No. 5,543,502 (e.g., col. 2, lines 17-46); U.S. Pat. Nos. 5,595,886; 5,610,278; 5,789,203 (e.g., col. 2, lines 26-51 and examples 5-8); U.S. Pat. No. 5,972,885 (e.g., col. 1, lines 25 to col. 2, line 40); U.S. Pat. No. 6,048,720 (e.g., col. 6, lines 1-22 and example 1); U.S. Pat. Nos. 6,060,447; 6,228,620; 6,316,226 (e.g., col. 4, line 4 to col. 5, line 28 and examples 1-5); U.S. Pat. Nos. 6,346,513; 6,458,563 (e.g., col. 4, lines 25-53) and U.S. Pat. No. 7,041,635 (e.g., col. 2, line 1 to col. 3, line 19, col. 3, line 40 to col. 4, line 67, col. 7, line 43 to col. 8, line 26, and col. 11, line 5 to col. 13, line 39).

In some embodiments, a FVIII-BDD protein produced by a particle described herein (e.g., expressed by engineered cells contained in the particle) has one or more of the following deletions of amino acids in the B-domain: (i) most of the B domain except for amino-terminal B-domain sequences essential for intracellular processing of the primary translation product into two polypeptide chains (WO 91/09122); (ii) a deletion of amino acids 747-1638 (Hoeben R. C., et al. *J. Biol. Chem.* 265 (13): 7318-7323 (1990)); amino acids 771-1666 or amino acids 868-1562 (Meulien P., et al. *Protein Eng.* 2(4):301-6 (1988); amino acids 982-1562 or 760-1639 (Toole et al., *Proc. Natl. Acad. Sci. U.S.A.* 83:5939-5942 (1986)); amino acids 797-1562 (Eaton et al., *Biochemistry* 25:8343-8347 (1986)); 741-1646 (Kaufman, WO 87/04187)), 747-1560 (Sarver et al., DNA 6:553-564 (1987)); amino acids 741-1648 (Pasek, WO 88/00831)), amino acids 816-1598 or 741-1689 (Lagner (Behring Inst. Mitt. (1988) No 82:16-25, EP 295597); a deletion that includes one or more residues in a furin protease recognition sequence, e.g., LKRHQR at amino acids 1643-1648, including any of the specific deletions recited in U.S. Pat. No. 9,956,269 at col. 10, line 65 to col. 11, line 36.

In other embodiments, a FVIII-BDD protein retains any of the following B-domain amino acids or amino acid sequences: (i) one or more N-linked glycosylation sites in the B-domain, e.g., residues 757, 784, 828, 900, 963, or optionally 943, first 226 amino acids or first 163 amino acids (Miao, H. Z., et al., *Blood* 103(a): 3412-3419 (2004), Kasuda, A., et al., *J. Thromb. Haemost.* 6: 1352-1359 (2008), and Pipe, S. W., et al., *J. Thromb. Haemost.* 9: 2235-2242 (2011).

In some embodiments, the FVIII-BDD protein is a single-chain variant generated by substitution of one or more amino acids in the furin protease recognition sequence (LKRHQR at amino acids 1643-1648) that prevents proteolytic cleavage at this site, including any of the substitutions at the R1645 and/or R1648 positions described in U.S. Pat. Nos. 10,023,628, 9,394,353 and 9,670,267.

In some embodiments, any of the above FVIII-BDD proteins may further comprise one or more of the following variations: a F3095 substitution to improve expression of the FVIII-BDD protein (Miao, H. Z., et al., Blood 103(a): 3412-3419 (2004); albumin fusions (WO 2011/020866); and Fc fusions (WO 04/101740).

All FVIII-BDD amino acid positions referenced herein refer to the positions in full-length human FVIII, unless otherwise specified.

"Factor IX protein" or "FIX protein", as used herein, means a polypeptide that comprises the amino acid sequence of a naturally occurring factor IX protein or variant thereof that has a FIX biological activity, e.g., coagulation activity, as determined by an art-recognized assay, unless otherwise specified. FIX is produced as an inactive zymogen, which is converted to an active form by factor XIa excision of the activation peptide to produce a heavy chain and a light chain held together by one or more disulfide bonds. FIX proteins that may be produced by a particle described herein (e.g., expressed by engineered RPE cells contained in the particle) include wild-type primate (e.g., human), porcine, canine, and murine proteins, as well as variants of such wild-type proteins, including fragments, mutants, variants with one or more amino acid substitutions and/or deletions and fusions of any of the foregoing wild-type or variant proteins with a half-life extending polypeptide. In an embodiment, cells are engineered to encode a full-length wild-type human factor IX polypeptide (e.g., with the signal sequence) or a functional variant thereof. A variant FIX protein preferably has at least 50%, 75%, 90% or more (including >100%) of the coagulation activity of wild-type factor VIX. Assays for measuring the coagulation activity of FIX proteins include the Biophen Factor IX assay (Hyphen BioMed) and the one stage clotting assay (activated partial thromboplastin time (aPTT), e.g., as described in EP 2 032 607 B2, thrombin generation time assay (TGA) and rotational thromboelastometry, e.g., as described in WO 2012/006624.

A number of functional FIX variants are known and may be expressed by engineered cells encapsulated in a particle described herein, including any of the functional FIX variants described in the following international patent publications: WO 02/040544 A3 at page 4, lines 9-30 and page 15, lines 6-31; WO 03/020764 A2 in Tables 2 and 3 at pages 14-24, and at page 12, lines 1-27; WO 2007/149406 A2 at page 4, line 1 to page 19, line 11; WO 2007/149406 A2 at page 19, line 12 to page 20, line 9; WO 08/118507 A2 at page 5, line 14 to page 6, line 5; WO 09/051717 A2 at page 9, line 11 to page 20, line 2; WO 09/137254 A2 at page 2, paragraph [006] to page 5, paragraph [011] and page 16, paragraph [044] to page 24, paragraph [057]; WO 09/130198 A2 at page 4, line 26 to page 12, line 6; WO 09/140015 A2 at page 11, paragraph [0043] to page 13, paragraph [0053]; WO 2012/006624; WO 2015/086406.

In certain embodiments, the FIX polypeptide comprises a wild-type or variant sequence fused to a heterologous polypeptide or non-polypeptide moiety extending the half-life of the FIX protein. Exemplary half-life extending moieties include Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. An exemplary FIX polypeptide is the rFIXFc protein described in WO 2012/006624, which is an FIXFc single chain (FIXF c-sc) and an Fc single chain (Fc-sc) bound together through two disulfide bonds in the hinge region of Fc.

FIX variants also include gain and loss of function variants. An example of a gain of function variant is the "Padua" variant of human FIX, which has a L (leucine) at position 338 of the mature protein instead of an R (arginine) (corresponding to amino acid position 384 of SEQ ID NO:2), and has greater catalytic and coagulant activity compared to wild-type human FIX (Chang et al., J. Biol. Chem., 273:12089-94 (1998)). An example of a loss of function variant is an alanine substituted for lysine in the fifth amino acid position from the beginning of the mature protein, which results in a protein with reduced binding to collagen IV (e.g., loss of function).

"Interleukin-2 protein" or "IL-2 protein", as used herein means a polypeptide comprising the amino acid sequence of a naturally occurring IL-2 protein or variant thereof that has an IL-2 biological activity, e.g., activate IL-2 receptor signaling in Treg cells, as determined by an art-recognized assay, unless otherwise specified. IL-2 proteins that may be produced by a particle described herein, e.g., a particle containing engineered RPE cells, include wild-type primate (e.g., human), porcine, canine, and murine proteins, as well as variants of such wild-type proteins. A variant IL-2 protein preferably has at least 50%, 75%, 90% or more (including >100%) of the biological activity of the corresponding wild-type IL-2. Biological activity assays for IL-2 proteins are described in U.S. Pat. No. 10,035,836, and include, e.g., measuring the levels of phosphorylated STAT5 protein in Treg cells compared to CD4+CD25−/low T cells or NK cells. Variant IL-2 proteins that may be produced by a particle of the present disclosure (e.g., a particle containing engineered RPE cells) include proteins with one or more of the following amino acid substitutions: N88R, N88I, N88G, D20H, Q126L, Q126F, and C125S or C125A.

"Islet cell" as used herein means a cell that comprises any naturally occurring or any synthetically created, or modified, cell that is intended to recapitulate, mimic or otherwise express, in part or in whole, the functions, in part or in whole, of the cells of the pancreatic islets of Langerhans. The term "islet cells" includes glucose-responsive, insulin producing cells derived from stem cells, e.g., from an induced pluripotent stem cell line.

"Mannitol", as used herein, refers to D-mannitol unless otherwise explicitly stated.

"Mesenchymal stem function cell" or "MSFC," as those terms are used herein, refers to a cell derived from, or having at least one characteristic specific to a cell of, mesodermal lineage, and wherein the MSFC is i) not in a terminal state of differentiation and ii) can terminally differentiate into one or more cell types. An MSFC does not comprise a cell of endodermal origin, e.g., a gut cell, or of ectodermal origin, e.g., a cell derived from skin, CNS, or a neural cell. In an embodiment, the MSFC is multipotent. In an embodiment, the MSFC is not totipotent. In an embodiment, an MSFC comprises one or more of the following characteristics:

a) it comprises a mesenchymal stem cell (MSC) or a cell derived therefrom, including a cell derived from a primary cell culture of MSC$_S$, a cell isolated directly (without long term culturing, e.g., less than 5 or 10 passages or rounds of cell division since isolation) from naturally occurring MSC$_S$, e.g., from a human or other mammal, a cell derived from a transformed, a pluripotent, an immortalized, or a long term (e.g., more than 5 or 10 passages or rounds of cell division) MSC culture. In an embodiment, the MSFC is derived from a human source, e.g., the blood (e.g., peripheral blood), bone marrow (e.g., the iliac crest, femora, tibiae, spine, rib, or knee), synovial tissue, adipose tissue, skin, fetal tissue, umbilical cord, or the placenta;

b) it comprises a cell that has been obtained from a less differentiated cell, e.g., a cell developed, programmed, or reprogramed (e.g., in vitro) into an MSC or a cell that is, except for any genetic engineering, substantially similar to one or more of a naturally occurring MSC or a cell from a primary or long term culture of MSC$_S$, or a cell described in a) above. Examples of less differentiated cells from which MSFC can be derived include IPS cells, embryonic stem cells, or other totipotent or pluripotent cells; see, e.g., Chen, Y. S. et al (2012) *Stem Cells Transl Med* 1(83-95); Frobel, J et al (2014) *Stem Cell Reports* 3(3):414-422; Zou, L et al (2013) Sci Rep 3:2243;

c) it is multipotent, e.g., as measured by any assay capable of providing information about cell multipotency, e.g., microscopy;

d) it exhibits a characteristic mononuclear ovoid, stellate shape or spindle shape, with a round to oval nucleus. The oval elongate nucleus may have prominent nucleoli and a mix of heterochromatin and euchromatin. An MSFC (e.g., an MSC) may have little cytoplasm, but many thin processes that appear to extend from the nucleus;

e) it is capable of cell division, e.g., as measured any assay capable of providing information about cell division, e.g., microscopy. In an embodiment, an MSFC is capable of cell division in culture (e.g., prior to being encapsulated or incorporated into a particle described herein). In an embodiment, it is capable of cell division after being encapsulated, e.g., encapsulated as described herein, or incorporated into a particle (e.g., a 2-compartment capsule described herein). In an embodiment, it is incapable of cell division after reaching confluence;

f) it is capable of differentiating into a mesenchymal cell lineage, e.g., an osteoblast, a chrondoblast, an adipocyte, or a fibroblast;

g) it expresses a mesenchymal cell marker, e.g., one, two, three, four, five or all of CD105, CD106, CD73, CD90, Stro-1, CD49a, CD29, CD44, CD146, CD166, TNAP+, THY-1+, Stro-2, Stro-4, and alkaline phosphatase;

h) it does not express significant levels of one, two, three, or any of CD34, CD31, VE-cadherin, CD45, HLA-DR, CD11b and a glycophorin or leukocyte differentiation antigen, e, g, CD14, CD33, CD3 and CD19;

i) it expresses one, two, or all of CD75, CD90, and CD105 and does not express one, two, or any of CD45, CD34, and CD14;

j) it is anti-inflammatory or immune-dampening, e.g., as measured by any method capable of providing information regarding inflammation, e.g., in vivo inhibition of T cell proliferation;

k) it is capable of being adherent, e.g., plastic adherent, e.g., as determined by, e.g., visual inspection; or l) can grow in three dimensions, e.g., as determined by, e.g., visual inspection.

"Parathyroid hormone" or "PTH" as used herein means a polypeptide or peptide that comprises the amino acid sequence of a naturally occurring parathyroid hormone polypeptide or peptide or variant thereof that has a PTH biological activity, e.g., as determined by an art recognized assay. PTH polypeptides and peptides that may be expressed by encapsulated cells described herein include wild-type primate (e.g., human), porcine, canine, and murine proteins, as well as variants of such wild-type proteins. Such PTH polypeptides and peptides may consist essentially of the wild-type human sequence for pre-pro-PTH polypeptide (115 amino acids), pro-PTH polypeptide (90 amino acids), the mature 84-amino acid peptide (PTH(1-84)), and biologically active variants thereof, such as the truncated variant peptide PTH(1-34). PTH peptide variants with/one or more amino acid substitutions in the human wild-type sequence have been described, e.g., in U.S. Pat. Nos. 7,410,948 and 8,563,513 and in US published patent application US20130217630. A PTH variant preferably has at least 50%, 75%, 90% or more (including >100%) of a biological activity of the corresponding wild-type PTH. An assay to detect certain PTH variants by tandem mass spectrometry is described in U.S. Pat. No. 8,383,417. A biological activity assay for PTH peptide variants—stimulation of adenylate cyclase as determined by measuring cAMP levels—is described in U.S. Pat. No. 7,410,948.

"Poloxamer", as used herein, refers to the standard generic term for a class of nonionic triblock linear copolymers composed of a central hydrophobic chain of polyoxypropylene (poly(propylene oxide)) flanked by two polyoxyethylene (poly(ethylene oxide)) moieties.

"Poloxamer 188" or "P 188", as used herein, refers to a poloxamer with an approximate molecular mass of 1800 g/mole for the polyoxypropylene core and an oxyethylene content of about 80% weight percent, e.g., 79.0 to 83.7 percent. In an embodiment, poloxamer 188 has an average molecular weight of 8350 g/mole. In an embodiment, poloxamer 188 has an average molecular weight of 7680 g/mole to 9510 g/mole, e.g., as determined by size exclusion chromatography, and an oxyethylene content of 81.8±1.9% weight percent. In an embodiment, each polyoxyethylene chain in poloxamer 188 has 75-85 (e.g., 80) ethylene oxide monomers and the polyoxypropylene core has 25-30 (e.g., 27) propylene oxide monomers. In an embodiment, poloxamer 188 used in a process described herein substantially meets the specifications set forth in a poloxamer monograph published by the United States Pharmacopeia-National Formulary (USP—NF) or the European Pharmacopoeia (Ph. Eur.) that is official at the time the process is performed.

"Poloxamer 407" or "P 407", as used herein, means a poloxamer with an approximate molecular mass of 4000 g/mole for the polypropylene core and an oxyethylene content of about 70% by weight. In an embodiment, poloxamer 407 has an average molecular weight of 9,840 g/mole to 14,600 g/mole and an oxyethylene content of 73.2±1.7% by weight. In an embodiment, each polyoxyethylene chain in poloxamer 407 has 95-105 (e.g., 101) ethylene oxide monomers (e.g., and the polyoxypropylene core has 54-60 (e.g., 56) propylene oxide monomers.

"Polypeptide", as used herein, refers to a polymer comprising amino acid residues linked through peptide bonds and having at least two, and in embodiments, at least 10, 50, 75, 100, 150 or 200 amino acid residues.

"Prevention," "prevent," and "preventing" as used herein refers to a treatment that comprises administering or applying a therapy, e.g., administering a composition of particles encapsulating cells (e.g., as described herein), prior to the onset of a disease, disorder, or condition to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

A "replacement therapy" or "replacement protein" is a therapeutic protein or functional fragment thereof that replaces or augments a protein that is diminished, present in insufficient quantity, altered (e.g., mutated) or lacking in a subject having a disease or condition related to the diminished, altered or lacking protein. Examples are certain blood clotting factors in certain blood clotting disorders or certain lysosomal enzymes in certain lysosomal storage diseases. In an embodiment, a replacement therapy or replacement protein provides the function of an endogenous protein. In an embodiment, a replacement therapy or replacement protein has the same amino acid sequence of a naturally occurring variant, e.g., a wild type allele or an allele not associated with a disorder, of the replaced protein. In an embodiment, or replacement therapy or a replacement protein differs in amino acid sequence from a naturally occurring variant, e.g., a wild type allele or an allele not associated with a disorder, e.g., the allele carried by a subject, at no more than about 1, 2, 3, 4, 5, 10, 15 or 20% of the amino acid residues.

"RPE cell" as used herein refers to a cell having one or more of the following characteristics: a) it comprises a retinal pigment epithelial cell (RPE) (e.g., cultured using the ARPE-19 cell line (ATCC® CRL-2302™)) or a cell derived therefrom, including a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogramed (e.g., in vitro) into an RPE cell or a cell that is, except for any genetic engineering, substantially similar to one or more of a naturally occurring RPE cell or a cell from a primary or long term culture of RPE cells (e.g., the cell can be derived from an IPS cell); or c) a cell that has one or more of the following properties: i) it expresses one or more of the biomarkers CRALBP, RPE-65, RLBP, BEST1, or αB-crystallin; ii) it does not express one or more of the biomarkers CRALBP, RPE-65, RLBP, BEST1, or αB-crystallin; iii) it is naturally found in the retina and forms a monolayer above the choroidal blood vessels in the Bruch's membrane; iv) it is responsible for epithelial transport, light absorption, secretion, and immune modulation in the retina; or v) it has been created synthetically, or modified from a naturally occurring cell, to have the same or substantially the same genetic content, and optionally the same or substantially the same epigenetic content, as an immortalized RPE cell line (e.g., the ARPE-19 cell line (ATCC® CRL-2302™)). In an embodiment, an RPE cell described herein is engineered, e.g., to have a new property, e.g., the cell is engineered to express a therapeutic protein. In other embodiments, an RPE cell is not engineered.

"Sequence identity" or "percent identical", when used herein to refer to two nucleotide sequences or two amino acid sequences, means the two sequences are the same within a specified region, or have the same nucleotides or amino acids at a specified percentage of nucleotide or amino acid positions within the specified when the two sequences are compared and aligned for maximum correspondence over a comparison window or designated region. Sequence identity may be determined using standard techniques known in the art including, but not limited to, any of the algorithms described in US Patent Publication No. 2017/02334455. In an embodiment, the specified percentage of identical nucleotide or amino acid positions is at least about 80%, 85%, 90%, 91%, 92%, 93%, 94%, 95%, 96%, 97%, 98%, 99% or higher.

"Spherical" as used herein, refers to a particle having a curved surface that forms a sphere (e.g., a completely round ball) or sphere-like shape. Spheres and sphere-like objects can be mathematically defined by rotation of circles, ellipses, or a combination around each of the three perpendicular axes, a, b, and c. For a sphere, the three axes a, b, and c are the same length. Generally, a sphere-like shape is an ellipsoid (for its averaged surface) with semi-principal axes a, b, and c that are within 10%, or 5%, or 2.5% of each other. The diameter of a sphere or sphere-like shape is the average diameter, such as the average of the semi-principal axes.

"Subject" as used herein refers to a human or non-human animal. In an embodiment, the subject is a human (i.e., a male or female), e.g., of any age group, a pediatric subject (e.g., infant, child, adolescent) or adult subject (e.g., young adult, middle-aged adult, or senior adult). In an embodiment, the subject is a non-human animal, for example, a mammal (e.g., a primate (e.g., a cynomolgus monkey or a rhesus monkey)). In an embodiment, the subject is a commercially relevant mammal (e.g., a cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Total volume," as used herein, refers to a volume within one compartment of a particle that includes the space occupied by another compartment. For example, the total volume of the second (e.g., outer) compartment of a two-compartment particle refers to a volume within the second compartment that includes space occupied by the first compartment.

"Treatment," "treat," and "treating" as used herein refers to one or more of reducing, reversing, alleviating, delaying the onset of, or inhibiting the progress of one or more of a symptom, manifestation, or underlying cause, of a disease, disorder, or condition. In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., considering a history of symptoms and/or in light of genetic or other susceptibility factors). Treatment may also be continued after symptoms have resolved, for example, to delay or prevent recurrence. In some embodiments, treatment comprises prevention and in other embodiments it does not.

"Von Willebrand factor protein" or "VWF protein", as used herein, means a polypeptide that comprises the amino acid sequence of a naturally occurring VWF polypeptide or variant thereof that has VWF biological activity, e.g., FVIII binding activity, as determined by an art-recognized assay, unless otherwise specified. VWF proteins that may be produced by a particle described herein (e.g., expressed by engineered cells contained in the particle) include wild-type primate (e.g., human), porcine, canine, and murine proteins, as well as variants of such wild-type proteins. The encapsulated cells may be engineered to encode any of the following VWF polypeptides: precursor VWF of 2813 amino acids, a VWF lacking the signal peptide of 22 amino acids and optionally the prepropeptide of 741 amino acids, mature VWF protein of 2050 amino acids, and truncated variants thereof, such as a VWF fragment sufficient to stabilize endogenous FVIII levels in VWF-deficient mice, e.g, a truncated variant containing the D'D3 region (amino acids 764-1247) or the D1D2D'D3 region; and VWF variants with one or more amino acid substitutions, e.g., in the D'region as described in U.S. Pat. No. 9,458,223. A variant VWF protein preferably has at least 50%, 75%, 90% or more (including >100%) of a biological activity of the corresponding wild-type VWF protein. Art-recognized assays for determining the biological activity of a VWF include ristocetin co-factor activity (Federici A B et al. 2004. *Haematologica* 89:77-85), binding of VWF to GP Ibα of the platelet glycoprotein complex Ib-V-IX (Sucker et al. 2006. *Clin Appl Thromb Hemost.* 12:305-310), and collagen binding (Kallas & Talpsep. 2001. *Annals of Hematology* 80:466-471).

In some embodiments, the VWF protein produced by a particle of the disclosure comprises a naturally-occurring or variant VWF amino acid sequence fused to a heterologous polypeptide or non-polypeptide moiety extending the half-life of theVWF protein. Exemplary half-life extending moieties include Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof.

Selected Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 10 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 12 carbon atoms ("$C_2$-$C_{12}$ alkenyl"), 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 12 carbon atoms ("$C_2$-$C_{10}$ alkynyl"), 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, —CH═CH—N($CH_3$)—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—Si($CH_3$)$_3$. Where "heteroalkyl" is recited, followed by recitations of specific heteroalkyl groups, such as —$CH_2O$, —$NR^CR^D$, or the like, it will be understood that the terms heteroalkyl and —$CH_2O$ or —$NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as —$CH_2O$, —$NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_2$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylene-diamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively. As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo [2.2.2]octanyl ($C_8$), bicyclo[2.1.1]hexanyl ($C_6$), bicyclo [3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5] decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom.

As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, $^{14}$C; O may be in any isotopic form, including $^{16}$O and $^{18}$O; and the like.

The term "pharmaceutically acceptable salt" is meant to include salts of the active compounds that are prepared with relatively nontoxic acids or bases, depending on the particular substituents found on the compounds described herein. When compounds used in the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the present disclosure contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

The present disclosure may employ compounds of Formula (I) in a prodrug form. Prodrugs are those compounds that readily undergo chemical changes under physiological conditions to provide the compounds useful in the present disclosure. Additionally, prodrugs can be converted to useful compounds of Formula (I) by chemical or biochemical methods in an ex vivo environment.

Certain compounds of Formula (I) described herein can exist in unsolvated forms as well as solvated forms, including hydrated forms. In general, the solvated forms are equivalent to unsolvated forms and are encompassed within the scope of the present disclosure. Certain compounds of Formula (I) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

The symbol "〰" as used herein refers to a connection to an entity, e.g., a polymer (e.g., hydrogel-forming polymer such as alginate) or an implantable element (e.g., a particle, device or material). The connection represented by "〰" may refer to direct attachment to the entity, e.g., a polymer or an implantable element, or may refer to linkage to the entity through an attachment group. An "attachment group," as described herein, refers to a moiety for linkage of a compound of Formula (I) to an entity (e.g., a polymer or an implantable element as described herein), and may comprise any attachment chemistry known in the art. A listing of exemplary attachment groups is outlined in *Bioconjugate Techniques* (3$^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N(R$^C$)—, —N(R$^C$)C(O)—, —C(O)N(R$^C$)—, —N(R$^C$)N(R$^D$)—, —NCN—, —C(=N(R$^C$)(R$^D$))O—, —S—, —S(O)$_x$—, —OS(O)$_x$—, —N(R$^C$)S(O)$_x$—, —S(O)$_x$N(R$^C$)—, —P(R$^F$)$_y$—, —Si(OR$^A$)$_2$—, —Si(R$^G$)(OR$^A$)—, —B(OR$^A$)—, or a metal, wherein each of R$^A$, R$^C$, R$^D$, R$^F$, R$^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)(C$_1$-C$_6$-alkylene)-, wherein alkylene is substituted with R$^1$, and R$^1$ is as described herein. In some embodiments, the attachment group is —C(O)(C$_1$-C$_6$-alkylene)-, wherein alkylene is substituted with 1-2 alkyl groups (e.g., 1-2 methyl groups). In some embodiments, the attachment group is —C(O)C(CH$_3$)$_2$—. In some embodiments, the attachment group is —C(O)(methylene)-, wherein alkylene is substituted with 1-2 alkyl groups (e.g., 1-2 methyl groups). In some embodiments, the attachment group is —C(O)CH(CH$_3$)—. In some embodiments, the attachment group is —C(O)C(CH$_3$)—.

Features of Particles

The present disclosure features particles comprising a first compartment, a second compartment, and a compound of Formula (I), e.g., a described herein. The particle may be spherical (e.g., a hydrogel capsule) or any other shape. The particle may comprise materials such as metals, metallic alloys, ceramics, polymers, fibers, inert materials, and combinations thereof. A particle may be completely made up of one type of material, or may comprise numerous other materials within the second compartment and any first compartments.

In some embodiments, the first compartment is modified with a compound of Formula (I). In some embodiments, the second compartment is modified with a compound of Formula (I). In some embodiments, both the first compartment and the second compartment are independently modified with a compound of Formula (I).

In some embodiments, a particle has a largest linear dimension (LLD), e.g., mean diameter, or size that is greater than 1 millimeter (mm), preferably 1.5 mm or greater. In some embodiments, a particle can be as large as 10 mm in diameter or size. For example, a particle described herein is in a size range of 0.5 mm to 10 mm, 1 mm to 10 mm, 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm. In some embodiments, the particle has a mean diameter or size between 1 mm to 8 mm. In some embodiments, the particle has a mean diameter or size between 1 mm to 4 mm. In some embodiments, the particle has a mean diameter or size between 1 mm to 2 mm. In some embodiments, the particle has a mean diameter or size between 1.5 mm to 2 mm.

In some embodiments, a particle has a largest linear dimension (LLD), e.g., mean diameter, or size that is 1 millimeter (mm) or smaller. In some embodiments, the particle is in a size range of 0.3 mm to 1 mm, 0.4 mm to 1 mm, 0.5 mm to 1 mm, 0.6 mm to 1 mm, 0.7 mm to 1 mm, 0.8 mm to 1 mm or 0.9 mm to 1 mm.

In some embodiments, the second (outer) compartment completely surrounds the first (inner) compartment, and the inner boundary of the second compartment forms an interface with the outer boundary of the first compartment, e.g., as illustrated in FIG. 1. In such embodiments, the thickness of the second (outer) compartment means the average distance between the outer boundary of the second compartment and the interface between the two compartments. In some embodiments, the thickness of the outer compartment is greater than about 10 nanometers (nm), preferably 100 nm or greater and can be as large as 1 mm. For example, the thickness of the outer compartment in a particle described herein may be 10 nanometers to 1 millimeter, 100 nanometers to 1 millimeter, 500 nanometers to 1 millimeter, 1 micrometer (μm) to 1 millimeter, 1 μm to 1 mm, 1 μm to 500 μm, 1 μm to 250 μm, 1 μm to 1 mm, 5 μm to 500 μm, 5 μm to 250 μm, 10 μm to 1 mm, 10 μm to 500 μm, or 10 μm to 250 μm. In some embodiments, the thickness of the outer compartment is 100 nanometers to 1 millimeters, between 1 μm and 1 mm, between 1 μm and 500 μm or between 5 μm and 1 mm.

In some embodiments, a particle comprises at least one pore or opening, e.g., to allow for the free flow of materials. In some embodiments, the mean pore size of a particle is between about 0.1 μm to about 10 μm. For example, the mean pore size may be between 0.1 μm to 10 μm, 0.1 μm to 5 μm, 0.1 μm to 2 μm, 0.15 μm to 10 μm, 0.15 μm to 5 μm, 0.15 μm to 2 μm, 0.2 μm to 10 μm, 0.2 μm to 5 μm, 0.25 μm to 10 μm, 0.25 μm to 5 μm, 0.5 μm to 10 μm, 0.75 μm to 10 μm, 1 μm to 10 μm, 1 μm to 5 μm, 1 μm to 2 μm, 2 μm to 10 μm, 2 μm to 5 μm, or 5 μm to 10 μm. In some embodiments, the mean pore size of a particle is between about 0.1 μm to 10 μm. In some embodiments, the mean pore size of a particle is between about 0.1 μm to 5 μm. In some embodiments, the mean pore size of a particle is between about 0.1 μm to 1 μm. In some embodiments, the mean pore size of the first compartment and the second compartment of the particle is substantially the same. In some embodiments, the mean pore size of the first compartment and the second compartment of the particle differ by about 1.5%, 2%, 5%, 7.5%, 10%, 15%, 20%, 25%, 30%, 35%, 40%, 45%, 50%, 55%, 60%, 65%, 70%, 75%, or more. In some embodiments, the mean pore size of the particle (e.g., mean pore size of the first compartment and/or mean pore size of the second compartment) is dependent on a number of factors, such as the material(s) within each compartment and the presence and density of a compound of Formula (I).

In some embodiments, the particle comprises a metal or a metallic alloy. The first compartment, the second compartment, or both compartments may comprise a metal or a metallic alloy. Exemplary metallic or metallic alloys include comprising titanium and titanium group alloys (e.g., nitinol, nickel titanium alloys, thermo-memory alloy materials), platinum, platinum group alloys, stainless steel, tantalum, palladium, zirconium, niobium, molybdenum, nickel-chrome, chromium molybdenum alloys, or certain cobalt alloys (e.g., cobalt-chromium and cobalt-chromium-nickel alloys, e.g., ELGILOY® and PHYNOX®). For example, a metallic material may be stainless steel grade 316 (SS 316L) (comprised of Fe, <0.3% C, 16-18.5% Cr, 10-14% Ni, 2-3% Mo, <2% Mn, <1% Si, <0.45% P, and <0.03% S). In metal-containing particles, the amount of metal (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the particle comprises a ceramic. The first compartment, the second compartment, or both compartments may comprise a ceramic. Exemplary ceramic materials include oxides, carbides, or nitrides of the transition elements, such as titanium oxides, hafnium oxides, iridium oxides, chromium oxides, aluminum oxides, and zirconium oxides.

Silicon based materials, such as silica, may also be used. In ceramic-containing particles, the amount of ceramic (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the particle comprises a polymer. The first compartment, the second compartment, or both compartments may comprise a polymer. A polymer may be a linear, branched, or cross-linked polymer, or a polymer of selected molecular weight ranges, degree of polymerization, viscosity or melt flow rate. Branched polymers can include one or more of the following types: star polymers, comb polymers, brush polymers, dendronized polymers, ladders, and dendrimers. A polymer may be a thermoresponsive polymer, e.g., gel (e.g., becomes a solid or liquid upon exposure to heat or a certain temperature) or a photocrosslinkable polymer. Exemplary polymers include polystyrene, polyethylene, polypropylene, polyacetylene, poly(vinyl chloride) (PVC), polyolefin copolymers, poly(urethane)s, polyacrylates and polymethacrylates, polyacrylamides and polymethacrylamides, poly(methyl methacrylate), poly(2-hydroxyethyl methacrylate), polyesters, polysiloxanes, polydimethylsiloxane (PDMS), polyethers, poly(orthoester), poly(carbonates), poly(hydroxyalkanoate)s, polyfluorocarbons, PEEK®, Teflon® (polytetrafluoroethylene, PTFE), PEEK, silicones, epoxy resins, Kevlar®, Dacron® (a condensation polymer obtained from ethylene glycol and terephthalic acid), polyethylene glycol, nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polyethylene glycol and 2-hydroxyethyl methacrylate (HEMA), polysaccharides, poly(glycolic acid), poly(L-lactic acid) (PLLA), poly(lactic glycolic acid) (PLGA), a polydioxanone (PDA), or racemic poly(lactic acid), polycarbonates, (e.g., polyamides (e.g., nylon)), fluoroplastics, carbon fiber, agarose, alginate, chitosan, and blends or copolymers thereof. In polymer-containing particles, the amount of a polymer (e.g., by % weight of the particle, actual weight of the polymer) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the polymer comprises a polyethylene. The first compartment, the second compartment, or both compartments may comprise a polyethylene. Exemplary polyethylenes include ultra-low-density polyethylene (ULDPE) (e.g., with polymers with densities ranging from 0.890 to 0.905 g/cm$^3$, containing comonomer); very-low-density polyethylene (VLDPE) (e.g., with polymers with densities ranging from 0.905 to 0.915 g/cm$^3$, containing comonomer); linear low-density polyethylene (LLDPE) (e.g., with polymers with densities ranging from 0.915 to 0.935 g/cm$^3$, contains comonomer); low-density polyethylene (LDPE) (e.g., with polymers with densities ranging from about 0.915 to 0.935 g/m$^3$); medium density polyethylene (MDPE) (e.g., with polymers with densities ranging from 0.926 to 0.940 g/cm$^3$, may or may not contain comonomer); high-density polyethylene (HDPE) (e.g., with polymers with densities ranging from 0.940 to 0.970 g/cm$^3$, may or may not contain comonomer).

In some embodiments, the particle comprises a polypropylene. The first compartment, the second compartment, or both compartments may comprise a polypropylene. Exemplary polypropylenes include homopolymers, random copolymers (homophasic copolymers), and impact copolymers (heterophasic copolymers), e.g., as described in McKeen, *Handbook of Polymer Applications in Medicine and Medical Devices,* 3—Plastics Used in Medical Devices, (2014): 21-53, which is incorporated herein by reference in its entirety.

In some embodiments, the particle comprises a polystyrene. The first compartment, the second compartment, or both compartments may comprise a polystyrene. Exemplary polystyrenes include general purpose or crystal (PS or GPPS), high impact (HIPS), and syndiotactic (SPS) polystyrene.

In some embodiments, the particle comprises a thermoplastic elastomer (TPE). The first compartment, the second compartment, or both compartments may comprise a TPE. Exemplary TPEs include (i) TPA-polyamide TPE, comprising a block copolymer of alternating hard and soft segments with amide chemical linkages in the hard blocks and ether and/or ester linkages in the soft blocks; (ii) TPC-co-polyester TPE, consisting of a block copolymer of alternating hard segments and soft segments, the chemical linkages in the main chain being ester and/or ether; (iii) TPO-olefinic TPE, consisting of a blend of a polyolefin and a conventional rubber, the rubber phase in the blend having little or no cross-linking; (iv) TPS-styrenic TPE, consisting of at least a triblock copolymer of styrene and a specific diene, where the two end blocks (hard blocks) are polystyrene and the internal block (soft block or blocks) is a polydiene or hydrogenated polydiene; (v) TPU-urethane TPE, consisting of a block copolymer of alternating hard and soft segments with urethane chemical linkages in the hard blocks and ether, ester or carbonate linkages or mixtures of them in the soft blocks; (vi) TPV-thermoplastic rubber vulcanizate consisting of a blend of a thermoplastic material and a conventional rubber in which the rubber has been cross-linked by the process of dynamic vulcanization during the blending and mixing step; and (vii) TPZ-unclassified TPE comprising any composition or structure other than those grouped in TPA, TPC, TPO, TPS, TPU, and TPV.

In some embodiments, the particle comprises a polysaccharide, and the polysaccharide is an alginate. Alginate is a polysaccharide made up of β-D-mannuronic acid (M) and α-L-guluronic acid (G). In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1. In some embodiments, the ratio of M:G is greater than 1. In alginate-containing particles, the amount of alginate (e.g., by % weight of the particle, actual weight of the alginate) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, both the first compartment and the second compartment comprise the same polymer. In some embodiments, the first compartment and the second compartment comprise different polymers. In some embodiments, the first compartment comprises an alginate. In some embodiments, the second compartment comprises an alginate. In some embodiments, both the first compartment and the second compartment comprise an alginate. In some embodiments, the alginate in the first compartment is different than the alginate in the second compartment. In some embodiments, the first compartment comprises an alginate and the second compartment comprises a different polymer (e.g., a polysaccharide, e.g., hyaluronate or chitosan). In some embodiments, the second compartment comprises an alginate and the first compartment comprises a different polymer (e.g., a polysaccharide, e.g., hyaluronate or chitosan).

Both the first compartment and the second compartment may include a single component (e.g., one polymer) or more than one component (e.g., a blend of polymers). In some embodiments, the first compartment comprises only alginate (e.g., chemically modified alginate, or a blend of an unmodified alginate and a chemically modified alginate). In some embodiments, the second compartment comprises only alginate (e.g., chemically modified alginate or a blend of an unmodified alginate and a chemically modified alginate). In some embodiments, both the first and the second compartment independently comprise only alginate (e.g., chemically modified alginate or blend of an unmodified alginate and a chemically modified alginate).

In some embodiments, the polymer in one or both of the first and second compartments is (i) a low-molecular weight alginate, e.g., has an approximate MW<75 kDa and G:M ratio≥1.5, (ii) a medium molecular weight alginate, e.g., has approximate molecular weight of 75-150 kDa and G:M ratio≥1.5, (iii) a high molecular weight alginate, e.g., has an approximate MW of 150 kDa-250 kDa and G:M ratio≥1.5, (iv) or a blend of two or more of these alginates. In an embodiment, the polymer in the first (inner) compartment is an unmodified, high molecular weight alginate or an unmodified, medium molecular weight alginate and the polymer in the second (outer) compartment is a blend of a chemically-modified alginate (e.g., alginate modified with Compound 101 shown in Table 2) and an unmodified alginate, e.g, a 70:30 blend or a 60:40 blend of CM-LMW-Alg-101:U-HMW-Alg, which may be prepared as described in the Examples below.

In some embodiments, the particle comprises alginate, and the compound of Formula (I) is covalently attached to some or all the monomers in the alginate. In some embodiments, some or all the monomers in the alginate are modified with the same compound of Formula (I). In some embodiments, some or all the monomers in the alginate are modified with different compounds of Formula (I).

In some embodiments, a polymer of the first compartment of the particle is modified with one compound of Formula (I), and a polymer of the second compartment of the particle is modified with a different compound of Formula (I). In some embodiments, the particle comprises a mixture of polymers modified with a compound of Formula (I) and unmodified polymers (e.g., polymers not modified with a compound of Formula (I)). In some embodiments, the first compartment comprises a mixture of polymers modified with a compound of Formula (I) and unmodified polymers (e.g., polymers not modified with a compound of Formula (I)). In some embodiments, the second compartment comprises a mixture of polymers modified with a compound of Formula (I) and unmodified polymers (e.g., polymers not modified with a compound of Formula (I)).

A polymer of a particle described herein may be modified with a compound of Formula (I) or a pharmaceutically acceptable salt thereof on one or more monomers of the polymer. The modified polymer of the particle may be present in the first (inner) compartment of the particle, the second (outer) compartment of the particle, or both the first (inner) and second (outer) compartments of the particle. In some embodiments, the modified polymer is present only in the second compartment (which includes the exterior particle surface). In some embodiments, at least 0.5% of the monomers of a polymer are modified with a compound of Formula (I) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of a polymer are modified with a compound of Formula (I)).

In some embodiments, 0.5% to 50%, 10% to 90%, 10% to 50%, or 25-75%, of the monomers of a polymer are modified with a compound of Formula (I). In some embodiments, 1% to 20% of the monomers of a polymer are modified with a compound of Formula (I). In some embodiments, 1% to 10% of the monomers of a polymer are modified with a compound of Formula (I).

In some embodiments, the polymer (e.g., alginate) (when modified with a compound of Formula (I), e.g., Compound 101 of Table 2) comprises an increase in % N (as compared with unmodified polymer, e.g., alginate) of any of the following values: (i) at least 0.1%, 0.2%, 0.5%, 1.0%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% N by weight; (ii) 0.1% to 10% by weight, (iii) 0.1% to 2% N by weight; (iv) 2% to 4% N by weight; (v) 4% to 8% N by weight; (vi) 5% to 9% N by weight; (vii) 6% to 9% N by weight, (viii) 6% to 8% N by weight; (ix) 7% to 9% N by weight; and (x) 8% to 9% N by weight where, in each case, % N is determined by combustion analysis (e.g., as described in Example 2 herein) and corresponds to the amount of compound of Formula (I) in the modified polymer.

A particle (e.g., a first compartment or second compartment therein) may comprise a compound of Formula (I) in an amount that confers a specific feature to the particle. For example, the particle surface (e.g., the exterior of the outer compartment) may comprise a concentration or density of a compound of Formula (I) such that the particle is afibrotic (i.e., mitigates the foreign body response) in a subject. In an embodiment, the particle surface comprises an alginate chemically modified with an afibrotic-effective amount of Compound 101. In an embodiment, the afibrotic-effective amount of Compound 101 produces an increase in % N (as compared with the unmodified alginate) of about 0.5% to 2% 2% to 4% N, about 4% to 6% N, about 6% to 8%, or about 8% to 10% N), where % N is determined by combustion analysis (e.g., as described in Example 2 herein) and corresponds to the amount of Compound 101 in the modified alginate.

As described in the examples below, certain higher concentrations of a compound of Formula (I) in the outer-compartment of two-compartment alginate hydrogel capsules compromised the mechanical strength of the capsules, possibly due to a reduction in sites on the alginate molecules that are available for cross-linking. Thus, in an embodiment, the particle surface (e.g., the exterior of the outer compartment) may comprise a concentration or density of a Formula (I) compound that is high enough to render the particle afibrotic but is lower than a threshold at which a desired mechanical strength is not achieved. In an embodiment, a desired mechanical strength refers to the ability of the particle to maintain its shape and/or remain intact when subjected to any one or more of the following stressors: (i) compression (e.g., at a constant rate); (ii) during administration (e.g., implantation) to a subject; and (iii) after a desired implantation period. The mechanical strength of a particle may be measured prior to implantation of the particle in a subject and/or after retrieval of the implanted particle (e.g., after 1 day, 2 days, 3 days, 4 days, 5 days, 6 days, 1 week, 2 weeks, 3 weeks, 4 weeks, 6 weeks, 8 weeks, 12 weeks, or longer after implant). In an embodiment, the desired mechanical strength of a particle (e.g., a hydrogel capsule) determined after manufacture but before implantation is determined by performing a fracture test using a texture analyzer.

In an embodiment, mechanical testing of hydrogel capsules is performed on a TA.XT plus Texture Analyzer (Stable Micro Systems, Surrey, United Kingdom) using a 5 mm probe attached to a 5 kg load cell. Individual capsules are placed on a platform and are compressed from above by the probe at a fixed rate of 0.5 mm/sec. Contact between the probe and capsule is detected when a repulsive force of 1 g is measured. The probe continues to travel 90% of the distance between the contact height of the probe and the platform, compressing the capsule to the point of bursting. The resistance to the compressive force of the probe is measured and can be plotted as a function of probe travel (force v. displacement curve). Typically, before a capsule bursts completely it will fracture slightly and the force exerted against the probe will decrease a small amount. An analysis macro can be programmed to detect the first time a decrease of 0.25-0.5 g occurs in the force v. displacement curve. The force applied by the probe when this occurs is termed the initial fracture force. In an embodiment, the desired mechanical strength of a particle described herein (e.g., a two-compartment hydrogel capsule) has an initial fracture force of greater than 1, 1.5, 2, 2.5 or 3 grams or at least 2 grams.

In an embodiment, the desired mechanical strength of a particle is the ability to remain intact at a desired timepoint after implantation in a subject, e.g., both the outer and inner compartments of a hydrogel capsule removed from a subject are visibly intact after retrieval from an immune competent mouse when observed by optical microscopy, e.g., by brightfield imaging as described in the Examples herein.

In an embodiment, the particle surface comprises an alginate chemically modified with Compound 101 in an amount that provides the particle with both an afibrotic property and a desired mechanical strength, e.g., a concentration or density of Compound 101 in the modified alginate that produces an increase in % N (as compared with the unmodified alginate) of any of the following values: (i) 1% to 3% by weight, (ii) 2% to 4% N by weight; (iii) 4% to 8% N by weight; (iv) 5% to 9% N by weight; (v) 6% to 9% N by weight, (vi) 6% to 8% N by weight; (vii) 7% to 9% N by weight; and (ix) 8% to 9% N by weight; where, in each case, % N is determined by combustion analysis (e.g., as described in Example 2 herein) and corresponds to the amount of compound of Formula (I) in the modified alginate.

When a particle (e.g., a first compartment or second compartment therein) comprises alginate, the alginate can be chemically modified with a compound of Formula (I) using any suitable method known in the art. For example, the alginate carboxylic acid moiety can be activated for coupling to one or more amine-functionalized compounds to achieve an alginate modified with a compound of Formula (I). The alginate polymer may be dissolved in water (30 mL/gram polymer) and treated with 2-chloro-4,6-dimethoxy-1,3,5-triazine (0.5 eq) and N-methylmorpholine (1 eq). To this mixture may be added a solution of the compound of Formula (I) dissolved in a buffer or solvent, such as acetonitrile (0.3 M). The reaction may be warmed, e.g., to 55° C. for 16 h, then cooled to room temperature and concentrated via rotary evaporation. The residue may then be dissolved in a buffer or solvent, e.g., water. The mixture may then be filtered, e.g., through a bed of cyano-modified silica gel (Silicycle) and the filter cake washed with water. The resulting solution may then be dialyzed (10,000 MWCO membrane) against a buffer or water for 24 hours, e.g., replacing the buffer or water at least one time, at least two times, at least three times, or more. The resulting solution can be concentrated, e.g., via lyophilization, to afford the desired chemically modified alginate.

In some embodiments, a particle described herein comprises a cell. In some embodiments, the cell is engineered to produce a therapeutic agent (e.g., a protein or polypeptide, e.g., an antibody, protein, enzyme, or growth factor). In some embodiments, the cell is disposed with the first compartment. In some embodiments, the cell is disposed within the second compartment. In some embodiments, the cell is disposed in the first compartment and the second compartment does not comprise a cell. A particle may comprise an active or inactive fragment of a protein or polypeptide, such as glucose oxidase (e.g., for glucose sensor), kinase, phosphatase, oxygenase, hydrogenase, reductase.

In some embodiments, a particle is capable of preventing materials over a certain size from passing through a pore or opening. In some embodiments, a particle is capable of preventing materials greater than 50 kD, 75 kD, 100 kD, 125 kD, 150 kD, 175 kD, 200 kD, 250 kD, 300 kD, 400 kD, 500 kD, 750 kD, or 1,000 kD from passing through.

A particle described herein may be configured to release a therapeutic agent, e.g., an exogenous substance, e.g., a therapeutic agent described herein. In some embodiments, the therapeutic agent is a compound of Formula (I) or a pharmaceutically acceptable salt thereof. In some embodiments, the therapeutic agent is a biological material. In some embodiments, the therapeutic agent is a nucleic acid (e.g., an RNA or DNA), protein (e.g., a hormone, enzyme, antibody, antibody fragment, antigen, or epitope), small molecule, lipid, drug, vaccine, or any derivative thereof.

A particle (e.g., as described herein) may be provided as a preparation or composition for implantation or administration to a subject. In some embodiments, at least 20%, 30%, 35%, 40%, 45%, 50%, 55%, 60%, 65%, 70%, 75%, 80%, 85%, 90%, 95% or 100% of the particles in a preparation or composition have a characteristic as described herein, e.g., mean diameter or mean pore size.

In some embodiments, a particle targets or is designed for a certain system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, a particle is targeted to the CNS. In some embodiments, a particle targets or is designed for a certain part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

A particle may be configured for implantation, or implanted or disposed into or onto any site of the body. In some embodiments, a particle is configured for implantation, implanted or disposed into the omentum of a subject, into the subcutaneous fat of a subject, or into the muscle tissue of a subject. A particle can be configured for implantation, or implanted, or disposed on or in the skin; a mucosal surface, a body cavity, the peritoneal cavity (e.g., the lesser sac); the central nervous system, e.g., the brain or spinal cord; an organ, e.g., the heart, liver, kidney, spleen, lung, lymphatic system, vasculature, the oral cavity, the nasal cavity, the teeth, the gums, the GI tract; bone; hip; fat tissue; muscle tissue; circulating blood; the eye (e.g., intraocular); breast, vagina; uterus, a joint, e.g., the knee or hip joint, or the spine.

In some embodiments, the particle is configured for implantation or implanted or disposed into the peritoneal cavity (e.g., the omentum). In some embodiments, the particle is configured for implantation or implanted or disposed into or onto the lesser sac, also known as the omental bursa or bursalis omentum. The lesser sac refers to a cavity located in the abdomen formed by the omentum, and is in close proximity to, for example, the greater omentum, lesser omentum, stomach, small intestine, large intestine, liver, spleen, gastrosplenic ligament, adrenal glands, and pancreas. Typically, the lesser sac is connected to the greater sac via the omental foramen (i.e., the Foramen of Winslow). In some embodiments, the lesser sac comprises a high concentration of adipose tissue. A particle may be implanted in the peritoneal cavity (e.g., the omentum, e.g., the lesser sac) or disposed on a surface within the peritoneal cavity (e.g., omentum, e.g., lesser sac) via injection or catheter. Additional considerations for implantation or disposition of a particle into the omentum (e.g., the lesser sac) are provided in M. Pellicciaro et al. (2017) *CellR*4 5(3): e2410, which is incorporated herein by reference in its entirety.

In some embodiments, the particle is configured for implantation or implanted or disposed into the central nervous system (CNS), e.g., the brain or spinal cord and their corresponding tissues and cavities. In vertebrates, the CNS is contained within the dorsal body cavity, including the cranial cavity and the spinal canal. In some embodiments, the particle is configured for implantation or implanted or disposed into an intracerebral space, e.g., the intraparenchymal space, the intraventricular space, or the subdural space. A particle may be implanted in the CNS or disposed on a surface within the CNS through a hole made in the skull and delivered via injection or catheter.

In some embodiments, the particle is configured for implantation or implanted in or disposed into the eye. Exemplary regions suitable for implantation or disposition of the particle include any surface or cavity within the eye, such as the retina, cornea, epithelium, aqueous humor, or vitreal space. In some embodiments, the particle is configured for implantation or implanted or disposed into the vitreal space. A particle may be implanted in the eye or disposed on a surface within the eye through incision and/or injection.

In some embodiments, the particle is easily retrievable from a subject, e.g., without causing injury to the subject or without causing significant disruption of the surrounding tissue. In an embodiment, the particle can be retrieved with minimal or no surgical separation of the particle from surrounding tissue, e.g., via minimally invasive surgical approach, extraction, or resection.

A particle can be configured for limited exposure (e.g., less than 2 days, 1 day, 24 hours, 20 hours, 16 hours, 12 hours, 10 hours, 8 hours, 6 hours, 5 hours, 4 hours, 3 hours, 2 hours, 1 hour or less). A particle can be configured for prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more) A particle can be configured for permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

In some embodiments, the particle is not a particle disclosed in any of WO2012/112982, WO2012/167223, WO2014/153126, WO2016/019391, WO2016/187225, US2012-0213708, US 2016-0030359, and US 2016-0030360.

Compounds

In some embodiments, the particles described herein comprise a compound of Formula (I). In some embodiments, the first compartment and/or second compartment of the particle comprise a compound of Formula (I):

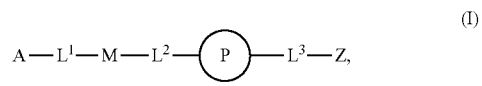

(I)

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_2$-$C_6$-alkenylene)-, —N($R^C$)N($R^D$)—, —NCN—, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —O$R^A$, —C(O)$R^A$, —C(O)O$R^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

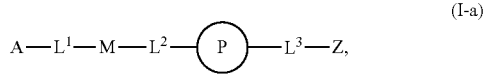
(I-a)

or a salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —N($R^C$)C(O)($C_1$-$C_6$-alkylene)-, —N($R^C$)C(O)($C_2$-$C_6$-alkenylene)-, —NCN—, —C(=N($R^C$))($R^D$))O—, —S—, —S(O)$_x$—, —OS(O)$_x$—, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O) $R^{B1}$, —N($R^{C1}$)($R^{D1}$), —N($R^{C1}$)C(O)$R^{B1}$, —C(O)N ($R^{C1}$), S$R^{E1}$, S(O)$_x$$R^{E1}$, —OS(O)$_x$$R^{E1}$, —N($R^{C1}$)S(O)$_x$ $R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) or (I-a), A is alkyl, alkenyl, alkynyl, heteroalkyl, cycloalkyl, heterocyclyl, aryl, heteroaryl, —O—, —C(O)O—, —C(O)—, —OC(O)—, —N($R^C$)C(O)—, —N($R^C$)C(O)($C_1$-$C_6$-alkylene)-, —N($R^C$) C(O)($C_1$-$C_6$-alkenylene)-, or —N($R^C$)—. In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —N($R^C$)—. In some embodiments, A is alkyl, alkenyl, alkynyl, heteroalkyl, —O—, —C(O)O—, —C(O)—, —OC(O)—, or —N($R^C$)—. In some embodiments, A is alkyl, —O—, —C(O)O—, —C(O)—, —OC(O), or —N($R^C$)—. In some embodiments, A is —N($R^C$)C(O)—, —N($R^C$)C(O)($C_1$-$C_6$-alkylene)-, or —N($R^C$)C(O)($C_1$-$C_6$-alkenylene)-. In some embodiments, A is —N($R^C$)—. In some embodiments, A is —N($R^C$)—, and $R^C$ an $R^D$ is independently hydrogen or alkyl. In some embodiments, A is —NH—. In some embodiments, A is —N($R^C$)C(O)($C_1$-$C_6$-alkylene)-, wherein alkylene is substituted with $R^1$. In some embodiments, A is —N($R^C$)C(O) ($C_1$-$C_6$-alkylene)-, and $R^1$ is alkyl (e.g., methyl). In some embodiments, A is —NHC(O)C(CH$_3$)$_2$—. In some embodiments, A is —N($R^C$)C(O)(methylene)-, and $R^1$ is alkyl (e.g., methyl). In some embodiments, A is —NHC(O)CH(CH$_3$)—. In some embodiments, A is —NHC(O)C(CH$_3$)—.

In some embodiments, for Formulas (I) or (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —CH$_2$—, —CH(CH$_3$)—, —CH$_2$CH$_2$CH$_2$, or —CH$_2$CH$_2$—. In some embodiments, $L^1$ is —CH$_2$— or —CH$_2$CH$_2$—.

In some embodiments, for Formulas (I) or (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —CH$_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —C(O)OCH$_2$—, —CH$_2$(OCH$_2$CH$_2$)$_2$—, —CH$_2$(OCH$_2$CH$_2$)$_3$—, CH$_2$CH$_2$O—, or —CH$_2$O—. In some embodiments, $L^3$ is —CH$_2$O—.

In some embodiments, for Formulas (I) or (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —CH$_2$—. In some embodiments, M is heteroalkyl (e.g., $C_1$-$C_6$ heteroalkyl). In some embodiments, M is (—OCH$_2$CH$_2$—)z, wherein z is an integer selected from 1 to 10. In some embodiments, z is an integer selected from 1 to 5. In some embodiments, M is —OCH$_2$CH$_2$—, (—OCH$_2$CH$_2$—)$_2$, (—OCH$_2$CH$_2$—)$_3$, (—OCH$_2$CH$_2$—)$_4$, or (—OCH$_2$CH$_2$—)$_5$. In some embodiments, M is —OCH$_2$CH$_2$—, (—OCH$_2$CH$_2$—)$_2$, (—OCH$_2$CH$_2$—)$_3$, or (—OCH$_2$CH$_2$—)$_4$. In some embodiments, M is (—OCH$_2$CH$_2$—)$_3$. In some embodiments, M is aryl. In some embodiments, M is phenyl. In some embodiments, M is unsubstituted phenyl. In some embodiments, M is

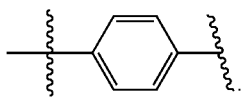

In some embodiments, M is phenyl substituted with R⁷ (e.g., 1 R⁷). In some embodiments, M is

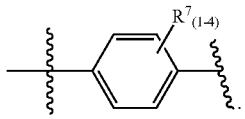

In some embodiments, R⁷ is $CF_3$.

In some embodiments, for Formulas (I) or (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

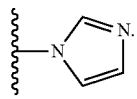

In some embodiments, P is triazolyl. In some embodiments, P is 1,2,3-triazolyl. In some embodiments, P is

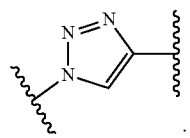 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

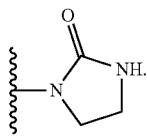 [SMILES: *N1CCNC1=O]

In some embodiments, P is thiomorpholinyl-1,1-dioxidyl. In some embodiments, P is

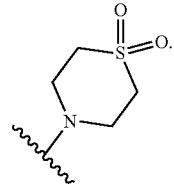 [SMILES: *N1CCS(=O)(=O)CC1]

In some embodiments, for Formulas (I) or (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

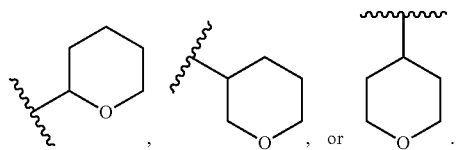

In some embodiments, Z is a 4-membered oxygen-containing heterocyclyl. In some embodiments, Z is

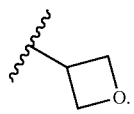

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

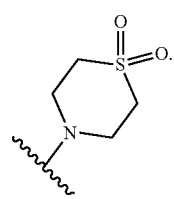 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

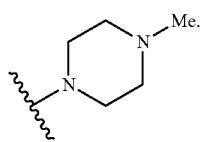 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

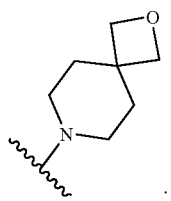 [SMILES: *N1CCC2(CC1)COC2]

In some embodiments, Z is 1-oxa-3,8-diazaspiro[4.5]decan-2-one. In some embodiments, Z is

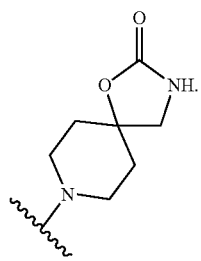 [SMILES: *N1CCC2(CC1)CNC(=O)O2]

In some embodiments, for Formulas (I) or (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) or (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —$C(O)OH$. In some embodiments, Z is —$CH_3$.

In some embodiments, for Formulas (I) or (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

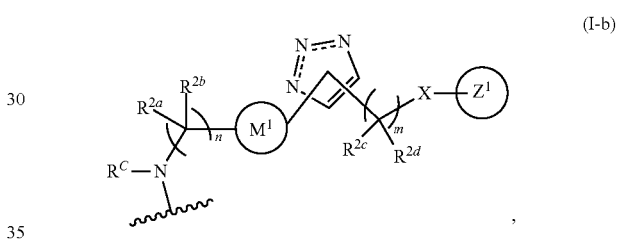

(I-b)

or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{11})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, $N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$ and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "⌇" refers to a connection to an attachment group or a polymer described herein. In some embodiments, for each $R^3$ and $R^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

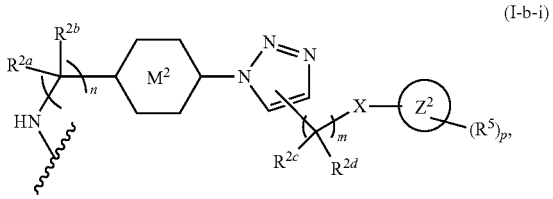
(I-b-i)

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and "∿∿∿" refers to a connection to an attachment group or a polymer described herein.

In some embodiments, the compound of Formula (I-b-i) is a compound of Formula (I-b-ii):

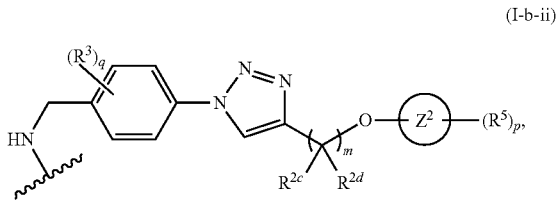
(I-b-ii)

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ and taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of p and q is independently 0, 1, 2, 3, 4, 5, or 6; and "∿∿∿" refers to a connection to an attachment group or a polymer described herein.

In some embodiments, the compound of Formula (I) is a compound of Formula (I-c):

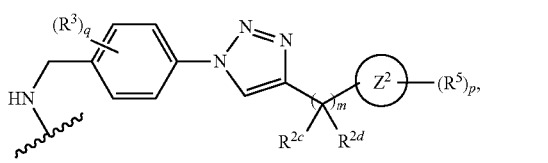
(I-c)

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ is taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; each of p and q is independently 0, 1, 2, 3, 4, 5, or 6; and "∿∿∿" refers to a connection to an attachment group or a polymer described herein.

In some embodiments, the compound of Formula (I) is a compound of Formula (I-d):

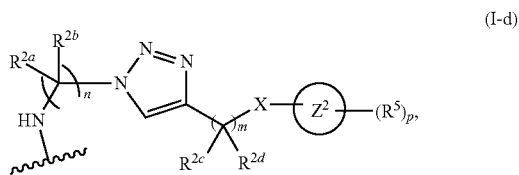
(I-d)

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "∿∿∿" refers to a connection to an attachment group or a polymer described herein.

In some embodiments, the compound of Formula (I) is a compound of Formula (I-e):

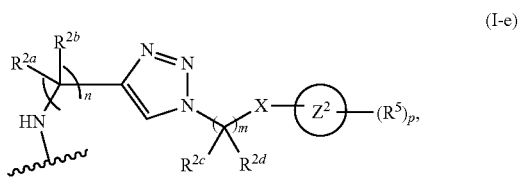
(I-e)

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "∿∿∿" refers to a connection to an attachment group or a polymer described herein.

In some embodiments, the compound of Formula (I) is a compound of Formula (I-f):

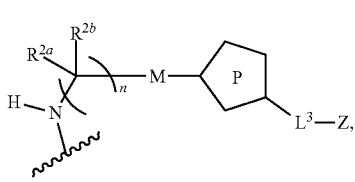

(I-f)

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "⁓" refers to a connection to an attachment group or a polymer described herein.

In some embodiments, the compound of Formula (I) is a compound of Formula (II):

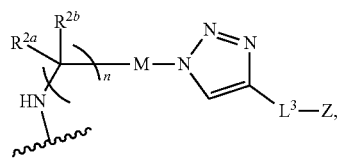

(II)

or a pharmaceutically acceptable salt thereof, wherein M is a bond, alkyl or aryl, wherein alkyl and aryl is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl or —$OR^A$, wherein alkyl, heteroalkyl, cycloalkyl, heterocyclyl, aryl, and heteroaryl is optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "⁓" refers to a connection to an attachment group or a polymer described herein.

In some embodiments, the compound of Formula (II) is a compound of Formula (II-a):

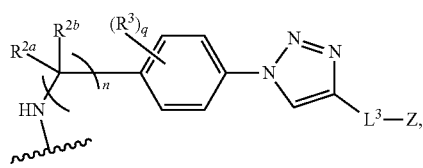

(II-a)

or a pharmaceutically acceptable salt thereof, wherein $L^3$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; $R^A$ is hydrogen; each $R^{A1}$ and $R^{B1}$ is independently hydrogen, alkyl, or heteroalkyl; n is independently 1, 2, 3, 4, 5, or 6; and "⁓" refers to a connection to an attachment group or a polymer described herein.

In some embodiments, the compound of Formula (I) is a compound of Formula (III):

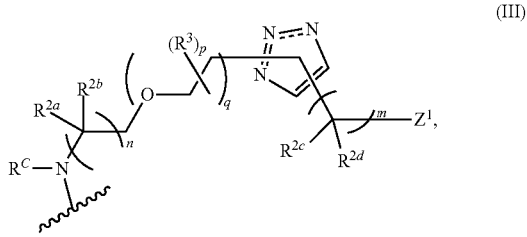

(III)

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and "⁓" refers to a connection to an attachment group or a polymer described herein.

In some embodiments, the compound of Formula (III) is a compound of Formula (III-a):

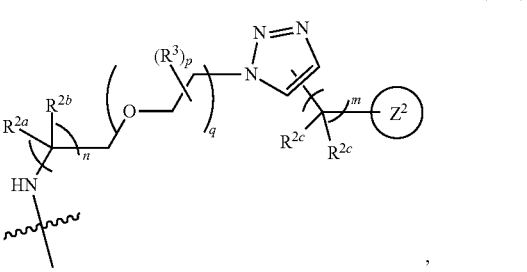

(III-a)

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —OR^{A1}, —C(O)OR^{A1}, or —C(O)R^{B1}; each R^{A1} and R^{B1} is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "〰" refers to a connection to an attachment group or a polymer described herein.

In some embodiments, the compound of Formula (III-a) is a compound of Formula (III-b):

(III-b)

or a pharmaceutically acceptable salt thereof, wherein Ring Z^2 is cycloalkyl, heterocyclyl, aryl, or heteroaryl, each of which is optionally substituted with 1-5 R^5; each of R^{2a}, R^{2b}, R^{2c}, and R^{2d} is independently hydrogen, alkyl, heteroalkyl, halo; or R^{2a} and R^{2b} or R^{2c} and R^{2d} are taken together to form an oxo group; each of R^3 and R^5 is independently alkyl, heteroalkyl, halogen, oxo, —OR^{A1}, —C(O)OR^{A1}, or —C(O)R^{B1}; each R^{A1} and R^{B1} is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "〰" refers to a connection to an attachment group or a polymer described herein.

In some embodiments, the compound of Formula (III-a) is a compound of Formula (III-c):

(III-c)

or a pharmaceutically acceptable salt thereof, wherein X is C(R')(R"), N(R'), or S(O)_x; each of R' and R" is independently hydrogen, alkyl, halogen, or cycloalkyl; each of R^{2a}, R^{2b}, R^{2c}, and R^{2d} is independently hydrogen, alkyl, heteroalkyl, or halo; or R^{2a} and R^{2b} or R^{2c} and R^{2d} are taken together to form an oxo group; each of R^3 and R^5 is independently alkyl, heteroalkyl, halogen, oxo, —OR^{A1}, —C(O)OR^{A1}, or —C(O)R^{B1}; each R^{A1} and R^{B1} is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "〰" refers to a connection to an attachment group or a polymer described herein.

In some embodiments, the compound of Formula (III-c) is a compound of Formula (III-d):

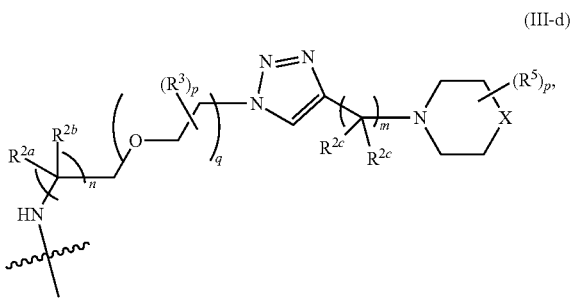

or a pharmaceutically acceptable salt thereof, wherein X is C(R')(R"), N(R'), or S(O)_x; each of R' and R" is independently hydrogen, alkyl, halogen, or cycloalkyl; each of R^{2a}, R^{2b}, R^{2c}, and R^{2d} is independently hydrogen, alkyl, heteroalkyl, or halo; or R^{2a} and R^{2b} or R^{2c} and R^{2d} are taken together to form an oxo group; each of R^3 and R^5 is independently alkyl, heteroalkyl, halogen, oxo, —OR^{A1}, —C(O)OR^{A1}, or —C(O)R^{B1}; each R^{A1} and R^{B1} is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "〰" refers to a connection to an attachment group or a polymer described herein.

In some embodiments, the compound is a compound of Formula (I). In some embodiments, L^2 is a bond and P and L^3 are independently absent.

In some embodiments, the compound is a compound of Formula (I-a). In some embodiments of Formula (II-a), L^2 is a bond, P is heteroaryl, L^3 is a bond, and Z is hydrogen. In some embodiments, P is heteroaryl, L^3 is heteroalkyl, and Z is alkyl. In some embodiments, L^2 is a bond and P and L^3 are independently absent. In some embodiments, L^2 is a bond, P is heteroaryl, L^3 is a bond, and Z is hydrogen. In some embodiments, P is heteroaryl, L^3 is heteroalkyl, and Z is alkyl.

In some embodiments, the compound is a compound of Formula (I-b). In some embodiments, P is absent, L^1 is —NHCH_2, L^2 is a bond, M is aryl (e.g., phenyl), L^3 is —CH_2O, and Z is heterocyclyl (e.g., a nitrogen-containing heterocyclyl, e.g., thiomorpholinyl-1,1-dioxide). In some embodiments, the compound of Formula (I-b) is Compound 116.

In some embodiments of Formula (I-b), P is absent, L^1 is —NHCH_2, L^2 is a bond, M is absent, L^3 is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-b) is Compound 105.

In some embodiments, the compound is a compound of Formula (I-b-i). In some embodiments of Formula (I-b-i), each of R^{2a} and R^{2b} is independently hydrogen or CH_3, each of R^{2c} and R^{2d} is independently hydrogen, m is 1 or 2, n is 1, X is O, p is 0, M^2 is phenyl optionally substituted with one or more R^3, R^3 is —CF_3, and Z^2 is heterocyclyl (e.g., an oxygen-containing heterocyclyl, e.g., tetrahydropyranyl, tetrahydrofuranyl, oxetanyl, or oxiranyl). In some embodiments, the compound of Formula (I-b-i) is Compound 100, Compound 106, Compound 107, Compound 108, Compound 109, or Compound 111.

In some embodiments, the compound is a compound of Formula (I-b-ii). In some embodiments of Formula (I-b-ii), each of R^{2a}, R^{2b}, R^{2c}, and R^{2d} is independently hydrogen, q is 0, p is 0, m is 1, and Z^2 is heterocyclyl (e.g., an oxygen-containing heterocyclyl, e.g., tetrahydropyranyl). In some embodiments, the compound of Formula (I-b-ii) is Compound 100.

In some embodiments, the compound is a compound of Formula (I-c). In some embodiments of Formula (I-c), each of $R^{2c}$ and $R^{2d}$ is independently hydrogen, m is 1, p is 1, q is 0, $R^5$ is —CH$_3$, and Z is heterocyclyl (e.g., a nitrogen-containing heterocyclyl, e.g., piperazinyl). In some embodiments, the compound of Formula (I-c) is Compound 113.

In some embodiments, the compound is a compound of Formula (I-d). In some embodiments of Formula (I-d), each of $R^{2a}$, $R^{2b}$, $R^{2c}$, and $R^{2d}$ is independently hydrogen, m is 1, n is 3, X is O, p is 0, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-d) is Compound 110 or Compound 114.

In some embodiments, the compound is a compound of Formula (I-f). In some embodiments of Formula (I-f), each of $R^{2a}$ and $R^{2b}$ is independently hydrogen, n is 1, M is —CH$_2$—, P is a nitrogen-containing heteroaryl (e.g., imidazolyl), $L^3$ is —C(O)OCH$_2$—, and Z is CH$_3$. In some embodiments, the compound of Formula (I-f) is Compound 115.

In some embodiments, the compound is a compound of Formula (II-a). In some embodiments of Formula (II-a), each of $R^{2a}$ and $R^{2b}$ is independently hydrogen, n is 1, q is 0, $L^3$ is —CH$_2$(OCH$_2$CH$_2$)$_2$—, and Z is —OCH$_3$. In some embodiments, the compound of Formula (II-a) is Compound 112.

In some embodiments of Formula (II-a), each of $R^{2a}$ and $R^{2b}$ is independently hydrogen, n is 1, $L^3$ is a bond or —CH$_2$, and Z is hydrogen or —OH. In some embodiments, the compound of Formula (II-a) is Compound 103 or Compound 104.

In some embodiments, the compound is a compound of Formula (III). In some embodiments of Formula (III), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —N(CH$_3$)(CH$_2$CH$_2$)S(O)$_2$CH$_3$). In some embodiments, the compound of Formula (III) is Compound 120.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 0, n is 2, q is 3, p is 0, and $Z^2$ is aryl (e.g., phenyl) substituted with 1 $R^5$ (e.g., —NH$_2$). In some embodiments, the compound of Formula (III-b) is Compound 102.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.t., 2-oxa-7-azaspiro[3.5]nonanyl). In some embodiments, the compound of Formula (III-b) is Compound 121.

In some embodiments, the compound is a compound of Formula (III-d). In some embodiments of Formula (III-d), each of $R^{2a}$, $R^{2b}$, $R^{2c}$, and $R^{2d}$ is independently hydrogen, m is 1, n is 2, q is 1, 2, 3, or 4, p is 0, and X is S(O)$_2$. In some embodiments of Formula (III-d), each of $R^{2a}$ and $R^{2b}$ is independently hydrogen, m is 1, n is 2, q is 1, 2, 3, or 4, p is 0, and X is S(O)$_2$. In some embodiments, the compound of Formula (III-d) is Compound 101, Compound 117, Compound 118, or Compound 119.

In some embodiments, the compound is a compound of Formula (I-b), (I-d), or (I-e). In some embodiments, the compound is a compound of Formula (I-b), (I-d), or (II). In some embodiments, the compound is a compound of Formula (I-b), (I-d), or (I-f). In some embodiments, the compound is a compound of Formula (I-b), (I-d), or (III).

In some embodiments, the compound of Formula (I) is not a compound disclosed in WO2012/112982, WO2012/167223, WO2014/153126, WO2016/019391, WO 2017/075630, US2012-0213708, US 2016-0030359 or US 2016-0030360.

In some embodiments, the compound of Formula (I) comprises a compound shown in Table 2, or a pharmaceutically acceptable salt thereof. In some embodiments, a particle described herein comprises a compound shown in Table 2, or a pharmaceutically acceptable salt thereof.

TABLE 2

Exemplary compounds

| Compound No. | Structure |
|---|---|
| 100 | 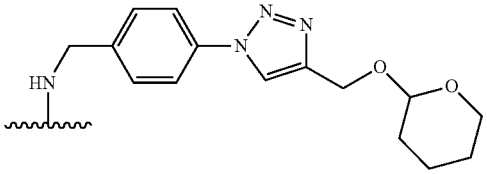 [SMILES: *NCc1ccc(-n2cc(COC3CCCCO3)nn2)cc1] |
| 101 | 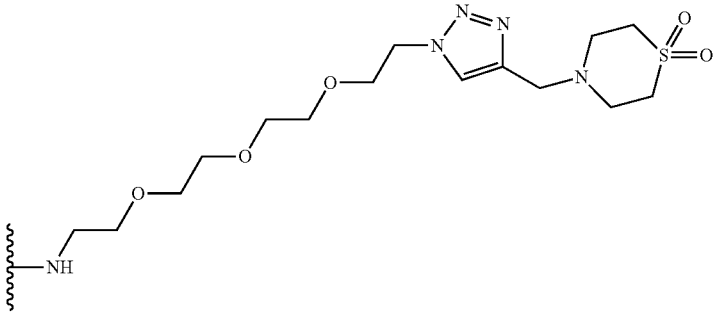 [SMILES: *NCCOCCOCCOCCn1cc(CN2CCS(=O)(=O)CC2)nn1] |

TABLE 2-continued

Exemplary compounds

| Compound No. | Structure |
| --- | --- |
| 102 | (structure) |
| 103 | (structure) |
| 104 | (structure) |
| 105 | (structure) |
| 106 | (structure) |
| 107 | (structure) |
| 108 | (structure) |
| 109 | (structure) |

TABLE 2-continued

Exemplary compounds

| Compound No. | Structure |
|---|---|
| 110 | [structure: ~NH-(CH2)3-triazole-CH2-O-tetrahydropyran-2-yl] |
| 111 | [structure: ~NH-CH2-phenyl-triazole-CH2-O-oxetan-3-yl] |
| 112 | [structure: ~NH-CH2-phenyl-triazole-CH2-O-CH2CH2-O-CH2CH2-OMe] |
| 113 | [structure: ~NH-CH2-phenyl-triazole-CH2-N(4-methylpiperazine)] |
| 114 | [structure: ~NH-(CH2)3-triazole-CH2-O-oxetan-3-yl] |
| 115 | [structure: ~NH-CH2CH2-imidazole-C(=O)-O-Et] |
| 116 | [structure: ~NH-CH2-phenyl-N(thiomorpholine-1,1-dioxide)] |
| 117 | [structure: ~NH-CH2CH2-O-CH2CH2-triazole-CH2-N(thiomorpholine-1,1-dioxide)] |
| 118 | [structure: ~NH-CH2CH2-O-CH2CH2-O-CH2CH2-triazole-CH2-N(thiomorpholine-1,1-dioxide)] |

TABLE 2-continued

Exemplary compounds

| Compound No. | Structure |
|---|---|
| 119 | 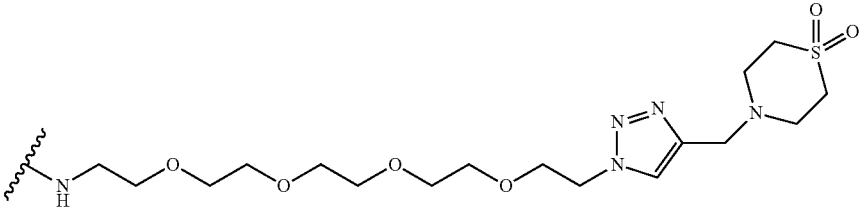 [SMILES: *NCCOCCOCCOCCOCCn1cc(CN2CCS(=O)(=O)CC2)nn1] |
| 120 | 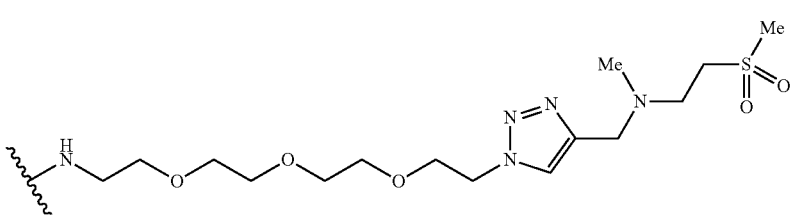 [SMILES: *NCCOCCOCCOCCn1cc(CN(C)CCS(C)(=O)=O)nn1] |
| 121 | 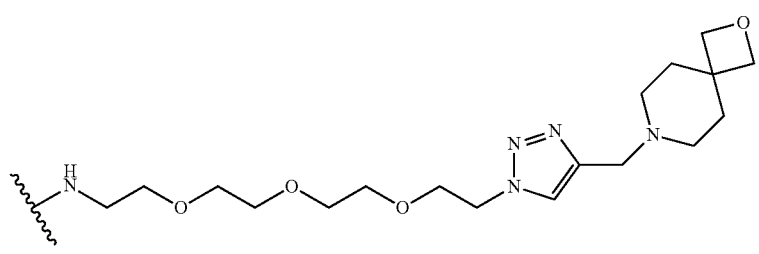 [SMILES: *NCCOCCOCCOCCn1cc(CN2CCC3(CC2)COC3)nn1] |

In some embodiments, the compound is a compound of Formula (I) (e.g., Formulas (I-a), (I-b), (I-c), (I-d), (I-e), (I-f), (II), (II-a), (III), (III-a), (III-b), (III-c), or (III-d)), or a pharmaceutically acceptable salt thereof, and is selected from:

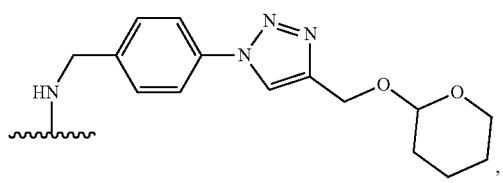

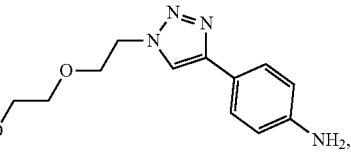

-continued or a pharmaceutically acceptable salt thereof.

In some embodiments, the particle described herein comprises the compound of

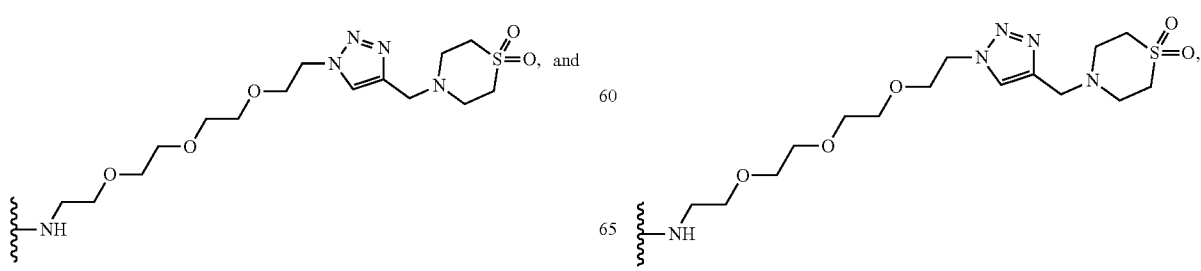

-continued

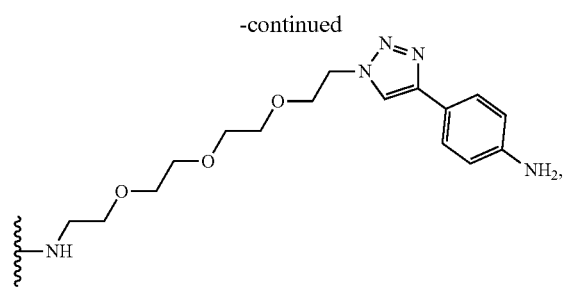

or a pharmaceutically acceptable salt thereof.

In an embodiment, a particle described herein comprises a compound of Formula (I) (e.g., a compound shown in Table 2) covalently bound to an alginate polymer. In an embodiment, a particle described herein comprises a compound of Formula (I) (e.g., a compound shown in Table 2, e.g., Compound 101) covalently bound to one or more guluronic acid and/or mannuronic acid monomers in an alginate polymer, e.g., by an amide bond.

In some embodiments, a compound of Formula (I) (e.g., Compound 101 in Table 2) is covalently attached to an alginate (e.g., an alginate with approximate MW<75 kDa, G:M ratio≥1.5) at a conjugation density of at least 2.0% and less than 9.0% nitrogen, or 2.0% to 5% nitrogen, 3.0% to 8.0% nitrogen, 5% to 8.0% nitrogen, 4.0% to 7.0% nitrogen, 5.0% to 7.0% nitrogen, or 6.0% to 7.0% nitrogen or about 6.8% nitrogen as determined by combustion analysis for percent nitrogen as described in the Examples below.

Cells

The particles of the present disclosure may comprise a wide variety of different cell types (e.g., human cells), including epithelial cells, endothelial cells, fibroblast cells, mesenchymal stem cells, keratinocyte cells, islet cells, and cells derived from any of the foregoing cell types. The cells may be derived from stem cells or induced pluripotent stem cells. Exemplary cell types include the cell types recited in WO 2017/075631. In some embodiments, the cells are derived from a cell-line shown in Table 3 below.

capable of producing insulin in a glucose-responsive manner; or (iii) not an induced pluripotent cell that is engineered into a differentiated insulin-producing pancreatic beta cell.

In an embodiment, the particles described herein comprise a plurality of cells. In an embodiment, the plurality of cells is in the form of a cell suspension prior to being encapsulated within a particle described herein. The cells in the suspension may take the form of single cells (e.g., from a monolayer cell culture), or provided in another form, e.g., disposed on a microcarrier (e.g., a bead or matrix) or as a three-dimensional aggregate of cells (e.g., a cell cluster or spheroid). The cell suspension can comprise multiple cell clusters (e.g., as spheroids) or microcarriers.

In some embodiments, the cells have been engineered to produce a therapeutic agent for the prevention or treatment of a disease, disorder, or condition described, e.g., in WO 2017/075631. The therapeutic agent may be any biological substance, such as a nucleic acid (e.g., a nucleotide, DNA, or RNA), a polypeptide, a lipid, a sugar (e.g., a monosaccharide, disaccharide, oligosaccharide, or polysaccharide), or a small molecule. Exemplary therapeutic agents include the agents listed in WO 2017/075631.

In some embodiments, the therapeutic agent is a peptide or polypeptide (e.g., a protein), such as a hormone, enzyme, cytokine (e.g., a pro-inflammatory cytokine or an anti-inflammatory cytokine), growth factor, clotting factor, or lipoprotein. A peptide or polypeptide (e.g., a protein, e.g., a hormone, growth factor, clotting factor or coagulation factor, antibody molecule, enzyme, cytokine, cytokine receptor, or a chimeric protein including cytokines or a cytokine receptor) produced by an engineered cell can have a naturally occurring amino acid sequence, or may contain a variant of the naturally occurring sequence. The variant can be a naturally occurring or non-naturally occurring amino acid substitution, mutation, deletion or addition relative to the reference naturally occurring sequence. The naturally occurring amino acid sequence may be a polymorphic variant. The naturally occurring amino acid sequence can be a human or a non-human amino acid sequence. In some

TABLE 3

Exemplary cell lines

| Cell Line | Cell Type | Germ Layer | Commercial Source |
|---|---|---|---|
| ARPE-19 | Epithelial (Retinal) | Ectoderm | ATCC (CRL-2302) |
| BJ | Fibroblast (Foreskin) | Ectoderm | ATCC (CRL-2522) |
| CCD-841-CoN | Epithelial (Colon) | Endoderm | ATCC (CRL-1790) |
| HaCat | Keratinocyte | Ectoderm | Addexbio (T0020001) |
| HHSEC | Endothelial (Hepatic Sinusoidal) | Endoderm | Sciencellonline.com (#5000) |
| Huv-EC-C | Endothelial (Embryonic umbilical) | Mesoderm | ATCC (CRL-1730) |
| MCF-10A | Epithelial (Mammary Gland) | Ectoderm | ATCC (CRL-10317) |
| MRC-5 | Fibroblast (Lung) | Mesoderm | ATCC (CCL-171) |
| MSC, human | Mesenchyme (Bone Marrow) | Mesoderm | ATCC (PCS-500-012) |
| MSC, mouse | Mesenchyme (Bone Marrow) | Mesoderm | Cyagen (MU BMX-01001) |
| WS-1 | Fibroblast (Skin) | Ectoderm | ATCC (CRL-1502) |
| 293F | Epithelial (Embryonic Kidney) | Mesoderm | Thermo Fisher (R790007) |

In some embodiments, the particle does not comprise any islet cells, as defined herein. In an embodiment, cells contained in a particle of the disclosure, e.g., RPE cells, MSFCs, including engineered RPE cells and MSFCs, have one or more of the following characteristics: (i) are not capable of producing insulin (e.g., insulin A-chain, insulin B-chain, or proinsulin) in an amount effective to treat diabetes or another disease or condition that may be treated with insulin; (ii) not embodiments, the naturally occurring amino acid sequence or naturally occurring variant thereof is a human sequence. In addition, a peptide or polypeptide (e.g., a protein) for use with the present disclosure may be modified in some way, e.g., via chemical or enzymatic modification (e.g., glycosylation, phosphorylation). In some embodiments, the peptide has about 2, 3, 4, 5, 6, 7, 8, 9, 10, 12, 14, 16, 18, 20, 25, 30, 35, 40, 45, or 50 amino acids. In some embodiments, the protein has an average molecular weight of 5 kD, 10 kD, 25 kD, 50 kD, 100 kD, 150 kD, 200 kD, 250 kD, 500 kD, or more.

In some embodiments, the protein is a hormone. Exemplary hormones include anti-diuretic hormone (ADH), oxytocin, growth hormone (GH), prolactin, growth hormone-releasing hormone (GHRH), thyroid stimulating hormone (TSH), thyrotropin-release hormone (TRH), adrenocorticotropic hormone (ACTH), follicle-stimulating hormone (FSH), luteinizing hormone (LH), luteinizing hormone-releasing hormone (LHRH), thyroxine, calcitonin, parathyroid hormone, aldosterone, cortisol, epinephrine, glucagon, insulin, estrogen, progesterone, and testosterone. In some embodiments, the protein is insulin (e.g., insulin A-chain, insulin B-chain, or proinsulin). In some embodiments, the protein is a growth hormone, such as human growth hormone (hGH), recombinant human growth hormone (rhGH), bovine growth hormone, methionine-human growth hormone, des-phenylalanine human growth hormone, and porcine growth hormone.

In some embodiments, the protein is a growth factor, e.g., vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

In some embodiments, the protein is a clotting factor or a coagulation factor, e.g., a blood clotting factor or a blood coagulation factor. In some embodiments, the protein is a protein involved in coagulation, i.e., the process by which blood is converted from a liquid to solid or gel. Exemplary clotting factors and coagulation factors include Factor I (e.g., fibrinogen), Factor II (e.g., prothrombin), Factor III (e.g., tissue factor), Factor V (e.g., proaccelerin, labile factor), Factor VI, Factor VII (e.g., stable factor, proconvertin), Factor VIII (e.g., antihemophilic factor A), Factor VIIIC, Factor IX (e.g., antihemophilic factor B), Factor X (e.g., Stuart-Prower factor), Factor XI (e.g., plasma thromboplastin antecedent), Factor XII (e.g., Hagerman factor), Factor XIII (e.g., fibrin-stabilizing factor), von Willebrand factor, prekallikrein, heparin cofactor II, high molecular weight kininogen (e.g., Fitzgerald factor), antithrombin III, and fibronectin. In some embodiments, the protein is an anti-clotting factor, such as Protein C.

In some embodiments, the protein is an antibody molecule. As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full-length antibody which has an immunoglobulin Fc region). In an embodiment, an antibody molecule comprises a full-length antibody, or a full-length immunoglobulin chain. In an embodiment, an antibody molecule comprises an antigen binding or functional fragment of a full-length antibody, or a full-length immunoglobulin chain. In an embodiment, an antibody molecule is a monospecific antibody molecule and binds a single epitope, e.g., a monospecific antibody molecule having a plurality of immunoglobulin variable domain sequences, each of which binds the same epitope. In an embodiment, an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

Various types of antibody molecules may be produced by the encapsulated engineered cells, including whole immunoglobulins of any class, fragments thereof, and synthetic proteins containing at least the antigen binding variable domain of an antibody. The antibody molecule can be an antibody, e.g., an IgG antibody, such as $IgG_1$, $IgG_2$, $IgG_3$, or $IgG_4$. An antibody molecule can be in the form of an antigen binding fragment including a Fab fragment, $F(ab')_2$ fragment, a single chain variable region, and the like. Antibodies can be polyclonal or monoclonal (mAb). Monoclonal antibodies may include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity. In some embodiments, the antibody molecule is a single-domain antibody (e.g., a nanobody). The described antibodies can also be modified by recombinant means, for example by deletions, additions or substitutions of amino acids, to increase efficacy of the antibody in mediating the desired function. Exemplary antibodies include anti-beta-galactosidase, anti-collagen, anti-CD14, anti-CD20, anti-CD40, anti-HER2, anti-IL-1, anti-IL-4, anti-IL6, anti-IL-13, anti-IL17, anti-IL18, anti-IL-23, anti-IL-28, anti-IL-29, anti-IL-33, anti-EGFR, anti-VEGF, anti-CDF, anti-flagellin, anti-IFN-α, anti-IFN-β, anti-IFN-γ, anti-mannose receptor, anti-VEGF, anti-TLR1, anti-TLR2, anti-TLR3, anti-TLR4, anti-TLR5, anti-TLR6, anti-TLR9, anti-PDF, anti-PD1, anti-PDL-1, or anti-nerve growth factor antibody. In some embodiments, the antibody is an anti-nerve growth factor antibody (e.g., fulranumab, fasinumab, tanezumab).

In some embodiments, the protein is a cytokine or a cytokine receptor, or a chimeric protein including cytokines or their receptors, including, for example tumor necrosis factor alpha and beta, their receptors and their derivatives, renin; lipoproteins; colchicine; corticotrophin; vasopressin; somatostatin; lypressin; pancreozymin; leuprolide; alpha-1-antitrypsin; atrial natriuretic factor; lung surfactant; a plasminogen activator other than a tissue-type plasminogen activator (t-PA), for example a urokinase; bombesin; thrombin; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19;

erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. Suitable proteins or peptides may be native or recombinant and include, e.g., fusion proteins.

Examples of a polypeptide (e.g., a protein) produced by particle described herein also include CCL1, CCL2 (MCP-1), CCL3 (MIP-1α), CCL4 (MIP-1β), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, IL5, IL6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A (IL1F1), IL1B (IL1F2), IL1Ra (IL1F3), IL1F5 (IL36RN), IL1F6 (IL36A), IL1F7 (IL37), IL1F8 (IL36B), IL1F9 (IL36G), IL1F10 (IL38), IL33 (IL1F11), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, C1qtnf4, Ccl21a, Ccl27a, Cd70, Cer1, Cklf, Clcf1, Cmtm2a, Cmtm2b, Cmtm3, Cmtm4, Cmtm5, Cmtm6, Cmtm7, Cmtm8, Crlf1, Ctf2, Ebi3, Edn1, Fam3b, Fas1, Fgf2, Flt31, Gdf10, Gdf11, Gdf15, Gdf2, Gdf3, Gdf5, Gdf6, Gdf7, Gdf9, Gm12597, Gm13271, Gm13275, Gm13276, Gm13280, Gm13283, Gm2564, Gpi1, Grem1, Grem2, Grn, Hmgb1, Ifna11, Ifna12, Ifna9, Ifnab, Ifne, Il17a, Il23a, Il25, Il31, Iltifb, Inhba, Lefty1, Lefty2, Mstn, Nampt, Ndp, Nodal, Pf4, Pglyrp1, Prl7d1, Scg2, Scgb3a1, Slurp1, Spp1, Thpo, Tnfsf10, Tnfsf11, Tnfsf12, Tnfsf13, Tnfsf13b, Tnfsf14, Tnfsf15, Tnfsf18, Tnfsf4, Tnfsf8, Tnfsf9, Tslp, Vegfa, Wnt1, Wnt2, Wnt5a, Wnt7a, Xcl1, epinephrine, melatonin, triiodothyronine, a prostaglandin, a leukotriene, prostacyclin, thromboxane, islet amyloid polypeptide, müllerian inhibiting factor or hormone, adiponectin, corticotropin, angiotensin, vasopressin, arginine vasopressin, atriopeptin, brain natriuretic peptide, calcitonin, cholecystokinin, cortistatin, enkephalin, endothelin, erythropoietin, folliclestimulating hormone, galanin, gastric inhibitory polypeptide, gastrin, ghrelin, glucagon, glucagon-like peptide-1, gonadotropin-releasing hormone, hepcidin, human chorionic gonadotropin, human placental lactogen, inhibin, somatomedin, leptin, lipotropin, melanocyte stimulating hormone, motilin, orexin, oxytocin, pancreatic polypeptide, pituitary adenylate cyclase-activating peptide, relaxin, renin, secretin, somatostatin, thrombopoietin, thyrotropin, thyrotropin-releasing hormone, vasoactive intestinal peptide, androgen, alpha-glucosidase (also known as acid maltase), glycogen phosphorylase, glycogen debrancher enzyme, phosphofructokinase, phosphoglycerate kinase, phosphoglycerate mutase, lactate dehydrogenase, carnitine palymityl transferase, carnitine, and myoadenylate deaminase.

In some embodiments, the protein is a replacement therapy or a replacement protein. In some embodiments, the replacement therapy or replacement protein is a clotting factor or a coagulation factor, e.g., Factor VIII (e.g., comprises a naturally occurring human Factor VIII amino acid sequence or a variant thereof) or Factor IX (e.g., comprises a naturally occurring human Factor IX amino acid sequence or a variant thereof). In some embodiments, the cell is engineered to express a human Factor VIII protein, e.g., a recombinant Factor VIII. In some embodiments, the recombinant Factor VIII is a B-domain-deleted recombinant Factor VIII (FVIII-BDD). In some embodiments, the cell is derived from a human RPE cell line and comprises an exogenous nucleic acid sequence which encodes the FVIII-BDD amino acid sequence shown in FIG. 2A (SEQ ID NO: 1).

In some embodiments, the cell is engineered to express a FIX, e.g., a wild-type human F IX, such as that shown in FIG. 2B (SEQ ID NO: 2) or a polymorphic variant thereof (e.g., alanine substituted for threonine at amino acid position 148 of SEQ ID NO: 2). In some embodiments, the cell is engineered to express a gain-in-function (GIF) variant of a wild-type FIX protein (FIX-GIF), wherein the GIF variant has higher specific activity than the corresponding wild-type FIX. In some embodiments, the cell is derived from a human RPE cell line and comprises an exogenous nucleic acid sequence which encodes SEQ ID NO: 2, except for having an amino acid substituted for arginine at a position corresponding to amino acid position 338 of SEQ ID NO: 2. In some embodiments, the substituting amino acid at a position corresponding to amino acid position 338 of SEQ ID NO: 2 is alanine, asparagine, aspartic acid, cysteine, glutamic acid, glutamine, histidine, leucine, lysine, or tyrosine. In some embodiments, the FIX protein encoded by cells contained in a particle described herein is a FIX-padua protein and comprises, consists essentially of, or consists of SEQ ID NO:36 (FIGS. 17A-17FF).

In some embodiments, the encapsulated cells are derived from a human RPE cell line and comprise an exogenous nucleic acid sequence which comprises a promoter sequence (e.g., nucleotides 337-2069 of SEQ ID NO:26) operably linked to a coding sequence for a polypeptide. In an embodiment, the coding sequence is a codon-optimized FVIII-BDD coding sequence shown in FIGS. 17A-17FF (SEQ ID NO: 9, 10, 11, 12, 13, 14, 15, 16 or 17) or a codon-optimized FIX-padua coding sequence shown in FIGS. 17A-17FF (SEQ ID NO:19, 20 or 21).

In some embodiments, the encapsulated cells are derived from a human RPE cell line and comprise a promoter sequence (e.g., SEQ ID NO:23 or a nucleotide sequence that iss at least 95%, 96%, 97%, 98% or 99% identical to SEQ ID NO:23) operably linked to a nucleotide sequence that encodes an amino acid sequence selected from the group consisting of SEQ ID NO:1, 2, 3, 4, 5,6, 7, 29, 30, 31, 32, 33, 34, 35 and 36.

In some embodiments, the particle is a two-compartment hydrogel capsule, in which the inner compartment was formed from a polymer solution comprising about 20 million cells/ml to about 40 million cells/ml, wherein the cells are derived from the ARPE-19 cell line and comprise nucleotides 337-2069 of SEQ ID NO:26 operably linked to a codon-optimized FVIII-BDD coding sequence shown in FIGS. 17A-17FF. In an embodiment, the FVIII-BDD coding sequence is SEQ ID NO:15.

In some embodiments, the replacement therapy or replacement protein is an enzyme, e.g., alpha-galactosidase, alpha-L-iduronidase (IDUA), or N-sulfoglucosamine sulfohydrolase (SGSH). In some embodiments, the replacement therapy or replacement protein is an enzyme, e.g., an alpha-galactosidase A (e.g., comprises a naturally occurring human alpha-galactosidase A amino acid sequence or a variant thereof). In some embodiments, the replacement therapy or replacement protein is a cytokine or an antibody.

In some embodiments, the therapeutic agent is a sugar, e.g., monosaccharide, disaccharide, oligosaccharide, or polysaccharide. In some embodiments, a sugar comprises a triose, tetrose, pentose, hexose, or heptose moiety. In some embodiments, the sugar comprises a linear monosaccharide or a cyclized monosaccharide. In some embodiments, the sugar comprises a glucose, galactose, fructose, rhamnose, mannose, arabinose, glucosamine, galactosamine, sialic acid, mannosamine, glucuronic acid, galactosuronic acid, mannuronic acid, or guluronic acid moiety. In some embodiments, the sugar is attached to a protein (e.g., an N-linked glycan or an O-linked glycan). Exemplary sugars include glucose, galactose, fructose, mannose, rhamnose, sucrose, ribose, xylose, sialic acid, maltose, amylose, inulin, a fructooligosaccharide, galactooligosaccharide, a mannan, a lectin, a pectin, a starch, cellulose, heparin, hyaluronic acid, chitin, amylopectin, or glycogen. In some embodiments, the therapeutic agent is a sugar alcohol.

In some embodiments, the therapeutic agent is a lipid. A lipid may be hydrophobic or amphiphilic, and may form a tertiary structure such as a liposome, vesicle, or membrane or insert into a liposome, vesicle, or membrane. A lipid may comprise a fatty acid, glycerolipid, glycerophospholipid, sterol lipid, prenol lipid, sphingolipid, saccharolipid, polyketide, or sphingolipid. Examples of lipids produced by the encapsulated cells include anandamide, docosahexaenoic acid, a prostaglandin, a leukotriene, a thromboxane, an eicosanoid, a triglyceride, a cannabinoid, phosphatidylcholine, phosphatidylethanolamine, a phosphatidylinositol, a phosohatidic acid, a ceramide, a sphingomyelin, a cerebroside, a ganglioside, estrogen, androsterone, testosterone, cholesterol, a carotenoid, a quinone, a hydroquinone, or a ubiquinone.

In some embodiments, the therapeutic agent is a small molecule. A small molecule may include a natural product produced by a cell. In some embodiments, the small molecule has poor availability or does not comply with the Lipinski rule of five (a set of guidelines used to estimate whether a small molecule will likely be an orally active drug in a human; see, e.g., Lipinski, C. A. et al (2001) *Adv Drug Deliv* 46:2-36). Exemplary small molecule natural products include an anti-bacterial drug (e.g., carumonam, daptomycin, fidaxomicin, fosfomycin, ispamicin, micronomicin sulfate, miocamycin, mupiocin, netilmicin sulfate, teicoplanin, thienamycin, rifamycin, erythromycin, vancomycin), an anti-parasitic drug (e.g., artemisinin, ivermectin), an anti-cancer drug (e.g., doxorubicin, aclarubicin, aminolaevulinic acid, arglabin, omacetaxine mepesuccinate, paclitaxel, pentostatin, peplomycin, romidepsin, trabectdin, actinomycin D, bleomycin, chromomycin A, daunorubicin, leucovorin, neocarzinostatin, streptozocin, trabectedin, vinblastine, vincristine), anti-diabetic drug (e.g., voglibose), a central nervous system drug (e.g., L-dopa, galantamine, zicontide), a statin (e.g., mevastatin), an anti-fungal drug (e.g., fumagillin, cyclosporin), 1-deoxynojirimycin, and theophylline, sterols (cholesterol, estrogen, testerone). Additional small molecule natural products are described in Newman, D. J. and Cragg, M. (2016) *J Nat Prod* 79:629-661 and Butler, M. S. et al (2014) *Nat Prod Rep* 31:1612-1661, which are incorporated herein by reference in their entirety.

In some embodiments, the cells are engineered to synthesize a non-protein or non-peptide small molecule. For example, in an embodiment an engineered cell can produce a statin (e.g., taurostatin, pravastatin, fluvastatin, or atorvastatin).

In some embodiments, the therapeutic agent is an antigen (e.g., a viral antigen, a bacterial antigen, a fungal antigen, a plant antigen, an environmental antigen, or a tumor antigen). An antigen is recognized by those skilled in the art as being immunostimulatory, i.e., capable of stimulating an immune response or providing effective immunity to the organism or molecule from which it derives. An antigen may be a nucleic acid, peptide, protein, sugar, lipid, or a combination thereof.

The particles comprising a cell may produce a single therapeutic agent or a plurality of therapeutic agents. The plurality of therapeutic agents may be related or may form a complex. In some embodiments, the therapeutic agent secreted or released from a particle comprising a cell is in an active form. In some embodiments, the therapeutic agent is secreted or released from a particle comprising a cell an inactive form, e.g., as a prodrug. In the latter instance, the therapeutic agent may be activated by a downstream agent, such as an enzyme.

Methods of Treatment

Described herein are methods for preventing or treating a disease, disorder, or condition in a subject through administration or implantation of particles comprising a first compartment, a second compartment, and a compound of Formula (I) (e.g., as described herein), or a composition comprising the same. In some embodiments, the methods described herein directly or indirectly reduce or alleviate at least one symptom of a disease, disorder, or condition. In some embodiments, the methods described herein prevent or slow the onset of a disease, disorder, or condition. In some embodiments, the subject is a human.

In some embodiments, the disease, disorder, or condition affects a system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, the disease, disorder, or condition affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

In some embodiments, the disease, disorder or condition is a neurodegenerative disease, diabetes, a heart disease, an autoimmune disease, a cancer, a liver disease, a lysosomal storage disease, a blood clotting disorder or a coagulation disorder, an orthopedic condition, an amino acid metabolism disorder.

In some embodiments, the disease, disorder or condition is a neurodegenerative disease. Exemplary neurodegenerative diseases include Alzheimer's disease, Huntington's disease, Parkinson's disease (PD) amyotrophic lateral sclerosis (ALS), multiple sclerosis (MS) and cerebral palsy (CP), dentatorubro-pallidoluysian atrophy (DRPLA), neuronal intranuclear hyaline inclusion disease (NIHID), dementia with Lewy bodies, Down's syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Jakob-Creutzfeldt disease, Niemann-Pick disease type 3, progressive supranuclear palsy, subacute sclerosing panencephalitis, spinocerebellar ataxias, Pick's disease, and dentatorubral-pallidoluysian atrophy.

In some embodiments, the disease, disorder, or condition is an autoimmune disease, e.g., scleroderma, multiple sclerosis, lupus, or allergies.

In some embodiments, the disease is a liver disease, e.g., hepatitis B, hepatitis C, cirrhosis, NASH.

In some embodiments, the disease, disorder, or condition is cancer. Exemplary cancers include leukemia, lymphoma, melanoma, lung cancer, brain cancer (e.g., glioblastoma), sarcoma, pancreatic cancer, renal cancer, liver cancer, testicular cancer, prostate cancer, or uterine cancer.

In some embodiments, the disease, disorder, or condition is an orthopedic condition. Exemplary orthopedic conditions include osteoporosis, osteonecrosis, Paget's disease, or a fracture.

In some embodiments, the disease, disorder or condition is a lysosomal storage disease. Exemplary lysosomal storage diseases include Gaucher disease (e.g., Type I, Type II, Type III), Tay-Sachs disease, Fabry disease, Farber disease, Hurler syndrome (also known as mucopolysaccharidosis type I (MPS I)), Hunter syndrome, lysosomal acid lipase deficiency, Niemann-Pick disease, Salla disease, Sanfilippo syndrome (also known as mucopolysaccharidosis type IIIA (MPS3A)), multiple sulfatase deficiency, Maroteaux-Lamy syndrome, metachromatic leukodystrophy, Krabbe disease, Scheie syndrome, Hurler-Scheie syndrome, Sly syndrome, hyaluronidase deficiency, Pompe disease, Danon disease, gangliosidosis, or Morquio syndrome.

In some embodiments, the disease, disorder, or condition is a blood clotting disorder or a coagulation disorder. Exemplary blood clotting disorders or coagulation disorders include hemophilia (e.g., hemophilia A or hemophilia B), Von Willebrand disease, thrombocytopenia, uremia, Bernard-Soulier syndrome, Factor XII deficiency, vitamin K deficiency, or congenital afibrinogenimia.

In some embodiments, the disease, disorder, or condition is an amino acid metabolism disorder, e.g., phenylketonuria, tyrosinemia (e.g., Type 1 or Type 2), alkaptonuria, homocystinuria, hyperhomocysteinemia, maple syrup urine disease.

In some embodiments, the disease, disorder, or condition is a fatty acid metabolism disorder, e.g., hyperlipidemia, hypercholesterolemia, galactosemia.

In some embodiments, the disease, disorder, or condition is a purine or pyrimidine metabolism disorder, e.g., Lesch-Nyhan syndrome.

In some embodiments, the disease, disorder, or condition is diabetes (e.g., Type I or Type II diabetes).

The present disclosure further comprises methods for identifying a subject having or suspected of having a disease, disorder, or condition described herein, and upon such identification, administering to the subject particles comprising a first compartment, a second compartment, and a compound of Formula (I) (e.g., as described herein), or a composition comprising such particles. In an embodiment, the subject is a human.

Pharmaceutical Compositions, Kits, and Administration

The present disclosure further comprises pharmaceutical compositions comprising the particles described herein, as well as kits thereof.

In some embodiments, a pharmaceutical composition comprises a particle comprising a first compartment, a second compartment, and a compound of Formula (I), as well as a pharmaceutically acceptable excipient. In some embodiments, the particles in the pharmaceutical composition comprise a cell (e.g., a human cell, e.g., an engineered human cell) and a pharmaceutically acceptable excipient. In some embodiments, the particles are provided in an effective amount in the pharmaceutical composition. In some embodiments, the effective amount is a therapeutically effective amount. In some embodiments, the effective amount is a prophylactically effective amount.

Pharmaceutical compositions described herein can be prepared by any method known in the art of pharmacology. In general, such preparatory methods include the steps of bringing the particles (e.g., particles, i.e., "the active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient (i.e., number of particles). The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the disclosure are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The particles described herein may be administered orally, parenterally (including subcutaneous, intramuscular, and intradermal), topically, rectally, nasally, intratumorally, intrathecally, buccally, vaginally or via an implanted reservoir. In some embodiments, provided particles or compositions are administrable subcutaneously or by implant.

In some embodiments, the particles and related compositions described herein may be administered or implanted in or on a certain region of the body, such as a mucosal surface or a body cavity. Exemplary sites of administration or implantation include the peritoneal cavity (e.g., lesser sac), adipose tissue, heart, eye, muscle, spleen, lymph node, esophagus, nose, sinus, teeth, gums, tongue, mouth, throat, small intestine, large intestine, thyroid, bone (e.g. hip or a joint), breast, cartilage, vagina, uterus, fallopian tube, ovary, penis, testicles, blood vessel, liver, kidney, central nervous system (e.g., brain, spinal cord, nerve), or ear (e.g., cochlea).

In some embodiments, the particles and related compositions described herein are administered or implanted at a site other than the central nervous system, e.g., the brain, spinal cord, nerve. In some embodiments, the particles and related compositions described herein are administered or implanted at a site other than the eye (e.g., retina).

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For ophthalmic use, provided pharmaceutically acceptable compositions may be formulated as micronized suspensions or in an ointment such as petrolatum.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The particles and related compositions described herein may be formulated in dosage unit form, e.g., single unit dosage form, for ease of administration and uniformity of dosage. It will be understood, however, that the total dosage and usage regimens of the compositions of the present disclosure will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a treatment required to achieve an effective amount will vary from subject to subject, depending, for example, on species, age, and general condition of a subject, severity of the side effects or disorder, identity of the particular particle(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be appreciated that the particles and related compositions, as described herein, can be administered in combination with one or more additional pharmaceutical agents. The particles or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

Also encompassed by the disclosure are kits (e.g., pharmaceutical packs). The inventive kits may be useful for preventing and/or treating any of the diseases, disorders or conditions described herein. The kits provided may comprise an inventive pharmaceutical composition or particle as described herein and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or particle described herein. In some embodiments, the inventive pharmaceutical composition or particle described herein provided in the container and the second container are combined to form one unit dosage form.

Methods of Making Particles

The present disclosure further comprises methods for making a particle described herein, e.g., a particle comprising a first compartment, a second compartment, and a compound of Formula (I). In some embodiments where the particle is a hydrogel capsule, the method of making the particle comprises contacting a plurality of droplets comprising first and second polymer solutions (e.g., each comprising a hydrogel-forming polymer) with an aqueous cross-linking solution. The droplets can be formed using any technique known in the art.

Each compartment of a particle described herein may comprise an unmodified polymer, a polymer modified with a compound of Formula (I), or a blend thereof. Briefly, in performing a method of preparing a particle configured as a two-compartment hydrogel capsule, a volume of a first polymer solution (e.g., comprising an unmodified polymer, a polymer modified with a compound of Formula (I), or a blend thereof, and optionally containing cells,) is loaded into a first syringe connected to the inner lumen of a coaxial needle. The first syringe may then be connected to a syringe pump oriented vertically above a vessel containing an aqueous cross-linking solution which comprises a cross-linking agent, a buffer, and an osmolarity-adjusting agent. A volume of the second polymer solution (e.g., comprising an unmodified polymer, a polymer modified with a compound of Formula (I), or a blend thereof, and optionally containing cells) is loaded into a second syringe connected to the outer lumen of the coaxial needle. The second syringe may then be connected to a syringe pump oriented horizontally with respect to the vessel containing the cross-linking solution. A high voltage power generator may then be connected to the top and bottom of the needle. The syringe pumps and power generator can then be used to extrude the first and second polymer solutions through the syringes with settings determined to achieve a desired droplet rate of polymer solution into the cross-linking solution. The skilled artisan may readily determine various combinations of needle lumen sizes, voltage range, flow rates, droplet rate and drop distance to create 2-compartment hydrogel capsule compositions in which the majority (e.g., at least 80%, 85%, 90% or more) of the capsules are within 10% of the target size and have a sphere-like in shape. After exhausting the first and second volumes of polymer solution, the droplets may be allowed to cross-link in the cross-linking solution for certain amount of time, e.g., about five minutes.

Exemplary process parameters for preparing a composition of millicapsules (e.g., 1.5 mm diameter millicapsules) include the following. A coaxial needle is disposed above the surface of the cross-linking solution at a distance sufficient to provide a drop distance from the needle tip to the solution surface. In an embodiment, the distance between the needle tip and the solution surface is between 1 to 5 cm. In an embodiment, the first and second polymer solutions are extruded through the needle with a total flow rate of between 0.05 mL/min to 5 mL/min, or 0.05 mL/min to 2.5 mL/min, or 0.05 mL/min to about 1 mL/min, or 0.05 mL/min to 0.5 mL/min, or 0.1 mL/min to 0.5 mL/min. In an embodiment, the first and second polymer solutions are extruded through the needle with a total flow rate of about 0.05 mL/min, 0.1 mL/min, 0.15 mL/min, 0.2 mL/min, 0.25 mL/min, 0.3 mL/min, 0.35 mL/min, 0.4 mL/min, 0.45 mL/min, or 0.5 mL/min. In an embodiment, the flow rate of the first and second polymer solutions through the needle are substantially the same. In an embodiment, the flow rate of the first and second polymer solutions through the needle are different.

In an embodiment, the voltage of the instrument is between 1 kV to 20 kV, or 1 to 15 kV, or 1 kV to 10 kV, or 5 kV to 10 kV. The voltage may be adjusted until a desired droplet rate is reached. In an embodiment, the droplet rate of the instrument is between 1 droplet/10 seconds to 50 droplets/10 seconds, or 1 droplet/10 seconds to 25 droplets/10 seconds.

In an embodiment, the number of non-particle debris on the surface of the cross-linking solution is determined. Particles that have fallen to the bottom of the cross-linking vessel may then be collected, e.g., by transferring cross-linking solution containing the particles to a separate container, leaving behind any non-particle debris on the solution surface in the original cross-linking vessel. The removed particles may then be allowed to settle, the cross-linking solution can be removed, and the particles may then be washed one or more times with a buffer (e.g., a HEPES buffer). In an embodiment, one or more aliquots of the resulting particle composition (e.g., preparation of particles) is inspected by microscopy to assess the quality of the composition, e.g., the number of particle defects and satellite particles.

In some embodiments, the cross-linking solution further comprises a process additive (e.g., a hydrophilic, non-ionic surfactant). A process additive may reduce surface tension of the cross-linking solution. Agents useful as the process additive in the present disclosure include polysorbate-type surfactants, copolymer of polyethyleneoxide (PEO) and polypropyleneoxide (PPO), poly(ethylene oxide)-poly(propylene oxide)-poly(ethylene oxide) (PEO-PPO-PEO) tri-block copolymers, and non-ionic surfactants, such as Tween® 20, Tween® 80, Triton™ X-100, IGEPAL® CA-630, poloxamer 188, or poloxamer 407, or surfactants with substantially the same chemical and physical properties listed in the Exemplary Surfactant Table immediately below.

Exemplary Surfactant Table

| Brand or Generic Name | Commercial Supplier | Approximate Average Molecular Weight (g/mole) | Hydro-philicity HLB[a] |
|---|---|---|---|
| Tween® 20[b] | Millipore Sigma | 1228 | 16.7 |
| Tween® 80[c] | Millipore Sigma | 1310 | 15 |
| Triton™ X-100[d] | Millipore Sigma | 625 | 13.4 |
| IGEPAL® CA-630[e] | Millipore Sigma | 603 | 13 |
| poloxamer 188[f] | Millipore Sigma | 8400 | >24 |
| poloxamer 407[g] | Millipore Sigma | 12,500 | 18-23 |

[a]hydrophilic-lipophilic balance
[b]Chemical names and synonyms: polyethylene glycol sorbitan monolaurate, polyoxyethylene (20) sorbitan monolaurate, polysorbate 20, polyoxyethylene 20 sorbitan monododecanoate
[c]Chemical names and synonyms: polyethylene glycol sorbitan monooleate, polyoxyethylene (20) sorbitan monooleate, polysorbate 80, (x)-sorbitan mono-9-octadecenoate poly (oxy-1,2-ethanediyl)
[d]Chemical names and synonyms: 4-(1,1,3,3-Tetramethylbutyl)phenyl-polyethylene glycol, t-octylphenoxypolyethoxyethanol, polyethylene glycol tert-octylphenyl ether; octylphenol ethoxylate, octylphenol ethylene oxide condensate
[e]Chemical names and synonyms: octylphenoxypolyethoxyethanol, octylphenoxy poly (ethyleneoxy)ethanol, branched
[f]Chemical name: Poly(ethylene glycol)-block-poly(propylene glycol)-block-poly(ethylene glycol)
[g]Chemical name: Poly(ethylene glycol)-block-poly(propylene glycol)-block-poly(ethylene glycol)

In some embodiments, the process additive is a non-ionic surfactant. In an embodiment, the process additive comprises more than one surfactant, e.g., more than one hydrophilic surfactant. In some embodiments, the process additive does not contain Tween® 20 (polysorbate 20) or Triton™ X-100. In an embodiment, the process additive is IGEPAL® CA-630 (polyethylene glycol sorbitan monooleate). In some embodiments, the process additive is poloxamer 188.

In some embodiments, the process additive (e.g., surfactant) is present in the cross-linking solution at a concentration of at least 0.0001% or more. In some embodiments, the cross-linking solution comprises at least 0.001%, 0.01%, or 0.1% of the process additive. In some embodiments, the process additive is present at a concentration selected from about 0.001% to about 0.1%, about 0.005% to about 0.05%, about 0.005% to about 0.01%, and about 0.01% to about 0.5%. In an embodiment, the process additive is a surfactant and is present at a concentration that is below the critical micelle concentration for the surfactant.

In some embodiments, the cross-linking agent comprises divalent cations of a single type or a mixture of different types, e.g., one or more of $Ba^{2+}$, $Ca^{2+}$, $Sr^{2+}$. In some embodiments, the cross-linking agent is $BaCl_2$, e.g., at a concentration of 1 mM to 100 mM or 7.5 mM to 20 mM. In some embodiments, the cross-linking agent is $CaCl_2$, e.g., at a concentration of 50 mM to 100 mM. In some embodiments, the cross-linking agent is $SrCl_2$, e.g., at a concentration of 37.5 mM to 100 mM. In some embodiments, the cross-linking agent is a mixture of $BaCl_2$ (e.g., 5 mM to 20 mM) and $CaCl_2$ (e.g., 37.5 mM to 12.5 mM) or a mixture of $BaCl_2$ (e.g., 5 mM to 20 mM) and $SrCl_2$ (e.g., 37.5 mM to 12.5 mM).

In some embodiments, the cross-linking agent is $SrCl_2$, and the process additive is Tween® 80 (or a surfactant with substantially the same chemical and physical properties listed in the Exemplary Surfactant Table) at a concentration of less than 0.1%, e.g., about 0.005% to 0.05%, about 0.005% to about 0.01%. In some embodiments, the concentration of $SrCl_2$ is about 50 mM. In some embodiments, the cross-linking agent is $SrCl_2$ and the process additive is poloxamer 188 at a concentration of 1%.

The type and concentration of buffer in the aqueous cross-linking solution is selected to maintain the solution pH at approximately neutral, e.g., from about 6.5 to about 7.5, about 7.0 to about 7.5, or about 7.0. In an embodiment, the buffer is compatible with a biological material to be encapsulated in the particle, e.g., cells. In some embodiments, the buffer in the aqueous cross-linking solution comprises HEPES (4-(2-hydroxyethyl)-1-piperazineethanesulfonic acid).

The osmolarity-adjusting agent in the aqueous cross-linking solution is selected to maintain the solution osmolarity at a value similar to the osmolarity of the polymer solution (which in some embodiments comprises a suspension of cells), e.g., an osmolarity that has a higher or lower variance of up to 20%, 10% or 5%. In some embodiments, the osmolarity agent is mannitol at a concentration of 0.1 M to 0.3 M.

In some embodiments, the cross-linking solution comprises 25 mM HEPES buffer, 20 mM $BaCl_2$, 0.2 M mannitol and 0.01% poloxamer 188.

In some embodiments, the cross-linking solution comprises 50 mM strontium chloride hexahydrate, 0.165 M mannitol, 25 mM HEPES and 0.01% of a surfactant with substantially the same chemical and physical properties listed in the Exemplary Surfactant Table for Tween 80.

In an embodiment, the process additive is poloxamer 188, which is present in the particle composition (e.g., preparation of particles) in a detectable amount after the wash steps. Poloxamer 188 may be detected by any technique known in the art, e.g., by partially or completely dissolving the particles in an aliquot of the composition by sodium sulfate precipitation and analyzing the supernatant by LC/MS.

Reduction in the surface tension of the cross-linking solution may be assessed by any method known in the art, for example, through the use of a contact angle goniometer or a tensiometer, e.g., via the du Nouy ring method (see, e.g., Davarci et al (2017) *Food Hydrocolloids* 62:119-127).

Enumerated Exemplary Embodiments

1. A particle comprising:
   a) a first compartment;
   b) a second compartment; and
   c) a compound of Formula (I-a):

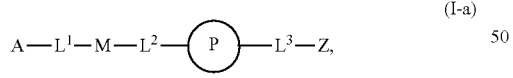

(I-a)

or a pharmaceutically acceptable salt thereof, wherein:
A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —N($R^C$)C(O)($C_1$-$C_6$-alkylene)-, —N($R^C$)C(O)($C_2$-$C_6$-alkenylene)-, —C(=N($R^C$))($R^D$))O—, —S—, —S(O)$_x$—, —OS(O)$_x$—, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;
$L^2$ is a bond;
M is absent, alkyl, heteroalkyl, cycloalkyl, heterocyclyl, aryl, or heteroaryl, each of which is optionally substituted by one or more $R^3$;
P is heteroaryl optionally substituted by one or more $R^4$;
Z is alkyl, alkenyl, alkynyl, heteroalkyl, cycloalkyl, heterocyclyl, aryl, or heteroaryl, each of which is optionally substituted by one or more $R^5$;
each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;
or $R^C$ and $R^D$, taken together with the nitrogen atom to which they are attached, form a ring (e.g., a 5-7 membered ring), optionally substituted with one or more $R^6$;
each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;
each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;
each $R^7$ is independently alkyl, alkenyl, alkynyl, heteroalkyl, halogen, cyano, oxo, hydroxyl, cycloalkyl, or heterocyclyl;
x is 1 or 2; and
y is 2, 3, or 4.

2. The particle of embodiment 1, wherein the first compartment is surrounded by the second compartment.
3. The particle of any one of embodiments 1-2, wherein the first compartment is disposed within the second compartment.
4. The particle of any one of embodiments 1-3, wherein the second compartment forms a barrier around the first compartment.
5. The particle of any one of embodiments 1-4, wherein the total volume of the second compartment is greater than, e.g. 1.5×, 2×, 3×, or 5×, the volume of the first compartment.
6. The particle of any one of embodiments 1-4, wherein the differential volume of the second compartment is greater than, e.g. 1.5×, 2×, 3×, or 5×, the volume of the first compartment.
7. The particle of any one of embodiments 1-4, wherein the total volume of the second compartment is about 1%, 2%, 5%, 7.5%, 10%, 15%, 20%, 25%, 30%, 35%, 40%, 45%, 50%, 55%, 60%, 65%, or 75% greater than the volume of the first compartment.
8. The particle of any one of embodiments 1-4, wherein the differential volume of the second compartment is about 1%, 2%, 5%, 7.5%, 10%, 15%, 20%, 25%, 30%, 35%, 40%, 45%, 50%, 55%, 60%, 65%, or 75% greater than the volume of the first compartment.
9. The particle of any one of embodiments 1-4, wherein the differential volume of the second compartment is less than, e.g. 1.5×, 2×, 3×, or 5×, the volume of the first compartment.
10. The particle of any one of embodiments 1-4, wherein the total volume of the second compartment is about 1%, 2%, 5%, 7.5%, 10%, 15%, 20%, 25%, 30%, 35%, 40%, 45%, 50%, 55%, 60%, 65%, or 75% less than the volume of the first compartment.
11. The particle of any one of embodiments 1-4, wherein the differential volume of the second compartment is about 1%, 2%, 5%, 7.5%, 10%, 15%, 20%, 25%, 30%, 35%, 40%, 45%, 50%, 55%, 60%, 65%, or 75% less than the volume of the first compartment.
12. The particle of embodiment 1, comprising a property selected from the following:
   a) the first compartment comprises a compound of Formula (I-a);
   b) the second compartment comprises a compound of Formula (I-a);
   c) a compound of Formula (I-a) is disposed on the exterior surface of the particle; and/or
   d) the particle comprises an interface between the first and second compartments and a compound of Formula (I-a) is disposed at the interface.
13. The particle of embodiment 12, comprising property a.
14. The particle of any one of embodiments 12-13, comprising property b.
15. The particle of any one of embodiments 12-14, comprising property c.
16. The particle of any one of embodiments 12-15, comprising property d.
17. The particle of embodiment 1, wherein the first compartment or the second compartment is substantially free of a compound of Formula (I-a).
18. The particle of embodiment 1, wherein the outer surface of the particle is substantially free of a compound of Formula (I-a).
19. The particle of embodiment 1, comprising a property selected from the following:
   a) the first compartment is substantially free of a compound of Formula (I-a);
   b) the second compartment is substantially free of a compound of Formula (I-a);
   c) the outer surface of the particle is substantially free of a compound of Formula (I-a); or
   d) the particle comprises an interface between the first and second compartment and the interface is substantially free of a compound of Formula (I-a).
20. The particle of embodiment 19, comprising property a.
21. The particle of any one of embodiments 19-20, comprising property b.
22. The particle of any one of embodiments 19-21, comprising property c.
23. The particle of any one of embodiments 19-22, comprising property d.
24. The particle of embodiment 19, comprising properties a and b.
25. The particle of any one of embodiments 1-24, wherein the particle has a largest linear dimension (LLD), e.g., diameter, of between 20 nanometers to 10 millimeters.
26. The particle of any one of embodiments 1-25, wherein the particle has a largest linear dimension (LLD), e.g., diameter, of between 500 nanometers to 10 millimeters.
27. The particle of any one of embodiments 1-26, wherein the particle has a largest linear dimension (LLD), e.g., diameter, of between 1 millimeter to 5 millimeters, e.g., between 1 millimeter to 4 millimeters, 1 millimeter to 3 millimeters, 1 millimeter to 2 millimeters, about 1.5 millimeters to 2 millimeters, or about 1.5 millimeters.
28. The particle of any one of embodiments 1-27, wherein the particle is configured as a hydrogel capsule with the first compartment surrounded by the second compartment.
29. The particle of embodiment 28, wherein the thickness of the second compartment is selected from the group consisting of:
   (a) 1 nanometers and 1 millimeter;
   (b) 100 nanometers and 1 millimeter; and
   (c) 500 nanometers and 500 micrometers.
30. The particle of embodiment 29, wherein the thickness of the second compartment is at least about 2.5%, 5%, 10%, 15%, 20%, 25%, 30%, 35%, 40%, 50%, 60%, 70%, or 80% of the diameter of the particle.
31. The particle of any one of embodiments 1-30, wherein the particle comprises a cell.
32. The particle of any one of embodiments 1-31, wherein the first compartment comprises a cell.
33. The particle of any one of embodiments 1-32, wherein the second compartment comprises a cell.
34. The particle of any one of embodiments 1-33, wherein the first compartment comprises a cell and the second compartment does not comprise a cell.
35. The particle of any one of embodiments 1-34, wherein the first compartment comprises a cell and the second compartment comprises a cell.
36. The particle of embodiment 35, wherein the first compartment and the second compartment comprise the same type of cell.
37. The particle of embodiment 35, wherein the cell in the first compartment is a different type of cell than the cell in the second compartment.
38. The particle of any one of embodiments 31-36, wherein the particle comprises an interface between the first compartment and the second compartment and a cell is disposed at the interface, e.g., a cell contacts both the first and second compartments.
39. The particle of any one of embodiments 31-37, wherein the number or density of cells in the second compartment is less than the number or density of cells in the first compartment.
40. The particle of any one of embodiments 31-39, wherein the first compartment is formed from a polymer solution comprising at least $0.5\times10^6$, $1\times10^6$, $5\times10^6$, $10\times10^6$, $15\times10^6$ or $20\times10^6$ cells per mL.
41. The particle of any one of embodiments 31-40, wherein the first compartment is formed from a polymer solution comprising at least $0.5\times10^6$, $1\times10^6$, $5\times10^6$, $10\times10^6$, $15\times10^6$, $20\times10^6$ or $25\times10^6$ cells per mL or from a polymer solution comprising 100 to 300 million cells per mL.
42. The particle of any one of embodiments 31-41, wherein the particle comprises at least 100; 250; 500; 750; 1,000; 2,500; 5,000; 10,000; 25,000; or 50,000 cells.

43. The particle of any one of embodiments 31-42, wherein the first compartment comprises at least 100; 250; 500; 750; 1,000; 2,500; 5,000; 10,000; 25,000; or 50,000 cells.

44. The particle of any one of embodiments 31-43, wherein the cells are present as single cells, one or more spheroids, or bound to one or more microcarriers.

45. The particle of any one of embodiments 31-44, wherein the exterior surface of the particle is substantially free of cells.

46. The particle of any one of embodiments 31-45, wherein:
   a) one or a plurality of cells is disposed within the first compartment;
   b) the number or density of cells in the second compartment is at least 2, 5, 10, $10^2$, $10^3$, or $10^4$ times less than the number of density of cells in the first compartment;
   c) the first compartment (e.g., the outer boundary of the first compartment) comprises a compound of Formula (I-a); or
   d) the second compartment (e.g., the outer boundary of the second compartment) comprises a compound of Formula (I-a).

47. The particle of embodiment 46, comprising property a.

48. The particle of any one of embodiments 46-47, comprising property b.

49. The particle of any one of embodiments 46-48, comprising property c.

50. The particle of any one of embodiments 46-49, comprising property d.

51. The particle of embodiment 50, comprising properties a and b.

52. The particle of embodiment 50, comprising properties a, b, and c.

53. The particle of embodiment 50, comprising properties a, b, and d.

54. The particle of embodiment 50, comprising properties a, b, c, and d.

55. The particle of any one of embodiments 31-54, wherein the second compartment is substantially free of cells.

56. The particle of any one of embodiments 31-55, wherein the cell is an epithelial cell, endothelial cell, fibroblast cell, mesenchymal stem cell, or keratinocyte cell.

57. The particle of any one of embodiments 31-56, wherein the cell is an RPE (e.g., ARPE-19) cell or an MSC.

58. The particle of any one of embodiments 31-56, wherein the cell is an islet cell.

59. The particle of any one of embodiments 31-58, wherein the cell expresses a therapeutic agent (e.g., a polypeptide).

60. The particle of embodiment 59, wherein the polypeptide is a Factor VIII protein or a variant thereof or a Factor IX protein or a variant thereof.

61. The particle of any one of embodiments 59-60, wherein the polypeptide comprises SEQ ID NO:1 or a variant thereof.

62. The particle of any one of embodiments 59-60, wherein the polypeptide comprises SEQ ID NO: 2 or a variant thereof, e.g., an alanine substituted for threonine at amino acid position 148 of SEQ ID NO:2 or a leucine substituted for arginine at amino acid position 338 of SEQ ID NO:2.

63. The particle of embodiment 59, wherein the polypeptide is insulin (e.g., insulin A-chain, insulin B-chain, or proinsulin).

64. The particle of any one of embodiments 1-63, wherein the particle comprises a polymer.

65. The particle of embodiment 64, wherein the polymer is a polysaccharide.

66. The particle of any one of embodiments 64-65, wherein the polymer is selected from alginate, chitosan, hyaluronate, gelatin, poly(L-lactic acid) (PLLA), or poly(lactic glycolic acid) (PLGA).

67. The particle of any one of embodiments 64-66, wherein the first compartment comprises a polymer (e.g., a polysaccharide, e.g., an alginate).

68. The particle of any one of embodiments 64-67, wherein the second compartment comprises a polymer (e.g., a polysaccharide, e.g., an alginate).

69. The particle of any one of embodiments 64-68, wherein both the first compartment and the second compartment comprise a polymer (e.g., a polysaccharide, e.g., an alginate).

70. The particle of any one of embodiments 64-69, wherein the first compartment and the second compartment comprise the same polymer.

71. The particle of any one of embodiments 64-70, wherein the first compartment and the second compartment comprise a different polymer.

72. The particle of any one of embodiments 64-71, wherein the first compartment does not comprise alginate and the second compartment comprises alginate.

73. The particle of any one of embodiments 64-72, wherein first compartment comprises an alginate and the second compartment comprises a polymer other than alginate.

74. The particle of any one of embodiments 64-73, wherein second compartment comprises an alginate and the first compartment comprises a polymer other than alginate.

75. The particle of embodiment 74, wherein the first compartment comprises hyaluronate or chondroitin and the second compartment comprises an alginate.

76. The particle of any one of embodiments 73-75, wherein the polymer of the first compartment is modified with a compound of Formula (I-a).

77. The particle of any one of embodiments 73-76, wherein the polymer of the second compartment is modified with a compound of Formula (I-a).

78. The particle of any one of embodiments 1-77, wherein the exterior surface of the particle and interior of the second compartment comprise a compound of Formula (I-a).

79. The particle of any one of embodiments 64-78, wherein the polymers of both the first compartment and second compartment are modified with a compound of Formula (I-a).

80. The particle of any one of embodiments 1-79, wherein the compound of Formula (I-a) is a compound of any one of Formulas (I-b), (I-c), (I-d), (I-e), (I-f), (II), (II-a), (III), (III-a), (III-b), (III-c), or (III-d), or a pharmaceutically acceptable salt thereof.

81. The particle of any one of embodiments 76-80, wherein the compound of Formula (I-a) is selected from Compound 110, Compound 112, Compound 113 or Compound 114 shown in Table 2.

82. The particle of any one of embodiments 76-80, wherein the compound of Formula (I-a) is Compound 112 shown in Table 2.

83. The particle of any one of embodiments 76-80, wherein the compound of Formula (I-a) is Compound 113 shown in Table 2.
84. The particle of any one of embodiments 76-80, wherein the compound of Formula (I-a) is Compound 114 shown in Table 2.
85. The particle of any one of embodiments 76-80, wherein the compound of Formula (I-a) is not Compound 100 shown in Table 2.
86. The particle of any one of embodiments 76-80, wherein the compound of Formula (I-a) is Compound 101 shown in Table 2.
87. The particle of any one of embodiments 76-86, wherein at least 0.5% of the monomers of a polymer are modified with a compound of Formula (I-a) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of a polymer are modified with a compound of Formula (I-a)).
88. The particle of any one of embodiments 76-86, wherein at least 0.5% of the monomers of a polymer in the first (inner) compartment of the particle are modified with a compound of Formula (I-a) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of a polymer in the first (inner) compartment of the particle are modified with a compound of Formula (I-a)).
89. The particle of any one of embodiments 76-86, wherein at least 0.5% of the monomers of a polymer in the second (outer) compartment of the particle are modified with a compound of Formula (I-a) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of a polymer in the second (outer) compartment of the particle are modified with a compound of Formula (I-a)).
90. The particle of any one of embodiments 76-86, wherein the polymer (when modified with a compound of Formula (I-a)) comprises an increase in % N (as compared with unmodified polymer) of 0.1% to 10% N by weight (e.g., 0.1% to 2% N, 2% to 4%, or 4% to 8% N by weight), where % N is determined by combustion analysis and corresponds to the amount of compound of Formula (I-a) in the modified polymer.
91. The particle of any one of embodiments 76-86, wherein the first (inner) compartment of the particle comprises a polymer (when modified with a compound of Formula (I-a)) that comprises an increase in % N (as compared with unmodified polymer) of 0.1% to 10% N by weight (e.g., 0.1% to 2% N, 2% to 4%, or 4% to 8% N by weight), where % N is determined by combustion analysis and corresponds to the amount of compound of Formula (I-a) in the modified polymer.
92. The particle of any one of embodiments 76-84, wherein the second (outer) compartment of the particle comprises a polymer (when modified with a compound of Formula (I-a)) that comprises increase in % N (as compared with unmodified polymer) of 0.1% to 10% N by weight (e.g., 0.1% to 2% N, 2% to 4%, or 4% to 8% N by weight), where % N is determined by combustion analysis and corresponds to the amount of compound of Formula (I-a) in the modified polymer.
93. The particle of any one of embodiments 76-84, wherein the particle is a hydrogel capsule and the second (outer) compartment of the capsule is formed using a mixture of an unmodified alginate and an alginate modified with a compound of Formula (I-a) (e.g., Compound 101) at a conjugation density of at least 2.0% and less than 9.0% nitrogen (N) as determined by combustion analysis for percent nitrogen as described in the Examples hereinbelow, or is 3.0% to 8.0%, 4.0% to 7.0%, 5.0% to 7.0%, or 6.0% to 7.0% or about 6.8%.
94. The particle of any one of embodiments 1-93, wherein the particle is a spherical particle.
95. The particle of any one of embodiments 1-94, wherein the particle is made by a method wherein the second compartment is formed around the first compartment.
96. The particle of any of embodiments 1-95, made by a method comprising contacting a plurality of droplets of a polymer solution with an aqueous cross-linking solution for a period of time sufficient to produce a particle, wherein the cross-linking solution comprises a cross-linking agent, a buffer, and an osmolarity-adjusting agent.
97. The particle of embodiment 96, wherein the cross-linking solution further comprises a process additive.
98. The particle of embodiment 97, wherein the process additive is a surfactant.
99. The particle of embodiment 98, wherein the surfactant is selected from a polysorbate-type surfactant, a copolymer of polyethyleneoxide (PEO) and polypropyleneoxide (PPO), a poly(ethylene oxide)-poly(propylene oxide)-poly(ethylene oxide) (PEO-PPO-PEO) triblock copolymer, polysorbate 20, polysorbate 80, 4-(1,1,3,3-Tetramethylbutyl)phenyl-polyethylene glycol, octylphenoxypolyethoxyethanol, poloxamer 188 and poloxamer 407.
100. The particle of any one of embodiments 98-99, wherein the surfactant has a hydrophilic-lipophilic balance (HLB) of at least 18 or at least 24, and optionally wherein the surfactant is poloxamer 188.
101. The particle of any one of embodiments 97-99, wherein the process additive is present in the cross-linking solution at a concentration of at least about 0.001% to about 0.1%, about 0.005% to about 0.05%, about 0.005% to about 0.01%, or about 0.01% to about 0.05%.
102. The particle of any one of embodiments 96-101, wherein the cross-linking agent comprises divalent cations of a single type or a mixture of different types, optionally wherein the cross-linking agent comprises one or more of $Ba^{2+}$, $Ca^{2+}$ and $Sr^{2+}$.
103. The particle of any one of embodiments 96-102, wherein the cross-linking agent is selected from the group consisting of:
   a. $BaCl_2$ at a concentration of 1 mM to 100 mM or 7.5 mM to 20 mM;
   b. $CaCl_2$ at a concentration of 50 mM to 100 mM;
   c. $SrCl_2$ at a concentration of 37.5 mM to 100 mM;
   d. a mixture of $BaCl_2$ at a concentration of 5 mM to 20 mM and $CaCl_2$ at a concentration of 37.5 mM to 12.5 mM; and
   e. a mixture of $BaCl_2$ at a concentration of 5 mM to 20 mM and $SrCl_2$ at a concentration of 37.5 mM to 12.5 mM.
104. The particle of any one of embodiments 96-103, wherein the buffer comprises 4-(2-hydroxyethyl)-1-piperazineethanesulfonic acid) (HEPES).

105. The particle of any one of embodiments 96-104, wherein the osmolarity-adjusting agent comprises mannitol at a concentration of 0.1 M to 0.3 M.
106. The particle of any of embodiments 96-105, wherein the cross-linking agent is not $SrCl_2$.
107. The particle of any one of embodiments 96-106, wherein the cross-linking agent is $BaCl_2$.
108. The particle of any one of embodiments 96-107, wherein the cross-linking solution comprises 25 mM HEPES buffer, 20 mM $BaCl_2$, 0.2 M mannitol and 0.01% poloxamer 188.
109. The particle of any one of embodiments 96-108, wherein the cross-linking agent is $SrCl_2$ and the process additive is a surfactant at a concentration of about 0.01%, wherein the surfactant is polysorbate 80.
110. The particle of embodiment 109, wherein the cross-linking solution comprises 50 mM strontium chloride hexahydrate, 0.165 M mannitol, 25 mM HEPES and 0.01% of polysorbate 80.
111. The particle of any one of embodiments 1 to 110, wherein the particle is a hydrogel millicapsule comprising a hydrogel forming polymer in each of the first and second compartments.
112. The particle of embodiment 111, wherein the only hydrogel forming polymer in the first compartment is a high molecular weight alginate and the hydrogel forming polymer in the second compartment is a mixture of a chemically modified low molecular weight alginate and an unmodified high molecular weight alginate.
113. A preparation of a plurality of particles, wherein the plurality comprises a particle of any one of embodiments 1-112
114. The preparation of embodiment 113, wherein at least 75%, 80%, 85%, 90%, 95%, 99%, or more of the particles in the plurality are spherical particles, and optionally wherein the preparation comprises a detectable amount of the process additive.
115. The preparation of embodiment 113 to 114, wherein the preparation is a pharmaceutically acceptable preparation.
116. A method of making a particle described herein, e.g., a particle of any of embodiments 1-115.
117. The method of embodiment 116, comprising forming the first compartment prior to formation of the second compartment.
118. The method of embodiment 117, comprising forming the first compartment at the same time as the formation of the second compartment.
119. The method of any one of embodiments 116-118, comprising contacting a plurality of droplets of first and second polymer solutions with an aqueous cross-linking solution for a period of time sufficient to produce a hydrogel capsule with first and second compartments, wherein the cross-linking solution comprises a cross-linking agent, a buffer, and an osmolarity-adjusting agent.
120. The method of any one of embodiments 116-119, wherein the method comprises use of a coaxial needle.
121. The method of any one of embodiments 116-120, wherein the first polymer solution comprises cells.
122. A method of implanting a particle in a subject comprising:
providing a particle described herein, e.g., in any of embodiments 1 to 112; and
disposing the particle in the body of the subject.
123. A method of providing a substance, e.g., a therapeutic substance, e.g., a polypeptide, to a subject comprising:
providing a particle described herein, e.g., in any of embodiments 1-112; which comprises or has the ability to produce the substance; and
disposing the particle in the body of the subject.
124. A method of evaluating a particle, e.g., in a subject comprising:
providing a particle described herein, e.g., in any of embodiments 1-112; and
disposing the particle in the body of the subject.
125. A method of treating a subject in need of a substance, e.g., a polypeptide, to a subject comprising:
providing a particle described herein, e.g., in any of embodiments 1-112; which comprises or has the ability to produce the substance; and
disposing the particle in the body of the subject.
126. A composition of particles for use in treating a subject in need of a substance, e.g., a polypeptide, to a subject comprising:
providing a particle described herein, e.g., in any of embodiments 1-112; which comprises or has the ability to produce the substance; and
disposing the particle in the body of the subject.

EXAMPLES

In order that the disclosure described herein may be more fully understood, the following examples are set forth. The examples described in this application are offered to illustrate the particles, chemical modifications, compositions and methods provided herein and are not to be construed in any way as limiting their scope.

Example 1

Synthesis of Exemplary Compounds for Preparation of Chemically Modified Implantable Elements General Protocols The procedures below describe methods of preparing exemplary compounds for preparation of chemically modified implantable elements. The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Huisgen Cycloaddition to Afford 1,4-Substituted Triazoles

The copper-catalyzed Huisgen [3+2] cycloaddition was used to prepare triazole-based compounds and compositions, devices, and materials thereof. The scope and typical protocols have been the subject of many reviews (e.g., Meldal, M. and Tornoe, C. W. Chem. Rev. (2008) 108:2952-3015; Hein, J. E. and Fokin, V. V. Chem. Soc. Rev. (2010) 39(4):1302-1315; both of which are incorporated herein by reference).

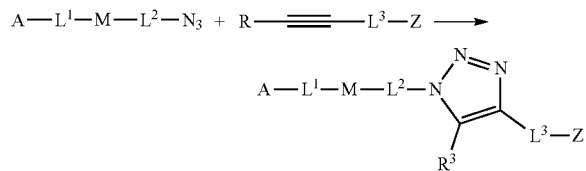

In the example shown above, the azide is the reactive moiety in the fragment containing the connective element A, while the alkyne is the reactive component of the pendant group Z. As depicted below, these functional handles can be exchanged to produce a structurally related triazole product. The preparation of these alternatives is similar, and do not require special considerations.

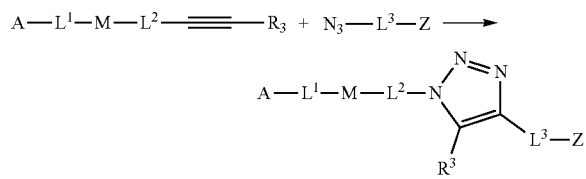

A typical Huisgen cycloaddition procedure starting with an iodide is outlined below. In some instances, iodides are transformed into azides during the course of the reaction for safety.

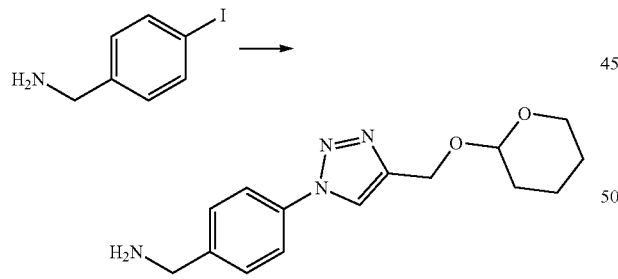

A solution of sodium azide (1.1 eq), sodium ascorbate, (0.1 eq) trans-N,N'-dimethylcyclohexane-1,2-diamine (0.25 eq), copper (I) iodide in methanol (1.0 M, limiting reagent) was degassed with bubbling nitrogen and treated with the acetylene (1 eq) and the aryl iodide (1.2 eq). This mixture was stirred at room temperature for 5 minutes, then warmed to 55° C. for 16 h. The reaction was then cooled to room temperature, filtered through a funnel, and the filter cake washed with methanol. The combined filtrates were concentrated and purified via flash chromatography on silica gel (120 g silica, gradient of 0 to 40% (3% aqueous ammonium hydroxide, 22% methanol, remainder dichloromethane) in dichloromethane to afford the desired target material.

A typical Huisgen cycloaddition procedure starting with an azide is outlined below.

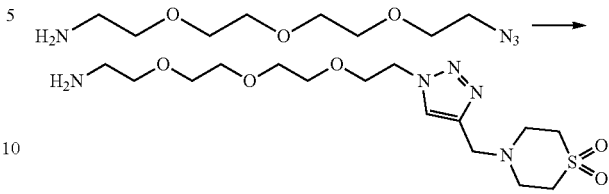

A solution of tris[(1-benzyl-1H-1,2,3-triazol-4-yl)methyl] amine (0.2 eq), triethylamine (0.5 eq), copper (I) iodide (0.06 eq) in methanol (0.4 M, limiting reagent) was treated with the acetylene (1.0 eq) and cooled to 0° C. The reaction was allowed to warm to room temperature over 30 minutes, then heated to 55° C. for 16h. The reaction was cooled to room temperature, concentrated, and purified with HPLC (C18 column, gradient of 0 to 100% (3% aqueous ammonium hydroxide, 22% methanol remainder dichloromethane) in dichloromethane to afford the desired target material.

Huisgen Cycloaddition to Afford 1,5-Substituted Triazoles

The Huisgen [3+2] cycloaddition was also performed with ruthenium catalysts to obtain 1,5-disubstituted products preferentially (e.g., as described in Zhang et al, J. Am. Chem. Soc., 2005, 127, 15998-15999; Boren et al, J. Am. Chem. Soc., 2008, 130, 8923-8930, each of which is incorporated herein by reference in its entirety).

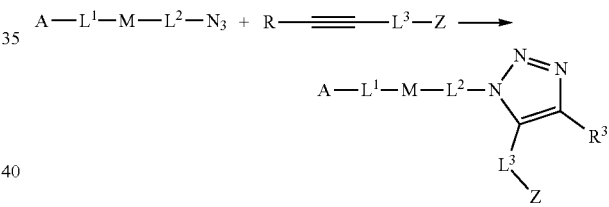

As described previously, the azide and alkyne groups may be exchanged to form similar triazoles as depicted below.

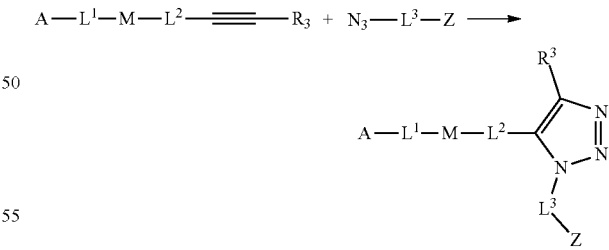

A typical procedure is described as follows: a solution of the alkyne (1 eq) and the azide (1 eq) in dioxane (0.8M) were added dropwise to a solution of pentamethylcyclo-pentadienylbis(triphenylphosphine) ruthenium(II) chloride (0.02 eq) in dioxane (0.16M). The vial was purged with nitrogen, sealed and the mixture heated to 60° C. for 12h. The resulting mixture was concentrated and purified via flash chromatography on silica gel to afford the requisite compound.

Experimental Procedure for (4-(4-((4-methylpiperazin-1-yl)methyl)-1H-1,2,3-triazol-1-yl)phenyl)methanamine (3)

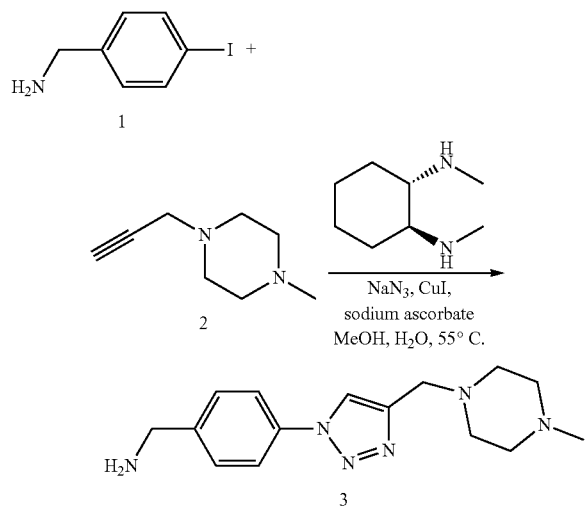

A mixture of (4-iodophenyl)methanamine (1, 843 mg, 3.62 mmol, 1.0 eq), (1S,2S)—N1,N2-dimethylcyclohexane-1,2-diamine (74 µL, 0.47 mmol, 0.13 eq), Sodium ascorbate (72 mg, 0.36 mmol, 0.1 eq), Copper Iodide (69 mg, 0.36 mmol, 0.1 eq), Sodium azide (470 mg, 7.24 mmol, 2.0 eq), and 1-methyl-4-(prop-2-yn-1-yl)piperazine (2, 0.5 g, 3.62 mmol, 1.0 eq) in Methanol (9 mL) and water (1 mL) were purged with nitrogen for 5 minutes and heated to 55° C. for over night. The reaction mixture was cooled to room temperature, concentrated under reduced pressure, and the brownish slurry was extracted with dichloromethane. Celite was added to the combined dichloromethane phases and the solvent was removed under reduced pressure. The crude product was purified over silica gel (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 7.5% to afford (4-(4-((4-methylpiperazin-1-yl)methyl)-1H-1,2,3-triazol-1-yl)phenyl)methanamine (3, 0.45 g, 43%). LCMS m/z: [M+H]$^+$ Calcd for $C_{15}H_{22}N_6$ 287.2; Found 287.1.

Experimental Procedure for N-(4-(4-((4-methylpiperazin-1-yl)methyl)-1H-1,2,3-triazol-1-yl)benzyl)methacrylamide (4)

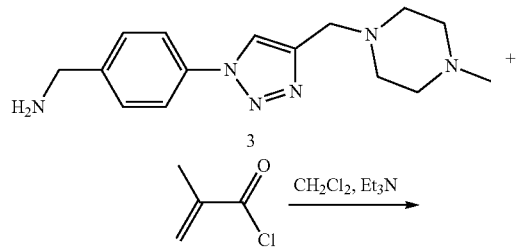

A solution of (4-(4-((4-methylpiperazin-1-yl)methyl)-1H-1,2,3-triazol-1-yl)phenyl)methanamine (3, 1.2 g, 4.19 mmol, 1.0 eq) and triethylamine (0.70 mL, 5.03 mmol, 1.2 eq) in CH$_2$Cl$_2$ (50 mL) was cooled to 0° C. with an ice-bath and methacryloyl chloride (0.43 mL, 4.40 mmol, 1.05 eq in 5 mL of CH$_2$Cl$_2$) was added. The reaction was stirred for a day while cooled with an ice-bath. 10 grams of Celite were added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 7.5%. The solvent was removed under reduced pressure and the resulting solid was triturated with diethyl ether, filtered and washed multiple times with diethyl ether to afford N-(4-(4-((4-methylpiperazin-1-yl)methyl)-1H-1,2,3-triazol-1-yl)benzyl)methacrylamide (4, 0.41 g, 28% yield) as a white solid. LCMS m/z: [M+H]$^+$ Calcd for $C_{19}H_{26}N_6O$ 355.2; Found 355.2.

Experimental Procedure for (4-(4-((2-(2-methoxyethoxy)ethoxy)methyl)-1H-1,2,3-triazol-1-yl)phenyl)methanamine (6)

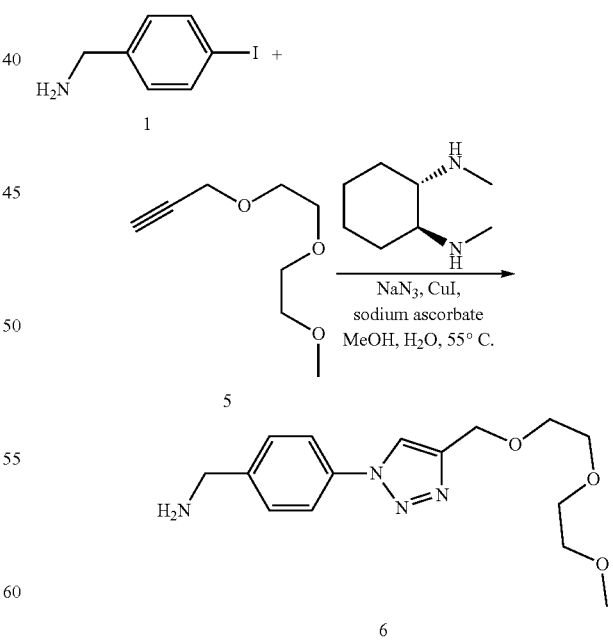

A mixture of (4-iodophenyl)methanamine (1, 2.95 g, 12.64 mmol, 1.0 eq), (1S,2S)—N1,N2-dimethylcyclohexane-1,2-diamine (259 µL, 1.64 mmol, 0.13 eq), sodium ascorbate (250 mg, 1.26 mmol, 0.1 eq), copper iodide (241 mg, 1.26 mmol, 0.1 eq), sodium azide (1.64 g, 25.29 mmol, 2.0 eq), and 3-(2-(2-methoxyethoxy)ethoxy)prop-1-yne (5, 2.0 g, 12.64 mmol, 1.0 eq) in methanol (40 mL) and water (4 mL) was purged with nitrogen for 5 minutes and then heated to 55° C. overnight. The reaction mixture was cooled to room temperature and concentrated under reduced pressure. The residue was dissolved in dichloromethane, filtered, and concentrated with Celite® (10 g). The crude product was purified on silica gel (220 g) using dichloromethane/(methanol containing 12% (v/v) aqueous ammonium hydroxide) as the eluent. The concentration of (methanol containing 12% (v/v) aqueous ammonium hydroxide) was gradually increased from 0% to 6.25% to afford (4-(4-((2-(2-methoxyethoxy)ethoxy)methyl)-1H-1,2,3-triazol-1-yl)phenyl)methanamine (6, 1.37 g, 35%). LCMS m/z: [M+H]$^+$ Calcd for $C_{15}H_{22}N_4O_3$ 307.2; Found 307.0.

Experimental Procedure for N-(4-(4-((2-(2-methoxyethoxy)ethoxy)methyl)-1H-1,2,3-triazol-1-yl)benzyl)methacrylamide (7)

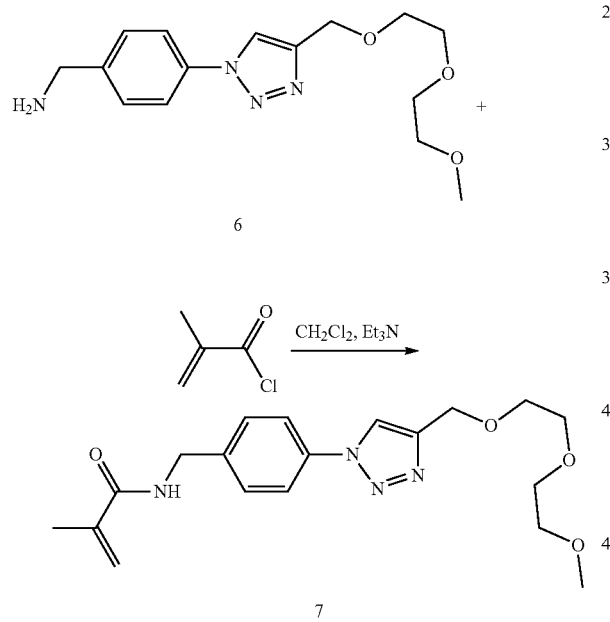

A solution of 4-(4-((2-(2-methoxyethoxy)ethoxy)methyl)-1H-1,2,3-triazol-1-yl)phenyl)methanamine (6, 1.69 g, 5.52 mmol, 1.0 eq) and triethylamine (0.92 mL, 6.62 mmol, 1.2 eq) in CH$_2$Cl$_2$ (50 mL) was cooled to 0° C. with an ice-bath and methacryloyl chloride (0.57 mL, 5.79 mmol, 1.05 eq) was added in a dropwise fashion. The reaction was stirred for 4 h at room temperature. 10 grams of Celite were added and the solvent was removed under reduced pressure. The residue was purified by silica gel (80 g) chromatography using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(4-(4-((2-(2-methoxyethoxy)ethoxy)methyl)-1H-1,2,3-triazol-1-yl)benzyl)methacrylamide (7, 1.76 g, 85% yield) as a white solid. LCMS m/z: [M+H]$^+$ Calcd for $C_{19}H_{26}N_4O_4$ 375.2; Found 375.0.

Experimental Procedure for 3-(prop-2-yn-1-yloxy)oxetane (9)

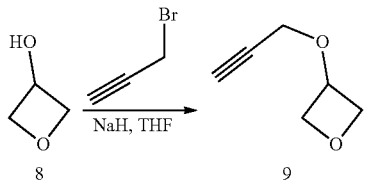

A suspension of sodium hydride (27.0 g, 675 mmol, 60% purity) in THF (200 mL) was cooled with an ice bath. Oexetan-3-ol (8, 25 g, 337 mmol) was added in a dropwise fashion and stirred for 30 minutes at 0° C. 3-Bromoprop1-yne (9, 41.2 mL, 371 mmol, 80% purity) was then added in a dropwise fashion. The mixture was stirred over night while allowed to warm to room temperature. The mixture was filtered over Celite, washed with THF, and concentrated with Celite under reduced pressure. The crude product was purified over silica gel (220 g) and eluted with Hexanes/EtOAc. The concentration of EtOAc in the mobile phase was increased from 0 to 25% to afford a yellow oil of (9, 18.25 g 48%).

Experimental Procedure for 3-(4-((oxetan-3-yloxy)methyl)-1H-1,2,3-triazol-1-yl)propan-1-amine (11)

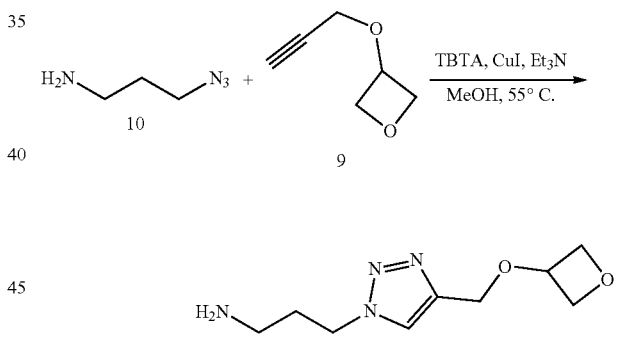

A mixture of 3-(prop-2-yn-1-yloxy)oxetane (9, 7.96 g, 71 mmol, 1.0 eq), 3-azidopropan-1-amine (10, 7.82 g, 78 mmol, 1.1 eq), Tris[(1-benzyl-1H-1,2,3-triazol-4-yl)methyl]-amine (8.29 g, 15.6 mmol, 0.22 eq), Copper Iodide (1.35 g, 7.1 mmol, 0.1 eq), and Triethylamine (2.47 mL, 17.8 mmol, 0.25 eq) in Methanol (80 mL) was warmed to 55° C. and stirred over night under Nitrogen atmosphere. The reaction mixture was cooled to room temperature, Celite (20 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 15% to afford 3-(4-((oxetan-3-yloxy)methyl)-1H-1,2,3-triazol-1-yl)propan-1-amine (11, 11.85 g, 79%) as a yellow oil. LCMS m/z: [M+H]$^+$ Calcd for $C_9H_{16}N_4O_2$ 213.1; Found 213.0.

Experimental Procedure for N-(3-(4-((oxetan-3-yloxy)methyl)-1H-1,2,3-triazol-1-yl)propyl)methacrylamide (12)

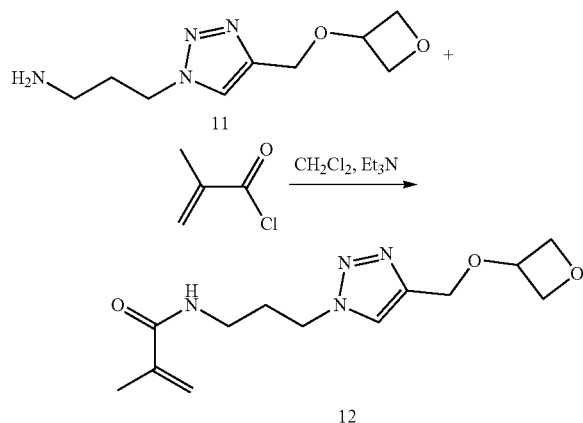

A solution of 3-(4-((oxetan-3-yloxy)methyl)-1H-1,2,3-triazol-1-yl)propan-1-amine (11, 3.94 g, 18.56 mmol, 1.0 eq) and triethylamine (3.1 mL, 22.28 mmol, 1.2 eq) in $CH_2Cl_2$ (100 mL) was cooled to 0° C. with an ice-bath and methacryloyl chloride (1.99 mL, 20.42 mmol, 1.1 eq) was added in a dropwise fashion. The reaction was stirred over night while allowed to warm to room temperature. 20 grams of Celite were added and the solvent was removed under reduced pressure. The residue was purified by silica gel chromatography (220 g) using dichloromethane/methanol as mobile phase. The concentration of methanol was gradually increased from 0% to 5% to afford N-(3-(4-((oxetan-3-yloxy)methyl)-1H-1,2,3-triazol-1-yl)propyl)methacrylamide (12, 3.22 g, 62% yield) as a solid. LCMS m/z: [M+H]$^+$ Calcd for $C_{13}H_{20}N_4O_3$ 281.2; Found 281.0.

Experimental Procedure for N-(4-(1H-1,2,3-triazol-1-yl)benzyl) methacrylamide (14)

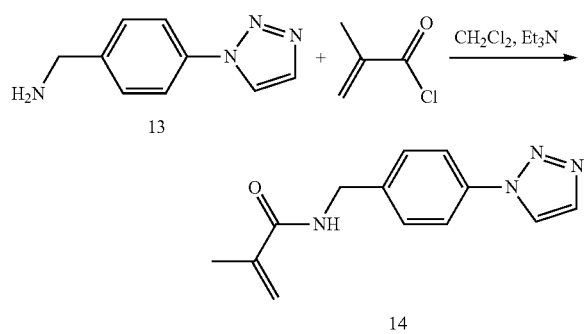

To a solution of (4-(1H-1,2,3-triazol-1-yl)phenyl)methanamine (13, obtained from WuXi, 1.2 g, 5.70 mmol, 1.0 eq) and triethylamine (15 mL, 107.55 mmol, 18.9 eq) in $CH_2Cl_2$ (100 mL) was slowly added methacryloyl chloride (893 mg, 8.54 mmol, 1.5 eq) in a dropwise fashion. The reaction was stirred over night. 20 grams of Celite were added and the solvent was removed under reduced pressure. The residue was purified by silica gel chromatography using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(4-(1H-1,2,3-triazol-1-yl)benzyl) methacrylamide (14, 1.38 g, 40% yield).

Experimental Procedure for (4-(4-(((tetrahydro-2H-pyran-2-yl)oxy)methyl)-1H-1,2,3-triazol-1-yl)phenyl)methanamine (15)

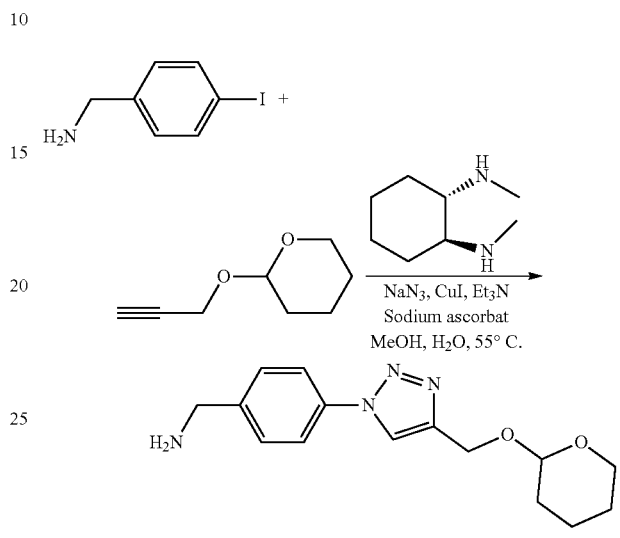

A mixture of (4-iodophenyl)methanamine hydrochloride (5.0 g, 18.55 mmol, 1.0 eq), (1S,2S)—N1,N2-dimethylcyclohexane-1,2-diamine (0.59 mL 3.71 mmol, 0.2 eq), Sodium ascorbate (368 mg, 1.86 mmol, 0.1 eq), Copper Iodide (530 mg, 2.78 mmol, 0.15 eq), Sodium azide (2.41 g, 37.1 mmol, 2.0 eq), $Et_3N$ (3.11 mL, 22.26 mmol, 1.2 eq) and 2-(prop-2-yn-1-yloxy)tetrahydro-2H-pyran (2.6 g, 18.55 mmol, 1.0 eq) in Methanol (50 mL) and water (12 mL) were purged with Nitrogen for 5 minutes and heated to 55° C. for over night. The reaction mixture was cooled to room temperature and filtered through 413 filter paper. Celite was added and the solvent was removed under reduced pressure and the residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 6.25% to afford (4-(4-(((tetrahydro-2H-pyran-2-yl)oxy)methyl)-1H-1,2,3-triazol-1-yl)phenyl)methanamine (15, 3.54 g, 66%) as a white solid. LCMS m/z: [M+H]$^+$ Calcd for $C_{15}H_{20}N_4O_2$ 289.2; Found 289.2.

Experimental Procedure for N-(4-(4-(((tetrahydro-2H-pyran-2-yl)oxy)methyl)-1H-1,2,3-triazol-1-yl)benzyl)methacrylamide (16)

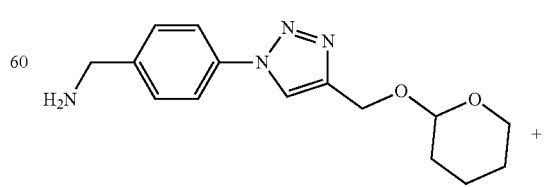

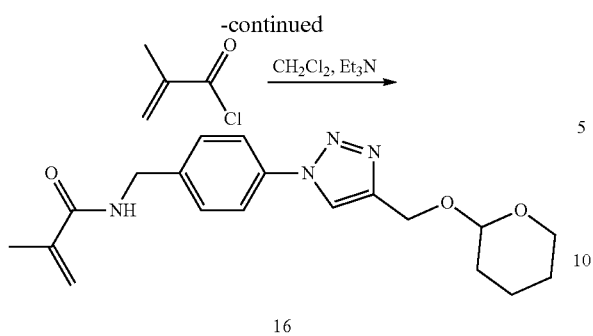

16

A solution of (4-(4-(((tetrahydro-2H-pyran-2-yl)oxy) methyl)-1H-1,2,3-triazol-1-yl)phenyl)methanamin (15, 3.46 g, 12.00 mmol, 1.0 eq) and triethylamine (2.01 mL, 14.40 mmol, 1.2 eq) in CH$_2$Cl$_2$ (40 mL) was cooled to 0° C. with an ice-bath and methacryloyl chloride (1.23 mL, 12.60 mmol, 1.05 eq, diluted in 5 mL of CH$_2$Cl$_2$) was added in a dropwise fashion. The cooling bath was removed and the reaction was stirred for 4 h. 20 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 3.75% to afford N-(4-(4-(((tetrahydro-2H-pyran-2-yl)oxy) methyl)-1H-1,2,3-triazol-1-yl)benzyl)methacrylamide (16, 2.74 g, 64% yield) as a white solid. LCMS m/z: [M+H]$^+$ Calcd for C$_{19}$H$_{24}$N$_4$O$_3$ 357.2; Found 357.3.

Experimental Procedure for N-(4-(4-(hydroxymethyl)-1H-1,2,3-triazol-1-yl)benzyl)methacrylamide (17)

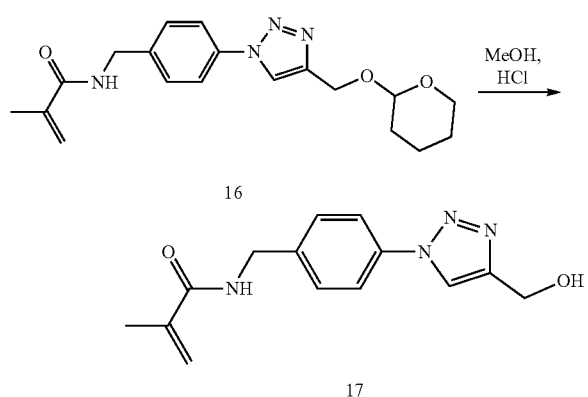

A solution of N-(4-(4-(hydroxymethyl)-1H-1,2,3-triazol-1-yl)benzyl)methacrylamide (16, 1.2 g, 3.37 mmol, 1.0 eq) was dissolved in Methanol (6 mL) and HCl (1N, aq., 9 mL) for over night at room temperature. Celite was added and the solvent was removed under reduced pressure. The crude product was purified over silica gel chromatography (24 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 12.5% to afford N-(4-(4-(hydroxymethyl)-1H-1,2,3-triazol-1-yl)benzyl)methacrylamide (17, 0.85 g, 92% yield) as a white solid. LCMS m/z: [M+H]$^+$ Calcd for C$_{14}$H$_{16}$N$_4$O$_2$ 273.1; Found 273.1.

Experimental Procedure for (4-(((tetrahydro-2H-pyran-2-yl)oxy)methyl)benzyl)carbamate (19)

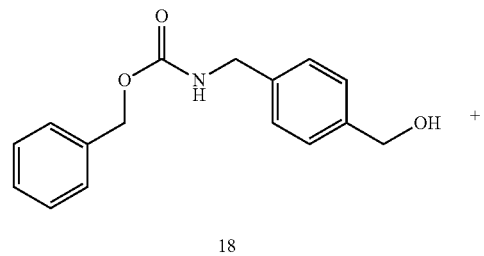

18

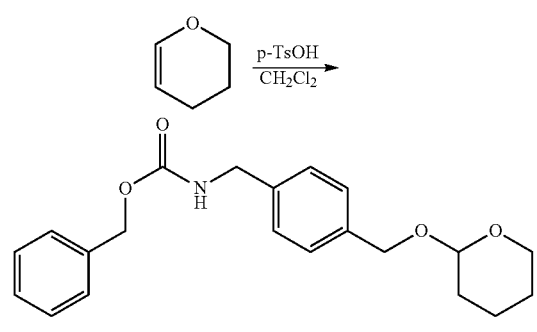

19

Benzyl (4-(hydroxymethyl)benzyl)carbamate (2.71 g, 10 mmol, 1 eq), 3,4-dihydro-2H-pyran (1.81 mL, 20 mmol, 2 eq), p-Toluenesulfonic acid monohydrate (285 mg, 1.5 mmol, 0.15 eq) in dichloromethane (100 mL) were stirred at room temperature over night. Celite was added and the solvent was removed under reduced pressure. The crude product was purified over silica gel (24 g) using Hexanes/ EtOAc as eluent starting at 100% Hexanes and increasing the concentration of EtOAc gradually to 100% to afford benzyl (4-(((tetrahydro-2H-pyran-2-yl)oxy)methyl)benzyl)-carbamate (19, 2.4 g, 68%) as a colorless oil. LCMS m/z: [M+Na]$^+$ Calcd for C$_{21}$H$_{25}$NO$_4$ 378.17 Found 378.17.

Experimental Procedure for (4-(((tetrahydro-2H-pyran-2-yl)oxy)methyl)-phenyl)methanamine (20)

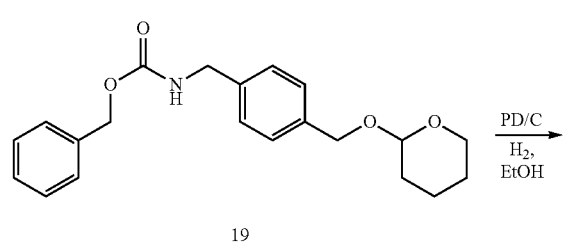

19

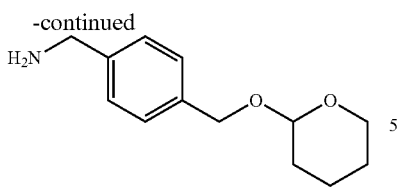

20

(4-(((tetrahydro-2H-pyran-2-yl)oxy)methyl)benzyl)carbamate (19, 1.5 g, 4.2 mmol, 1 eq), Palladium on carbon (160 mg, 10 wt. %) in EtOH was briefly evacuated and then Hydrogen was added via a balloon and the mixture was stirred for 1 hour at room temperature. Celite was added and the solvent was removed under reduced pressure. The crude product was purified over silica gel (12 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(((tetrahydro-2H-pyran-2-yl)oxy)methyl)phenyl)methanamine (20, 890 mg, 95%) as a colorless oil. LCMS m/z: [M+H]$^+$ Calcd for C$_{13}$H$_{19}$NO$_2$ 222.15 Found 222.14.

Experimental Procedure for N-(4-(((tetrahydro-2H-pyran-2-yl)oxy)methyl)benzyl)-methacrylamide (21)

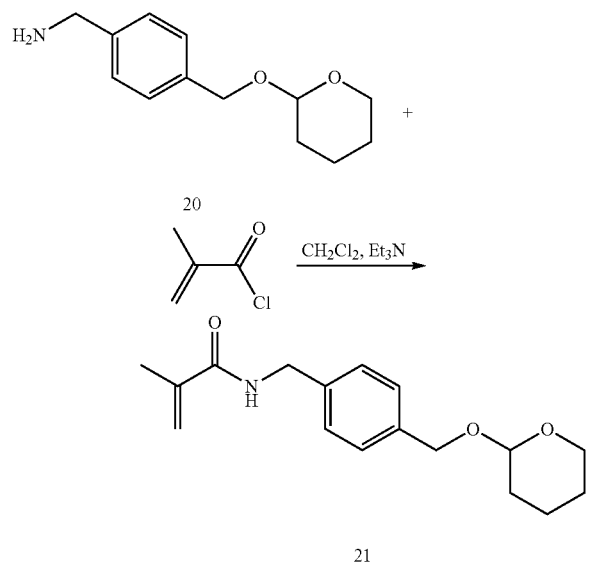

21

A solution of (4-(((tetrahydro-2H-pyran-2-yl)oxy)methyl)phenyl)methanamine (20, 0.5 g, 2.26 mmol, 1.0 eq) and triethylamine (0.47 mL, 3.39 mmol, 1.5 eq) in CH$_2$Cl$_2$ (10 mL) were briefly evacuated and flushed with Nitrogen. Methacryloyl chloride (0.33 mL, 3.39 mmol, 1.5 eq) was added in a dropwise fashion. The reaction mixture was stirred over night at room temperature. 10 grams of Celite was added and the solvent was removed under reduced pressure. The residue was purified by silica gel chromatography (12 g) using Hexanes/EtOAc as eluent starting at 100% Hexanes and increasing the concentration of EtOAc gradually to 100% to afford N-(4-(((tetrahydro-2H-pyran-2-yl)oxy)methyl)benzyl)methacrylamide (21, 0.47 g, 72% yield) as a colorless solid. LCMS m/z: [M+Na]$^+$ Calcd for C$_{17}$H$_{23}$NO$_3$ 312.16; Found 312.17.

Experimental Procedure (4-(4-(2-((tetrahydro-2H-pyran-2-yl)oxy)ethyl)-1H-1,2,3-triazol-1-yl)phenyl)methanamine (22)

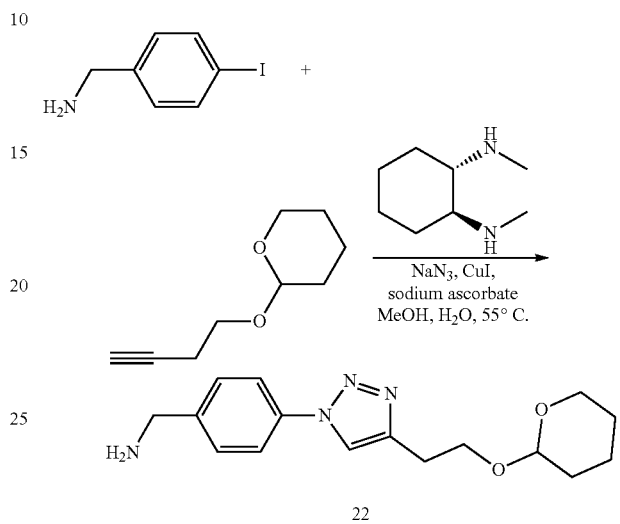

22

A mixture of (4-iodophenyl)methanamine (5.0 g, 21.45 mmol, 1.0 eq), (1S,2S)—N1,N2-dimethylcyclohexane-1,2-diamine (0.44 mL 2.79 mmol, 0.13 eq), Sodium ascorbate (425 mg, 2.15 mmol, 0.1 eq), Copper Iodide (409 mg, 2.15 mmol, 0.1 eq), Sodium azide (2.79 g, 42.91 mmol, 2.0 eq), and 2-(but-3-yn-1-yloxy)tetrahydro-2H-pyran (3.36 mL, 21.45 mmol, 1.0 eq) in Methanol (20 mL) and water (5 mL) were purged with Nitrogen for 5 minutes and heated to 55° C. for over night. The reaction mixture was cooled to room temperature and filtered through 413 filter paper. Celite (10 g) was added and the solvent was removed under reduced pressure and the residue was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 5% to afford (4-(4-(2-((tetrahydro-2H-pyran-2-yl)oxy)ethyl)-1H-1,2,3-triazol-1-yl)phenyl)methanamine (22, 3.15 g, 49%) as a solid. LCMS m/z: [M+H]$^+$ Calcd for C16H22N402 303.18; Found 303.18.

Experimental Procedure for N-(4-(4-(2-((tetrahydro-2H-pyran-2-yl)oxy)ethyl)-1H-1,2,3-triazol-1-yl)benzyl)methacrylamide (23)

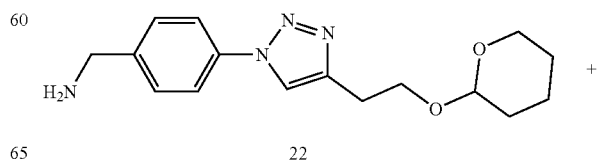

22

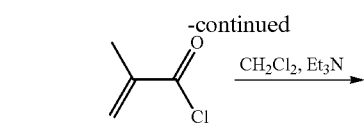

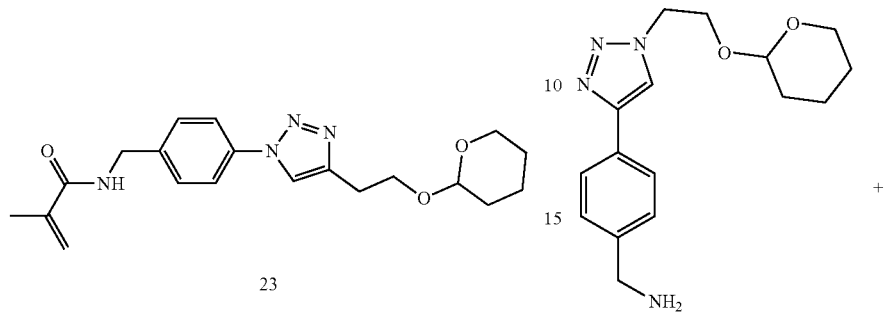

A solution of (4-(4-(2-((tetrahydro-2H-pyran-2-yl)oxy)ethyl)-1H-1,2,3-triazol-1-yl)phenyl)methanamine (22, 3.10 g, 10.25 mmol, 1.0 eq) and triethylamine (1.71 mL, 12.30 mmol, 1.2 eq) in CH$_2$Cl$_2$ (55 mL) was cooled to 0° C. with an ice-bath and methacryloyl chloride (1.05 mL, 12.30 mmol, 1.2 eq, diluted in 5 mL of CH$_2$Cl$_2$) was added in a dropwise fashion. The cooling bath was removed and the reaction was stirred for 4 h. 8 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 2.5% to afford N-(4-(4-(2-((tetrahydro-2H-pyran-2-yl)oxy)ethyl)-1H-1,2,3-triazol-1-yl)benzyl)methacrylamide (23, 2.06 g, 54% yield) as a white solid. LCMS m/z: [M+H]$^+$ Calcd for C$_{20}$H$_{26}$N$_4$O$_3$ 371.2078; Found 371.2085.

Experimental Procedure (4-(1-(2-((tetrahydro-2H-pyran-2-yl)oxy)ethyl)-1H-1,2,3-triazol-4-yl)phenyl)methanamine (24)

A mixture of (4-ethynylphenyl)methanamine (2.36 g, 18.00 mmol, 1.0 eq), (1S,2S)—N1,N2-dimethylcyclohexane-1,2-diamine (0.56 mL, 3.60 mmol, 0.2 eq), Sodium ascorbate (357 mg, 1.80 mmol, 0.1 eq), Copper Iodide (514 mg, 2.70 mmol, 0.15 eq), and 2-(2-azidoethoxy)tetrahydro-2H-pyran (3.08, 18.00 mmol, 1.0 eq) in Methanol (24 mL) and water (6 mL) were purged with Nitrogen for 5 minutes and heated to 55° C. for over night. The reaction mixture was cooled to room temperature and filtered over Celite and rinsed with MeOH (3×50 mL). The solvent was removed under reduced pressure and the residue was redissolved in dichloromethane, Celite (20 g) was added and the solvent was removed under reduced pressure and the residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(1-(2-((tetrahydro-2H-pyran-2-yl)oxy)ethyl)-1H-1,2,3-triazol-4-yl)phenyl)methanamine (24, 3.51 g, 64%) as a yellowish oil. LCMS m/z: [M+H]$^+$ Calcd for C$_{16}$H$_{22}$N$_4$O$_2$ 303.1816; Found 303.1814.

Experimental Procedure for N-(4-(1-(2-((tetrahydro-2H-pyran-2-yl)oxy)ethyl)-1H-1,2,3-triazol-4-yl)benzyl)methacrylamide (25)

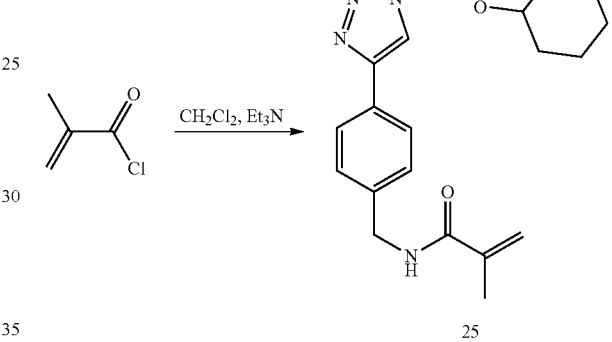

A solution of (4-(1-(2-((tetrahydro-2H-pyran-2-yl)oxy)ethyl)-1H-1,2,3-triazol-4-yl)phenyl)methanamine (24, 1.5 g, 4.96 mmol, 1.0 eq) and triethylamine (1.04 mL, 7.44 mmol, 1.5 eq) in CH$_2$Cl$_2$ (30 mL) were briefly evacuated and flushed with Nitrogen. Methacryloyl chloride (0.72 mL, 7.44 mmol, 1.5 eq) was added in a dropwise fashion. The reaction mixture was stirred for 2 h at room temperature. 10 grams of Celite was added and the solvent was removed under reduced pressure. The residue was purified by silica gel chromatography (40 g) using Hexanes/EtOAc as eluent starting at 100% Hexanes and increasing the concentration of EtOAc gradually to 100% to afford N-(4-(1-(2-((tetrahydro-2H-pyran-2-yl)oxy)ethyl)-1H-1,2,3-triazol-4-yl)benzyl)methacrylamide (25, 0.9 g, 49% yield) as a colorless solid. LCMS m/z: [M+Na]$^+$ Calcd for C$_{20}$H$_{26}$N$_4$O$_3$ 371.2078; Found 371.2076.

Experimental Procedure for 1-(4-(4-(((tetrahydro-2H-pyran-2-yl)oxy)methyl)-1H-1,2,3-triazol-1-yl)phenyl)ethan-1-amine (26)

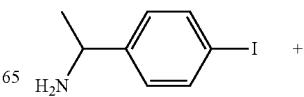

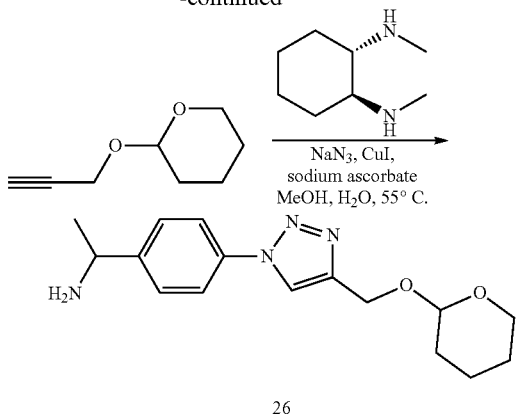

26

A mixture of 1-(4-iodophenyl)ethan-1-amine hydrochloride (1.0 g, 4.05 mmol, 1.0 eq), (1S,2S)—N1,N2-dimethylcyclohexane-1,2-diamine (0.08 mL 0.53 mmol, 0.13 eq), Sodium ascorbate (80 mg, 0.40 mmol, 0.1 eq), Copper Iodide (77 mg, 0.40 mmol, 0.1 eq), Sodium azide (526 g, 8.09 mmol, 2.0 eq), and 2-(prop-2-yn-1-yloxy)tetrahydro-2H-pyran (0.57 g, 4.05 mmol, 1.0 eq) in Methanol (9 mL) and water (1 mL) were purged with Nitrogen for 5 minutes and heated to 55° C. for over night. The reaction mixture was cooled to room temperature and the solvent was removed under reduced pressure. The residue was redissolved in dichloromethane and filtered over a plug of Celite. Celite was added to the filtrate and the solvent was removed under reduced pressure. The residue was purified over silica gel (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 5% to afford 1-(4-(4-(((tetrahydro-2H-pyran-2-yl)oxy)methyl)-1H-1,2,3-triazol-1-yl)phenyl)ethan-1-amine (26, 0.62 g, 51%) as a yellowish solid. LCMS m/z: [M+H]+ Calcd for $C_{16}H_{22}N_4O_2$ 303.2; Found 303.2.

Experimental Procedure for N-(1-(4-(4-(((tetrahydro-2H-pyran-2-yl)oxy) methyl)-1H-1,2,3-triazol-1-yl)phenyl)ethyl)methacrylamide (27)

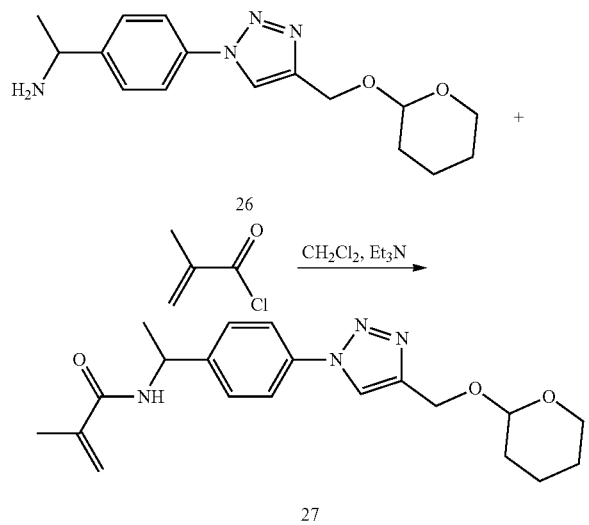

A solution of 1-(4-(4-(((tetrahydro-2H-pyran-2-yl)oxy)methyl)-1H-1,2,3-triazol-1-yl)phenyl)ethan-1-amine (26, 0.52 g, 1.7 mmol, 1.0 eq) and triethylamine (0.29 mL, 2.1 mmol, 1.2 eq) in $CH_2Cl_2$ (11 mL) was cooled to 0° C. with an ice-bath and methacryloyl chloride (0.18 mL, 1.8 mmol, 1.05 eq, diluted in 11 mL of $CH_2Cl_2$) was added in a dropwise fashion. The cooling bath was removed and the reaction was stirred for 4 h. 5 grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 2.5% to afford N-(1-(4-(4-(((tetrahydro-2H-pyran-2-yl)oxy)methyl)-1H-1,2,3-triazol-1-yl)phenyl)ethyl)methacrylamide (27, 0.49 g, 76% yield) as a white solid. LCMS m/z: [M+H]+ Calcd for $C_{20}H_{26}N_4O_3$ 371.2078; Found 371.2087.

Experimental Procedure for (4-(4-(((tetrahydro-2H-pyran-2-yl)oxy)methyl)-1H-1,2,3-triazol-1-yl)-2-(trifluoromethyl)phenyl)methanamine (28)

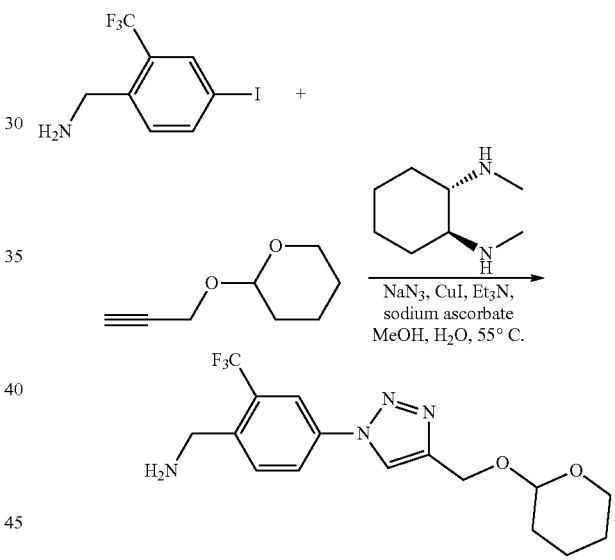

28

A mixture of (4-iodo-2-(trifluoromethyl)phenyl)methanamine (3.0 g, 9.97 mmol, 1.0 eq), (1S,2S)—N1,N2-dimethylcyclohexane-1,2-diamine (0.31 mL 1.99 mmol, 0.2 eq), Sodium ascorbate (197 mg, 1.00 mmol, 0.1 eq), Copper Iodide (285 mg, 1.49 mmol, 0.15 eq), Sodium azide (1.30 g, 19.93 mmol, 2.0 eq), $Et_3N$ (1.67 mL, 11.96 mmol, 1.2 eq) and 2-(prop-2-yn-1-yloxy)tetrahydro-2H-pyran (1.40 g, 9.97 mmol, 1.0 eq) in Methanol (24 mL) and water (6 mL) were purged with Nitrogen for 5 minutes and heated to 55° C. for over night. The reaction mixture was cooled to room temperature and filtered through a plug of Celite and rinsed with Methanol (3×50 mL). Celite was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(4-(((tetrahydro-2H-pyran-2-yl)oxy)methyl)-1H-1,2,3-triazol-1-yl)-2-(trifluoromethyl)phenyl)methanamine (28, 2.53 g, 71%) as a green oil. LCMS m/z: [M+H]+ Calcd for $C_{16}H_{19}N_4O_2F_3$ 357.2; Found 357.1.

Experimental Procedure for N-(4-(4-(((tetrahydro-2H-pyran-2-yl)oxy)methyl)-1H-1,2,3-triazol-1-yl)-2(trifluoromethyl)benzyl) methacrylamide (29)

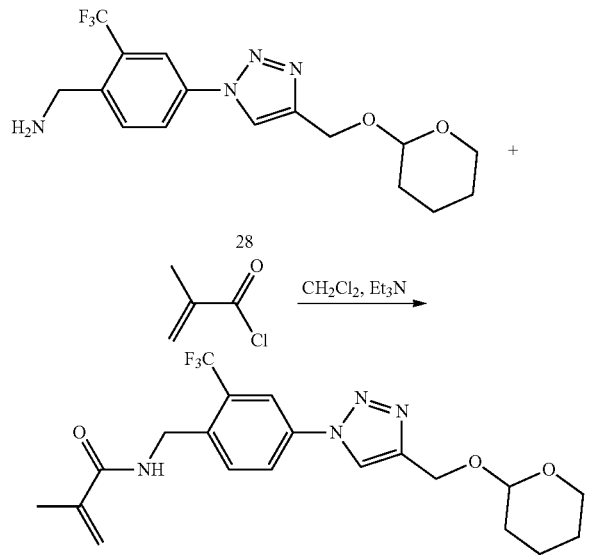

A solution of (4-(4-(((tetrahydro-2H-pyran-2-yl)oxy)methyl)-1H-1,2,3-triazol-1-yl)-2-(trifluoromethyl)phenyl)methanamine (28, 1.0 g, 2.81 mmol, 1.0 eq) and triethylamine (0.59 mL, 4.21 mmol, 1.5 eq) in $CH_2Cl_2$ (25 mL) were briefly evacuated and flushed with Nitrogen. Methacryloyl chloride (0.41 mL, 4.21 mmol, 1.5 eq) was added in a dropwise fashion. The reaction mixture was stirred for 6 h at room temperature. 10 grams of Celite was added and the solvent was removed under reduced pressure. The residue was purified by silica gel chromatography (40 g) using Hexanes/EtOAc as eluent starting at 100% Hexanes and increasing the concentration of EtOAc gradually to 100% to afford N-(4-(4-(((tetrahydro-2H-pyran-2-yl)oxy)methyl)-1H-1,2,3-triazol-1-yl)-2(trifluoromethyl)benzyl) methacrylamide (29, 0.65 g, 55% yield) as a colorless solid. LCMS m/z: [M+H]+ Calcd for $C_{20}H_{23}N_4O_3F_3$ 425.2; Found 425.1.

Experimental Procedure for 3-(4-(((tetrahydro-2H-pyran-2-yl)oxy)methyl)-1H-1,2,3-triazol-1-yl)propan-1-amine (30)

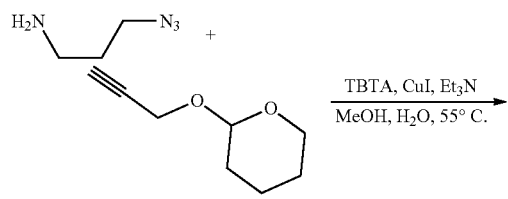

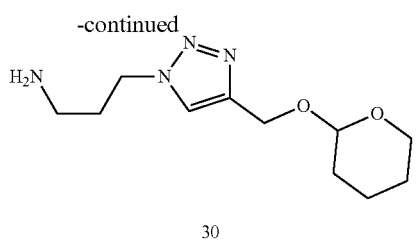

A mixture of 3-azidopropan-1-amine hydrochloride (1.5 g, 14.98 mmol, 1.0 eq), Tris[(1-benzyl-1H-1,2,3-triazol-4-yl)methyl]-amine (1.99 g, 3.75 mmol, 0.25 eq), Copper Iodide (0.29 g, 1.50 mmol, 0.1 eq), and Triethylamine (0.52 mL, 3.75 mmol, 0.25 eq) in Methanol (50 mL) and water (6 mL) were purged with Nitrogen for 5 minutes and cooled to 0 C. 2-(prop-2-yn-1-yloxy)tetrahydro-2H-pyran (2.10 g, 14.98 mmol, 1.0 eq) was added and the reaction mixture was warmed to 55° C. and stirred over night under Nitrogen atmosphere. The reaction mixture was cooled to room temperature, filtered over a plug of Celite and rinsed with Methanol (3×50 mL). Celite (20 g) was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 20% to afford 3-(4-(((tetrahydro-2H-pyran-2-yl)oxy)methyl)-1H-1,2,3-triazol-1-yl)propan-1-amine (30, 2.36 g, 66%). LCMS m/z: [M+H]+ Calcd for $C_{11}H_{20}N_4O_2$ 241.2; Found 241.2.

Experimental Procedure for N-(3-(4-(((tetrahydro-2H-pyran-2-yl)oxy)methyl)-1H-1,2,3-triazol-1-yl)propyl)methacrylamide (31)

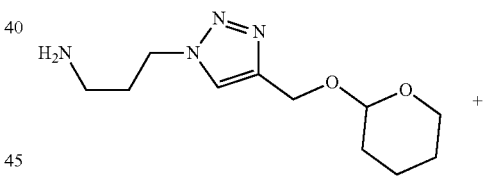

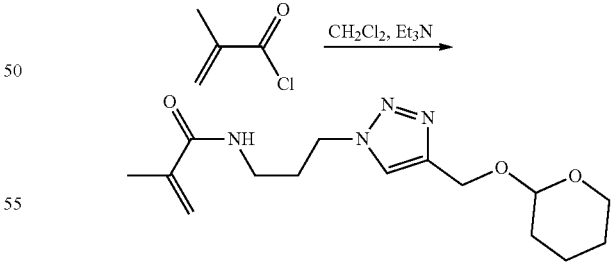

A solution of 3-(4-(((tetrahydro-2H-pyran-2-yl)oxy)methyl)-1H-1,2,3-triazol-1-yl)propan-1-amine (30, 1.0 g, 4.16 mmol, 1.0 eq) and triethylamine (0.58 mL, 4.16 mmol, 1.0 eq) in $CH_2Cl_2$ (20 mL) were briefly evacuated and flushed with Nitrogen. Methacryloyl chloride (0.40 mL, 4.16 mmol, 1.0 eq) was added in a dropwise fashion. The reaction mixture was stirred at room temperature over night. 10 grams of Celite was added and the solvent was removed under reduced pressure. The residue was purified by silica gel chromatography (40 g) using using dichloromethane/(methanol containing 12% (v/v) aqueous ammonium hydroxide) as mobile phase. The concentration of (methanol containing 12% (v/v) aqueous ammonium hydroxide) was gradually increased from 0% to 20% to afford N-(3-(4-(((tetrahydro-2H-pyran-2-yl)oxy)methyl)-1H-1,2,3-triazol-1-yl)propyl)methacrylamide (31, 0.96 g, 75% yield) as a colorless oil. LCMS m/z: [M+H]$^+$ Calcd for $C_{15}H_{24}N_4O_3$ 309.2; Found 309.4.

Experimental Procedure for (4-(4-((oxetan-3-yloxy)methyl)-1H-1,2,3-triazol-1-yl)phenyl)methanamine (32)

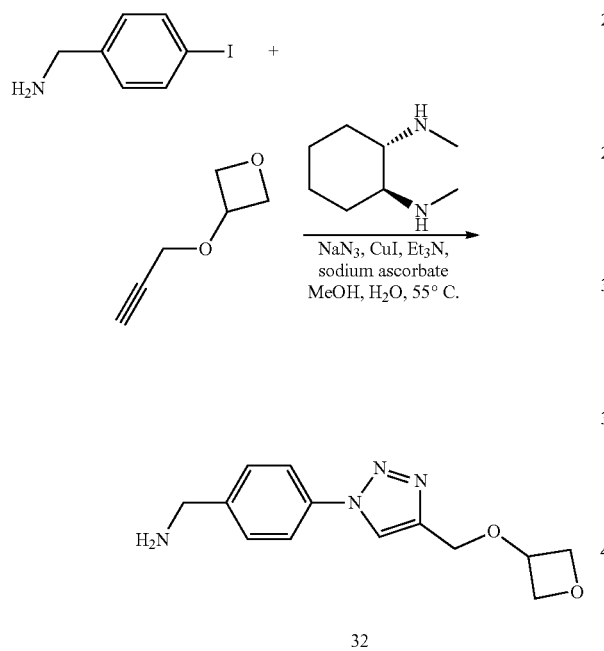

A mixture of (4-iodophenyl)methanamine hydrochloride (2.64 g, 9.80 mmol, 1.0 eq), (1S,2S)—N1,N2-dimethylcyclohexane-1,2-diamine (0.31 mL 1.96 mmol, 0.2 eq), Sodium ascorbate (198 mg, 0.98 mmol, 0.1 eq), Copper Iodide (279 mg, 1.47 mmol, 0.15 eq), Sodium azide (1.27 g, 19.59 mmol, 2.0 eq), Et$_3$N (1.64 mL, 11.75 mmol, 1.2 eq) and 3-(prop-2-yn-1-yloxy)oxetane (9, 1.10 g, 9.80 mmol, 1.0 eq) in Methanol (24 mL) and water (6 mL) were purged with Nitrogen for 5 minutes and heated to 55° C. for overnight. The reaction mixture was cooled to room temperature and filtered through a plug of Celite and rinsed with Methanol (3×50 mL). Celite was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(4-((oxetan-3-yloxy)methyl)-1H-1,2,3-triazol-1-yl)phenyl)methanamine (32, 1.43 g, 56%) as an oil. LCMS m/z: [M+H]$^+$ Calcd for $C_{13}H_{16}N_4O_2$ 261.1346; Found 261.1342.

Experimental Procedure for N-(4-(4-((oxetan-3-yloxy)methyl)-1H-1,2,3-triazol-1-yl)benzyl)methacrylamide (33)

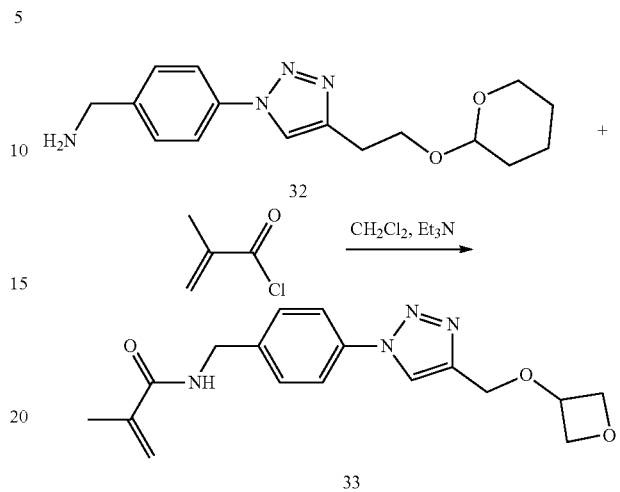

A solution of (4-(4-((oxetan-3-yloxy)methyl)-1H-1,2,3-triazol-1-yl)phenyl)methanamine (32, 0.58 g, 2.23 mmol, 1.0 eq) and triethylamine (0.47 mL, 3.34 mmol, 1.5 eq) in CH$_2$Cl$_2$ (20 mL) were briefly evacuated and flushed with Nitrogen. Methacryloyl chloride (0.32 mL, 3.34 mmol, 1.5 eq) was added in a dropwise fashion. The reaction mixture was stirred for 6 h at room temperature. 10 grams of Celite was added and the solvent was removed under reduced pressure. The residue was purified by silica gel chromatography (24 g) using Hexanes/EtOAc as eluent starting at 100% Hexanes and increasing the concentration of EtOAc gradually to 100% to afford N-(4-(4-((oxetan-3-yloxy)methyl)-1H-1,2,3-triazol-1-yl)benzyl)methacrylamide (33, 0.48 g, 66% yield) as a colorless solid. LCMS m/z: [M+H]$^+$ Calcd for $C_{17}H_{20}N_4O_3$ 329.1608; Found 329.1611.

Experimental Procedure for ethyl 1-(2-methacrylamidoethyl)-1H-imidazole-4-carboxylate (35)

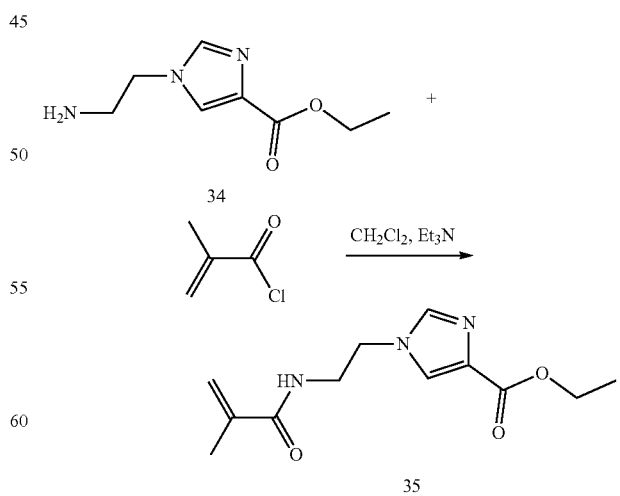

A solution of ethyl 1-(2-aminoethyl)-1H-imidazole-4-carboxylate (34, 2.0 g, 10.91 mmol, 1.0 eq) and triethylamine (3.80 mL, 27.29 mmol, 2.5 eq) in CH$_2$Cl$_2$ (20 mL) were briefly evacuated and flushed with Nitrogen. Methacryloyl chloride (1.60 mL, 16.37 mmol, 1.5 eq) was added in a dropwise fashion. The reaction mixture was stirred for 3 h at room temperature. 15 grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford ethyl 1-(2-methacrylamidoethyl)-1H-imidazole-4-carboxylate (35, 1.28 g, 47% yield) as a colorless solid. LCMS m/z: $[M+H]^+$ Calcd for $C_{12}H_{17}N_3O_3$ 252.1; Found 252.1.

Experimental Procedure for N-(4-(1,1-dioxidothiomorpholino)benzyl)methacrylamide (37)

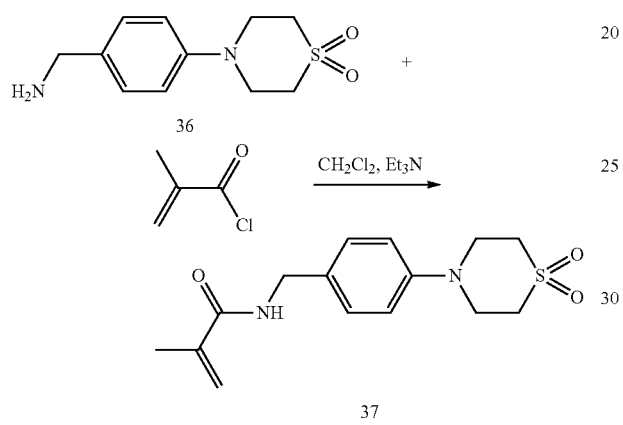

To a solution of 4-(4-(aminomethyl)phenyl)thiomorpholine 1,1-dioxide hydrochloride (36, 1.15 g, 4.15 mmol, 1.0 eq) and triethylamine (1.39 mL, 9.97 mmol, 2.4 eq) in $CH_2Cl_2$ (80 mL) was added a solution of methacryloyl chloride (0.43 mL, 4.36 mmol, 1.05 eq, in $CH_2Cl_2$, 5 mL) in a dropwise fashion. The reaction mixture was stirred for 22 h at room temperature. 8 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 3.75% to afford N-(4-(1,1-dioxidothiomorpholino)benzyl) methacrylamide (37, 0.32 g, 25% yield) as a solid.

Experimental Procedure for N-methyl-N-(2-(methylsulfonyl)ethyl)prop-2-yn-1-amine (38)

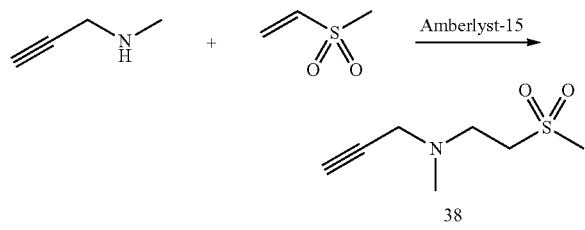

To a mixture of 1-methylsulfonylethylene (4.99 g, 47.03 mmol, 4.13 mL) and Amberlyst-15 ((30% w/w)), N-methylprop-2-yn-1-amine (2.6 g, 37.62 mmol) was added in a dropwise fashion. The mixture was stirred at room temperature for 12 hours. The catalyst was removed by filtration and the filtrate was concentrated under reduced pressure to afford: N-methyl-N-(2-(methylsulfonyl)ethyl)prop-2-yn-1-amine (38, 6.43 g, 98%) as an oil. LCMS m/z: $[M+H]^+$ Calcd for $C_7H_{13}NSO_2$ 176.11; Found 176.1.

Experimental Procedure for N-((1-(2-(2-(2-(2-aminoethoxy)ethoxy)ethoxy) ethyl)-1H-1,2,3-triazol-4-yl)methyl)-N-methyl-2-(methylsulfonyl)ethan-1-amine (40)

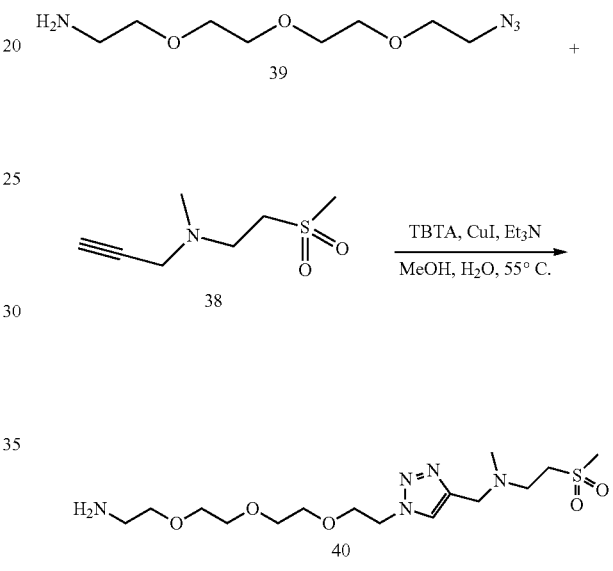

A mixture of N-methyl-N-(2-(methylsulfonyl)ethyl)prop-2-yn-1-amine (38, 5.02 g, 28.64 mmol, 1.25 eq), Tris[(1-benzyl-1H-1,2,3-triazol-4-yl)methyl]-amine (3.04 g, 5.73 mmol, 0.25 eq), Copper Iodide (436 mg, 2.29 mmol, 0.1 eq), and Triethylamine (0.8 mL, 5.7 mmol, 0.25 eq) in Methanol (50 mL) and water (6 mL) was evacuated and flushed with Nitrogen (3 times) and cooled with an ice bath. 2-(2-(2-(2-azidoethoxy)ethoxy)ethoxy)ethan-1-amine (39, 5.02 g, 22.91 mmol, 1.0 eq) was added in a dropwise fashion, the cooling bath was removed and the mixture was stirred for 5 minutes. The reaction was warmed to 55° C. and stirred overnight under Nitrogen atmosphere. The reaction mixture was cooled to room temperature, Celite (20 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford N-((1-(2-(2-(2-(2-aminoethoxy)ethoxy)ethoxy)ethyl)-1H-1,2,3-triazol-4-yl)methyl)-N-methyl-2-(methylsulfonyl)ethan-1-amine (40, 4.98 g, 55%) as an oil. LCMS m/z: $[M+H]^+$ Calcd for $C_{15}H_{31}N_5O_5S$ 394.2; Found 394.2.

Experimental Procedure N-(2-(2-(2-(2-(4-((methyl (2-(methylsulfonyl)ethyl) amino)methyl)-1H-1,2,3-triazol-1-yl)ethoxy)ethoxy)ethoxy) ethyl)methacrylamide (41)

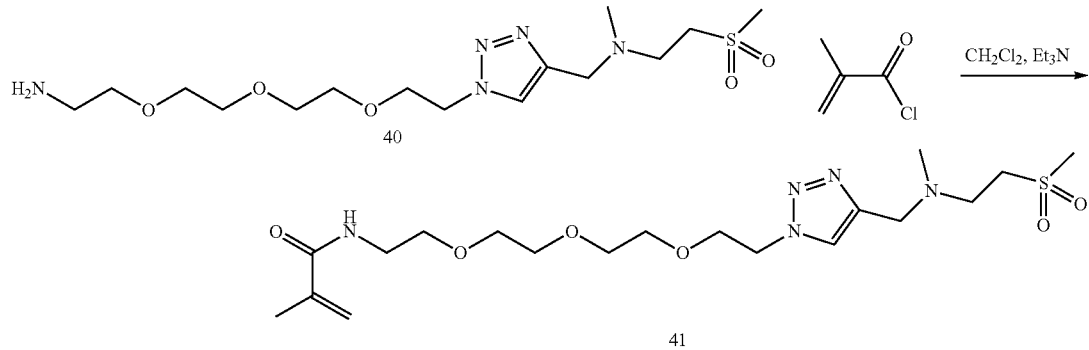

To a solution of N-((1-(2-(2-(2-(2-aminoethoxy)ethoxy)ethoxy)ethyl)-1H-1,2,3-triazol-4-yl)methyl)-N-methyl-2-(methylsulfonyl)ethan-1-amine (40, 1.0 g, 2.54 mmol, 1.0 eq) and triethylamine (0.43 mL, 3.05 mmol, 1.2 eq) in CH$_2$Cl$_2$ (15 mL) was added a solution of methacryloyl chloride (0.30 mL, 3.05 mmol, 1.5 eq) in a dropwise fashion. The reaction mixture was stirred for 5 h at room temperature. Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 12.5% to afford N-(2-(2-(2-(2-(4-((methyl(2-(methylsulfonyl)ethyl) amino)methyl)-1H-1,2,3-triazol-1-yl)ethoxy)ethoxy)ethoxy) ethyl)methacrylamide (41, 0.86 g, 73% yield) as an oil. LCMS m/z: [M+H]$^+$ Calcd for C$_{19}$H$_{35}$N$_5$O$_6$S 462.2; Found 462.2.

Experimental Procedure for 7-(prop-2-yn-1-yl)-2-oxa-7-azaspiro[3.5]nonane (42)

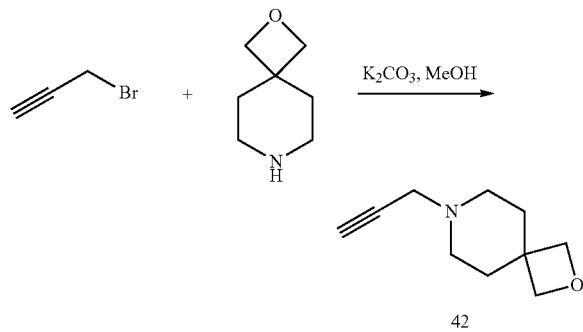

3-Bromoprop-1-yne (4.4 mL, 39.32 mmol 1.0 eq) was added to a mixture of 2-oxa-7-azaspiro[3.5]nonane (8.54 g, 39.32 mmol, 1.0 eq), potassium carbonate (17.9 g, 129.7 mmol, 3.3 eq) in Methanol (200 mL) and stirred over night at room temperature. The mixture was filtered, Celite was added and the solvent was removed under reduced pressure. The residue was purified by silica gel chromatography (220 g) using dichloromethane/methanol as mobile phase. The concentration of methanol was gradually increased from 0% to 5% to afford 7-(prop-2-yn-1-yl)-2-oxa-7-azaspiro[3.5]nonane (42, 4.44 g, 68%) as an oil. Experimental Procedure for 2-(2-(2-(2-(4-((2-oxa-7-azaspiro[3.5]nonan-7-yl)methyl)-1H-1,2,3-triazol-1-yl)ethoxy)ethoxy)ethoxy)ethan-1-amine (43)

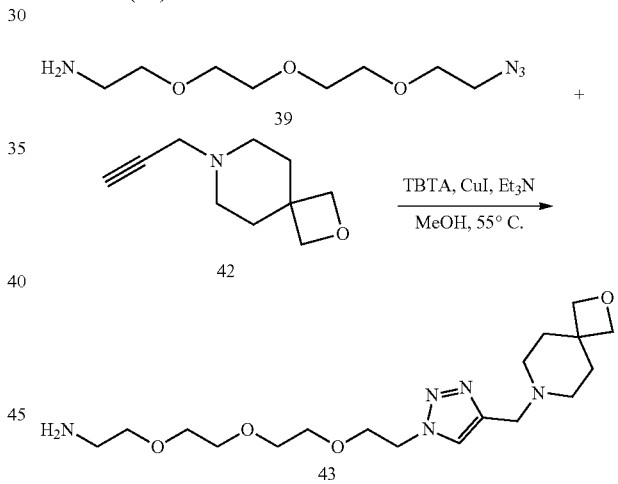

A mixture of 7-(prop-2-yn-1-yl)-2-oxa-7-azaspiro[3.5]nonane (42, 2.5 g, 15.13 mmol, 1.0 eq), Tris[(1-benzyl-1H-1,2,3-triazol-4-yl)methyl]-amine (1.77 g, 3.33 mmol, 0.22 eq), Copper Iodide (288 mg, 1.51 mmol, 0.1 eq), and Triethylamine (0.53 mL, 3.8 mmol, 0.25 eq) in Methanol (50 mL) was cooled with an ice bath. 2-(2-(2-(2-azidoethoxy)ethoxy)ethoxy)ethan-1-amine (39, 3.86 g, 17.70 mmol, 1.17 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (10 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 2-(2-(2-(2-(4-((2- oxa-7-azaspiro[3.5]nonan-7-yl) methyl)-1H-1,2,3-triazol-1-yl)ethoxy)ethoxy)ethoxy)ethan-1-amine (43, 4.76 g, 82%) as an oil. LCMS m/z: [M+H]+ Calcd for $C_{18}H_{33}N_5O_4$ 384.3; Found 384.2.

Experimental Procedure for N-(2-(2-(2-(2-(4-((2-oxa-7-azaspiro[3.5]nonan-7-yl)methyl)-1H-1,2,3-triazol-1-yl)ethoxy)ethoxy)ethoxy)ethyl)methacrylamide (44)

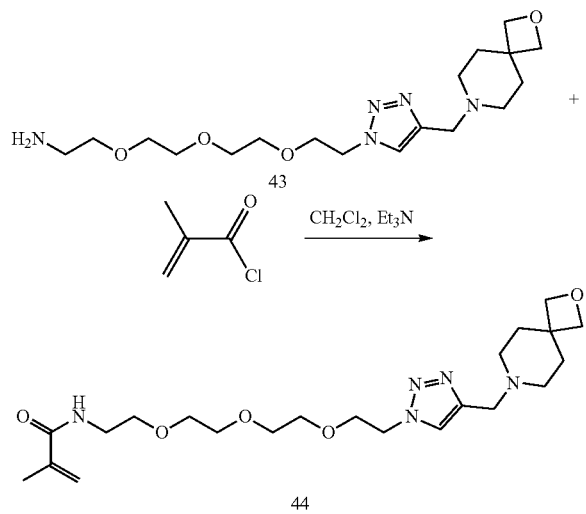

A solution of 2-(2-(2-(2-(4-((2-oxa-7-azaspiro[3.5]nonan-7-yl) methyl)-1H-1,2,3-triazol-1- yl)ethoxy)ethoxy)ethoxy) ethan-1-amine (43, 2.65 g, 6.91 mmol, 1.0 eq) and triethylamine (1.16 mL, 8.29 mmol, 1.2 eq) in $CH_2Cl_2$ (100 mL) was cooled with an ice-bath under Nitrogen atmosphere. Methacryloyl chloride (0.74 mL, 7.6 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (120 g) using dichloromethane/methanol as mobile phase. The concentration of methanol was gradually increased from 0% to 10% to afford N-(2-(2-(2-(2-(4-((2-oxa-7-azaspiro[3.5]nonan-7-yl)methyl)-1H-1,2,3-triazol-1- yl)ethoxy)ethoxy)ethoxy)ethyl)methacrylamide (44, 1.50 g, 48% yield) as a colorless oil. LCMS m/z: [M+H]+ Calcd for $C_{22}H_{37}N_5O_5$ 452.29; Found 452.25.

Experimental Procedure for 4-((1-(2-(2-aminoethoxy)ethyl)-1H-1,2,3-triazol-4-yl)methyl)thiomorpholine 1,1-dioxide (45)

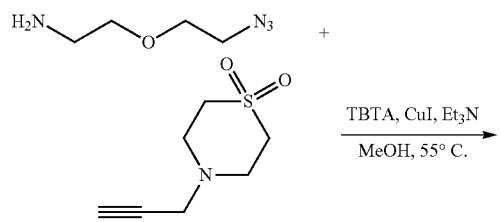

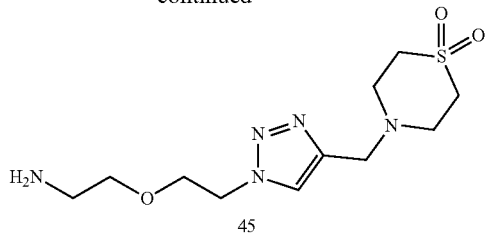

A mixture of 4-(prop-2-yn-1-yl)thiomorpholine 1,1-dioxide (1.14 g, 6.58 mmol, 1.0 eq), Tris[(1-benzyl-1H-1,2,3-triazol-4-yl)methyl]-amine (768 mg, 1.45 mmol, 0.22 eq), Copper Iodide (125 mg, 0.66 mmol, 0.1 eq), and Triethylamine (0.23 mL, 1.65 mmol, 0.25 eq) in Methanol (20 mL) was cooled with an ice bath. 2-(2-azidoethoxy)ethan-1-amine (1.00 g, 7.70 mmol, 1.17 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (10 g) was added, and concentrated under reduced pressure. The crude product was purified over silica gel (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 9.5% to afford for 4-((1-(2-(2-aminoethoxy)ethyl)-1H-1,2,3-triazol-4-yl)methyl)thiomorpholine 1,1-dioxide (45, 1.86 g, 93%) as a white solid. LCMS m/z: [M+H]+ Calcd for $C_{11}H_{21}N_5O_4S$ 304.1438; Found 304.1445.

Experimental Procedure for N-(2-(2-(4-((1,1-dioxidothiomorpholino)methyl)-1H-1,2,3-triazol-1-yl)ethoxy)ethyl)methacrylamide (46)

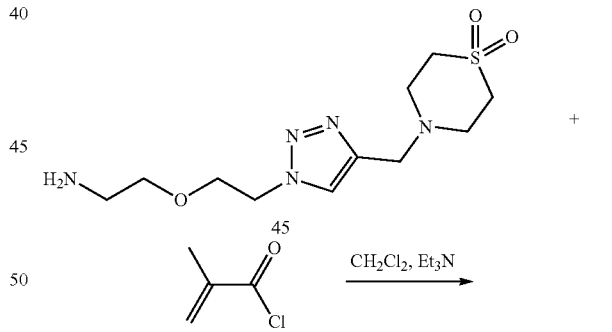

A solution of 4-((1-(2-(2-aminoethoxy)ethyl)-1H-1,2,3-triazol-4-yl)methyl)thiomorpholine 1,1-dioxide (45, 1.32 g, 4.35 mmol, 1.0 eq) and triethylamine (0.73 mL, 5.22 mmol, 1.2 eq) in CH$_2$Cl$_2$ (100 mL) was cooled with an ice-bath under Nitrogen atmosphere. Methacryloyl chloride (0.47 mL, 4.8 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(2-(2-(4-((1,1-dioxidothiomorpholino)methyl)-1H-1,2,3-triazol-1-yl)ethoxy)ethyl)-methacrylamide (46, 0.90 g, 56% yield) as a colorless oil. LCMS m/z: [M+H]$^+$ Calcd for C$_{15}$H$_{25}$N$_5$O$_4$S 372.17; Found 372.15.

Experimental Procedure for 4-((1-(2-(2-(2-aminoethoxy)ethoxy)ethyl)-1H-1,2,3-triazol-4-yl)methyl)thiomorpholine 1,1-dioxide (47)

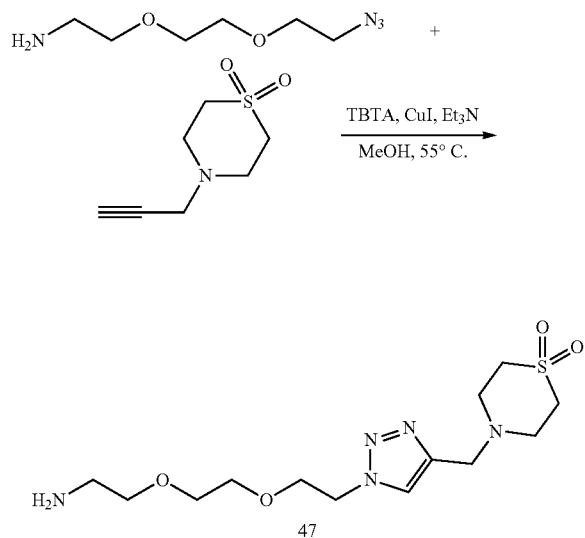

A mixture of 4-(prop-2-yn-1-yl)thiomorpholine 1,1-dioxide (4.6 g, 26.55 mmol, 1.0 eq), Tris[(1-benzyl-1H-1,2,3-triazol-4-yl)methyl]-amine (3.1 g, 5.84 mmol, 0.22 eq), Copper Iodide (506 mg, 2.66 mmol, 0.1 eq), and Triethylamine (0.93 mL, 6.64 mmol, 0.25 eq) in Methanol (80 mL) was cooled with an ice bath. 2-(2-(2-azidoethoxy)ethoxy)ethan-1-amine (5.00 g, 28.68 mmol, 1.08 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 4-((1-(2-(2-(2-aminoethoxy)ethoxy)ethyl)-1H-1,2,3-triazol-4-yl)methyl)thiomorpholine 1,1-dioxide (47, 5.26 g, 57%) as a yellowish oil. LCMS m/z: [M+H]$^+$ Calcd for C$_{13}$H$_{25}$N$_5$O$_4$S 348.1700; Found 348.1700.

Experimental Procedure N-(2-(2-(2-(4-((1,1-dioxidothiomorpholino)methyl)-1H-1,2,3-triazol-1-yl)ethoxy)ethoxy)ethyl)methacrylamide (48)

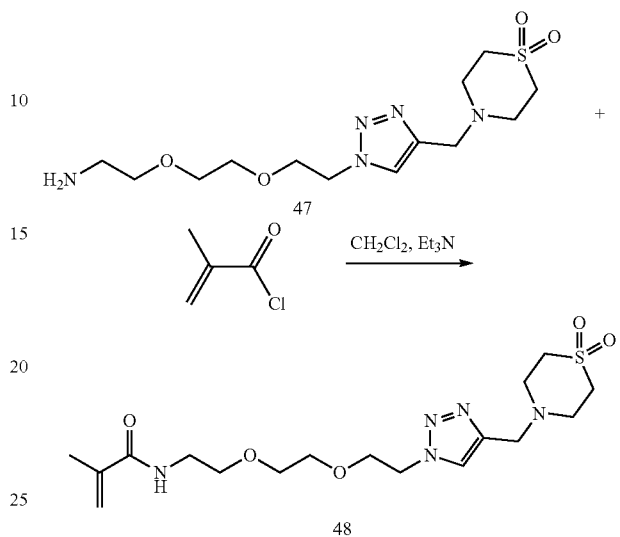

A solution of 4-((1-(2-(2-(2-aminoethoxy)ethoxy)ethyl)-1H-1,2,3-triazol-4-yl)methyl)thiomorpholine 1,1-dioxide (47, 1.49 g, 4.29 mmol, 1.0 eq) and triethylamine (0.72 mL, 5.15 mmol, 1.2 eq) in CH$_2$Cl$_2$ (50 mL) was cooled with an ice-bath under Nitrogen atmosphere. Methacryloyl chloride (0.46 mL, 4.7 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (80 g) using dichloromethane/methanol as mobile phase. The concentration of methanol was gradually increased from 0% to 5% to afford N-(2-(2-(2-(4-((1,1-dioxidothiomorpholino)methyl)-1H-1,2,3-triazol-1-yl)ethoxy)ethoxy)ethyl)-methacrylamide (48, 0.67 g, 38% yield) as a colorless oil. LCMS m/z: [M+H]$^+$ Calcd for C$_{17}$H$_{29}$N$_5$O$_5$S 416.20; Found 416.20.

Experimental Procedure for 4-((1-(14-amino-3,6,9,12-tetraoxatetradecyl)-1H-1,2,3-triazol-4-yl)methyl)thiomorpholine 1,1-dioxide (49)

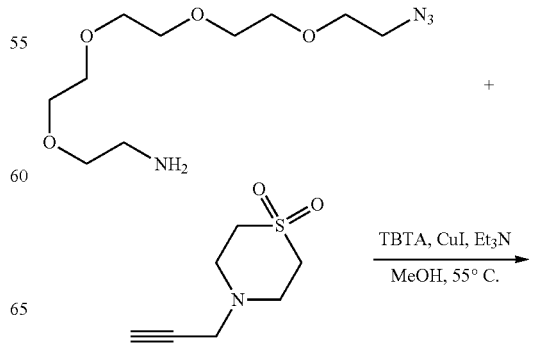

111

-continued

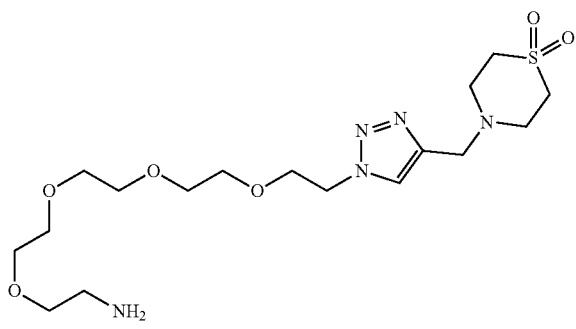

49

A mixture of 4-(prop-2-yn-1-yl)thiomorpholine 1,1-dioxide (5.0 g, 28.86 mmol, 1.0 eq), Tris[(1-benzyl-1H-1,2,3-triazol-4-yl)methyl]-amine (3.37 g, 6.35 mmol, 0.22 eq), Copper Iodide (550 mg, 2.89 mmol, 0.1 eq), and Triethylamine (1.01 mL, 7.22 mmol, 0.25 eq) in Methanol (90 mL) was cooled with an ice bath. 14-azido-3,6,9,12-tetraoxatetradecan-1-amine (8.86 g, 33.77 mmol, 1.17 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (15 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 4-((1-(14-amino-3,6,9,12-tetraoxatetradecyl)-1H-1,2,3-triazol-4-yl)methyl)thiomorpholine 1,1-dioxide (49, 7.56 g, 60%) as an oil. LCMS m/z: [M+H]$^+$ Calcd for $C_{17}H_{33}N_5O_6S$ 436.2224; Found 436.2228.

Experimental Procedure N-(14-(4-((1,1-dioxidothiomorpholino)methyl)-1H-1,2,3-triazol-1-yl)-3,6,9,12-tetraoxatetradecyl)methacrylamide (50)

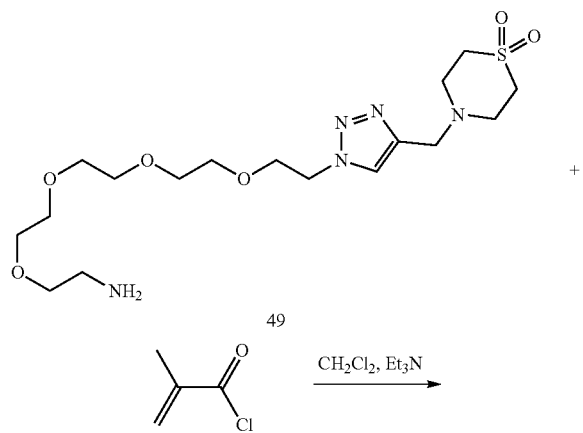

112

-continued

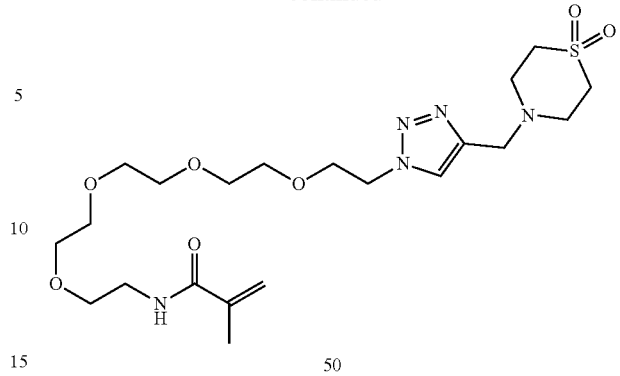

50

A solution of 4-((1-(14-amino-3,6,9,12-tetraoxatetradecyl)-1H-1,2,3-triazol-4-yl)methyl)thiomorpholine 1,1-dioxide (49, 1.95 g, 4.79 mmol, 1.0 eq) and triethylamine (0.80 mL, 5.74 mmol, 1.2 eq) in $CH_2Cl_2$ (50 mL) was cooled with an ice-bath under Nitrogen atmosphere. Methacryloyl chloride (0.51 mL, 5.26 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (80 g) using dichloromethane/methanol as mobile phase. The concentration of methanol was gradually increased from 0% to 5% to afford N-(14-(4-((1,1-dioxidothiomorpholino)methyl)-1H-1,2,3-triazol-1-yl)-3,6,9,12-tetraoxatetradecyl)methacrylamide (50, 0.76 g, 32% yield) as a colorless oil. LCMS m/z: [M+H]$^+$ Calcd for $C_{21}H_{37}N_5O_7S$ 504.25; Found 504.20.

Example 2

Chemical Modification of Exemplary Polymers

A polymeric material may be chemically modified with a compound of Formula (I) (or pharmaceutically acceptable salt thereof) prior to formation of a particle (e.g., a hydrogel capsule described herein). Synthetic protocols of exemplary compounds for modification of polymeric materials are outlined above in Example 1. These compounds, or others, may be used to chemically modify any polymeric material.

For example, in the case of alginate, the alginate carboxylic acid is activated for coupling to one or more amine-functionalized compounds to achieve an alginate modified with an afibrotic compound, e.g., a compound of Formula (I). The alginate polymer is dissolved in water (30 mL/gram polymer) and treated with 2-chloro-4,6-dimethoxy-1,3,5-triazine (0.5 eq) and N-methylmorpholine (1 eq). To this mixture is added a solution of the compound of interest (e.g., Compound 101 shown in Table 2) in acetonitrile (0.3M).

The amounts of the compound and coupling reagent added depends on the desired concentration of the compound bound to the alginate, e.g., conjugation density. A medium conjugation density of Compound 101 typically ranges from 2% to 5% N, while a high conjugation density of Compound 101 typically ranges from 5.1% to 8% N. To prepare a CM-LMW-Alg-101-Medium polymer solution, the dissolved unmodified low molecular weight alginate (approximate MW<75 kDa, G:M ratio≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate). To prepare a CM-LMW-Alg-101-High polymer solution, the dissolved unmodified low-molecular weight alginate (approximate MW<75 kDa, G:M ratio≥1.5) is treated with 2-chloro-4,6-dimethoxy-1,3,5-triazine (10.2 mmol/g alginate) and N-methylmorpholine (20.4 mmol/g alginate) and Compound 101 (10.8 mmol/g alginate).

The reaction is warmed to 55° C. for 16h, then cooled to room temperature and gently concentrated via rotary evaporation, then the residue is dissolved in water. The mixture is filtered through a bed of cyano-modified silica gel (Silicycle) and the filter cake is washed with water. The resulting solution is then extensively dialyzed (10,000 MWCO membrane) and the alginate solution is concentrated via lyophilization to provide the desired chemically-modified alginate as a solid or is concentrated using any technique suitable to produce a chemically modified alginate solution with a viscosity of 25 cP to 35 cP.

The conjugation density of a chemically modified alginate is measured by combustion analysis for percent nitrogen. The sample is prepared by dialyzing a solution of the chemically modified alginate against water (10,000 MWCO membrane) for 24 hours, replacing the water twice followed by lyophilization to a constant weight.

Example 3

Preparation of Exemplary Alginate Solutions

70:30 mixture of chemically-modified and unmodified alginate. A low molecular weight alginate (PRONOVA™ VLVG alginate, NovaMatrix, Sandvika, Norway, cat. #4200506, approximate molecular weight<75 kDa; G:M ratio≥1.5) was chemically modified with Compound 101 in Table 2 to produce chemically modified low molecular weight alginate (CM-LMW-Alg-101) solution with a viscosity of 25 cp to 35 cP. A solution of high molecular weight unmodified alginate (U-HMW-Alg) was prepared by dissolving unmodified alginate (PRONOVA™ SLG100, NovaMatrix, Sandvika, Norway, cat. #4202106, approximate molecular weight of 150 kDa-250 kDa) at 3% weight to volume in 0.9% saline. The CM-LMW-Alg solution was blended with the U-HMW-Alg solution at a volume ratio of 70% CM-LMW-Alg to 30% U-HMW-Alg (referred to herein as a 70:30 CM-Alg:UM-Alg solution).

Unmodified alginate control solution. An unmodified medium molecular weight alginate (SLG20, NovaMatrix, Sandvika, Norway, cat. #4202006, approximate molecular weight of 75-150 kDa), was dissolved at 1.4% weight to volume in 0.9% saline to prepare a U-MMW-Alg solution.

Example 4

Culturing Exemplary Cells for Encapsulation as Single Cells

4A. ARPE-19 cells. These RPE cells were cultured and subsequently encapsulated in one-compartment or two-compartment hydrogel millicapsules. ARPE-19 cells may be cultured according to any method known in the art, such as according to the following protocol. ARPE-19 cells in a 75 cm$^2$ culture flask were aspirated to remove culture medium, and the cell layer was briefly rinsed with 0.05% (w/v) trypsin/0.53 mM EDTA solution ("TrypsinEDTA") to remove all traces of serum containing a trypsin inhibitor. 2-3 mL Trypsin/EDTA solution was added to the flask, and the cells were observed under an inverted microscope until the cell layer was dispersed, usually between 5-15 minutes. To avoid clumping, cells were handled with care and hitting or shaking the flask during the dispersion period was minimized. If the cells did not detach, the flasks were placed at 37° C. to facilitate dispersal. Once the cells dispersed, 6-8 mL complete growth medium was added and the cells were aspirated by gentle pipetting. The cell suspension was transferred to a centrifuge tube and spun down at approximately 125×g for 5-10 minutes to remove TrypsinEDTA. The supernatant was discarded, and the cells were re-suspended in fresh growth medium. Appropriate aliquots of cell suspension was added to new culture vessels, which were incubated at 37° C. The medium was renewed 2-3 times weekly.

4B. HEK293F cells. These cells, marketed as FreeStyle™ 293 F (Thermo Fisher Scientific, Waltham, MA, USA) were grown in suspension using a 125 ml Erlenmeyer flask with a working volume of 25 ml of FreeStyle 293 Expression Medium. Flasks were incubated at 37° C. on a shaker plate set for 125 RPM. Cells were grown to a density between 2 and 3×10$^6$ cells/ml at which time the cells are re-seeded to a density between 2 and 3×10$^5$ cells/ml, typically every 3-4 days. To avoid clumping, cells were handled with care, placed into a 50 ml falcon tube and vortexed for 5-10 seconds to maximize cell homogeneity. After counting the cell density, appropriate aliquots of cell suspension was added to new culture vessels.

Example 5

Preparation of Cell Clusters for Encapsulation

Spheroid clusters of exemplary cells (e.g., ARPE-19 cells) are prepared using AggreWell™ spheroid plates (STEMCELL Technologies) and the protocol outlined herein. On Day 1, rinsing solution (4 mL) is added to each plate, and the plates is spun down for 5 minutes at 3,000 RPM in a large centrifuge. The rinsing solution is removed by pipet, and 4 mL of the complete growth medium is added. The ARPE-19 cells are seeded into the plates at the desired cell density and pipetted immediately to prevent aggregation, with the general rule of thumb that 3.9 million cells per well will generate 150 µm diameter clusters. The plate is spun down for 3 minutes at 800 RPM, and the plate is placed into an incubator overnight.

On Day 2, the plate is removed from incubation. Using wide bore pipet tips, the cells are gently pipetted to dislodge the spheroid clusters. The clusters are filtered through a 40 µm or 80 µm cell strainer to remove extraneous detached single cells and then spun down in a centrifuge for 2×1 minute. The clusters are resuspended gently using wide bore pipet tips and are gently stirred to distribute them throughout the medium or another material (e.g., alginate).

Alternatively, ARPE-19 spheroids are prepared using the following protocol. On Day 1, AggreWell™ plates are removed from the packaging in a sterile tissue culture hood. 2 mL of Aggrewell™ Rinsing solution is added to each well. The plate is centrifuged at 2,000 g for 5 minutes to remove air bubbles, and the AggreWell™ Rinsing Solution is removed from the wells. Each well is rinsed with 2 mL of the complete growth medium, and 2 million ARPE-19 cells in 3.9 mL of the complete growth medium is added to each well. The plate is centrifuged at 100 g for 3 minutes, then the cells are incubated the cells at 37° C. for 48 hours. On Day 3, the same protocol described above is used to dislodge the spheroid clusters.

Example 6

Formation of One-Compartment and Two-Compartment Hydrogel Capsules

Suspensions of single cells (ARPE-19 cells or HEK293F cells as described in Example 4) were encapsulated in one-compartment or two-compartment hydrogel capsules according to the protocols described below.

Immediately before encapsulation, single cells were centrifuged at 1,400 r.p.m. for 1 min and washed with calcium-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH≈7.4, ≈290 mOsm). After washing, the cells were centrifuged again and all of the supernatant was aspirated. In some experiments, the cell pellet was then resuspended in the 70:30 CM-Alg:UM-Alg solution described in Example 3 at a range of densities of suspended single cells per ml alginate solution. In some experiments, cells were used directly without suspension (e.g, dilution) in the alginate solution ("undiluted cells").

Prior to fabrication of one-compartment and two-compartment hydrogel capsules, buffers and alginate solutions were sterilized by filtration through a 0.2-μm filter using aseptic processes.

To prepare particles configured as two-compartment hydrogel millicapsules of about 1.5 mm diameter, an electrostatic droplet generator was set up as follows: an ES series 0-100-kV, 20-watt high-voltage power generator (EQ series, Matsusada, NC, USA) was connected to the top and bottom of a coaxial needle (inner lumen of 22G, outer lumen of 18G, Ramé-Hart Instrument Co., Succasunna, NJ, USA). The inner lumen was attached to a first 5-ml Luer-lock syringe (BD, NJ, USA), which was connected to a syringe pump (Pump 11 Pico Plus, Harvard Apparatus, Holliston, MA, USA) that was oriented vertically. The outer lumen was connected via a luer coupling to a second 5-ml Luer-lock syringe which was connected to a second syringe pump (Pump 11 Pico Plus) that was oriented horizontally. When preparing two-compartment capsules that encapsulate cells only in the inner compartment, a first alginate solution comprising the cells (as single cell suspension) was placed in the first syringe and a second alginate solution lacking cells was placed in the second syringe. The two syringe pumps move the first and second alginate solutions from the syringes through both lumens of the coaxial needle and single droplets containing both alginate solutions are extruded from the needle into a glass dish containing a cross-linking solution. The settings of each Pico Plus syringe pump were 12.06 mm diameter and the flow rates of each pump were adjusted to achieve various test flow rates in the Examples below, but keeping the total flow rate set at 10 ml/h.

For fabrication of one-compartment hydrogel capsules of about 1.5 mm diameter, the 70:30 CM-Alg:UM-Alg solution described in Example 3 (with or without a suspension of single cells) was loaded into a syringe and capped with an 18-gauge blunt tipped needle (SAI Infusion Technologies). The syringe was placed into a syringe pump oriented vertically above a dish containing the crosslinking buffer. A high voltage power generator was connected to the needle and grounded to the biosafety cabinet. The syringe pump and power generator were turned on to extrude the alginate solution through the needle with a flow-rate of 0.16 mL/min or 10 mL/hr and adjusting the voltage in a range of 5-9 kV until there was a droplet rate of 12 droplets per 10 seconds.

For fabrication of both the two-compartment and one-compartment millicapsules, after extrusion of the desired volumes of alginate solutions, the alginate droplets were crosslinked for five minutes in a cross-linking solution which contained 25 mM HEPES buffer, 20 mM $BaCl_2$, and 0.2M mannitol. In some experiments, the cross-linking solution also contained 0.01% of poloxamer 188. Capsules that had fallen to the bottom of the crosslinking vessel were collected by pipetting into a conical tube. After the capsules settled in the tube, the crosslinking buffer was removed, and capsules were washed. Capsules without cells were washed four times with HEPES buffer (NaCl 15.428 g, KCl 0.70 g, $MgCl_2 \cdot 6H_2O$ 0.488 g, 0 ml of HEPES (1 M) buffer solution (Gibco, Life Technologies, California, USA) in 2 liters of deionized water) and stored at 4° C. until use. Capsules encapsulating cells were washed four times in HEPES buffer, two times in 0.9% saline, and two times in culture media and stored in an incubator at 37° C.

In some experiments, the quality of capsules in a composition of two-compartment or one-compartment capsules was examined. An aliquot containing at least 200 capsules was taken from the composition and transferred to a well plate and the entire aliquot examined by optical microscopy for quality by counting the number of spherical capsules out of the total.

In some experiments, the mechanical strength of capsules in a composition of two-compartment capsules was examined using a texture analyzer to determine the initial fracture force as described herein above.

Example 7

Assessing the Effect of Cell Loading on Capsule Quality

Capsule compositions (comprising two-compartment capsules or one-compartment capsules) were prepared as described in Example 6 using the 70:30 CM-Alg:UM-Alg solution described in Example 3 and various loading amounts of cells in the alginate solution used to form the first (inner) compartment. The cross-linking solution included 0.01% poloxamer 188. Two-compartment capsules (1.5 mm diameter) with equal volume first and second compartments formed from the 70:30 alginate solution were prepared using a flow rate of 5 ml/hour for the alginate solutions in each of the first and second syringes. In addition, a composition of two-compartment, 1.5 mm capsules was prepared in substantially the same manner except the inner compartment was formed using undiluted cells (concentration equiv. to 500 million cells/ml) in the first syringe (e.g., no alginate solution.) Engineered ARPE19 cells expressing Factor VIII were encapsulated at 10-50 million cells/ml alginate solution in one-compartment capsules or 10-500 million cells/ml alginate solution (concentration equiv. to one-compartment capsules) in 2-compartment capsules. The different capsule compositions were examined for quality and the results are shown in FIG. 3.

For the one-compartment millicapsules, it was generally observed that capsule quality (i.e., spherical shape) decreased as cell loading increased. Quality of compositions comprising one-compartment millicapsules was below the acceptable threshold of 95% spherical particles in the examined aliquot at cell loadings greater than 20 million cells/ml alginate. Compositions comprising two-compartment millicapsules had very high spherical quality up to a loading cell amount of undiluted cells equivalent to 500 million cells/ml alginate solution, which is about a 25× higher cell loading capacity than the highest acceptable cell loading capacity for the one-compartment particles. For this particular configuration of 70:30 CM-Alg:UM-Alg and capsule size, a cell loading equivalent to 500 million cells/ml alginate solution appears to be the upper loading limit for the first (inner) compartment. Therefore, the two-compartment millicapsules permitted encapsulation of a significantly greater number of cells without affecting the spherical morphology of the capsules.

Example 8

Altering the Effect of Flow Rate Ratio on the Thickness of the Second Compartment Compositions containing two-compartment hydrogel millicapsules (about 1.5 mm in diameter) were prepared with a 70:30 mixture of CM-Alg:U-Alg in both compartments. The combined flow rates of alginate solutions through the outer and inner lumens was held constant at 10 ml/h, while the ratio of these flow rates was varied to prepare capsules with varying compartment thicknesses. To visualize the compartments in the resulting capsules, ARPE19-FVIII cells were encapsulated at 20 million cells/ml alginate solution in the first (inner) compartment. Compartment thickness was measured via image analysis.

Figures 4A, 4B:
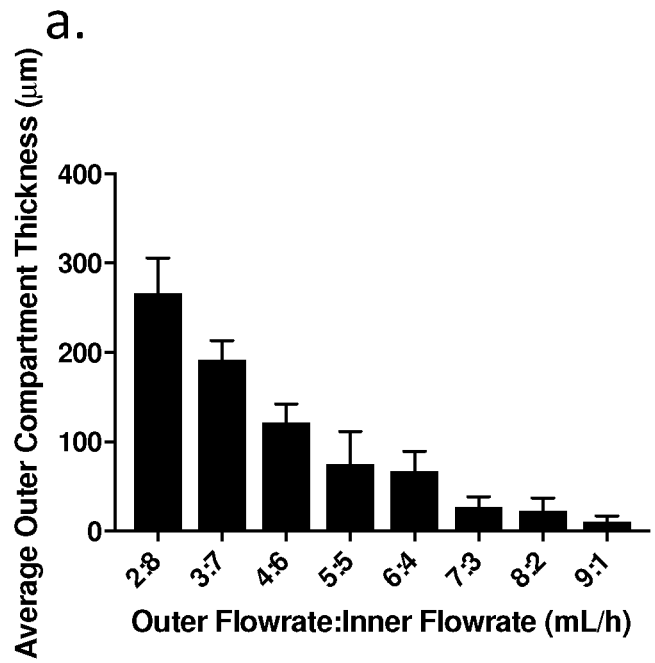
FIGS. 4A-4B show the effect of altering the flow rate of extruded alginate on the thickness of the second (outer) compartment of an exemplary particle of the disclosure (i.e., a two-compartment hydrogel millicapsule).

By changing the outer:inner lumen flow rate ratio, the mean thickness of the second (outer) compartment of a 1.5 mm two-compartment capsule was varied from 11-267 microns as shown in FIGS. 4A-4B. In all cases, spherical capsules of about 1.5 mm were formed. The smallest second (outer) compartment created was about 11 microns in diameter, and increasing the ratio of outer:inner lumen flow rates increased the second (outer) compartment thickness from about 11 microns to a maximum of 267 microns. Therefore, the second (outer) compartment thickness of hydrogel capsules may be altered by varying inner and outer flow rates to generate a composition of uniform spherical millicapsules.

Example 9

Effect of Varying the Composition and Size of the First Compartment on the Mechanical Properties of Particles Compositions of two-compartment hydrogel millicapsules were prepared by extruding first and second alginate solutions through a coaxial needle as described in Example 6. The second (outer) compartment was prepared using the 70:30 CM-Alg:U-Alg solution described in Example 3 and the first (inner) compartment was prepared using the U-HMW-Alg solution described in Example 3. While keeping the total (e.g., combined) flow rate at 10 ml/h, the inner: outer flow rate ratios (I:O) were varied from 1 ml to 9 ml per hour and 9 ml to 1 ml per hour to produce millicapsules with different inner and outer compartment thicknesses. Control capsule compositions were also prepared. One control contained one-compartment capsules made from the same 70:30 CM-Alg:U-Alg solution. A second control composition contained one-compartment capsules made from the same U-HMW-Alg solution. Mechanical testing was performed on aliquots from each of the compositions using a texture analyzer to measure initial fracture of individual capsules.

Figure 5:
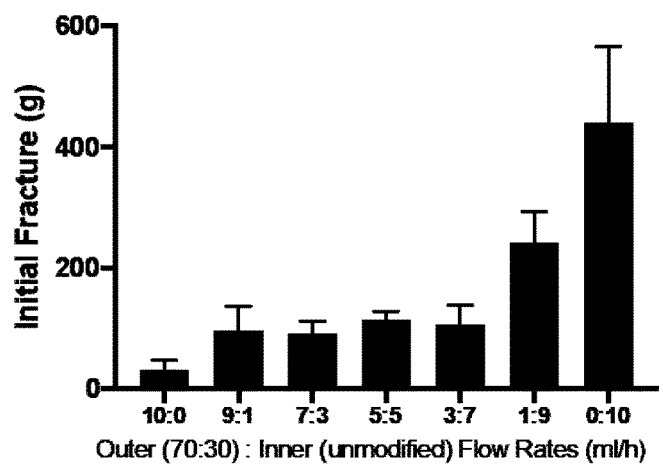
FIG. 5 is a graph showing the initial fracture of exemplary particles of the disclosure (i.e., two-compartment hydrogel millicapsules) with varying ratios of inner:outer flow rates (ml/h). The polymer in the first compartment (Inner) is an unmodified high molecular weight alginate and the polymer in the second compartment (Outer) is a mixture of a chemically modified low molecular weight alginate and an unmodified high molecular weight alginate at a 70:30 ratio of chemically modified to unmodified alginate.
Figures 6A, 6B, 6C, 6D:
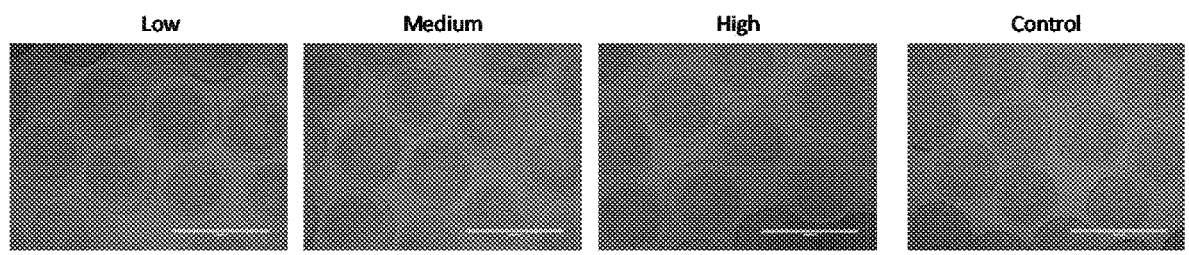
FIGS. 6A-6D are brightfield images of exemplary particles (i.e., two-compartment hydrogel millicapsules) with a 50:50 volume ratio of inner:outer compartments. Second (outer) compartments contain low, medium or high conjugation alginate or a control (unmodified), alginate. Exemplary RPE cells engineered to express an exogenous protein were encapsulated in the first (inner) compartment for visualization of the two-compartment architecture.

Two-compartment capsules of about 1.5 mm in diameter were created in all conditions. One-compartment capsules prepared from the 70:30 mixture had the lowest initial fracture compared to all of the two-compartment capsule configurations. The mechanical strength of two-compartment capsules with an inner compartment of U-HMW-Alg increased with increasing volume fraction of the inner compartment to the entire capsule (see FIG. 5). Capsules in the second control composition (one-compartment U-HMW-Alg capsules) had higher initial fracture than all two-compartment particles with inner and outer compartments composed of U-HMW-Alg and 70:30 CM-Alg:U-Alg, respectively. As the volume fraction of the inner compartment (U-HMW-Alg) increased, mean initial fracture increased. Therefore, changing the configuration of the inner compartment (identity of the alginate and/or thickness) of a 2-compartment millicapsule can alter its mechanical properties. Thus, 2-compartment hydrogel millicapsules can present the same capsule surface with respect to chemical modification (e.g., to mitigate FBR) but have stronger mechanical strength by changing the alginate composition in the first (inner) compartment.

Example 10

Preparation of Two-Compartment Hydrogel Capsules with Varying Amounts of Chemical Modification in the $2^{nd}$ (Outer) Compartment Chemically modified alginate solutions were prepared with varying amounts of conjugation of compound 101. Polymers were prepared with low (2.03% N), medium (4.42% N), or high (6.72% N) levels of compound 101 conjugation, where % nitrogen is determined by combustion analysis and corresponds to the amount of small molecule conjugated to the polymer. Compositions of two-compartment hydrogel millicapsules were prepared as follows. The outer compartment was formed using (i) a solution containing one of these conjugated polymers blended with U-HMW-Alg at a 70:30 ratio of CM-Alg-101 to U-HMW-Alg or (ii) the U-MMW-Alg solution described in Example 3 as a control. The inner compartment was formed using a solution containing the medium CM-Alg-101 conjugation blended with U-HMW-Alg. The inner and outer flow rates were both 5 ml/h. To visualize the first (inner) compartment, 20 million ARPE19-FVIII cells/ml alginate solution were encapsulated in the first (inner) compartment of the capsule.

FIGS. 6A-6D show the capsules created with low, medium, high conjugation CM-Alg polymers or the control (unmodified) polymer in the second (outer) compartment. Compositions of spherical, uniform millicapsules of about 1.5 mm in diameter were formed regardless of which CM-A polymer solution was used to form the outer compartment, demonstrating that high quality capsules can be prepared with the same polymer used in the first (inner) compartment and varying amounts of chemical modification in the second (outer) compartment.

Example 11

Effect of Varying the Level of Chemical Modification in the Second Compartment on Biocompatibility The hydrogel capsules prepared in Example 10 were examined for fibrosis in vivo by implanting the capsules into the IP space of C57/BL6 mice for one week. In this mouse model, encapsulated xenogeneic cell lines, such as human RPE cells, generally induce a fibrotic response. At retrieval, particles were imaged for the presence of fibrosis, and initial fracture measured using a texture analyzer. The results are shown in FIGS. 7A-7F.

Upon retrieval, the empty capsules (no cells) had no visible fibrosis (FIG. 7D). Control capsules (U-MMW-Alg outer compartment) had fibrotic buildup surrounding the particles (FIG. 7E). For capsules with a CM-Alg-101 in the outer compartment, a fibrotic response was only observed on the low conjugation CM-Alg capsules (FIG. 7A), with minimal fibrosis observed on the medium and high conjugation CM-Alg capsules (FIGS. 7B-7C). Initial fracture was measured prior to implantation and at retrieval, and all 2-compartment capsules had similar initial fracture at each time point (FIG. 7F). Therefore, altering the chemical modification profile only on the second (outer) compartment of the capsule may be used to modulate an afibrotic property, i.e., increasing the concentration of a compound of Formula I in the outer compartment can substantially reduce fibrosis without affecting mechanical strength.

Example 12

Effect of Varying the Level of Chemical Modification in the Second Compartment on Macrophage Adhesion Over Time The degree of mouse macrophage adhesion in vivo over 1-4 weeks on hydrogel capsules with varying amounts (low, medium, or high) of chemical modification in the second (outer) compartment was examined as follows. Capsules were prepared as described in Example 10, and implanted in C57/BL6 mice as in Example 11, then retrieved at 1, 2, and 4 weeks post-implantation. At retrieval, particles were imaged for the presence of mouse macrophages using immunofluorescent staining (anti-F4/80). The results are shown in FIGS. 9A-9K.

After 1 week of implantation, macrophage adhesion was observed on the positive control capsules (unmodified medium molecular weight alginate) and the low conjugation capsules (FIGS. 9A-9B). Some macrophage adhesion was observed on the medium conjugation capsules (FIG. 9C), and there was minimal macrophage adhesion on the high conjugation (FIG. 9D), or empty capsules (FIG. 9E). At 2 and 4 weeks post-implantation, there was no macrophage adhesion on the empty capsules (FIGS. 9H and 9K), and macrophage adhesion was higher on the medium conjugation capsules (FIGS. 9F and 9I), compared to the high conjugation capsules (FIGS. 9G and 9J), demonstrating a dose response between the level of chemical modification in the second (outer) compartment of the capsule and macrophage adhesion (fibrosis) in vivo.

Example 13

Effect of Varying the Level of Chemical Modification in the Second Compartment on Fibrosis The level of chemical modification in the second (outer) compartment of exemplary particles was investigated for its impact on fibrosis using the method described below. The low, medium, and high conjugation capsules prepared in Example 10 were used. Additionally, medium-high (4.79% N) and double-high (9.00% N) conjugation capsules were prepared using methods described in Example 10, where % nitrogen is determined by combustion analysis and corresponds to the amount of small molecule conjugated to the polymer. The capsules were then implanted in C57/BL6 mice as described in Example 11, and retrieved at 2 weeks post-implantation. Fibrosis of the retrieved capsules was analyzed with brightfield imaging, where an opaque layer around the capsule indicates fibrosis. The results are shown in FIGS. 10A-10E.

Empty capsules with medium conjugation were used as a control, and showed no fibrosis (FIG. 10A). Capsules with medium conjugation or medium-high conjugation showed higher levels of fibrosis (FIGS. 10B-10C), compared with the high-conjugation capsules (FIG. 10D). Many of the double high conjugation capsules were not intact spheres after retrieval, some appeared fibrosed, or reduced in size, and there was significant capsule debris (FIG. 10E). This suggests that the second (outer) compartment containing the high levels of a compound of Formula (I) was not intact, demonstrating that there is an upper limit to the amount of a compound of Formula (I) that can effectively resist fibrosis.

Example 14

Effect of Varying the Level of Chemical Modification in the Second Compartment on Mechanical Strength The mechanical strength of the capsules used in Example 13 were measured by initial fracture using a texture analyzer. Each of the control, medium, medium high, high, and double high conjugated capsules were tested for mechanical strength at both pre- and post-implantation stages. The results are shown in FIG. 11.

Initial mechanical strength was higher in the control (empty) capsules compared to cell-loaded capsules. The medium, medium-high, and high conjugation capsules had similar strength at both pre- and post-implantation, with a decrease in strength observed after implantation. The capsules with the highest level of conjugation (double high) were the weakest capsules, and most of these capsules were not intact at retrieval (FIG. 11), as noted in Example 13. This further demonstrates that there is an upper limit to the amount of afibrotic small molecule conjugation that is efficacious, as very high levels of conjugation compromise mechanical strength.

Example 15

Effect of Covalent and Non-Covalent Chemical Modification of the Second (Outer) Compartment on Fibrosis The difference between conjugated or non-conjugated compounds of Formula (I) in the second (outer) compartment of hydrogel capsules as a means to confer resistance to fibrosis was determined using the following experiment.

Capsules with medium and high amounts of compounds of Formula (I) were prepared as in Example 10. In addition, a third type of capsule featuring non-conjugated afibrotic small molecules (denoted "amine added back") was prepared in a similar manner to the method of Example 10, where the second (outer) compartment of the capsule was made from alginate solution containing unconjugated compounds of Formula (I). This solution was prepared by adding unconjugated small molecule to a medium conjugation alginate solution, using an amount of unconjugated small molecule necessary to achieve an overall amount of compounds of Formula (I) equivalent to the high conjugation alginate solution. The 70:30 CM-Alg:U-Alg was used for the first (inner) compartment of the "amine added back" capsules. All capsules were then implanted in vivo using C57/BL6 mice as in Example 11, and were retrieved at 2 weeks post-implantation. Retrieved capsules were imaged with brightfield microscopy to detect the presence of an opaque outer layer of adhered cells, indicating the beginning of fibrosis. The results are shown in FIGS. 12A-12C.

There was a layer of adhered cells observed on the medium conjugation capsules (FIG. 12A), while only minimal adhesion to the high conjugation capsules was observed (FIG. 12B). The "amine added back" capsules also appeared opaque, indicating a layer of fibrotic cell adhesion on the capsule (FIG. 12C). Therefore, this data demonstrates that only conjugated small molecules contribute to the afibrotic properties of the capsules.

Example 16

Effect of Varying Level of Small Molecule Conjugation and Polymer Blend Ratio in the Second Compartment on Macrophage Adhesion Capsules prepared from alginate solutions of two polymer blends (containing different ratios of low molecular weight alginate (CM-LMW) to unmodified high molecular weight alginate (U-HMW)), and varying amounts (medium, medium high, or high) of compounds of Formula (I) were compared in terms of their fibrosis resistance in vivo with the following experiment.

Three polymer blends were prepared at a 70% CM-LMW-Alg to 30% U-HMW-Alg ratio (70:30) as described in Example 3, with medium, medium high, or high levels of compounds of Formula (I). An additional three polymer blends were also prepared at a 60% CM-LMW-Alg to 40% U-HMW-Alg ratio (60:40), again with medium, medium high, or high levels of compounds of Formula (I). Each polymer blend was then used to form the second (outer) compartment of capsules using the method described in Example 10, providing a set of six hydrogel capsules, featuring medium, medium-high, or high-levels of conjugation from either 70:30 or 60:40 ratio polymer blends. The inner compartments of all the capsules contained the 70:30 CM-Alg:U-Alg solution. The capsules were then implanted in vivo, as described in Example 11, and were retrieved at 1 week post-implantation and analyzed via immunofluorescent staining for mouse macrophages adhesion (fibrosis) on the capsules. The results are shown in FIGS. 13A-13F A trend of decreasing levels of adhered macrophages was observed from the medium to high conjugated capsules, across both the 70:30 (FIGS. 13A-13C) and the 60:40 ratio blends (FIGS. 13D-13F). Also, a larger amount of adhered macrophages was observed in the 60:40 ratio blend capsules, compared with the relatively lower amount of macrophage adhesion in the capsules form the 70:30 ratio blend. As the change in ratio affects the total dose of small molecules on the capsule, the results infer that the amount of small molecule conjugated to the polymer and the amount of chemically modified polymer used to prepare the capsules can independently alter macrophage adhesion and fibrosis.

Example 17

Comparison of Capsule Architecture on the Fibrotic Response

Compositions of one-compartment or two-compartment hydrogel millicapsules encapsulating single ARPE-19 cells expressing FVIII-BDD were prepared by extruding droplets of the 70:30 CM-Alg:U-Alg solution described in Example 3 with various cell loading concentrations into a crosslinking solution. One-compartment capsules with either no cells or 5000 cells dispersed throughout the entire capsule were prepared as the controls. The two-compartment capsules had a cell-free second (outer) compartment and a first (inner) compartment containing 5000 or 2500 cells per capsule. Capsules with 2500 and 5000 cells were prepared using an outer:inner volume ratio of 50%:50%. Capsules with 2500 cells and a thicker second (outer) compartment were prepared using an outer:inner volume ratio of 75%:25%. The capsules were implanted into the IP space of C57/BL6 mice at 0.5 ml capsules/mouse. Capsules were retrieved after 14 days and imaged to observe presence or absence of fibrosis. In this mouse model, the xenogeneic ARPE-19 cells in the capsule were expected to induce a FBR.

The results of this experiment showed that all capsules encapsulating ARPE-19 cells, fabricated with either one or two compartments, were fibrosed in the C57/BL6 mouse model (data not shown). No fibrosis was observed on the empty one-compartment control capsules. Thus, in C57/BL6 mice, the configuration of capsules as one-compartment or two-compartments had no apparent effect on FBR induced by the xenogeneic RPE cells.

Example 18

Assessing Cell Proliferation in Exemplary Particles Configured as Two-Compartment Hydrogel Capsules HEK293F cells, which grow in suspension, were encapsulated within the inner compartment of two-compartment hydrogel millicapsules of about 1.5 mm in diameter. The capsules were prepared using the 70:30 CM-Alg:U-MW-Alg solution described in Example 3 to form both inner and outer compartments. The cell loading concentration in the inner compartment was 20 million HEK293F cells/ml (equivalent of 10 million cells/ml alginate solution in a 1.5 mm one-compartment capsule). Two-compartment capsules were fabricated using 5 ml/h inner and outer flow rates. As a control, one-compartment capsules of about 1.5 mm diameter were prepared using the same 70:30 CM-Alg:U-MW-Alg alginate solution comprising 10 million HEK293F cells/ml. Capsules were incubated at 37° C., 5% $CO_2$ for 7 days and then observed by microscopy.

Observation of the capsule edges revealed the presence of cells protruding from the edges of the one-compartment capsules, but not the two-compartment capsules, after one week of culture (FIGS. 14A-9B). Free floating and adhered cells were observed on the surface of the tissue culture plate containing the one-compartment capsules, demonstrating incomplete encapsulation and/or escape of cells (FIG. 14C). In contrast, no cells were observed outside of the two-compartment capsules in the culture plate after one week of culture (FIG. 14D). Similar results were obtained when one-compartment and two-compartment capsules were prepared with ARPE19 cells instead of HEK293F cells (data not shown). Thus, the two-compartment capsules are more effective than one-compartment capsules in containing cells, e.g., without cell leakage or protrusion through the capsule surface.

Example 19

Assessing Protein Release From One- and Two-Compartment Capsules

To determine if protein molecules expressed by encapsulated cells can be released from two-compartment hydrogel capsules, engineered ARPE19 cells expressing FVIII-BDD were encapsulated in two-compartment capsules and protein secretion was measured after 24 hours.

The capsules were prepared using the 70:30 CM-alg:U-HMW-Alg solution described in Example 3 in each of the first and second syringes and 5 ml/h inner and outer flow rates. The alginate solution to prepare the inner compartment also contained ARPE19-FVIII at 20, 50 or 100 million cells/ml. Capsules were incubated for 24 h at 37° C. in a known volume of medium, and medium supernatant was collected and FVIII was detected by FVIII ELISA.

After 24 h, FVIII was detected in medium supernatant samples for each cell loading concentration. An increasing trend between cell loading concentration and amount of FVIII detected from the 2-compartment particles was observed (data not shown). These results suggest that FVIII expressed by cells encapsulated in the inner compartment of a two-compartment capsule diffuses through the second compartment and then exits the capsule.

Example 20

Cell Concentration in Capsules Can be Increased to Increase FIX Levels in Plasma and IP Fluid of Nude Mice Compositions of two-compartment hydrogel millicapsules (1.5 mm) encapsulating single ARPE-19:FIX cells were prepared by extruding droplets of the 70:30 CM-Alg:U-Alg solution described in Example 3 with various cell loading concentrations into a crosslinking solution. Cells were encapsulated at 2, 20, 100, 300 million cells/ml alginate in the inner compartment (equivalent of 1, 10, 50, 150 million cells/ml alginate solution in a 1.5 mm one-compartment capsule). Capsules were implanted into the IP space of nude mice (0.5 ml/mouse) and were retrieved after 5 days. Levels of FIX in the plasma and IP fluid was measured by ELISA.

Figure 15A:
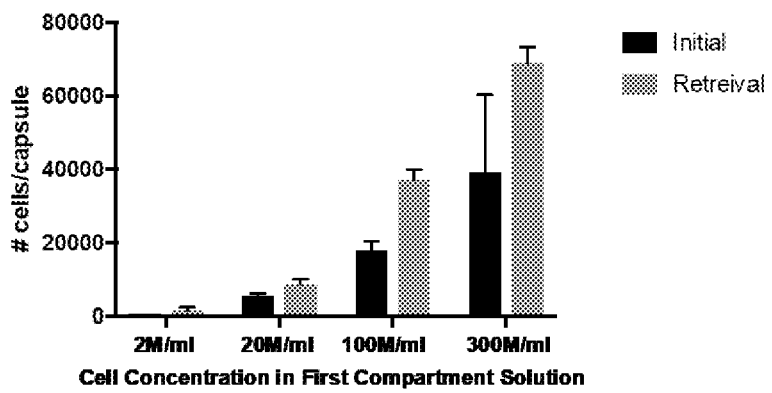
FIGS. 15A-15C illustrate a correlation between expression levels in vivo of FIX by two-compartment hydrogel millicapsules and concentration of ARPE-19:FIX cells in the inner compartment of the capsules.
Figure 15B:
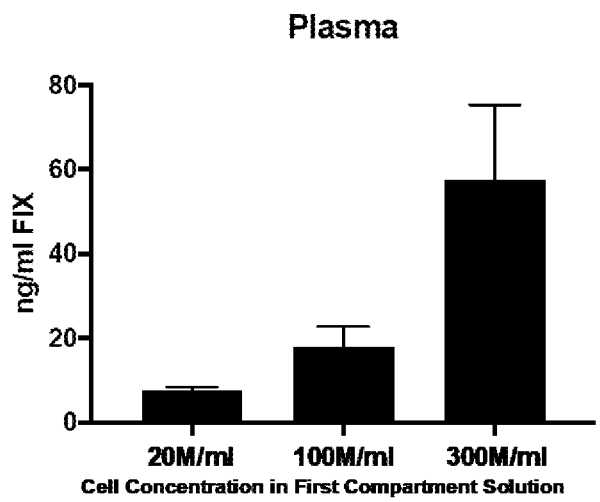
Figure 15C:
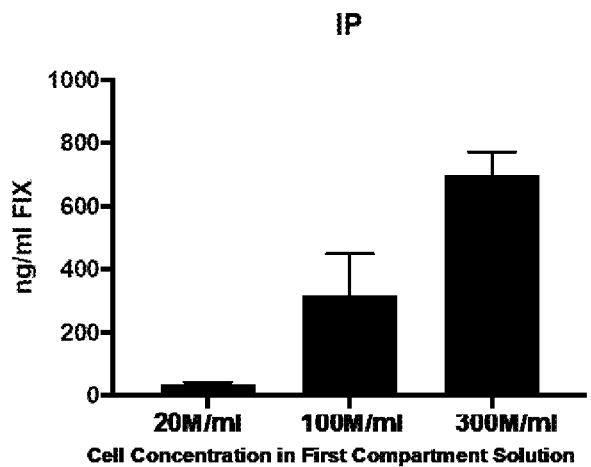

By varying the encapsulated cell concentration, the total number of encapsulated cells was varied from 500 to 39,000 cells/capsule as shown in FIG. 15A. At all cell concentrations, capsules were created with spherical morphology (data not shown). Some proliferation of cells was observed during implant (FIG. 15A). The levels of FIX in the plasma and IP fluid increased with increasing cell concentration, with the exception of 2 million cells/ml, which was at the lower limit of detection of the ELISA assay (FIG. 15. B, C and data not shown). There was an approximately 10-fold increase in FIX levels in the IP fluid, where the capsules are in the local environment, compared to the plasma. Capsules at all cell concentrations were retrieved intact (data not shown). Therefore, a dose response for FIX expression in both the IP and plasma was observed between 2 and 300 M cells/ml alginate solution used to form the inner compartment. In addition, the successful encapsulation of 39,000 cell/capsule is significantly greater than what has been reported in the scientific literature.

Example 21

Optimal Cell Concentration Maximized FIX Levels and Maintained Capsule Integrity Compositions of two-compartment hydrogel millicapsules encapsulating single ARPE-19:FIX cells were prepared as in the previous examples, with cells encapsulated at 100, 200, 300 and 646 million cells/ml of the alginate solution used to form the inner compartment (equivalent of 50, 100, 150, 323 million cells/ml alginate solution in a 1.5 mm one-compartment capsule). Capsules were implanted into the IP space of nude mice (0.5 ml/mouse) and were retrieved after 4 weeks. Levels of FIX in the IP fluid was measured by ELISA.

Figure 16A:
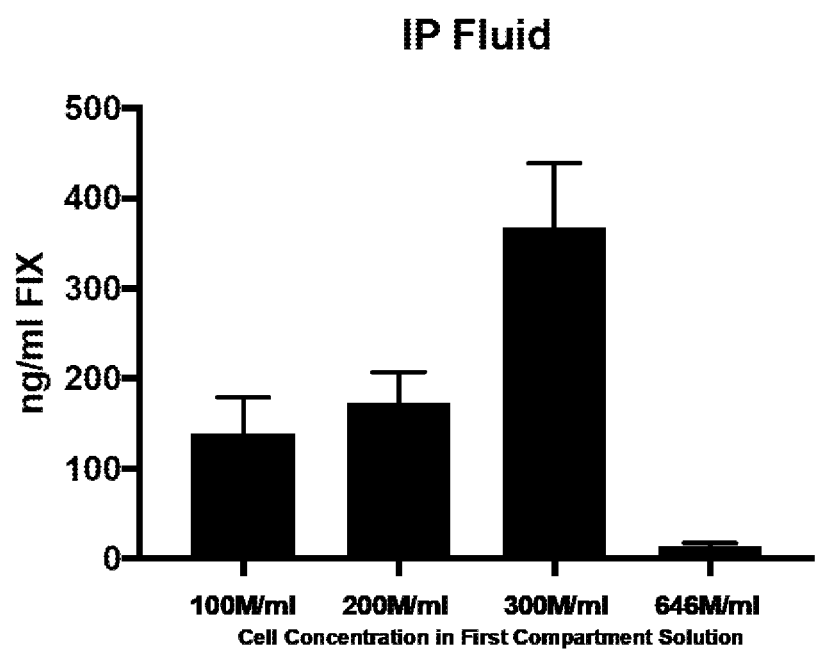
FIGS. 16A-16C illustrate a correlation between expression levels in vivo of FIX by two-compartment hydrogel millicapsules, concentration of ARPE-19:FIX cells in the inner compartment of the capsules and capsule integrity.
Figures 16B, 16C:
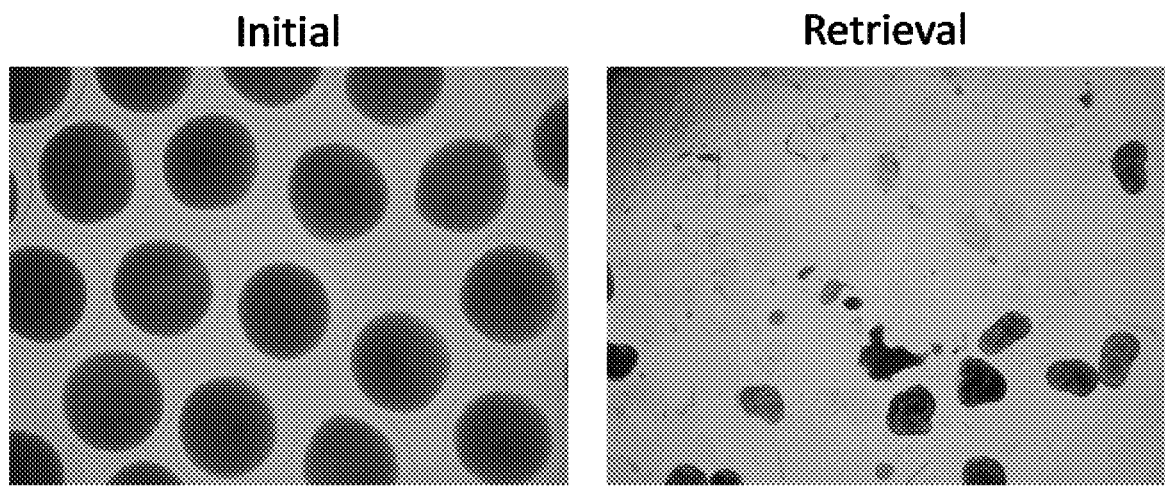

By varying the encapsulated cell concentration, the total number of encapsulated cells was varied from 24,000 to 54,000 cells/capsule (data not shown). At all cell concentrations, capsules were created with spherical morphology (data not shown). The levels of FIX in the IP fluid increased with increasing cell concentration to 150 million cells/ml (FIG. 16A). At the highest loading cell concentration (646 million cells/ml), the FIX levels were low and the retrieved capsules were no longer intact (FIG. 16B). The majority of the capsules prepared with 100 million cells/ml had greatest number of capsules retrieved intact (data not shown). This demonstrates that there is an optimal cell concentration where protein levels are maximized and capsules maintain their integrity.

Example 22

Preparation of Two-Compartment Capsules with a Target Size of 0.75 mm Diameter or 1.0 mm Diameter Two-compartment capsule compositions with a capsule target size of 1.0 mm or 0.75 mm were prepared as described in the previous examples, but with the following adjustments. The alginate solution used to form the second (outer) compartment contained CM-Alg-101 with a medium conjugation level of Compound 101 (e.g., prepared as described in Example 10) blended with U-HMW-Alg at a 70:30 ratio of CM-Alg-101 to U-HMW-Alg. The same blended alginate solution with a suspension of ARPE19 cells (50 million cells per ml) engineered to express human FVIII was used to form the first (inner) compartment. Capsule compositions with a capsule target size of 1.0 mm capsules were generated using a coaxial needle (20G OD/26G ID), a voltage of 7.3 kV, first and second compartment flow rates each of 5 mL/h, and a capsule droplet rate of 30-35 droplets per 10 seconds. Capsule compositions with a target size of 0.75 mm were prepared using a coaxial needle (20G OD/26G ID), a voltage of approximately 7.5 kV, first and second compartment flow rates each of 5 mL/h, and a capsule droplet rate of 35-40 droplets per 10 seconds.

Figure 18A:
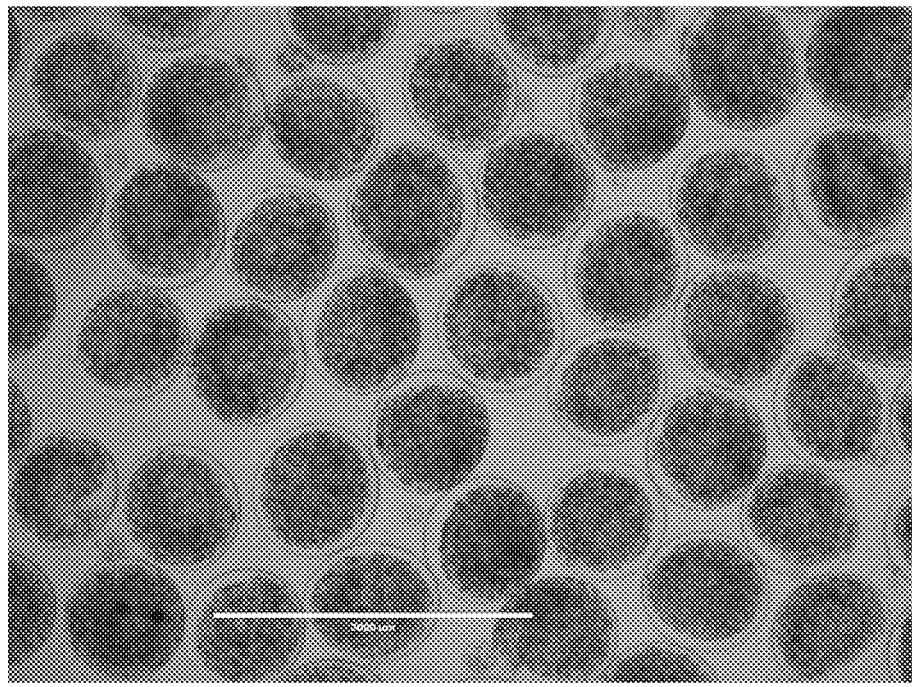
FIG. 18A-18B are brightfield images of exemplary particles (i.e., two-compartment hydrogel capsules about 0.75 mm in diameter (FIG. 18A) or about 1.0 mm in diameter (FIG. 18B) with a 50:50 volume ratio of inner:outer compartments. Each of the first (inner) and second (outer) compartments contain medium conjugation alginate. Exemplary RPE cells engineered to express an exogenous protein were encapsulated in the first (inner) compartment for visualization of the two-compartment architecture.
Figure 18B:
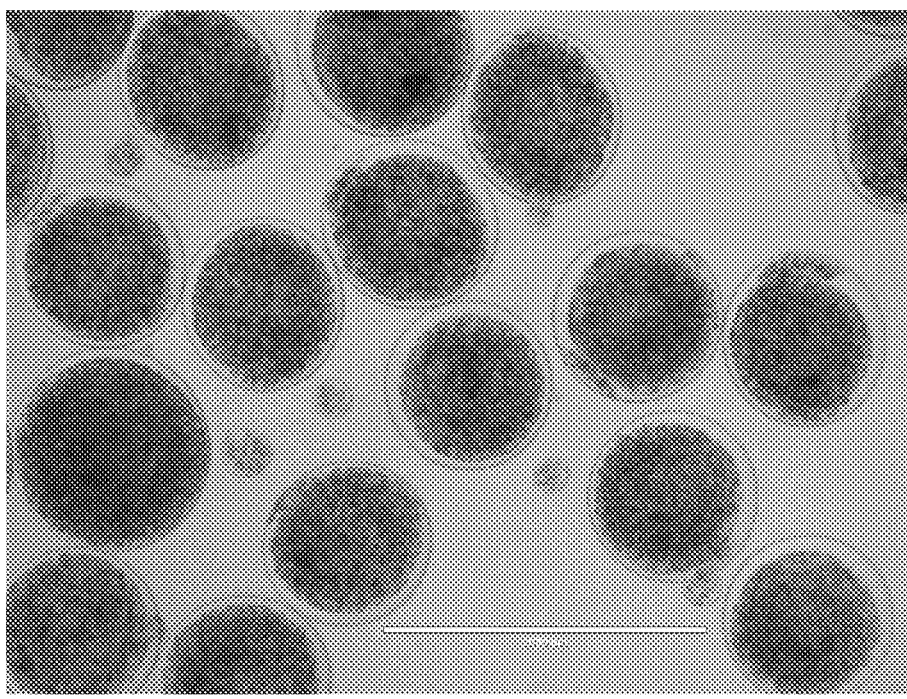

As shown in FIGS. 18A-18B, spherical 0.75 mm and 1.0 mm two compartment capsules with cells in the inner compartment were produced. These capsules had outer compartments that completely encapsulated the cells in the inner compartment. Therefore, two-compartment capsules can be prepared at 0.75 and 1.0 mm mean diameters.

EQUIVALENTS AND SCOPE

This application refers to various issued patents, published patent applications, journal articles, and other publications, all of which are incorporated herein by reference in their entirety. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present disclosure, as defined in the following claims.

The invention claimed is:

1. A particle comprising:

a) a first compartment comprising an alginate polymer and a cell;

b) a second compartment comprising an alginate polymer; and c) a compound of Formula (I-a):

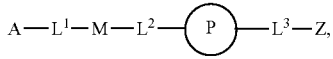

$$A-L^1-M-L^2-\boxed{P}-L^3-Z,$$  (I-a)

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —N($R^C$)C(O)($C_1$-$C_6$-alkylene)-, —N($R^C$)C(O)($C_2$-$C_6$-alkenylene)-, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$) or a metal, each of which is optionally linked to an attachment group and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring, optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4; wherein:

the first compartment is surrounded by the second compartment; and, the alginate polymer of the second compartment is modified with a compound of Formula (I-a).

2. The particle of claim 1, wherein the differential volume of the second compartment is about 1%, 2%, 5%, 7.5%, 10%, 15%, 20%, 25%, 30%, 35%, 40%, 45%, 50%, 55%, 60%, 65%, or 75% less than the volume of the first compartment.

3. The particle of claim 1, wherein the first compartment is substantially free of a compound of Formula (I-a).

4. The particle of claim 1, wherein the particle has a largest linear dimension (LLD), of between 1 millimeter to 5 millimeters, between 1 millimeter to 4 millimeters, 1 millimeter to 3 millimeters, 1 millimeter to 2 millimeters, or 1.5 millimeters to 2 millimeters.

5. The particle of claim 1, wherein the average distance between the outer boundary of the first compartment and the outer boundary of the second compartment is between 500 nanometers and 500 micrometers.

6. The particle of claim 1, wherein:

a) one or a plurality of cells is disposed within the second compartment;

b) the number or density of cells in the second compartment is at least 2, 5, 10, $10^2$, $10^3$, or $10^4$ times less than the number of density of cells in the first compartment; and/or c) the first compartment comprises a compound of Formula (I-a).

7. The particle of claim 1, wherein the cell is an epithelial cell, endothelial cell, fibroblast cell, mesenchymal stem cell, or keratinocyte cell.

8. The particle of claim 1, wherein the cell is an RPE cell or a mesenchymal stem cell (MSC).

9. The particle of claim 1, wherein the cell is an islet cell.

10. The particle of claim 1, wherein the cell expresses a therapeutic agent.

11. The particle of claim 10, wherein the therapeutic agent is a Factor VIII protein or a variant thereof or a Factor IX protein or a variant thereof.

12. The particle of claim 10, wherein the therapeutic agent is insulin.

13. The particle of claim 1, wherein the alginate is a high guluronic acid alginate (G) alginate.

14. The particle of claim 1, wherein the compound of Formula (I-a) is a compound of any one of Formulas (I-b), (I-c), (I-d), (I-e), (I-f), (II), (II-a), (III), (III-a), (III-b), (III-c), or (III-d), or a pharmaceutically acceptable salt thereof.

15. The particle of claim 1, wherein the compound of Formula (I-a) is selected from:

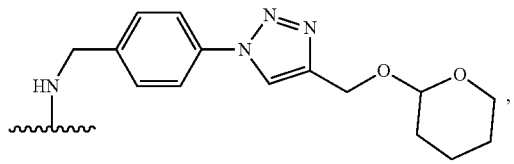

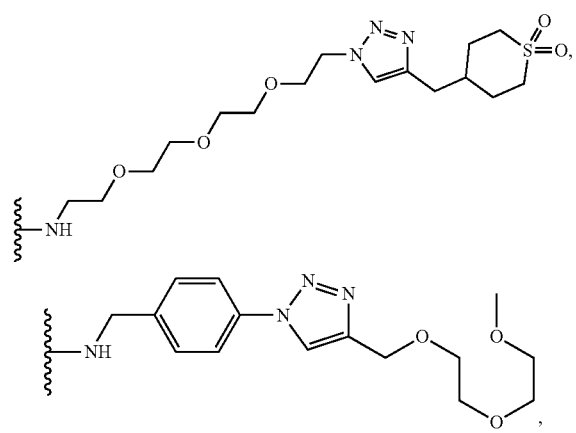

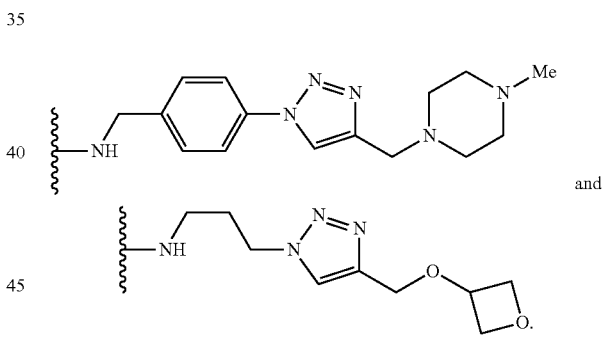

and

16. The particle of claim 1, wherein the particle is a hydrogel capsule and wherein:

a) the first compartment comprises a plurality of cells engineered to express a polypeptide;

b) the first compartment is surrounded by the second compartment;

c) the second compartment is substantially free of cells; and d) wherein the second compartment and exterior surface of the particle comprise an alginate chemically-modified with the compound of Formula (I-a).

17. The particle of claim 16, wherein the chemically-modified alginate comprises the compound of Formula (I-a) in an amount that provides the particle with both an afibrotic property and a desired mechanical strength.

18. The particle of claim 16, wherein the compound of Formula (I-a) is Compound 101, which has the structure:

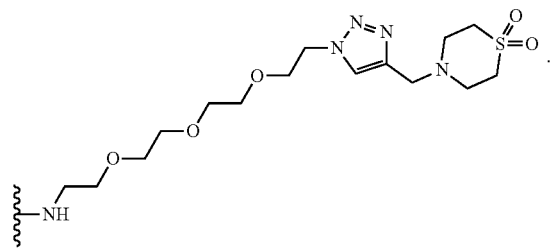 [SMILES: *NCCOCCOCCOCCn1cc(CN2CCS(=O)(=O)CC2)nn1]

19. The particle of claim 16, wherein Compound 101 is present in the chemically-modified alginate at a density of at least 2.0% and less than 9.0% nitrogen (N) as determined by combustion analysis for percent nitrogen.

20. The particle of claim 16, which has a mean diameter of about 1 mm to about 2 mm or a mean diameter of about 0.75 to about 1.0 mm and wherein the first compartment is formed from an alginate solution that lacks an afibrotic compound.

21. The particle of claim 16, wherein the first compartment is formed from an alginate solution comprising about 10 to about 50 million cells/ml, 50 to about 500 million cells/ml, about 75 million to about 450 million cells/ml, about 100 to about 450 million cells/ml, about 100 to about 400 million cells/ml, or about 100 to about 300 million cells/ml.

22. The particle of claim 16, wherein the cells are derived from ARPE19 cells and comprise an exogenous nucleotide sequence which comprises SEQ ID NO:9, SEQ ID NO:10, SEQ ID NO:11, of SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:23, SEQ ID NO:26, SEQ ID NO:27, and SEQ ID NO:28.

23. A particle comprising:
a) a first compartment comprising an alginate polymer and an islet cell;
b) a second compartment comprising an alginate polymer; and
c) a compound of Formula (III-a):

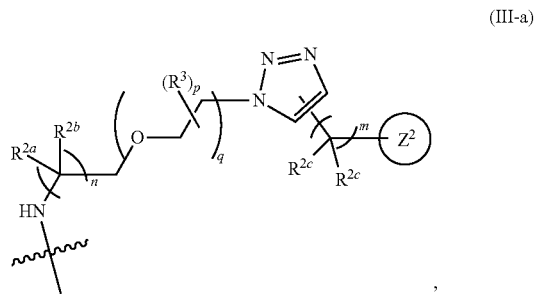

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{41}$, —$C(O)OR^{41}$, or —$C(O)R^{B1}$; each $R^{41}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; and "⌇" refers to a connection to an alginate polymer; wherein:
the first compartment is surrounded by the second compartment; and,
the alginate polymer of the second compartment is modified with a compound of Formula (III-a).

24. The particle of claim 23, wherein the compound of Formula (III-a) is selected from:

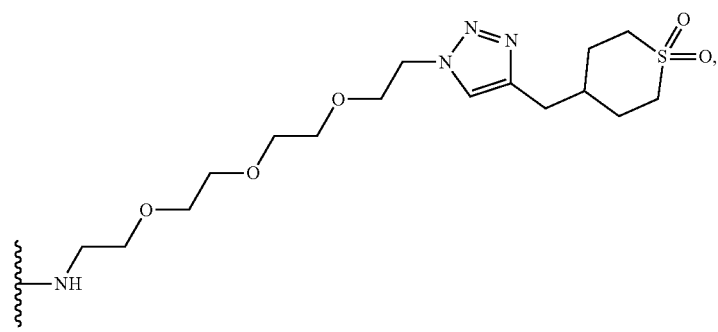 [SMILES: *NCCOCCOCCOCCn1cc(CC2CCS(=O)(=O)CC2)nn1]

-continued
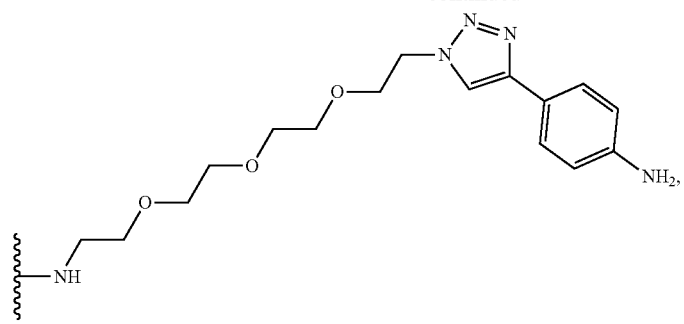
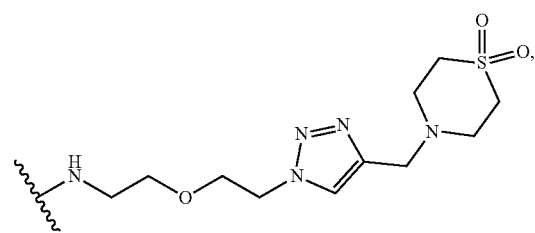
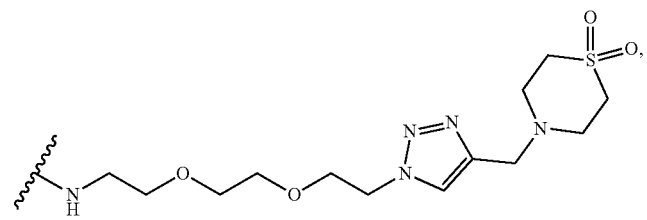
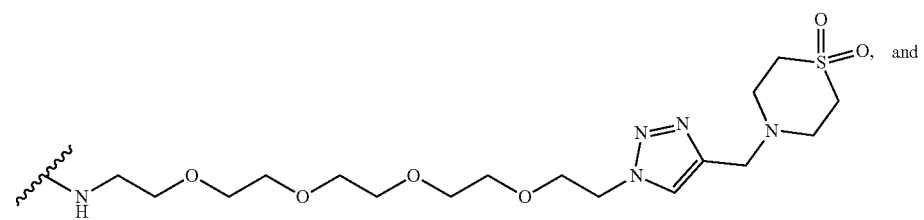
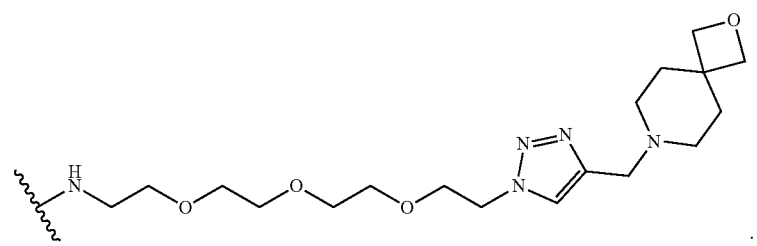

25. The particle of claim 23, wherein the compound of Formula (III-a) is
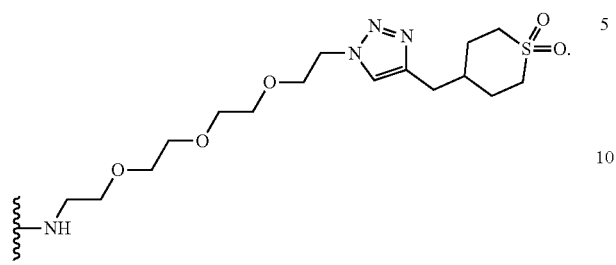
26. The particle of claim 23, wherein the islet cell produces a therapeutic agent.
27. The particle of claim 26, wherein the therapeutic agent is insulin.
* * * * *